United States Patent
Collard et al.

(10) Patent No.: US 10,604,755 B2
(45) Date of Patent: Mar. 31, 2020

(54) TREATMENT OF LIPID TRANSPORT AND METABOLISM GENE RELATED DISEASES BY INHIBITION OF NATURAL ANTISENSE TRANSCRIPT TO A LIPID TRANSPORT AND METABOLISM GENE

(71) Applicant: CuRNA, Inc., Miami, FL (US)

(72) Inventors: Joseph Collard, Delray Beach, FL (US); Olga Khorkova Sherman, Tequesta, FL (US); Carlos Coito, West Palm Beach, FL (US)

(73) Assignee: CuRNA, Inc., Miami, FL (US)

( * ) Notice: Subject to any disclaimer, the term of this patent is extended or adjusted under 35 U.S.C. 154(b) by 0 days.

(21) Appl. No.: 14/814,895

(22) Filed: Jul. 31, 2015

(65) Prior Publication Data

US 2016/0024505 A1 Jan. 28, 2016

Related U.S. Application Data

(62) Division of application No. 13/318,713, filed as application No. PCT/US2010/033908 on May 6, 2010, now Pat. No. 9,155,754.

(60) Provisional application No. 61/248,212, filed on Oct. 2, 2009, provisional application No. 61/235,227, filed on Aug. 19, 2009, provisional application No. 61/180,646, filed on May 22, 2009, provisional application No. 61/176,267, filed on May 7, 2009, provisional application No. 61/175,930, filed on May 6, 2009.

(51) Int. Cl.
| | |
|---|---|
| *C12N 15/113* | (2010.01) |
| *A61K 31/7115* | (2006.01) |
| *A61K 31/7125* | (2006.01) |
| *A61K 31/713* | (2006.01) |
| *A61K 48/00* | (2006.01) |

(52) U.S. Cl.
CPC .......... *C12N 15/113* (2013.01); *A61K 31/713* (2013.01); *C12N 15/1137* (2013.01); *C12N 15/1138* (2013.01); *C12Y 203/01043* (2013.01); *A61K 48/00* (2013.01); *C12N 2310/11* (2013.01); *C12N 2310/14* (2013.01); *C12N 2310/313* (2013.01); *C12N 2310/314* (2013.01); *C12N 2310/315* (2013.01); *C12N 2310/321* (2013.01); *C12N 2310/322* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,754,065 A | 6/1988 | Levenson et al. |
| 4,800,159 A | 1/1989 | Mullis et al. |
| 5,034,506 A | 7/1991 | Summerton et al. |
| 5,138,045 A | 8/1992 | Cook et al. |
| 5,218,105 A | 6/1993 | Cook et al. |
| 5,288,512 A | 2/1994 | Seiden |
| 5,288,514 A | 2/1994 | Ellman |
| 5,319,080 A | 6/1994 | Leumann |
| 5,393,878 A | 2/1995 | Leumann |
| 5,432,272 A | 7/1995 | Benner et al. |
| 5,457,189 A | 10/1995 | Crooke et al. |
| 5,459,255 A | 10/1995 | Cook et al. |
| 5,474,796 A | 12/1995 | Brennan |
| 5,491,084 A | 2/1996 | Chalfie et al. |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |
| 5,576,302 A | 11/1996 | Cook et al. |
| 5,593,853 A | 1/1997 | Chen et al. |
| 5,605,662 A | 2/1997 | Heller et al. |
| 5,661,134 A | 8/1997 | Cook et al. |
| 5,708,161 A | 1/1998 | Reese |
| 5,739,119 A | 4/1998 | Galli et al. |
| 5,739,311 A | 4/1998 | Lackey et al. |
| 5,756,710 A | 5/1998 | Stein et al. |
| 5,849,902 A | 12/1998 | Arrow et al. |
| 5,891,725 A | 4/1999 | Soreq et al. |
| 5,902,880 A | 5/1999 | Thompson |
| 5,908,779 A | 6/1999 | Carmichael et al. |

(Continued)

FOREIGN PATENT DOCUMENTS

| | | |
|---|---|---|
| CA | 2686933 | 4/2008 |
| EP | 335451 A3 | 3/1988 |

(Continued)

OTHER PUBLICATIONS

Girard et al (Nature 442: 199-202, 2006).*

(Continued)

*Primary Examiner* — Richard A Schnizer

(74) *Attorney, Agent, or Firm* — CuRNA, Inc.; Monte R. Browder

(57) ABSTRACT

The present invention relates to antisense oligonucleotides that modulate the expression of and/or function of a Lipid transport and metabolism gene, in particular, by targeting natural antisense polynucleotides of a Lipid transport and metabolism gene. The invention also relates to the identification of these antisense oligonucleotides and their use in treating diseases and disorders associated with the expression of a Lipid transport and metabolism genes.

15 Claims, 29 Drawing Sheets

Specification includes a Sequence Listing.

(56) References Cited

U.S. PATENT DOCUMENTS

| | | |
|---|---|---|
| 5,965,721 A | 10/1999 | Cook et al. |
| 5,985,663 A | 11/1999 | Bennett et al. |
| 6,005,095 A | 12/1999 | Capaccioli et al. |
| 6,013,639 A | 1/2000 | Peyman et al. |
| 6,013,786 A | 1/2000 | Chen et al. |
| 6,034,233 A | 3/2000 | Ecker et al. |
| 6,100,090 A | 8/2000 | Monia et al. |
| 6,140,492 A | 10/2000 | Morelli et al. |
| 6,147,200 A | 11/2000 | Manoharan et al. |
| 6,165,712 A | 12/2000 | Foulkes et al. |
| 6,165,990 A | 12/2000 | Singh et al. |
| 6,175,409 B1 | 1/2001 | Nielsen et al. |
| 6,221,587 B1 | 4/2001 | Ecker et al. |
| 6,239,265 B1 | 5/2001 | Cook |
| 6,242,589 B1 | 6/2001 | Cook et al. |
| 6,268,490 B1 | 7/2001 | Imanishi et al. |
| 6,303,374 B1 | 10/2001 | Zhang et al. |
| 6,307,040 B1 | 10/2001 | Cook et al. |
| 6,316,198 B1 | 11/2001 | Skouv et al. |
| 6,335,434 B1 | 1/2002 | Guzaev et al. |
| 6,376,541 B1 | 4/2002 | Nixon et al. |
| 6,403,566 B1 | 6/2002 | Wang |
| 6,444,464 B1 | 9/2002 | Wyatt |
| 6,451,991 B1 | 9/2002 | Martin et al. |
| 6,525,191 B1 | 2/2003 | Ramassamy |
| 6,528,262 B1 | 3/2003 | Gilad et al. |
| 6,528,631 B1 | 3/2003 | Cook et al. |
| 6,617,122 B1 | 9/2003 | Hayden et al. |
| 6,617,442 B1 | 9/2003 | Crooke et al. |
| 6,630,315 B1 | 10/2003 | Miwa et al. |
| 6,639,059 B1 | 10/2003 | Kochkine et al. |
| 6,656,730 B1 | 12/2003 | Manoharan |
| 6,667,337 B2 | 12/2003 | Wilson |
| 6,670,461 B1 | 12/2003 | Wengel et al. |
| 6,710,174 B2 | 3/2004 | Bennett et al. |
| 6,734,291 B2 | 5/2004 | Kochkine et al. |
| 6,762,169 B1 | 7/2004 | Manoharan |
| 6,794,499 B2 | 9/2004 | Wengel et al. |
| 6,821,724 B1 * | 11/2004 | Mittman ............ C07H 21/02 422/68.1 |
| 6,833,361 B2 | 12/2004 | Hong et al. |
| 6,861,514 B2 | 3/2005 | Cook et al. |
| 6,867,294 B1 | 3/2005 | Sanghvi et al. |
| 6,936,467 B2 | 8/2005 | Kmiec et al. |
| 6,936,593 B1 | 8/2005 | Agrawal et al. |
| 6,977,295 B2 | 12/2005 | Belotserkovskii et al. |
| 6,986,988 B2 | 1/2006 | Gilad et al. |
| 7,034,133 B2 | 4/2006 | Wengel et al. |
| 7,034,145 B2 | 4/2006 | Shen et al. |
| 7,053,195 B1 | 5/2006 | Goff |
| 7,053,199 B2 | 5/2006 | Imanishi et al. |
| 7,053,207 B2 | 5/2006 | Wengel |
| 7,060,809 B2 | 6/2006 | Wengel et al. |
| 7,084,125 B2 | 8/2006 | Wengel |
| 7,087,589 B2 | 8/2006 | Jacobson et al. |
| 7,125,982 B1 | 10/2006 | Frayne |
| 7,144,995 B2 | 12/2006 | Wise et al. |
| 7,144,999 B2 | 12/2006 | Ward et al. |
| 7,148,204 B2 | 12/2006 | Bennett et al. |
| 7,153,954 B2 | 12/2006 | Koch et al. |
| 7,169,916 B2 | 1/2007 | Krotz et al. |
| 7,199,107 B2 | 4/2007 | Dobie et al. |
| 7,202,357 B2 | 4/2007 | Crooke et al. |
| 7,217,572 B2 | 5/2007 | Ward et al. |
| 7,220,549 B2 | 5/2007 | Buzby |
| 7,226,785 B2 | 6/2007 | Kmiec et al. |
| 7,229,974 B2 | 6/2007 | Peyman et al. |
| 7,229,976 B2 | 6/2007 | Dobie et al. |
| 7,235,534 B2 | 6/2007 | Tauguay et al. |
| 7,235,653 B2 | 6/2007 | Bennett et al. |
| 7,238,858 B2 | 7/2007 | Marraccini et al. |
| 7,276,599 B2 | 10/2007 | Moore et al. |
| 7,285,288 B1 | 10/2007 | Tormo et al. |
| 7,297,786 B2 | 11/2007 | McCray et al. |
| 7,314,923 B2 | 1/2008 | Kaneko et al. |
| 7,320,965 B2 | 1/2008 | Sah et al. |
| 7,321,828 B2 | 1/2008 | Cowsert et al. |
| 7,335,764 B2 | 2/2008 | Crooke et al. |
| 7,335,765 B2 | 2/2008 | Kaneko et al. |
| 7,339,051 B2 | 3/2008 | Crooke et al. |
| 7,371,833 B1 | 5/2008 | Weiss |
| 7,399,845 B2 | 7/2008 | Seth et al. |
| 7,402,434 B2 | 7/2008 | Newman et al. |
| 7,402,574 B2 | 7/2008 | Iversen et al. |
| 7,420,050 B2 | 9/2008 | Park et al. |
| 7,423,142 B2 | 9/2008 | Vornlocher |
| 7,425,545 B2 | 9/2008 | Crooke et al. |
| 7,427,675 B2 | 9/2008 | Capaldi et al. |
| 7,456,154 B2 | 11/2008 | Soreq et al. |
| 7,462,642 B2 | 12/2008 | Wang et al. |
| 7,468,431 B2 | 12/2008 | Bhanot et al. |
| 7,510,830 B2 | 3/2009 | Baguley et al. |
| 7,541,344 B2 | 6/2009 | Bhat et al. |
| 7,547,684 B2 | 6/2009 | Seth et al. |
| 7,569,575 B2 | 8/2009 | Sorensen et al. |
| 7,569,686 B1 | 8/2009 | Bhat et al. |
| 7,572,582 B2 | 8/2009 | Wengel et al. |
| 7,582,745 B2 | 9/2009 | Sah et al. |
| 7,585,893 B2 | 9/2009 | Baguley et al. |
| 7,589,190 B2 | 9/2009 | Westergaard et al. |
| 7,598,227 B2 | 10/2009 | Crooke et al. |
| 7,605,251 B2 | 10/2009 | Tan et al. |
| 7,622,453 B2 | 11/2009 | Frieden et al. |
| 7,662,948 B2 | 2/2010 | Kurreck et al. |
| 7,666,854 B2 | 2/2010 | Seth et al. |
| 7,674,895 B2 | 3/2010 | Reich et al. |
| 7,687,617 B2 | 3/2010 | Thrue et al. |
| 7,691,995 B2 | 4/2010 | Zamore et al. |
| 7,695,902 B2 | 4/2010 | Crooke |
| 7,696,345 B2 | 4/2010 | Allerson et al. |
| 7,709,456 B2 | 5/2010 | Corey et al. |
| 7,709,630 B2 | 5/2010 | Gaarde et al. |
| 7,713,738 B2 | 5/2010 | Hansen et al. |
| 7,718,629 B2 | 5/2010 | Bamcrot et al. |
| 7,723,508 B2 | 5/2010 | Crooke et al. |
| 7,732,422 B2 | 6/2010 | Gleave et al. |
| 7,732,590 B2 | 6/2010 | Bhanot et al. |
| 7,737,264 B2 | 6/2010 | Thrue et al. |
| 7,737,265 B2 | 6/2010 | Akinc et al. |
| 7,741,305 B2 | 6/2010 | Crooke et al. |
| 7,741,309 B2 | 6/2010 | Hansen et al. |
| 7,741,457 B2 | 6/2010 | Seth et al. |
| 7,745,609 B2 | 6/2010 | Bennett et al. |
| 7,749,978 B2 | 7/2010 | Sah et al. |
| 2003/0139359 A1 | 7/2003 | Dobie |
| 2003/0170699 A1 * | 9/2003 | Fan ............ C07K 14/72 435/6.11 |
| 2003/0186920 A1 | 10/2003 | Sirois |
| 2003/0191075 A1 | 10/2003 | Cook et al. |
| 2003/0228618 A1 | 12/2003 | Levanon et al. |
| 2003/0233670 A1 | 12/2003 | Edgerton et al. |
| 2004/0006031 A1 | 1/2004 | Dean et al. |
| 2004/0033480 A1 | 2/2004 | Wong |
| 2004/0101858 A1 | 5/2004 | Ward et al. |
| 2004/0137423 A1 | 7/2004 | Hayden et al. |
| 2004/0138155 A1 | 7/2004 | Baird et al. |
| 2004/0175803 A1 | 9/2004 | Meritet et al. |
| 2004/0180336 A1 | 9/2004 | Gilad et al. |
| 2004/0254137 A1 | 12/2004 | Ackermann et al. |
| 2005/0009771 A1 | 1/2005 | Levanon et al. |
| 2005/0026160 A1 | 2/2005 | Allerson et al. |
| 2005/0108783 A1 * | 5/2005 | Koike ............ A01K 67/0276 800/17 |
| 2005/0113326 A1 | 5/2005 | Siwkowski et al. |
| 2005/0143357 A1 | 6/2005 | Pousette et al. |
| 2005/0153286 A1 | 7/2005 | Clements |
| 2005/0215504 A1 | 9/2005 | Bennett et al. |
| 2005/0222029 A1 | 10/2005 | Bartel et al. |
| 2006/0009410 A1 | 1/2006 | Crooke et al. |
| 2006/0142196 A1 | 6/2006 | Klein et al. |
| 2006/0178333 A1 | 8/2006 | Soreq et al. |
| 2006/0281699 A1 * | 12/2006 | Merchiers ............ C12Q 1/25 514/44 A |
| 2007/0082848 A1 | 4/2007 | Alitalo et al. |

(56) References Cited

U.S. PATENT DOCUMENTS

| | | |
|---|---|---|
| 2007/0197459 A1 | 8/2007 | Milner |
| 2007/0213274 A1 | 9/2007 | Salonen |
| 2007/0213292 A1 | 9/2007 | Stoffel et al. |
| 2007/0231816 A1 | 10/2007 | Chaussabel et al. |
| 2007/0248590 A1 | 10/2007 | Milne et al. |
| 2008/0146788 A1 | 6/2008 | Bhat et al. |
| 2008/0221051 A1 | 9/2008 | Becker et al. |
| 2008/0293136 A1* | 11/2008 | Quay ............... C12N 15/1137 435/375 |
| 2008/0293142 A1 | 11/2008 | Liu et al. |
| 2009/0149403 A1* | 6/2009 | MacLachlan ........ C12N 15/113 514/44 R |
| 2009/0191263 A1 | 7/2009 | Reich et al. |
| 2009/0192106 A1 | 7/2009 | Dobie et al. |
| 2009/0208479 A1 | 8/2009 | Jaye et al. |
| 2009/0258925 A1 | 10/2009 | Wahlestedt |
| 2009/0318536 A1 | 12/2009 | Freier et al. |
| 2009/0326041 A1 | 12/2009 | Bhanot et al. |
| 2010/0105760 A1 | 4/2010 | Collard et al. |

FOREIGN PATENT DOCUMENTS

| | | | |
|---|---|---|---|
| EP | 335451 A2 | 10/1989 | |
| WO | WO-1984/03564 | 9/1984 | |
| WO | WO-1991/19735 | 12/1991 | |
| WO | WO-1992/00091 | 1/1992 | |
| WO | WO-1992/08796 | 5/1992 | |
| WO | WO-1993/20242 | 10/1993 | |
| WO | WO-1994-026887 A1 | 11/1994 | |
| WO | WO-1994/28143 | 12/1994 | |
| WO | WO-1995-015373 A2 | 6/1995 | |
| WO | WO-1995/22618 | 8/1995 | |
| WO | WO-1995/25116 | 10/1995 | |
| WO | WO-1995/35505 | 12/1995 | |
| WO | WO-1996-027663 A2 | 9/1996 | |
| WO | WO-1997-039120 A1 | 10/1997 | |
| WO | WO-9854359 A1 * | 12/1998 | ........... C12Q 1/6883 |
| WO | WO-1999-014226 A1 | 3/1999 | |
| WO | WO-1999-039352 A1 | 8/1999 | |
| WO | WO-2000-057837 A1 | 10/2000 | |
| WO | WO-2000-061770 A2 | 10/2000 | |
| WO | WO-2001-000669 A2 | 1/2001 | |
| WO | WO-2001-21631 A2 | 3/2001 | |
| WO | WO-2001-025488 A2 | 4/2001 | |
| WO | WO-2001-051630 A1 | 7/2001 | |
| WO | WO-2002-062840 A1 | 8/2002 | |
| WO | WO-2002-068688 A1 | 9/2002 | |
| WO | WO-2004-016255 A1 | 2/2004 | |
| WO | WO-2004-024079 A2 | 3/2004 | |
| WO | WO-2004-030750 A1 | 4/2004 | |
| WO | WO-2004-041838 A1 | 5/2004 | |
| WO | WO-2004-104161 A2 | 12/2004 | |
| WO | WO-2005-045034 A2 | 5/2005 | |
| WO | WO-2005-070136 A2 | 8/2005 | |
| WO | WO-2005-079862 A1 | 9/2005 | |
| WO | WO-2007-028065 A2 | 3/2007 | |
| WO | WO-2007-071182 A1 | 6/2007 | |
| WO | WO-2007-087113 A2 | 8/2007 | |
| WO | WO-2007-138023 A1 | 12/2007 | |
| WO | WO-2008-057556 A2 | 5/2008 | |
| WO | WO-2008-066672 A2 | 6/2008 | |
| WO | WO-2008-087561 A2 | 7/2008 | |
| WO | WO-2010-002984 A1 | 1/2010 | |
| WO | WO-2010-040571 A2 | 4/2010 | |
| WO | WO-2010-054364 A1 | 5/2010 | |
| WO | WO-2010-058227 A2 | 5/2010 | |
| WO | WO 2010/088668 | * 8/2010 | |

OTHER PUBLICATIONS

GenBank Accession DQ577347.1 (2008).*
Simon et al (Structure 19(2): 172-180, 2011).*
GenBank Accession AK_311445.1 (2008).*
Shibata et al (Genome Res. 5: 400-403, 1995) (Year: 1995).*
Ausubel, Current Protocols in Molecular Biology vol. 1, 1994, 6.0.1-6.4.10.
Barak, et al., "A β-Arrestin/Green Fluorescent Protein Biosensor for Detecting G Protein-Coupled Receptor Activation," J. Biol. Chem. 272:27497-27500 (1997).
Barber, et al., "Delivery of membrane-impermeant fluorescent probes into living neural cell populations by lipotransfer," Neuroscience Letters 207:17-20 (1996).
Baum, "Solid-phase synthesis of benzodiazepines," C&EN News, Jan. 18, p. 33-34 (1993).
Bernstein, E., et al., "Role for a Bidentate Ribonuclease in the Initiation Step of RNA Interference," Nature 409:363-366 (2001).
Boutla, A., et al., "Short 5'-phosphorylated double-stranded RNAs induce RNA interference in *Drosophila*," Curr. Biol. 11:1776-1780 (2001).
Boyd-Kimball, et al., "Proteomic Identification of Proteins Specifically Oxidized by Intracerebral Injection of Amyloid β-Peptide (1-42) into Rat Brain: Implications for Alzheimer's Disease," Neuroscience 132, 313-324 (2005).
Brazma & Vilo, "Gene expression data analysis," FEBS Lett., 480:17-24 (2000).
Bright, et al., "Chapter 6. Fluorescence Ratio Imaging Microscopy," Methods in Cell Biology vol. 30, Taylor and Wang (eds) p. 157-192 (1989).
Bright, et al., "Delivery of Macromolecules Into Adherent Cells via Electroporation for Use in Fluorescence Spectroscopic Imaging and Metabolic Studies," Cytometry 24:226-233 (1996).
Bright, et al., "Fluorescence Ratio Imaging Microscopy: Temporal and Spatial Measurements of Cytoplasmic pH," J. Cell Biology 104:1019-1033 (1987).
Campbell, et al., "Phosphonmate Ester Synthesis Using a Modified Mitsunobu Condensation," J. Org. Chem. 59:658-660 (1994).
Caplen, N. J., et al., "Specific inhibition of gene expression by small double-stranded RNAs in invertebrate and vertebrate systems," PNAS Sci. USA 98:9742-9747 (2001).
Carninci, et al., "The transcriptional landscape of the mammalian genome," Science 309:1559-1563 (2005).
Carulli, et al., "High Throughput Analysis of Differential Gene Expression," J. Cell Biochem. Suppl., 3:286-296 (1998).
Celis, et al., "Gene expression profiling: monitoring transcription and translation products using DNA microarrays and proteomics," FEBS Lett., 480:2-16 (2000).
Chabala, J.C., "Solid-phase combinatorial chemistry and novel tagging methods for identifying leads," Curr Opin Biotechnol. 6:632-639 (1995).
Cech, J., "Ribozymes and Their Medical Implications," American. Med Assoc. 260:3030-3035 (1988).
Chen, et al., "Expression of ssDNA in Mammalian Cells," BioTechniques 34:167-171 (2003).
Chen, et al., "Analogous Organic Synthesis of Small-Compound Libraries: Validation of Combinatorial Chemistry in Small-Molecule Synthesis," J. Amer. Chem. Soc. 116:2661-2662 (1994).
Cheng, J. et al., "Transcriptional maps of 10 human chromosomes at 5-nucleotide resolution," Science 308:5725:1149-1154 (2005).
Cho, et al., "An Unnatural Biopolymer," Science 261:1303-1305 (1993).
Christiensen, N.K. et al., "A Novel Class of Oligonucleotide Analogues Containing 2'-O,3'-C-Linked [3.2.0]Bicycloarabinonucleoside Monomers: Synthesis, Thermal Affinity Studies, and Molecular Modeling," J. Am. Chem. Soc., 120:5458-5463 (1998).
Cubitt, et al., "Understanding, improving and using green fluorescent proteins," Trends in Biochemical Science 20:448-455 (1995).
Curiel, D. T. et al., "Adenovirus enhancement of transferrin-polylysine-mediated gene delivery," PNAS 88:8850-8854 (1991).
Dai et al., "SIRT1 Interacts With p73 and Suppresses p73-Dependent Transcriptional Activity," J Cell Physiol 210(1):161-165 (2007).
Davidson, et al., "A model system for in vivo gene transfer into the central nervous system using an adenoviral vector," Nat. Genet 3:219-223 (1993).
Davis, et al., "Direct Gene Transfer into Skeletal Muscle In Vivo: Factors Affecting Efficiency of Transfer and Stability of Expression," Hum Gene Ther 4:151-159 (1993).

(56) References Cited

OTHER PUBLICATIONS

De Mesmaeker, et al., "Antisense Oligonucleotides," Acc. Chem. Res. 28:366-374 (1995).
Deng et al., "Small Interfering RNA Targeting the PINK1 Induces Apoptosis in Dopaminergic Cells SH-SY5Y", Biochemical and Biophysical Research Communications, vol. 337, No. 4, pp. 1133-1138 (2005).
Dixon, et al., "Anthrax," New England J. Med. 341:815-826 (1999).
Dolle, "Discovery of Enzyme inhibitors through combinatorial chemistry," Mol Divers. 2:223-236 (1997).
Dykxhoorn, D., et al., "Determinants of Specific RNA Interference-Mediated Silencing of Human β-Globin Alleles Differing by a Single Nucleotide Polymorphism," PNAS, vol. 103, No. 15, pp. 5953-5958, (2006).
Eguchi, et al., "Antisense RNA," Annu Rev. Biochem 60:631-652 (1991).
Eichler, et al., "Generation and utilization of synthetic combinatorial libraries," Mol Med Today 1:174-180 (1995).
Eichler, et al., "Peptide Peptidomimetic and organic synthetic combinatorial libraries," Med Res Rev 15:481-496 (1995).
Espeseth, et al., A genome wide analysis of ubiquitin ligases in APP processing identifies a novel regulator of BACE1 mRNA levels, Mol. Cell Neurosci. 33: 227-235 (2006).
Faghihi, M. & Wahlestedt, C., "RNA interference is not involved in natural antisense mediated regulation of gene expression in mammals," Genome Biol (2005).
Fauchere, et al., "Peptide and nonpeptide lead discovery using robotically synthesized soluble libraries," Can J. Physiol Pharmacol 75:683-689 (1997).
Felgner and Holm, "Cationic Liposome-Mediated Transfection," Bethesda Res. Lab Focus, 11:2:21 (1989).
Fields, et al., "How many genes in the human genome?" Nature Genetics 7:345-346 (1994).
Freier & Altman, "The ups and downs of nucleic acid duplex stability: structure-stability studies on chemically-modified DNA:RNA duplexes," Nucl. Acid Res., 25:22:4429-4443 (1997).
Fuchs, et al., "Identification of Differentially Expressed Genes by Mutually Subtracted RNA Fingerprinting," Anal. Biochem., 286:91-98 (2000).
Gebeyehu, G., et al., "Novel biotinylated nucleotide-analogs for labeling and colorimetric detection of DNA," Nucl. Acids Res. 15:4513 (1987).
Geller, A.I. et al., "An HSV-1 Vector Expressing Tyrosine Hydroxylase Causes Production and Release of L-DOPA from Cultured Rat Striatal Cells," J. Neurochem 64:487-496 (1995).
Geller, A.I. et al., "Long-term increases in neurotransmitter release from neuronal cells expressing a constitutively active adenylate cyclase from a herpes simplex virus type 1 vector," PNAS U.S.A. :90:7603-7607 (1993).
Geller, A.I., et al., "Infection of cultured central nervous system neurons with a defective herpes simplex virus 1 vector results in stable expression of Escherichia coli β-galactosidase," PNAS USA 87:1149-1153 (1990).
GenBank Accession No. NM_000559, Homo Sapiens Hemoglobin, Gamma A (HBG1), mRNA, (2008).
Giuliano, et al., "FLuorescent Protein Biosensors: Measurement of Molecular Dynamics in Living Cells," Ann. Rev. of Biophysics and Biomolecular Structure 24:405-434 (1995).
Giuliano, et al., "Light-Optical-Based Reagents for the Measurement and Manipulation of Ions, Metabolites, and Macromolecules in Living Cells," Methods in Neuroscience 27:1-16 (1995).
Giuliano, et al., "Determination of Intracellular pH of BALB/c-3T3 Cells Using the Fluorescence of Pyranine," Anal. Biochem 167:362-371 (1987).
Going & Gusterson, "Molecular Pathology and Future Developments," Eur. J. Cancer, 35:1895-1904 (1999).
Hagihara, et al., "Vinylogous Polypeptides: An Alternate Peptide Backbone," J. Amer. Chem. Soc. 114:6568-6571 (1992).

Haussecker, D., et al., "Dicer-Dependent Turnover of Intergenic from the Human β-Globin Gene Cluster," Molecular and Cellular Biology, vol. 25, No. 21, pp. 9724-9733, (2005).
Heller, et al., "Discovery and Analysis of Inflammatory Disease-Related Genes Using cDNA Microarrays," PNAS U.S.A. 94:2150-2155 (1997).
Herdewijn P., "Heterocyclic Modifications of Oligonucleotides and Antisense Technology," Antisense & Nucleic Acid Drug Dev., 10:297-310 (2000).
Hirschmann, et al., J. Amer. Chem. Soc., 114:9217-9218 (1992).
Hobbs-DeWitt, et al., "Diversomers: An approach to nonpeptide, nonoligomeric chemical diversity," Proc. Nat. Acad. Sci. USA 90;6909-6913 (1993).
Houghton AN, Gold JS, Blachere NE, Immunity against cancer: lessons learned from melanoma,. Curr Opin Immunol 13:134-140 (2001).
International Human Genome Sequencing Consortium "Finishing the euchromatic sequence of the human genome." Nature 431:7011:931-945 (2004).
Janda, K.D. "Tagged versus untagged libraries: Methods for the generation and screening of combinatorial chemical libraries," PNAS 91:10779-10785 (1994).
Janowski, et al., "Inhibiting gene expression at transcription start sites in chromosomal DNA with antigen RNAs," Nature Chemical Biology, 1(4):216-222 (2005).
Jungblut, et al., "Proteomics in human disease: Cancer, heart and infectious diseases," Electrophoresis 20:2100-2110 (1999).
Jurecic & Belmont, "Long-distance DD-PCR and cDNA microarrays," Curr. Opin. Microbiol., 3:316-321 (2000).
Kabanov, et al., "A new class of antivirals: antisense oligonucleotides combined with a hydrophobic substituent effectively inhibit influenza virus reproduction and synthesis of virus-specific proteins in MDCK cells," FEBS Lett. 259:327-330 (1990).
Kaplitt, M.G., et al., "Long-term gene expression and phenotypic correction using adeno-associated virus vectors in the mammalian brain," Nat. Genet. 8:148-154 (1994).
Kapranov, P. et al., "Examples of the complex architecture of the human transcriptome revealed by RACE and high-density tiling arrays," Genome Res 15:7:987-997 (2005).
Katayama, S. et al., "Antisense Transcription in the Mammalian Transcriptome," Science 309:1564-1566 (2005).
Kawahara & Nishikura, "Extensive adenosine-to-inosine editing detected in Alu repeats of antisense RNAs reveals scarcity of sense-antisense duplex formation," FEBS Lett 580:2301-2305 (2006).
Kay, et al., "Identification of enzyme inhibitors from phage-displayed combinatorial peptide libraries," Comb Chem High Throughput Screen 4:535-543 (2001).
Kenan, et al., "Exploring molecular diversity with combinatorial shape libraries," Trends Biochem Sci 19:57-64 (1994).
Kornberg, A., DNA Replication, W.H. Freeman & Co., San Francisco, pp. 75-77, (1980).
Larson, et al., "Rapid DNA Fingerprinting of Pathogens by Flow Cytometry," Cytometry, 2000, 41:203-208 (2000).
Larsson, et al., "High-Throughput Protein Expression of cDNA Products as a Tool in Functional Genomics," J. Biotechnology., 80:143-157 (2000).
Lebl, et al., "One-bead-one-structure combinatorial libraries," Biopolymers 37:177-198 (1995).
LeGal Lasalle et al., "An Adenovirus Vector for Gene Transfer into Neurons and Glia in teh Brain," Science 259:988-990 (1993).
Letsinger, et al., "Cholesteryl-conjugated oligonucleotides: Synthesis, Properties, and Activity as Inhibitors of Replication of Human Immunodeficiency Virus in Cell Culture," PNAS 86:6553-6556 (1989).
Li et al., "Control of APP processing and Aβ generation level by BACE1 enzymatic activity and transcription," Faseb J 20; 285-292 (2006).
Li, et al., J. Neurochem 89 1308-1312 (2004).
Liang, et al., "Parallel Synthesis and Screening of a Solid Phase Carbohydrate Library," Science 274:1520-1522 (1996).
Luther, "Role of endogenous antisense RNA in cardiac gene regulation," J. Mol. Med. 83:26-32 (2005).

(56) References Cited

OTHER PUBLICATIONS

Madden, et al., "Serial analysis of gene expression: from gene discovery to target identification," Drug Discov. Today 5:415-425 (2000).
Makalowska I, Lin CF, Makalowski W., "Overlapping genes in vertebrate genomes," Comput Biol. Chem 29:1:1-12 (2005).
Mannino and Gould-Fogerite, "Liposome Mediated Gene Transfer," BioTechniques 6:682-690 (1988).
Manoharan et al., "Lipidic Nucleic Acids," Tetrahedron Lett 36:3651-3654 (1995).
Manoharan, et al., "Chemical Modifications to Improve Uptake and Bioavailability of Antisense Oligonucleotides," Ann. N.Y. Acad. Scie 660:306-309 (1992).
Manoharan, et al., "Introduction of a Lipophilic Thioether in teh Minor Groove of Nucleic Acids for Antisense Applications," Bioorg. Med. Chem. Let 3:2765-2770 (1993).
Manoharan, et al., "Cholic Acid-Oligonucleotide Conjugates for Antisense Applications," Bioorg. Med. Chem. Let 4;1053 (1994).
Manoharan, et al., "Oligonucleotide Conjugates: Alteration of the Pharmacokinetic Properties of Antisense Agents," Nucleosides & Nucleotides 14:969-973 (1995).
Manoharan, M., "2'-Carbohydrate modifications in antisense oligonucleotide therapy: importance of conformation, configurationj and conjugation," Biochemica et Biophysica Acta 1489:117-139 (1999).
Mattick, J. S. "RNA regulation: a new genetics?" Nat. Rev. Genet 5:4:316-323 (2004).
Maurer, R.A., "Cationic Liposome-Mediated Transfection of Primary Cultures of Rat Pituitary Cells," Bethesda Res. Lab. Focus 11:2:25 (1989).
Mcneil in Methods in Cell Biology vol. 29, Taylor and Wang (eds.) p. 153-173 (1989).
Morelli et al., "The antisense bcl-2-IgH transcript is an optimal target for synthetic oligonucleotides," PNAS USA 94:8150-8155 (1997).
Nielsen, et al., "Sequence-Selective Recognition of DNA by Strand Displacement with a Thymine-Substituted Polyamide," Science 254:1497-1500 (1991).
Oberhauser, et al., "Effective incorporation of 2'-O-methyl-oligoribonucleotides into liposomes and enhanced cell association through modification with thiocholesterol," Nucl. Acids Res. 20:533-538 (1992).
Petit et al., "Wild-type PINK1 Prevents Basal and Induced Neuronal Apoptosis, a Protective Effect Abrogated by Parkinson Disease-Related Mutations", Journ. Biol. Chem., vol. 280, No. 40, pp. 34025-334032 (2005).
Prasanth, et al., "Regulating Gene Expression through RNA Nuclear Retention," Cell 123, 249-263 (2005).
Prashar & Weissman, "READS: A Method for Display of 3'-End Fragments of Restriction Enzyme-Digested cDNAs for Analysis of Differential Gene Expression," Methods Enzymol., 303:258-272 (1999).
Quantin, et al., "Adenovirus as an expression vector in muscle cells in vivo," PNAS 89:2581-2584 (1992).
Rosenfeld, et al., "In Vivo Transfer of the Human Cystic Fibrosis Transmembrane Conductance Regulator Gene to the Airway Epithelium," Cell, 68:143-155 (1992).
Rosok and Sioud, "Systematic identification of sense-antisense transcripts in mammalian cells," Nature Biotech. 22(1):104-108 (2004).
Saison-Behmoaras, et al., "Short modified antisense oligonucleotides directed against Ha-ras point mutation induce selective cleavage of the mRNA and inhibit T24 cells proliferation," EMBO J. 10:1111-1118 (1991).
Sanghvi, Y.S., in Crooke, S.T. and Lebleu, B., eds., Antisense Research and Applications, CRC Press, Boca Raton, 1993, p. 276-278.
Scheele et al., "The Human PINK1 Locus is Regulated and Vivo by a Non-Coding Natural Antisense RNA During Modulation of Mitochondrial Function", BMC Genomics, vol. 8, No. 1, p. 74 (2007).

Schena, et al., "Parallel human genome analysis: Microarray-based expression monitoring of 1000 genes," PNAS 93:10614-10619(1996).
Shea, et al., "Synthesis, hybridization properties and antiviral activity of lipid-oligodeoxynucleotide conjugates," Nucl. Acids Res 18:3777-3783 (1990).
Shen, T., et al., "Modification of Globin Gene Expression by RNA Targeting Strategies," Experimental Hematology, vol. 35, No. 8, pp. 1209-1218, (2007).
Shimomura, et al., "Semi-synthetic aequorin," J. of Biochemistry (Tokyo) 251:405-410 (1988).
Singer, et al., "Targeting BACE1 with siRNAs ameliorates Alzheimer disease neuropathology in a transgenic model," Nat Neurosci 8:1343-1349 (2005).
Southwick, et al., "Cyanine Dye Labeling Reagents-Carboxymethylindocyanine Succinimidyl Esters," Cytometry 11:418-430 (1990).
Stratford-Perricadet, et al., "Widespread Long-term Gene Transfer to Mouse Skeletal Muscles and Heart," J. Clin. Invest., 90:626-630 (1992).
Sullenger, et al., "Overexpression of TAR sequences Renders Cells Resistant to Human Immunodeficiency Virus Replication," Cell63:601-608 (1990).
Sun, et al., "Downregulation of Sirt1 by antisense oligonucleotides induces apoptosis and enhances radiations sensitization in A549 lung cancer cells," Lung Cancer 58(1):21-29 (2007).
Sutcliffe, et al., "TOGA: An automated parsing technology for analyzing expression of nearly all genes," PNAS, 97:1976-1981 (2000).
Sutton, et al., "TIGR Assembler: A New Tool for Assembling Large Shotgun Sequencing Projects," Genome Science & Tech., 1:9-19 (1995).
Svinarchuk, et al., "Inhibition of HIV proliferation in MT-4 cells by antisense oligonucleotide conjugated to lipophilic groups," Biochimie 75:49-54 (1993).
Tamagno, et al., "The various aggregation states of β-amyloid 1-42 mediate different effects on oxidative stress, neurodegeneration, and BACE-1 expression," Free Radic Biol Med 41:202-212 (2006).
Thakker, D.R., et al., "siRNA-mediated knockdown of the serotonin transporter in the adult mouse brain," Mol Psychiatry 10:782-789 (2005).
Thakker, et al., "Neurochemical and behavioral consequences of widespread gene knockdown in the adult mouse brain by using nonviral RNA interference," PNAS 101:17270-17275 (2004).
Thomas et al., "Intracellular pH Measurements in Ehrlich Ascites Tumor Cells Utilizing Spectroscopic Probes Generated in Situ," Biochemistry 18:2210-2218 (1979).
Thompson, et al., "Synthesis and Applications of Small Molecule Libraries" Chem Rev 96:555-600 (1996).
To, Ky, "Identification of Differential Gene Expressionm by High Throughput Analysis," Comb. Chem. High Throughput Screen 3:235-241 (2000).
Tong, et al., "Oxidative stress potentiates BACE1 gene expression," Neural Transm 112, 455-469 (2005).
Toulme, J.J., "New candidates for true antisense," Nature Biotechnology 19:17-18 (2001).
Tsien in Methods in Cell Biology vol. 30 Taylor and Wang (eds) p. 127-156 (1989).
Ulhman, E., "Recent advances in the medical chemistry of antisense oligonucleotide," Current Opinions in Drug Discovery & Development 3:203-213 (2000).
Van Den Eynde BJ, "T cell defined tumor antigens," Curr Opin Immunol 9:684-693 (1997).
Van Der Bruggen, et al., "Tumor-specific shared antigenic peptides recognized by human T cells," Immunol Rev188:51-64 (2002).
Vanhee-Brossolet and Vaquero, "Do natural antisense transcripts make sense in eukaryotes?" Gene 211:1-9 (1998).
Vaughn, et al., "Human Antibodies with Sub-nanomolar Affinities Isolated from a Large Non-immunized Phage Display Library," Nature Biotechnology, 14:3:309-314 (1996).
Velculescu, et al., "Serial Analysis of Gene Expression," Science 270:484-487 (1995).

(56) References Cited

OTHER PUBLICATIONS

Wahlestedt, "Natural antisense and noncoding RNA transcripts as potential drug targets," Drug Discovery Today 11 (11/12):503-508 (2006).

Wahlestedt, C., "Antisense oligonucleotide strategies in neuropharmacology," Trends Pharmacol Sci 15:2:42-46 (1994).

Walsh, et al., The role of cell-derived oligomers of Aβ in Alzheimer's disease and avenues for therapeutic intervention, Biochem Soc Trans 33: 1087-1090 (2005).

Wang, B.B. et al., "Identification of a nuclear-specific cyclophilin which interacts with the proteinase inhibitor eglin c," Biochem J. 314 (Pt 1) 313-319 (1996).

Wiesenhofer, et al., "Glial cell line-derived neurotrophic factor (GDNP) is a proliferation factor for rat C6 glioma cells: evidence from antisense experiments," Antisense & Nucleic Acid Drug Development 10(5):311-321 (2000).

Xue, et al., "Hypoxia and reoxygenation increased BACE1 mRNA and protein levels in human neuroblastoma SH-SY5Y cells," Neurosci Lett 405,231-235 (2006).

Yamada, et al., "Endothelial Nitric-Oxide Synthase Antisense (NOS3AS) Gene Encodes an Autophagy-Related Protein (APG9-like2) Highly Expressed in Trophoblast" (2005).

Yang, et al., "Cellular and Humoral Immune Responses to Viral Antigens Create Barriers to Lung-Directed Gene Therapy with Recombinant Adenoviruses," J. Virol 69:2004-2015 (1995).

Yoshigai, et al., "Characterization of Natural Antisense Transcripts Expressed from Interleukin 1β-inducible Genes in Rat Hepatocytes," HOAJ Biology; 1-10 (2012).

EP Application No. 06850393.7 Examination Report dated Oct. 18, 2011.

International Search Report and Written Opinion for PCT Application No. PCT/US2010/033078 dated Jun. 29, 2011.

PCT/US2010/026119 Search Report and Written Opinion dated Feb. 7, 2011.

PCT/US2010/024079 Search Report and Written Opinion dated Jan. 31, 2011.

PCT/US2010/027394 Search Report and Written Opinion dated Nov. 5, 2010.

PCT/US96/10287 (WO97/000271) The Regents of the University of California 1.3.97.

\* cited by examiner

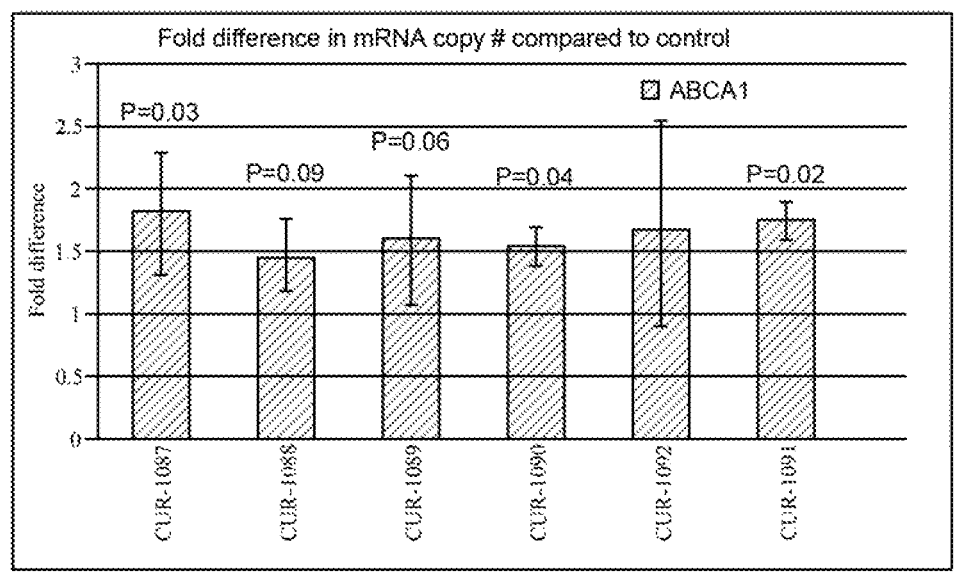
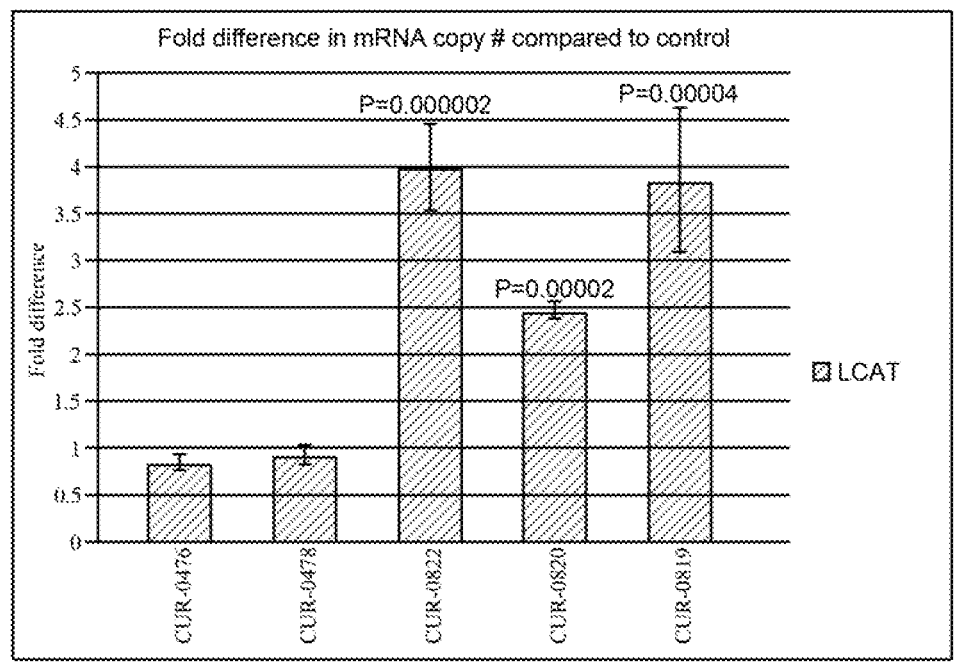

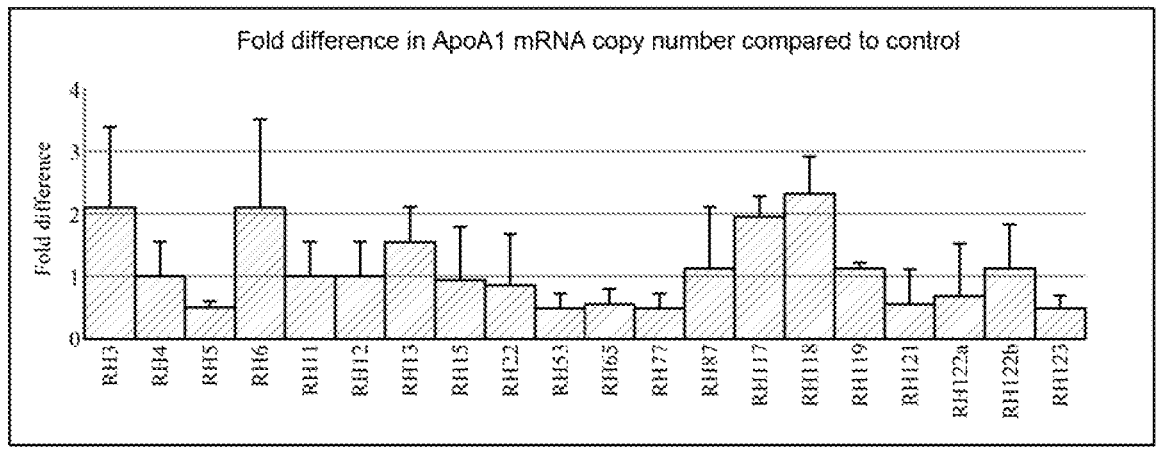
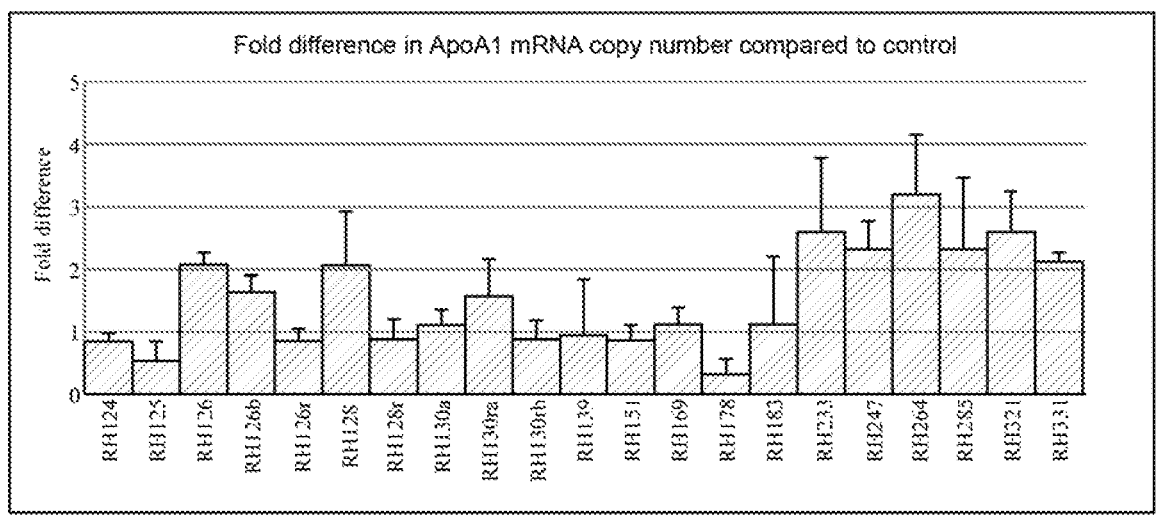
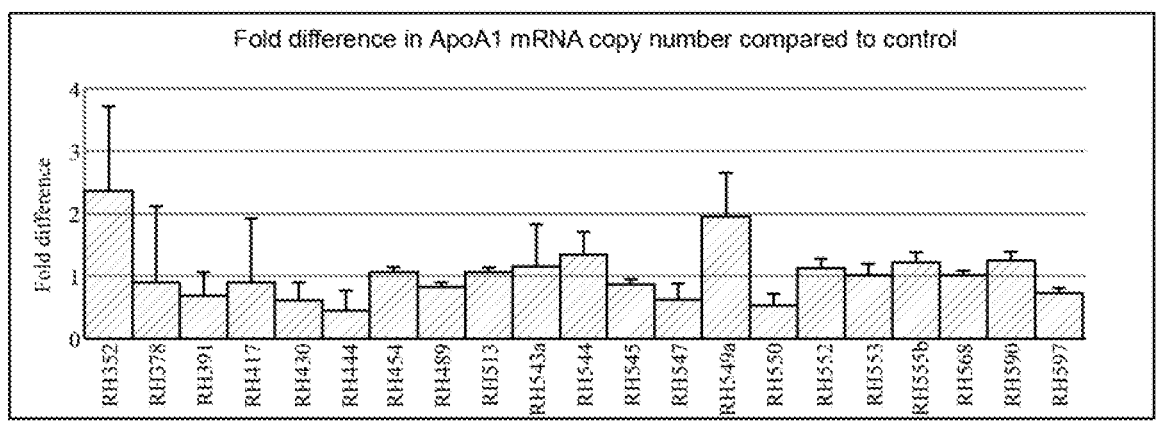

Fold difference in mRNA copy number compared to control (primary monkey hepatocytes)

FIG.2

(SEQ ID NO: 1)

>gi|21536375 | ref |NM_005502 | Homo sapiens ATP-binding cassette, sub –family A (ABC1), member 1 (ABCA1), mRNA
gtaattgcgagcgagagtgagtggggccgggacccgcagagccgagccgacccttctctcccgggctgcggcagggcagggcggggagctccgc
gcaccaacagagccggttctcagggcgctttgctccttgttttttccccggttctgttttctcccctctccggaaggcttgtcaaggggtaggagaaagaga
cgcaaacacaaaagtggaaaacagttaatgaccagccacggcgtccctgctgtgagctctggccgctgccttccagggctcccgagccacacgctggg
ggtgctggctgagggaacatggcttgttggcctcagctgaggttgctgctgtggaagaacctcactttcagaagaagacaaacatgtcagctgctgctgg
aagtggcctggcctctatttatcttcctgatcctgatctctgttcggctgagctacccaccctatgaacaacatgaatgccatttccaaataaagccatgccct
ctgcaggaacacttccttggggttcaggggattatctgtaatgccaacaacccctgtttccgttacccgactcctggggaggctcccggagttgttggaaact
ttaacaaatccattgtggctcgcctgttctcagatgctcggaggcttctttatacagccagaaagacaccagcatgaaggacatgcgcaaagttctgagaa
cattacagcagatcaagaaatccagctcaaacttgaagcttcaagatttcctggtggacaatgaaaccttctctgggttcctgtatcacaacctctctctccca
aagtctactgtggacaagatgctgagggctgatgtcattctccacaaggtatttttgcaaggctaccagttacatttgacaagtctgtgcaatggatcaaaatc
agaagagatgattcaacttggtgaccaagaagtttctgagctttgtggcctaccaagggagaaactggctgcagcagagcgagtacttcgttccaacatg
gacatcctgaagccaatcctgaacactaaactctacatctcccttcccgagcaaggagctggctgaagccacaaaaacattgctgcatagtcttggga
ctctggcccaggagctgttcagcatgagaagctggagtgacatgcgacaggaggtgatgtttctgaccaatgtgaacagctccagctcctccacccaaat
ctaccaggctgtgtctcgtatgtctgcgggcatcccgagggagggggctgaagatcaagtctctcaactggtatgaggacaacaactacaaagccctc
tttggaggcaatggcactgaggaagatgctgaaaccttctatgacaactctacaactccttactgcaatgatttgatgaagaattggagtctagtcctctttcc
cgcattatctggaaagctctgaagccgctgctcgttgggaagatcctgtatacacctgacactccagccacaaggcaggtcatggctgaggtgaacaag
accttccaggaactggctgtgttccatgatctggaaggcatgtgggaggaactcagcccaagatctggacctcatggagaacagccaagaaatggac
cttgtccggatgctgttggacagcagggacaatgaccactttgggaacagcagttggatggcttagattggacagcccaagacatcgtggcgttttttggc
caagcacccagaggatgtccagtccagtaatggttctgtgtacacctggagagaagctttcaacgagactaaccaggcaatccggaccatatctgcttc
atggagtgtgtcaacctgaacaagctagaacccatagcaacagaagtctggctcatcaacaagtccatggagctgctggatgagaggaagttctgggct
ggtattgtgttcactggaattactccaggcagcattgagctgccccatcatgtcaagtacaagatccgaatggacattgacaatgtggagaggacaaataa
aatcaaggatgggtactgggaccctggtcctcgagctgacccctttgaggacatgcggtacgtctgggggggggcttcgcctacttgcaggatgtggtgga
gcaggcaatcatcagggtgctgacgggcaccgagaagaaaactggtgtctatatgcaacagatgccctatcctgttacgttgatgacatctttctgcggg
tgatgagccggtcaatgcccctcttcatgacgctggcctggatttactcagtggctgtgatcatcaagggcatcgtgtatgagaaggaggcacggctgaa
agagaccatgcggatcatgggcctggacaacagcatcctctgttagctggttcattagtagcctcattcctcttcttgtgagcgctggcctgctagtggtc
atcctgaagttaggaaacctgctgccctacagtgatcccagcgtggtgtttgtcttcctgtccgtgtttgctgtggtgacaatcctgcagtgcttcctgattagc
acactctctccagagccaacctggcagcagcctgtggggggcatcatctacttcacgctgtacctgccctacgtcctgtgtgtggcatggcaggactacgt
gggcttcacactcaagatcttcgctagcctgctgtctcctgtggcttttgggtttggctgtgagtactttgcccttttgaggagcagggcattggagtgcagt
gggacaacctgtttgagagtcctgtggaggaagatggcttcaatctcaccacttcggtctccatgatgctgtttgacaccttcctctatgggtgatgacctg
gtacattgaggctgtcttccaggccagtacggaattcccaggccctggtattttccttgcaccaagtcctactggttggcgaggaaagtgatgagaagag
ccaccctggttccaaccagaagagaatatcagaaatctgcatggaggaggaacccacccacttgaagctgggcgtgtccattcagaacctggtaaaagt
ctaccgagatgggatgaaggtggctgtcgatggcctggcactgaatttttatgaggccagatcacctccttcctgggccacaatggagcggggaagac
gaccaccatgtcaatcctgaccgggttgttccccccgacctcgggcaccgcctacatcctgggaaaagacattgctctgagatgagcaccatccggca
gaacctgggggtctgtcccagcataacgtgctgtttgacatgctgactgtcgaagaacacatctggtctatgcccgcttgaaagggctctctgagaagc
acgtgaaggcggagatggagcagatggcctgatgttggtttgccatcaagcaagctgaaaagcaaaacaagccagctgtcaggtggaatgcagag
aaagctatctgtggccttggcctttgtcgggggatctaaggttgtcattctggatgaaccacagctggtgtggaccttactcccgcaggggaatatggg
agctgctgctgaaataccgacaaggccgcaccattattctctacacaccacatggatgaagcggacgtcctggggggacaggattgccatcatctccca
tgggaagctgtgctgtgtgggctcctccctgttctgaagaaccagctgggaacaggctactacctgacctggtcaagaaagatgtggaatcctcctca
gttcctgcagaaacagtagtagcactgtgtcatacctgaaaaaggaggacagtgtttctcagagcagttctgatgctggcctgggcagcgaccatgagag
tgacacgctgaccatcgatgtctctgctatcccaacctcatcaggaagcatgtgtctgaagcccggctggtgaagacatagggcatgagctgacctatg
tgctgccatataagctgctaaggaggggagccttgtgaactctttcatgagattgatgaccggctctcagacctggcatttctagttatggcatctcaga
gacgaccctggaagaaatattcctcaaggtggccgaagagagtgggggtggatgctgagacctcagatggtaccttgccagcaagacgaaacaggcgg
gccttcggggacaagcagagctgtcttcgcccgttcactgaagatgatgctgctgatccaaatgattctgacatagacccagaatccagagagacagact

FIG.2 (Continued)

tgctcagtgggatggatggcaaagggtcctaccaggtgaaaggctggaaacttacacagcaacagtttgtggccctttttgtggaagagactgctaattgc
cagacggagtcggaaaggatttttgctcagattgtcttgccagctgtgtttgtctgcattgcccttgtgttcagcctgatcgtgccacccttggcaagtaccc
cagcctggaacttcagccctggatgtacaacgaacagtacacatttgtcagcaatgatgctcctgaggacacgggaaccctggaactcttaaacgccctc
accaaagaccctggcttcgggacccgctgtatggaaggaaacccaatcccagacacgccctgccaggcaggggaggaagagtggaccactgcccca
gttccccagaccatcatggacctcttccagaatgggaactggacaatgcagaacccttcacctgcatgccagtgtagcagcgacaaaatcaagaagatg
ctgcctgtgtgtcccccagggggcagggggctgcctcctccacaaagaaaacaaaacactgcagatatccttcaggacctgacaggaagaaacatttcg
gattatctggtgaagacgtatgtgcagatcatagccaaaagcttaaagaacaagatctgggtgaatgagtttaggtatggcggctttcctgggtgtcagt
aatactcaagcacttcctccgagtcaagaagttaatgatgccatcaaacaaatgaagaaacacctaaagctggccaaggacagttctgcagatcgatttct
caacagcttggaagatttatgacaggactggacaccaaaaataatgtcaaggtgtggttcaataacaagggctggcatgcaatcagctcttcctgaatgt
catcaacaatgccattctccggccgcaacctgcaaaaggggagagaaccctagccattatggaattactgcttcaatcatccctgaatctcaccaagcagc
agctctcagaggtggctctgatgaccacatcagtggatgtccttgtgtccatctgtgtcatctttgcaatgtccttcgtcccagccagcttgtcgtattcctgat
ccaggagcgggtcagcaaagcaaaacacctgcagttcatcagtggagtgaagcctgtcatctactggctctctaattttgtctgggatatgtgcaattacgtt
gtccctgccacactggtcattatcatcttcatctgcttccagcagaagtcctatgtgtcctccaccaatctgcctgtgctagcccttctactttgctgtatgggt
ggtcaatcacacctctcatgtacccagcctcctttgtgttcaagatccccagcacagcctatgtggtgctcaccagcgtgaacctcttcattggcattaatgg
cagcgtggccaccttttgtgctggagctgttcaccgacaataagctgaataatatcaatgatatcctgaagtccgtgttcttgatcttcccacattttgcctggg
acgagggctcatcgacatggtgaaaaaccaggcaatggctgatgccctggaaaaggtttgggagaatcgctttgtgtcaccattatcttgggacttggtgg
gacgaaacctcttcgccatggccgtggaaggggtggtgttcttcctcattactgttctgatccagtacagattcttcatcaggcccagacctgtaaatgcaaa
gctatctcctctgaatgatgaagatgaagatgtgaggcgggaaagacagagaattcttgatggtggaggccagaatgacatcttagaaatcaaggagttg
acgaagatatatagaaggaagcggaagcctgctgttgacaggatttgcgtgggcattcctcctggtgagtgctttgggctcctgggagttaatggggctg
gaaaatcatcaactttcaagatgttaacaggagataccactgttaccagaggagatgcttccttaacaaaaatagtatcttatcaaacatccatgaagtacat
cagaacatgggctactgccctcagtttgatgccatcacagagctgttgactgggagagaacacgtggagttctttgccctttgagaggagtcccagagaa
agaagttggcaaggttggtgagtgggcgattcggaaactgggcctcgtgaagtatggagaaaaatatgctggtaactatagtggaggcaacaaacgcaa
gctctctacagccatggctttgatcggcgggcctcctgtggtgtttctggatgaacccaccacaggcatggatcccaaagcccggcggttcttgtggaatt
gtgccctaagtgttgtcaaggaggggagatcagtagtgcttacatctcatagtatgaagaatgtgaagctcttgcactaggatggcaatcatggtcaatg
gaaggttcaggtgccttggcagtgtccagcatctaaaaaataggtttggagatggttatacaatagttgtacgaatagcagggtccaacccggacctgaag
cctgtccaggatttctttggacttgcattcctggaagtgttctaaaagagaaacaccggaacatgctacaataccagcttccatcttcattatcttctctggcc
aggatattcagcatcctctcccagagcaaaaagcgactccacatagaagactactctgtttctcagacaacacttgaccaagtatttgtgaactttgccaag
gaccaaagtgatgatgaccacttaaaagacctctcattacacaaaaaccagacagtagtggacgttgcagttctcacatcttttctacaggatgagaaagtg
aaagaaagctatgtatgaagaatcctgttcatacggggtggctgaaagtaaagaggaactagactttccctttgcaccatgtgaagtgttgtggagaaaaga
gccagaagttgatgtgggaagaagtaaactggatactgtactgatactattcaatgcaatgcaattcaatgcaatgaaaacaaaattccattacaggggca
gtgcctttgtagcctatgtcttgtatggctctcaagtgaaagacttgaattttagtttttttacctataccctatgtgaaactctattatggaacccaatggacatatgg
gtttgaactcacacttttttttttttttttttgttcctgtgtattctcattgggtttgcaacaataattcatcaagtaatcatggccagcgattattgatcaaaatcaaaag
gtaatgcacatcctcattcactaagccatgccatgcccaggagactggtttcccggtgacacatccattgctggcaatgagtgtgccagagttattagtgcc
aagttttcagaaagttgaagcaccatggtgtgtcatgctcactttgtgaaagctgctctgctcagagtctatcaacattgaatatcagttgacagaatggtgc
catgcgtggctaacatcctgctttgattccctctgataagctgttctggtggcagtaacatgcaacaaaaatgtggtgtctccaggcacgggaaacttggtt
ccattgttatattgtcctatgcttcgagccatgggtctacagggtcatcctatgagactcttaaatatactagatcctggtaagaggcaaagaatcaacagc
caaactgctggggctgcaagctgctgaagccagggcatgggattaaagagattgtgcgttcaaacctagggaagcctgtgcccatttgtcctgactgtct
gctaacatggtacactgcatctcaagatgtttatctgacacaagtgtattatttctggcttttgaattaatctagaaaatgaaagatggagttgtattttgacaa
aaatgtttgtactttttaatgttattggaatttaagttctatcagtgacttctgaatccttagaatggcctctttgtagaacccctgtggtatagaggagtatggcca
ctgccccactattttttattttctttatgtaagtttgcatatcagtcatgactagtgcctagaaagcaatgtgatggtcaggatctcatgacattatatttgagtttcttt
cagatcatttaggatactcttaatctcacttcatcaatcaaatatttttgagtgtatgctgtagctgaaagagtatgtacgtacgtataagactagagagatatta
agtctcagtacacttcctgtgccatgttattcagctcactggtttacaaatataggttgtcttgtggttgtaggagcccactgtaacaatactgggcagcctttt
tttttttttttaattgcaacaatgcaaaagccaagaaagtataagggtcacaagtctaaacaatgaattcttcaacagggaaaacagctagcttgaaaacttgc
tgaaaaacacaacttgtgtttatggcatttagtaccttcaaataattggcttgcagatattggatacccattaaatctgacagtctcaaattttttcatctcttcaat
cactagtcaagaaaaatataaaaacaacaaatacttccatatggagcattttcagagttttctaacccagtctatttttctagtcagtaaacatttgtaaaaata
ctgtttcactaatacttactgttaactgtcttgagagaaaagaaaaatatgagagaactattgtttggggaagttcaagtgatctttcaatatcattactaacttctt
ccactttttccagaatttgaatattaacgctaaaggtgtaagacttcagatttcaaattaatctttctatattttttaaatttacagaatattatataacccactgctga

FIG.2 (Continued)

aaaagaaaaaaatgattgtttttagaagttaaagtcaatatttgattttaaatataagtaatgaaggcatatttccaataactagtgatatggcatcgttgcatttac
agtatcttcaaaaatacagaatttatagaataattctcctcatttaatattttcaaaatcaaagttatggtttcctcatttactaaaatcgtattctaattcttcattat
agtaaatctatgagcaactccttacttcggttcctctgatttcaaggccatattttaaaaaatcaaaaggcactgtgaactattttgaagaaaacacaacatttta
atacagattgaaaggacctcttctgaagctagaaacaatctatagttatacatcttcattaatactgtgttaccttttaaaatagtaattttttacattttcctgtgtaa
acctaattgtggtagaaattttttaccaactctatactcaatcaagcaaaattctgtatattcccctgtggaatgtacctatgtgagtttcagaaattctcaaaatac
gtgttcaaaaattctgctttgcatctttgggacacctcagaaaactattaacaactgtgaatatgagaaatacagaagaaaataataagccctctatacata
aatgcccagcacaattcattgttaaaaaacaaccaaacctcacactactgtatttcattatctgtactgaaagcaaatgctttgtgactattaaatgttgcacatc
attcattcactgtatagtaatcattgactaaagccatttgtctgtgttttcttcttgtggttgtatatatcaggtaaaatattttccaaagagccatgtgtcatgtaata
ctgaaccactttgatattgagacattaatttgtaccctgttattatctactagtaataatgtaatactgtagaaatattgctctaattctttttcaaaattgttgcatccc
ccttagaatgtttctatttccataaggatttaggtatgctattatcccttcttatacccctaagatgaagctgtttttgtgctctttgttcatcattggccctcattccaa
gcactttacgctgtctgtaatgggatctatttttgcactggaatatctgagaattgcaaaactagacaaaagtttcacaacagattctaagttaaatcatttcat
taaaaggaaaaagaaaaaaaattttgtatgtcaataactttatatgaagtattaaaatgcatatttctatgttgtaatataatgagtcacaaaataaagctgtga
cagttctgttggtctacagaaa

(SEQ ID NO: 2)

>gi|4557891| ref| NM_000229.1| Home sapiens lecithin-cholesterol acyltransferase (LCAT), Mrna CCAGGGCTGGAATGGGGCCGCCCGGCTCCCCATGGCAGTGGGTGACGCTGCTGCTGGGCTGCTGCTCCCTCCTCCGCCCCCTTC
TGGCTCCTCAATGTGCTCTTCCCCCCGCACACCACGCCCAAGGCTGAGCTCAGTAACCACACACGGCCCGTCATCCTCGTGCCCGG
CTGCCTGGGGAATCAGCTAGAAGCCAAGCTGGACAAAACCAGATGTGGTGAACTGGATGTGCTACCGCAAGACAGAGGACTTCTTC
ACCATCTGGCTGGATCTCAACATGTTCCTACCCCTTGGGGTAGACTGCTGGATCGATAACACCAGGGTTGTCTACAACCGGAGCTC
TGGGCTCGTGTCCAACGCCCCTGGTGTCCAGATCCGCGTCCCTGGCTTTGGCAAGACCTACTCTGTGGAGTACCTGGACAGCAGCA
AGCTGGCAGGGTACCTGCACACTGGTGCAGAAGCTGGTCAACAATGGCTACGTGCGGGACGAGACTGTGCGCGCCGCCCCCTA
TGACTGGCGGCTGGAGCCCGGCCAGCAGGAGGAGTACTACCGCAAGCTCGCAGGGCTGGTGGAGGAGATGCACGCTGCCTATGG
GAAGCCTGTCTTCCTCATTGGCCACAGCCTCGGCTGTCTACACTTGCTCTATTTCCTGCTGCGCCAGCCCCAGGCCTGGAAGGACC
GCTTTATTGATGCCTTCATCTCTCTTGGGGCTCCCTGGGGTGGCTCCATCAAGCCCATGCTGGTCTTGGCCTCAGGTGACAACCAG
GGCATCCCCATCATGTCCAGCATCAAGCTGAAAGAGGAGCAGCGCATAACCACCACCTCCCCCTGGATGTTCCCTCTCGCATGG
CGTGGCCTGAGGACCACGTGTTCATTTCCACACCCAGCTTCAACTACACAGGCCGTGACTTCCAACGCTTCTTGCAGACCTGCAC
TTTGAGGAAGGCTGGTACATGTGGCTGCAGTCACGTGACCTCCTGGCACAGGACTCCCAGCACCTGGTGTGGAAGTATACTGTCTTTA
CGGCGTGGGCCTGCCCACGCCCCGCACCTACATCTACGACCACGGCTTCCCCTACACGGACCCTGTGGGTGTGCTCTATGAGGAT
GGTGATGACACGGTGGCGACCCCGCAGCACCGAGCTCTGTGGCCTGTGGCAGGGCCGCCAGCCACAGCCTGTGCACCTGCTGCCCC
TGCACCGGGATACAGCATCTCAACATGGTCTTCAGCAACCTGACCCTGGAGCACATCAATGCCATCCTGCTGGGTGCCTACCGCCA
GGGTCCCCCTGCATCCCCGACTGCCAGCCCAGAGCCCCCGCCTCCTGAATAAAGACCTTCCTTTGCTACCGT

(SEQ ID NO: 3)

>gi|126012561| ref|NM_002332.2|Homo sapiens low density lipoprotein receptor-related protein 1 (LRP1), mRNA CAGCGGTGCGAGCTCCAGGCCCATGCACTGAGGAGGCGGAAACAAGGGGAGCCCCCAGAGCTCCATCAAGCCCCCTCCAAAGGC
TCCCCTACCCGGTCCACGCCCCCCACCCCCCCTCCCCGCCTCCTCCCCAATTGTGCATTTTTGCAGCCGGAGGCGGCTCCGAGATGG
GGCTGTGAGCTTCGCCCGGGGAGGGGGAAAGAGCAGCGAGGAGTGAAGCGGGGGGGTGGGGTGAAGGGTTTGGATTTCGGGGC
AGGGGGCGCACCCCCGTCAGCAGGCCCTCCCCAAGGGGCTCGGAACTCTACCTCTTCACCCACGCCCCTGGTGCGCTTTGCCGAA
GGAAAGAATAAGAACAGAGAAGGAGGAGGGAGGAGGGAGGAAAAGGGGGACCCCCCAACTGGGGGGGGTGAAGGACGAGAAGT
AGCAGGAACCAGAGGGGGAAGGGGCTGCTGCTTTGCATCAGCCCACACCATGCTGACCCCGCCGTTGCTCCTGCTGCCCCTGCTC
TCAGCTCTGGTCGCGGCGGGCTATCGACGCCCCTAAGACTTGCAGCCCCAAGCAGTTTGCCTGCAGAGATCAAATAACCCTGTATCTC
AAAGGGCTGGCGGTGCGACGGTGAGAGGGACTGCCCAGACGGATCTGACGAGGCCCCTGAGATTTGTCCACAGAGTAAGGCCCA
GCGATGCCAGCCAAACGAGCATAACTGCCTGGGTACTGAGCTGTGTGTTCCCATGTCCCGCCTCTCGCAATGGGGTCAGGACTGC
ATGGACGGCTCAGATGAGGGGCCCCACTGCCGAGAGCTCCAAGGCAACTGCTCTCGCCTGGGCTGCCAGCACCATTGTGTCCCA
CACTCGATGGGCCCACTGCTACTGCAACAGCAGCAGCTTTCAGCTTCCAGGCAGATGGCAAGACCTGCAAAGATTTTGATGAGTGCTC
AGTGTACCGGCACCTGCAGCCAGCTATGCACCAACACAGACGGCTCCTTCATATGTGGCTGTGTTGAAGGATACCTCCTGCAGCCC
GATAACCGCTCCTGCAAGGCCAAGAACGAGCCAGTAGACCGGCCCCCTGTGCTGTTGATAGCCAACTCCCAGAACATCTTGGCCA
CGTACCTGAGTGGGGCCCAGGTGTCTACCATCACACCTACGACCACGCGGCAGACCACAGCCATGGACTTCAGCTATGCCAACGA
GACCGTATGCTGGGTGCATGTTGGGACAGTGCTGCTCAGACGCAGCTCAAGTGTGCCCGCATGCCTGGCCTAAAGGGCTTCGTG

FIG.2 (Continued)

GATGAGCACACCATCAACATCTCCCTCAGTCTGCACCACGTGGAACAGATGGCCATCGACTGGCTGACAGGCAACTTCTACTTTG
TGGATGACATCGATGATAGGATCTTTGTCTGCAACAGAAATGGGGACACATGTGTCACATTGCTAGACCTGGAACTCTACAACCC
CAAGGGCATTGCCCTGGACCCTGCCATGGGGAAGGTGTTTTTCACTGACTATGGGCAGATCCCAAAGGTGGAACGCTGTGACATG
GATGGGCAGAACCGCACCAAGCTCGTCGACAGCAAGATTGTGTTTCCTCATGGCATCACGCTGGACCTGGTCAGCCGCCTTGTCT
ACTGGGCAGATGCCTATCTGGACTATATTGAAGTGGTGGACTATGAGGGCAAGGGCCGCCAGACCATCATCCAGGGCATCCTGAT
TGAGCACCTGTACGGCCTGACTGTGTTTGAGAATTATCTCTATGCCACCAACTCGGACAATGCCAATGCCCAGCAGAAGACGAGT
GTGATCCGTGTGAACCGCTTTAACAGCACCGAGTACCAGGTTGTCACCCGGGTGGACAAGGGTGGTGCCCTCCACATCTACCACC
AGAGGCGTCAGCCCCGAGTGAGGAGCCATGCCTGTGAAAACGACCAGTATGGGAAGCCGGGTGGCTGCTCTGACATCTGCCTGCT
GGCCAACAGCCACAAGGCGCGGACCTGCCGCTGCCGTTCCGGCTTCAGCCTGGGCAGTGACGGGAAGTCATGCAAGAAGCCGGA
GCATGAGCTGTTCCTCGTGTATGGCAAGGGCCGGCCAGGCATCATCCGGCGCATGGTATGGGGGCCAAGGTCCCGGATGAGCA
CATGATCCCATTGAAAACCTCATGAACCCCCGAGCCCTGGACTTCCACGCTGAGACCGGCTTCATCTACTTTGCCGACACCACCA
GCTACCTCATTGGCCGCCAGAAGATTGATGGCACTGAGCGGGAGACCATCCTGAAGGACGGCATCCACAATGTGGAGGGTGTGG
CCGTGGACTGGATGGGAGACAATCTGTACTGGACGGACAGATGGGGCCCAAAAAGACAATCAGCGTGGGCCAGGCTGGAGAAAGCTG
CTCAGACCCGCAAGACTTTAATCGAGGGCAAAATGACACACCCCAGGGCTATTGTGGTGGATCCACTCAATGGGTGGATGTACTG
GACAGACTGGGAGGAGGACCCCAAGGACAGTCGGCGTGGGCGGCTGGAGAGGGCGTGGATGGATGGCTCACACCGAGACATCTT
TGTCACCTCCAAGACAGTGCTTTGGCCCAATGGGCTAAGCCTGGACATCCCGGCTGGGCGCCTCTACTGGGTGGATGCCTTCTACG
ACCGCATCGAGACGATACTGCTCAATGGCACAGACCGGAAGATTGTGTATGAAGGTCCTGAGCTGAACCACGCCTTTGGCCTGTG
TCACCATGGCAACTACCTCTTCTGGACTGAGTATCGGAGTGGCAGTGTCTACCGCTTGGAACGGGGTGTAGGAGGCGCACCCCCC
ACTGTGACCCTTCTGCGCAGTGAGCGGCCCCCCATCTTTGAGATCCGAATGTATGATGCCCAGCAGCAGCAAGTTGGCACCAACA
AATGCCGGGTGAACAATGGCGGCTGCAGCAGCCTGTGCTTGGCCACCCCTGGGAGCCGCCAGTGCGCCTGTGCTGAGGACCAGGT
GTTGGACGCAGACGGCGTCACTTGCTTGGCGAACCCATCCTACGTGCCTCCACCCCAGTGCCAGCCAGGCGAGTTTGCCTGTGCC
AACAGCCGCTGCATCCAGGAGCGCTGGAAGTGTGACGGAGACAACGATTGCCTGGACAACAGTGATGAGGCCCCAGCCCTCTGC
CATCAGCACACCTGCCCCTCGGACCCGATTCAAGTGCGAGAACAACCGGTGCATCCCCAACCGCTGGCTCTGCGACGGGGACAATG
ACTGTGGGAACAGTGAAGATGAGTCCAATGCCACTTGTTCAGCCCGCACCTGCCCCCCCAACCAGTTCTCCTGTGCCAGTGGCCG
CTGCATCCCCATCTCCTGGACGTGTGATCTGGATGACGACTGTGGGGACCGCTCTGATGAGTCTGCTTCGTGTGCCTATCCCACCT
GCTTCCCCCTGACTCAGTTTACCTGCAACAATGGCAGATGTATCAACATCAACTGGAGATGCGACAATGACAATGACTGTGGGGA
CAACAGTGACGAAGCCGGCTGCAGCCACTCCTGTTCTAGCACCCAGTTCAAGTGCAACAGCGGGCGTTGCATCCCCGAGCACTGG
ACCTGCCGATGGGGACAATGACTGCGGAGACTACAGTGATGAGACACACGCCAACTGCACCAACCAGGCCACGAGGCCCCCTGGT
GGCTGCCACACTGATGAGTTCCAGTGCCGGCTGGATGGACTATGCATCCCCCTGCGGTGGCGCTGCGATGGGGACACTGACTGCA
TGGACTCCAGCGATGAGAAGAGCTGTGAGGGAGTGACCCGCTGCCAGTGTCAAGTTTGGCTGCAAGGACTCAGCTCG
GTGCATCAGCAAAGCGTGGGTGTGTGATGGCGACAATGACTGTGAGGATAACTCGGACGAGGAACTGCGAGTCCCTGGCCTG
CAGGCCACCCTCGCACCCTTGTGCCAACAACACCTCAGTCTGCCTGCCCCTGACAAGCTGTGTGATGGCAACGACGACTGTGGC
GACGGCTCAGATGAGGGCGAGCTCTGCGACCAGTGCTCTCTGAATAACGGTGGCTGCAGCCACAACTGCTCAGTGGCACCTGGCG
AAGGCATTGTGTGTTCCTGCCCTCTGGGCATGGAGCTGGGGCCCGACAACCACACCTGCCAGATCCAGAGCTACTGTGCCAAGCA
TCTCAAATGCAGCCAAAAGTGCGACCAGAACAAGTTCAGCGTGAAGTGCTCCTGCTACGAGGGCTGGGTCCTGGAACCTGACGGC
GAGAGCTGCCGCAGCCGTGGACCCCTTCAAGCCGGTTCATCATTTTCTCCAACCGCCATGAAATCCGGCGCATCGATCTTCACAAAGG
AGACTACAGCGTCCTGGTGCCCGGCCTGCGCAACACCATCGCCCTGGACTTCCACCTCAGCCAGACGCCCCTCTACTGGACCGAC
GTGGTGGAGGACAAGATCTACCGCGGGAAGCTGCTGGACAACGGAGCCCTGACTAGTTTCGAGGTGGTGATTCAGTATGGCCTGG
CCACACCCGAGGGCCTGGCTGTAGACTGGATTGCAGGCAACATCTACTGGGTGGAGAGTAACCTGGATCAGATCGAGGTGGCCA
AGCTGGATGGGACCCTCCGGACCCACCCCTGCTGGCCGGTGACATTGAGCACCCAAGGGCAATCGCACTGGATCCCCGGGATGGGAT
CCTGTTTTGGACAGACTGGGATGCCAGCCTGCCCCGCATTGAGGCAGCCTCCATGAGTGGGGCTGGGGCCGCACCGTGCACCGGG
GAGACCGGCTCTGGGGGCTGGCCCAACGGGCTCACCGTGGACTACCTGGAGAAGCCCATCCTTTGGATTGACGCCAGGTCAGATG
CCATTTACTCAGCCCCGTTACGACGGCTCTGGCCACACATGGAGGTGCTTCGGGGACACGAGTTCCTGTCGCACCCGTTTGCAGTGACG
CTGTACGGGGGGGAGTCTACTGGACTGACTGGCGAACAAAACACACTGGCTAAGGCCAACAAGTGGACCGGCCACAATGTCACC
GTGGTACAGAGGACCAACACCCAGCCCTTTGACCTGCAGGTGTACCACCCCTCCCGCCAGCCCATGGCTCCCAATCCCTGTGAGG
CCAATGGGGCCAGGGCCCCTGCTCCCACCTTTTGTCTCATCAACTACAACCGGACCGTGTCCTGCGCCTGCCCCCACCTCATGAAG
CTCCACAAGGACAACACCCTGCTATGAGTTTAAGGATTTCCTGCTGTACGCACGTCAGATGGAGATCCGAGGTGTGGACCTGG
ATGCTCCCTACTACAACTACATCATCTCCTTCACGGTGCCCGACATCGACAACGTCACAGTGCTAGACTACGATGCCCGCGAGCA
GCGTGTGTACTGGTCTGACGTGCGGACACAGGCCATCAAGCGGGCCTTCATCAACGGCACAGGCGTGGAGACAGTCGTCTCTGCA
GACTTGCCAAATGCCCACGGGCTGGCTGTGGACTGGGTCTCCCGAAACCTGTTCTGGACAAGCTATGACACCAATAAGAAGCAGA
TCAATGTGGCCCGGCTGGATGGCTCCTTCAAGAACGCAGTGGTGCAGGGCCTGGAGCAGCCCCATGGCCTTGTCGTCCACCCTCT
GCGTGGGAAGCTCTACTGGACCGATGGTGACAACATCAGCATGGCCAACATGGATGGCAGCAATCGCACCCTGCTCTTCAGTGGC
CAGAAGGGCCCCGTGGGCCTGCTATTGACTTCCCTGAAACCTCTACTGGATCAGCTCCGGGAACCCATACCATCAACCCGCT
GCAACCTGGATGGGAGTGGGCTGGAGGTCATCGATGCCATGCGCAGCCAGCTGGCCAAGGCCACCGCCCTGGCCATCATGGGGG
ACAAGCTGTGGTGGCTGATCAGGTGTCGGAAAAGATGGGCACATGCAGCAAGGCTGACGGCTCGGGCTCCGTGGTCCTTCGGA
ACAGCCACCACCCTGGTGATGCACATGAAGGTCTATGACGAGAGCATCCAGCTGGACCATAAGGGCACCAACCCCTGCAGTGTCA
ACAACGGTGACTGCTCCAGCTCTGCCTGCCCACGTCAGAGACGACCCGCTCCTGCATGTGCACAGCCGGCTATAGCCTCCGGAG
TGGCCAGCAGGCCTGCGAGGGCGTAGGTTCCTTTCTCCTGTACTCTGTGCATGAGGGAATCAGGGGAATTCCCCTGGATCCCAATG
ACAAGTCAGATGCCCTGGTCCCAGTGTCCGGGACCCTGCCTGCTGCTGCGCAAATGACCATCTACTG
GGTGGACATGGGCCTGAGCACGATCAGCCGGGGCCAAGCGGGACCAGACGTGGCCGTGAAGACGTGGTGACCAATGGCATTGGCCG
TGTGGACGGCATTGCAGTGGACTGGATCGCAGGCAACATCTACTGGACAGACCAGGGCTTTGATGTCATCGAGGTCGCCCGGCTC
AATGGCTCCTTCCGCTACGTGGTGATCTCCCAGGGTCTAGACAAGCCCCGGGCCATCACCGTCCACCCGGAGAAAGGGTACTTGT
TCTGGACTGAGTGGGGTCAGTATCCGCGTATTGAGCGGTCTCGGCTAGATGGCACGGAGCGTGTGGTGCTGGTCAACGTCAGCAT
CAGCTGGCCCAACGGCATCTCAGTGGACTACCAGGATGGCAAGCTGTACTGGTGCGATGCACGGACAGACAAGATTGAACGGAT
CGACCTGGAGACAGGTGAGAACCGCGAGGTGGTTCTGTCCAGCAACAATGGACATGTTTTCAGTGTCTGTGTTTGAGGATTTC
ATCTACTGGAGTGACAGGACTCATGCCAACGGCTCTATCAAGCGCGGGAAAGACAATGCCACAGCTCCGTGCCCCTGCGA
ACCGGCATCGGCGTCCAGCTTAAAGACATCAAAGTCTTCAACCGGGACCGGCAGAAAGGCACCAACGTGTGCGCGGTGGCCAAT

```
GGCTGTACTGGGGCAGACGCCAAGCTTTCAGTCATCGGCAGCATCCGGCTCAATGGCACGGACCCCATTGTGGCTGCTGACAGCAA
ACGAGGGCTAAGTCACCCCTTCAGCATCGACGTCTTTGAGGATTACATCTATGGTGTCACCTACATCAATAATCGTGTCTTCAAGA
TCCATAAGTTTGGCCACAGCCCCTTGGTCAACCTGACAGGGGGCCTGAGCCACGCCTCTGACGTGGTCCTTTACCATCAGCACAA
GCAGCCCGAAGTGACCAACCCATGTGACCGCAAGAAATGCGAGTGGCTCTGCCTGCTGAGCCCAGTGGGCCTGTCTGCACCTGT
CCCAATGGAAGCGGCTGGACAACGGCACATGCGTGCCTGTGCCCTCTCCAACGCCCCCCCAGATGCTCCCCGGCCTGGAACCT
GTAACCTGCAGTGCTTCAACGGTGGCAGCTGTTCCTCAATGCACGGAGGCAGCCCAAGTGCCGCTGCCAACCCCGCTACACGGG
TGACAAGTGTGAACTGGACCAGTGCTGGGAGCACTGTCGCAATGGGGGCACCTGTGCTGCCTCCCCCTCTGGCATGCCCACGTGC
CGGTGCCCCACGGGCTTCACGGGCCCCAAATGCACCCAGCAGGTGTGTGCGGGCGTACTGTGCCAACAACAGCACCTGCACTGTCA
ACCAGGGCAACCAGCCCCAGTGCCGATGCCTACCCGGCTTCCTGGGCGACCGCTGCCAGTACCGGCAGTGCTCTGGCTACTGTGA
GAACTTTGGCACATGCCAGATGGCTGCTGATGGCTCCCGACAATGCCGCTGCACTGCCTACTTTGAGGGATCGAGGTGTGAGGTG
AACAAGTGCAGCCGCTGTCTCGAAGGGGCCTGTGTGGTCAACAAGCAGAGTGGGGATGTCACCTGCAACTGCACGGATGGCCGG
GTGGGCCCCCAGCTGTCTGACCTGCGTCGGCCACTGCAGCAATGGCGGCTCCTGTACCATGAACAGCAAAATGATGCCTGAGTGCC
AGTGCCCACCCGACATGACAGGGCCCCGGTGTGAGGAGCAGTCTTCAGCCAGCAGCAGCCAGGACATATAGCCTCCATCCTAAT
CCCTCTGCTGTTGCTGCTGCTGCTGGTTCTGGTGGCCGGAGTGGTATTCTGGTATAAGCGGCGAGTCCAAGGGGCTAAGGGCTTCC
AGCACCAACGGATGACCAACGGGGCCATGAACGTGGAGATTGGAAACCCCACCTACAAGATGTACGAAGGCGGAGAGCCTGATG
ATGTGGGAGGCCTACTGGACGCTGACTTTGCCCTGGACCCTGACAAGCCCACCAACTTCACCAACCCCGTGTATGCCACACTCTAC
ATGGGGGGCCATGGCAGTCGCCACTCCCTGGCCAGCACGGACGAGAAGCGAGAACTCCTGGGCCGGGGCCCTGAGGACGAGATA
GGGGACCCCTTGGCATAGGGCCCTGCCCCGTCGGACTGCCCCCAGAAAGCCTCCTGCCCCCTGCCGGTGAAGTCCTTCAGTGAGC
CCCTCCCCAGCCAGCCCTTCCCTGGCCCCGGCCGGATGTATAAATGTAAAAATGAAGGAATTACATTTTATATGTGAGCGAGCAAG
CCGGCAAGCGAGCACAGTATTTATTTCTCCATCCCCTCCCTGCCTGCTCCTTGGCACCCCATGCTGCCTTCAGGGAGACAGGCAGG
GAGGGCTTGGGGCTGCACCTCCTACCCTCCCACCAGAACGCACCCCACTGGGAGAGCTGGTGGTGCAGCCTTCCCCTCCCTGTAT
AAGCACACTTTGCCAAGGCTCTCCCCTCTCGCCCCATCCCTGCTTGCCCGCTCCCACAGCTTCCTGAGGGCTAATTCTGGGAAGGGA
GAGTTCTTTGCTGCCCCTGTCTGGAAGACGTGGCTCTGGGTGAGGTAGGCGGGAAAGGATGGAGTGTTTTAGTTCTTGGGGGAGG
CCACCCCAAACCCCAGCCCCAACTCCAGGGGCACCTATGAGATGGCCATGCTCAACCCCCTCCCAGACAGGCCCTCCCTGTCTC
CAGGGCCCCACCGAGGTTCCCAGGGCTGGAGACTTCCTCTGGTAAACATTCCTCCAGCACTCTCAGAACGCCAAGGA
GGTGGGCCACACCCAGGAAGGGAAAGCGGGCAGCCCCGTTTTGGGGACGTGAACGTTTTAATAATTTTTGCTGAATTCCTTTACA
ACTAAATAACACAGATATTGTTATAAATAAAATTGTAAAAAAAAAAAAAAAAAA
```

(SEQ ID NO: 4)

>gi|124494255|ref|NM_008512.2| Mus musculus low density lipoprotein receptor- related protein (Lrp1), mRNA

```
AGTCAGGGGAGCAGCGGTGCGAGCTCCAGGCCAGTGCACTGAGGAGGCGGAAACGGGGGAGCCCCTAGTGCTCCATCAGGCCCC
TACCAAGGCACCCCCATCGGGGTCCACGCCCCCCACCCCCTCCCCAATTGTGCATTTTGCAGCCAGAGGGCGGCTC
CGAGATGGGGCTGTGAGCTTCGCCCTGGGAGGGGGAGAGGAGCGAGGAGTAAAGCAGGGGTGAAGGGTTCGAATTTGGGGGCA
GGGGGCGCACCCGCGTCAGCAGGCCCTTCCCAGGGGGCTCGGAACTGTACCATTTCACCTATGCCCCTGGTTCGCTTTGCTTAAGG
AAAGGATAAGAATAGAAGAGTCGGGGAGAGGAAGATAAAGGGGGACCCCCAATTGGGGGGGGCGAGGACAAGAAGTAACAG
GACCAGAGGGTGGGGGCTGCTGTTGCATCGGCCCACACCATGCTGACCCCGCCGTTGCTGCTGCTGCTGCCGCTGCTTTCAGCTC
TGGTCTCCGGGGCCACTATGGATGCCCCTAAAACTTGCAGCCCTAAGCAGTTTGCCTGCAGAGACCAAAATCACCTGTATCTCAAA
GGGCTGGCGGTGTGACGGTGAAAGACATTGCCCCGACGGCTCTGATGGAGCCCTGAGATCTGTCCAGAGAGTAAAGCCCAGAG
ATGCCCGCCAAATGAGCACAGTTGTCTGGGGACTGAGCTATGTGTCCCCATGTCTCGTCTCTGCAACGGGATCCAGGACTGCATG
GATGGCTCAGACGAGGGTGCTCAACTGCCGAGAGCTCCGAGCCAACTGTTCTCGAATGGGTTGTCAACACCATTGTGTACCTACAC
CCAGTGGGCCCACGTGCTACTGTAACAGCAGCTTCCAGCTGCAGGCAGATGGCAAGACGTGCAAAGATTTTGACGAGTGTTCCGT
GTATGGCACCTGCAGCCAGCTTTGCACCAACACAGATGGCTCCTTCACATGTGGCTGTGTTGAAGGCTACCTGCTGCAACCGGAC
AACCTGCTCCTGCAAGGCCAAGAATGAGCCAGTGAGCCAGTAGATCGGCCGCCAGTGCTACTGATGCCAACTCTCAGAACATCCTAGCTACGT
ACCTGAGTGGGGCCCAAGTGTCTACCATCACACCCACCAGCACCGACAAACCCACGGCCATGGACTTCAGTTATGCCAATGAGAC
CGTATGCTGGGTGCACGTTGGGGACAGTGCTGCCCAGACACAGCTCAAGTGTGCCCGGATGCCTGGCCTGAAGGGCTTTGTGGAT
GAGCATACCATCAACATCTCCCTCAGCCTGCACCACGTGGAGCAGATGGCAATCGACTGGCTGACGGGAAACTTCTACTTTGTCG
ACGACATTGACGACAGGATCTTTGTCTGTAACCGAAACGGGGACACCTGTGTCACTCTGCTGGACCTGGAACTCTACAACCCCAA
AGGCATCGCCTTGGACCCGGCCATGGGGAAGGTGTTCTTCACTGACTACGGGCAGATCCCAAAGGTGGAGCGCTGTGACATGGAT
GGACAGAACCGCCACCAAGCTGGTGGATAGCAAGATCGTGTTTCCACACCGGCATCACCCTGGACCTGGTCAGCGCCTCGTCTACT
GGGCGGACGCCTACCTAGACTACATCGAGGTGGTAGACTACGAAGGGAAGGGTCGCCATCATCCAAGGCATCCTGATCG
AGCACCTGTACGGCCTGACCGTGTTTGAGAACTATCTCTACGCCACCAACTCGGACAATGCCAACACGCAGCAGAAGACGAGCGT
GATCCGAGTGAACCGGTTCAACAGTACTGAGTACCAGGTCGTCACCCGTGTGGACAAGGGTGGTGCCCTGCATATCTACCACCAG
CGACGCCAGCCCCGAGTGCGGAGTCACGCCTGTGAGAATGACCAGTACGGGAAGCCAGGTGGCTGCTCCGACATCTGCCTCCTGG
CCAACAGTCACAAGGCAAGGACCTGCAGGTTGCAGGTCTGCAGGTCTGGGCTTCCACGGTCTGGGAAGTGATGGCAAAGTCTTGTAAGAAACCTGAAC
ATGGCTGTTCCTCGTGTATGGCAAGGCCGACCAGGCATCATTAGAGGCATGGACATGGGGGCCAAGGTCCCAGATGAGCACAT
GATCCCCATCGAGAACCTTATGAATCCACGCGCTCTGGACTTCCACGCCGAGACCGGCTTCATCTACTTTGCTGACACCACCAGCT
ACCTCATTGGCCGCCAGAAAATTGATGGCACGGAGAGAGAGACTATCCTGAAGGATGGCATCCACAATGTGGAGGGCGTAGCCG
TGGACTGGATGGGAGACAATCTTTACTGGACTGATGATGGCCCCAAGAAGACCATTAGTGTGGCCAGCCTGGAGAAAGCCGCTCA
GACCCGGAAGACTCTAATTGAGGGCAAGATGACACACCCCAGGGCCATTGTAGTGGATCCACTCAAGGGTGGATGTACTGGACA
GACTGGGGAGGAGCCCACAGATCGGCGAGGGCGGTTGGATGGACGGCTCACACCGAGATATCTTTGTC
ACCTCCAAGAGTGCTTTGGCCCAATGGGCTAAGCCTGGATATCCCAGCCGGACCGCCTCTACTGGGTGGATGCCTTCTATGACC
GAATTGAGACCATACTGCTCAATGGCACAGACCGGAAGATTGTATATGAGGGTCCTGAACTGAATCATGCCTCGGCCTGTGTCA
CCATGGCAACTACCTCTTTTGGACCGAGTACCGGAGCGGCAGCGTCTACCGCTTGGAACGGGGCGTGGCAGGCGCACCGCCCACT
```

FIG.2 (Continued)

```
GTGACCCTTCTGCGCAGCGAGAGACCGCCTATCTTTGAGATCCGAATGTACGACGCGCAGCAGCAGCAAGTGGGTACCAACAAAT
GCCGGGTAAATAACGGAGGCTGCAGCAGCCTGTGCCTCGCCACCCCCGGGAGCCGCCAGTGTGCCTGTGCCGAGGACCAGGTGTT
GGACACAGATGGTGTCACCTGCTTGGCGAACCCATCCTACGTGCCCCACCCCAGTGCCAGCCGGGCGAGTTTGCCTGTGCCAAC
AACCGCTGCATCCAGGAGCGCTGGAAGTGTGACGGAGACAACGACTGTCTGGACAACAGCGATGAGGCCCCAGCACTGTGCCAT
CAACACACCTGTCCCTCGGACCGATTCAAGTGTGAGAACAACCGGTGTATCCCCAACCGCTGGCTCTGTGATGGGGATAATGATT
GTGGCAACAGCGAGGACGAATCCAATGCCACGTGCTCAGCCCGCACCTGTCCACCCAACCAGTTCTCCTGTGCCAGTGGCCGATG
CATTCCTATCTCATGGACCTGTGATCTGGATGATGACTGTGGGGACCGGTCCGATGAGTCAGCCTCATGCGCCTACCCCACCTGCT
TCCCCCTGACTCAATTTACCTGCAACAATGGCAGATGTATTAACATCAACTGGCGGTGTGACAACGACAATGACTGTGGGGACAA
CAGCGACGAAGCCGGCTGCAGTCACTCCTGCTCCAGTACCCAGTTCAAGTGCAACAGTGGCAGATGCATCCCCGAGCACTGGACG
TGTGATGGGGACAATGATTGTGGGGACTTACAGCGACGAGACACCGCCAACTGTACCAACCAGGCTACAAGACCTCCTGGTGGC
TGCCACTCGGATGAGTTCCAGTGCCGCCTAGATGGCCTGTGCATCCCCCTGAGGTGGCGCTGCGACGGGACACCGACTGCATGG
ATTCCAGCGATGAGAAGAGCTGTGAGGGCGTGACCCATGTTTGTGACCCGAATGTCAAGTTTGGCTGCAAGGACTCCGCCCGGTG
CATCAGCAAGGCGTGGGTGTGTGATGGCGACAGCGACTGTGAAGATAACTCCGACGAGGAGAACTGTGAGGCCCTGGCCTGCAG
GCCACCCTCCCATCCCTGCGCCAACAACACCTCTGTCTGCCTGCCTCCTGACAAGCTGTGCGACGGCAAGGATGACTGTGGAGAC
GGCTCGGATGAGGGCGAGCTCTGTGACCAGTGTTCTCTGAATAATGGTGGCTGTAGTCACAACTGCTCAGTGGCCCCTGGTGAAG
GCATCGTGTGCTCTTGCCCTCTGGGCATGGAGCTGGGCTCTGACAACCACACCTGCCAGATCCAGAGCTACTGTGCCAAGCACCTC
AAATGCAGCCAGAAGTGTGACCAGAACAAGTTCAGTGTGAAGTGCTCCTGGCTACGAGGGCTGGGTCTTGAGCCTGACGGGGAA
AGCTGCCGCAGTCTGGATCCCTTCAAACCGTTCATCATCTTCTCCAACCGCCACGAGATCAGGCGCATTGACCTTCACAAGGGGG
ACTACAGCGTCCTAGTGCCTGGCCTGCGCAACACTATTGCCCTGGACTTCCACCTCAGCCAGAGTGCCCTCTACTGGACCGACGTG
GTAGAGGACAAGATCTACCGTGGGAAACTCCTGGACAACGGAGCCCTGACCAGCTTTGAGGTGGTGATTCAGTATGCCTTGGCCA
CACCAGAGGGCCTGGCTGTAGATTGGATTGCAGGCAACATCTACTGGGTGGAGAGCAACCTGGACCAGATCGAAGTGGCCAAGC
TGGACGGAACCCTCCGAACCACTCTGCTGGCGGGTGACATTGAGCACCCGAGGGCCATCGCTCTGGACCCTCGGGATGGGATTCT
GTTTTGGACAGACTGGGATGCCAGCCTGCCACGAATCGAGGCTGCGTCCATGAGTGGGGCTGGCCGCCGAACCATCCACCGGGAG
ACAGGCTCTGGGGGCTGGCCCAACGGGCTCACCGTGGATTACCTGGAGAAGCGCATCCTCTGGATTGATGCTAGGTCAGATGCCA
TCTATTCAGCCCGGTATGACGGCTCCGGCCACATGGAGGTGCTTCGGGGACACGAGTTCCTGTCACACCCATTTGCCGTGACACTG
TACGGTGGGGAGGTGTACTGGACCGACTGGCGAACAAATACACTGGCTAAGGCCAACAAGTGGACTGGCCACAACGTCACCGTG
GTACAGAGGACCAACACCCAGCCCTTCGACCTGCAGGTGTATCACCTTCCCGGCAGCCCATGGCTCCAAACCCATGTGAGGCCA
ATGGCGGCCGGGGCCCCTGTTCCCATCTGTGCCTCATCAACTACAACCGGACCGTCTCCTGCGCCTGTCCCCACCTCATGAAGCTG
CACAAGGACAACACCACCTGCTATGAGTTTAAGAAGTTCCTGCTGTACGCACGTCAGATGGAGATCCGGGGCGTGGACCTGGATG
CCCCGTACTACAATTATATCATCTCCTTCACGGTGCCTGATATCGACAATGTCACGGTGCTGGACTATGATGCCCGAGAGCAGCGA
GTTTACTGGTCTGATGTGCGGACTCAAGCCATCAAAAGGGCATTTATCAACGGCACTGGCGTGGAGACCGTTGTCTCTGCAGACTT
GCCCAACGCCCACGGGCTGGCTGTGGACTGGGTCTCCCGAAATCTGTTTGGACAAGTTACGACACCAACAAGAAGCAGATTAAC
GTGGCCCGGCTGGACGGCTCCCTTCAAGAATGCAGTGGTGGTGCAGGGCCTGGAGCAGCCCCACGGCCTGGTCGTCCACCCGCTTCGTG
GCAAGCTCTACTGGACTGATGGGGACAACATCAGCATGGCCAACATGGATGGGAGCAACCACACTCTGCTCTTCAGTGGCCAGAA
GGGCCCTGTGGGGGTTGGCCATTGACTTCCCTGAGAGCAAACTCTACTGGATCAGCTCTGGGAACCACACAATCAACCGTTGCAAT
CTGGATGGGAGCGAGCTGGAGGTCATCGACACCATGCGGAGCCAGCTGGGCAAGGCCACTGCCCTGGCCATCATGGGGGACAAG
CTGTGGTGGGCAGATCAGGTGTCAGAGAAGATGGGCACGTGCAACAAAGCCGATGGCTCTGGGTCCGTGGTGCTGCGGAACAGT
ACCACGTTGGTTATGCACATGAAGGTGTATGACGAGACCATCCAGCTAGAGCATGAGGGCACCAACCCTGCAGTGTCAACAAC
GGAGACTGTTCCCAGCTCTGCCTGCCAACATCAGAGACGACTCGCTCCTGTATGTGTACAGCCGGTTACAGCCTCCGGAGCGGAC
AGCAGGCCTGTGAGGGTGTGGGCTCTTTTCTCCTGTACTCTGTACATGAGGGAATTCGGGGGATTCCACTAGATCCCAATGACAAG
TCGGATGCCCTGGTCCCAGTGTCCGGAACTTCACTGGCTGTCGGAATCGACTTCCATGCCGAAAATGACACTATTTATTGGGTGGA
TATGGGCCTAAGCACCATCAGCAGGGCCAAGCGTGACCAGACATGGCGAGAGGATGTGGTGACCAACGGTATTGGCCGTGTGGA
GGGCATCGCGGTGGACTGGATCGCAGGCAACATATACTGGACGGACCAGGGCTTCGATGTCATCGAGGTTGCCCGGCTCAATGGC
TCTTTTCGTTATGTGGTCATTTCCCAGGGTCTGGACAAGCCTCGGGCCATCACTGTCCACCCAGAGAAGGGGTACTTGTTCTGGAC
CGAGTGGGGTCATTACCCACGTATTGAGCGGTCTCGCCTTGATGGCACAGAGAGAGTGGTGTTGGTTAATGTCAGCATCAGCTGG
CCCAATGGCATCTCAGTAGACTATCAGGGCGGCAAGCTCTACTGGTGTGATGCTCGGATGGACAAGATCGAGCGCATCGACCTGG
AAACGGGCGAGAACCGGGAGGTGGTCCTGTCCAGCAATAACATGGATATGTTCTCCGTGTCCGTGTTTGAGGACTTCATCTACTG
GAGTGACAGAACTCACGCCAATGGCTCCATCAAGCGCGGCTGCAAAGACAATGCTACAGACTCCGTGCCTCTGAGGACAGGCATT
GGTGTTCAGCTTAAAGACATCAAGGTCTTCAACAGGGACAGGCAGAAGGGTACCAATGTGTGCGCGGTAGCCAACGGCGGGTGC
CAGCAGCTCTGCTTGTATCGGGGTGGCGGCAGCGAGCCTGTGCCTGTGCCCACGGGATGCTGGCAGAAGACGGGGCCTCATGCC
GAGAGTACGCTGGCTACCTGCTCTACTCAGAGCGGACCATCCTCAAGAGCATCCACCTGTCGGATGAGCGTAACCTCAACGCACC
GGTGCAGCCCTTTGAAGACCCCGAGCACATGAAAAATGTCATCGCCCTGGCCTTTGACTACCGAGCAGGCACCTCCCCGGGGACC
CCTAACCGCATCTTCTTCAGTGACATCCACTTTGGGAACATCCAGCAGATCAATGACGATGGCTCGGCCAGGACCACCATCGTGG
AAAATGTGGGCTCTGTGGAAGGCCTGGCCTATCACCGTGGCTGGGACACACTGTACTGGACAAGCTACACCACATCCACCATCAC
CCGCCACACCGTGGACCAGACTCGCCCAGGGCCTTCGAGAGGGGAGACAGGTCATCACCCATGTCGGAGCACCACCCGGAGAGC
CTTTGTGCCTGGATGAGTGCCAGAACCCTGATGTTCTGGACCAATTGGAACGAGCTCCATCCAAGCATCATGCGGGCAGCCCTATCC
GGAGCCAACGTCCTGACCCTCATTGAGAAGGACATCCGCACGCCCAATGGGTTGGCCATCGACCACCGGGCGGAGAAGCTGTACT
TCTCGGATACCACCTTGGACAAGATCGAGCGCTGCGAGTACGACGGCTCCCACCGCTATGTGATCCTAAAGTCGGAGCCCGTCCA
CCCCTTTGGGTTGGCCGGTGTACGGAGAGCACATTTCTGGACTGACTGGGTGCCGGCGGGCTGTGCAGCGAGCCAACAAGTATGTG
GGCAGCGACATGAAGCTGCTTCGGGTGGACATTCCCCAGCAACCCATGGGCATCATCGCCGTGGCCAACGACACCAACAGCTGTG
AACTCTCCCCCTGCCGTATCAACAATGGAGGCTGCCAGGATCTGTGCTGCTCACCCACCAAGGCCACGTCAACTGTTCCTGTCGA
GGGGCCCGGATCCTCCAGGAGGACTTCACCTGCCGGGCTGTGAACTCCTCTTGTCGGGCACCAAGATGAGTTTGAGTGTGCCAATG
GGGAATGTATCAGCTTCAGCCTCACCTGTGATGGCGTCTCCCACTGCAAGGACAAGTCCGATGAGAAGCCCTCCTACTGCAACTC
ACGCCGCTGCAAGAAGACTTCCGCCAGTGTAACAATGGTCGCTGTGTATCCAACATGCTGTGGTGCAATGGGGTGGATGACTGT
GGGGATGGCTCTGATGAGATTCCTTGCAACAAGACTGCCTGTGGTGTGGGTGAGTTCCGCTGCCGGGATGGGTCCTGCATCGGGA
ACTCCAGTCGCTGCAACCAGTTTGTGGATTGTGAGGATGCCTCGGATGAGATGAATTGCAGTACCACAGACTGCAGCAGCTATTT
```

FIG.2 (Continued)

```
CCGCCTGGGCGTGAAAGGTGTCCTCTTCCAGCCGTGCGAGCGGACATCCCTGTGCTACGCACCTAGCTGGGTGTGTGATGGCGCC
AACGACTGTGGAGACTACAGCGATGAACGTGACTGTCCAGGTGTGAAGCGCCCTAGGTGCCCGCTCAATTACTTTGCCTGCCCCA
GCGGGCGCTGTATCCCCATGAGCTGGACGTGTGACAAGGAGGATGACTGTGAGAACGGCGAGGACGAGACCCACTGCAACAAGT
TCTGCTCAGAGGCACAGTTCGAGTGCCAGAACCACCGGTGTATCTCCAAGCAGTGGCTGTGTGACGGTAGCGATGATTGCGGGGA
TGGCTCCGATGAGGCAGCTCACTGTGAAGGCAAGACATGTGGCCCCTCCTCCTTCTCCTGTCCCGGCACCCACGTGTGTGTCCCTG
AGCGCTGGCTCTGTGATGGCGACAAGGACTGTACCGATGGCGCGGATGAGAGTGTCACTGCTGGCTGCCTGTACAACAGCACCTG
TGATGACCGTGAGTTCATGTGCCAGAACCGCTTGTGTATTCCCAAGCATTTCGTGTGCGACCATGACCGTGACTGTGCTGATGGCT
CTGATGAATCCCCTGAGTGTGAGTACCCAACCTGCGGCCCCAATGAATTCCGCTGTGCCAATGGGCGTTGTCTGAGCTCCCGTCAG
TGGGAATGTGATGGGGAGAATGACTGTCACGACCACAGCGATGAGGCTCCCAAGAACCCACACTGCACCAGCCCAGAGCACAAA
TGCAATGCCTCATCACAGTTCCTGTGCAGCAGCGGGCGCTGCGTGGCTGAGGCGTTGCTCTGCAACGGCCAGGACGACTGTGGGG
ACGGTTCAGACGAACGCGGGTGCCATGTCAACGAGTGTCTCAGCCGCAAGCTCAGTGGCTGCAGTCAGGACTGCGAGGACCTCA
AGATAGGCTTTAAGTGCCGCTGTCGCCCGGGCTTCCGGCTAAAGGACGATGGCAGGACCTGTGCCGACCTGGATGAGTGCAGCAC
CACCTTCCCCTGCAGCCAGCTCTGCATCAACACCCACGGAAGTTACAAGTGTCTGTGTGTGGAGGGCTATGCACCCCGTGGCGGT
GACCCCCACAGCTGCAAAGCTGTGACCGATGAGGAGCCATTTCTCATCTTTGCCAACCGGTACTACCTGCGGAAGCTCAACCTGG
ACGGCTCCAACTACACACTGCTTAAGCAGGGCCTGAACAATGCGGTCGCCTTGGACTTTGACTACCGAGCAGATGATCTACTG
GACGGACGTGACCACCCAGGGCAGCATGATTCGCAGGATGCACCTCAACGGCAGCAACGTGCAGGTTCTGCACCGGACGGGCCT
TAGTAACCCAGATGGGCTGGCTGTGGACTGGGTGGGTGGCAACCTGTACTGGTGTGACAAGGGCAGAGATACCATTGAGGTGTCC
AAGCTTAACCGGGGCCTATCGGACAGTGCTGGTCAGCTCTGGCCTCCGGGAGCCCAGAGCTCTGGTAGTGGATGTACAGAATGGGT
ACCTGTACTGGACAGACTGGGGTGACCACTCACTGATCGGCCGGATTGGCATGGATGGATCTGGCCGCAGCATCATCGTGGACAC
TAAGATCACATGGCCCAATGGCCTGACCGTGGACTACGTCACGGAACGCATCTACTGGGCTGACGCCCGTGAGGACTACATCGAG
TTCCGCAGCCTGGATGGCTCCAACCGTCACGTTGTGCTGACGCCCAAGACATCCCACACATCTTTGCGCTGACCCTATTTGAAGACTA
CGTCTACTGGACAGACTGGGGAAACGAAGTCCATCAACCGGGCCCACAAGACCACGGGTGCCAACAAAACACTCCTCATCAGCAC
CCTGCACCGGCCCATGGACTTACATGTATTCCACGCCCTGCGCCAGCCAGATGTGCCCAATCACCCCTGCAAAGTCAACAATGGT
GGCTGCAGCAACCTGTGCCTGCTGTCCCCTGGGGGTGGTCATAAATGCGCCTGCCCCACCAACTTCTATCTGGGTGGCGATGGCCG
TACCTGTGTGTCCAACTGCACAGCAAGCCAGTTTGTGTGCAAAAATGACAAGTGCATCCCCTTCTGGTGGAAGTGTGACACGGAG
GACGACTGTGGGGATCACTCAGACGAGCCTCCAGACTGTCCCGAGTTCAAGTGCCGCCCAGGCCAGTTCCAGTGCTCCACCGGCA
TCTGCACCAACCCCTGCCTTCATCTGTGATGGGGACAATGACTGCCAAGACAATAGTGATGAGGCCAATTGCGACATTCACGTCTG
CTTGCCCAGCCAATTCAAGTGCACCAACACCAACCGCTGCATTCCTGGCATCTTCCGTTGCAATGGGCAGGACAACTGCGGGGAC
GGCGAGGATGAGCGGGATTGCCCTGAGGTGACCTGCGCCCCCAACCAGTTCCAGTGCTCCATCACCAAGCGCTGCATCCCTCGCG
TCTGGGTCTGTGACAGGGATAATGACTGTGTGGACGGCAGTGATGAGCCTGCCAACTGTACCCAAATGACCTGTGGAGTGGATGA
GTTCCGCTGCAAGGATTCTGGCCGCTGCATCCCCGCGCGCTGGAAGTGTGACGGAGAAGATGACTGTGGGGATGGTTCAGATGAG
CCCAAGGAAGAGTGTGATGAGCGCACCTGTGAGCCATACCAGTTCCGCTGCAAAAACAACCGCTGTGTCCCAGGCCGTTGGCAAT
GTGACTACGACAACGACTCGGAGATAACTCGGACGAGGAGAGCTGCACACCTCGGCCCTGCTCTGAGAGTGAGTTTTCCTGTGC
CAATGGCCGCTGCATCGCTGGGCGCTGGAAGTGTGATGGGGACCATGACTGTGCCGACGGCTCAGACGAGAAAGACTGCACCCC
CCGCTGTGATATGGACCAGTTCCAGTGCAAGAGTGGCCACTGCATCCCCCTGCGCTGGCGCTGTGACGCGGATGCTGACTGTATG
GACGGCAGTGACGAGGAAGCCTGTGGCACTGGGGTGAGGACCTGCCCATTGGATGAGTTTCAATGTAACAACACCTTGTGCAAGC
CGCTGGCCTGGAAGTGTGATGGAGAGGACGACTGTGGGGACAACTCAGATGAGAACCCCGAGGAATGCGCCCGGTTCATCTGCC
CTCCCAACCGGCCTTTCCGCTGCAAGGAATGACCGAGCTGCCTGTGGATTGGGCGCCAGTGTGATGGCGTGGACAACTGTGGAGA
TGGGACTGACGAGGAGGACTGTGAGCCCCCCACGGCCCAGAAGTCCACCACTGCAAAGACAAGAAGGAGTTCCTGTGCCGAAACCA
GCGCTGTCTATCATCCTCCCTGCGCTGTAACATGTTCGATGACTGCGGCGATGGCTCCGATGAAGAAGATTGCAGCATCGACCCCA
AGCTGACCAGCTGTGCCACCAATGCCAGCATGTGTGGGGACGAAGCTCGTTGTGTGCGCACTGAGAAAGCTGCCTACTGTGCCTG
CCGCTCGGGCTTCCATACTGTGCCGGGCCAGCCCGGATGCCAGGACATCAACGAGTGCCTGCGCTTTGGTACCTGCTCTCAGCTCT
GCAACAACACCAAGGGGAGGCCACCTCTGCAGCTGTGCCCGCAACTTCATGAAGACACACAACACCTGCAAAGCTGAAGGCTCCG
AGTACCAGGTGCTATACACATCCGCGGATGACAACGAGATCCGCACGCTTGTTCCCGGGCCACCCCCACTCAGCCTACGAGCAGACATT
CCAGGGCGATGAGAGTGTCCGCATAGATGCCATGGATGTCCATGTCAAGGCCGGCCGTGTCTACTGGACTAACTGGCACACGGGC
ACAATCCCTACAGGAGCCTGCCCCCTGCCGCCCCCTCCTACCACTTCCAACCGCCACCGGACAGATCGACCGGGGTGTCACCCC
ACCTCAATATTTCAGGGCTGAAGATGCCGAGGGGTATCGCTATCGACTGGGTGGCCGGGAATGTGTACTGGACCGATTCCGGCCG
AGACGTGATTGAGGTGGCGCAAATGAAGGGCGAGAACCGCAAGACGCTCATCTCGGGCATGATTGATGAGCCCCATGCCATCGT
GGTGGACCCTCTGAGGGGGCACCATGTACTTGGTCAGACTGGGGGAACCACCCCAAGATTGAAACAGCAGCGATGGATGCACCCT
TCGGGAGACTCTCGTGCAAGACAACATTCAGTGGCCTACAGGGCTGGCTGTGGATATCACAATGAACGGCTCTACTGGGCAGAT
GCCAAGCTTTCGGTCATCGGCAGCATCCGGCTCAACGGCACTGACCCCATTGTGGCTGCTGACAGCAAACGAGGCCTAAGTCACC
CCTTCAGCATCGATGTGTTTGAAGACTACATCTACGGAGTCACTTACATCAATAATCGTGTCTTCAAGATCCACAAGTTTGGACAC
AGCCCCTTGATCAACCTAACTGGGGGCCTGAGCCATGCCTCTGATGTAGTCCTTTACCATCAACACAAGCAGCCTGAAGTGACCA
ACCCCTGTGACCGCAAGAAATGTGAATGGCTGTGTCTGCTGAGCCCCAGCGGGCCTGTCTGCACCCTGTCCCAATGGAAAGAGGCT
GGATAATGGCACCTGTGTGGCCTGTCCCTCCAACACCCCCTCCAGATGCCCCTAGGCCTGCAGTGCCACTGCAGTGCTTCA
ATGGTGGTAGTTGTTTCCTCAATGCTCGGAGGCAGCCAAGTGCCGTTGCCAGCCCGTTACACAGGCGATAAGTGTGAGCTGGA
TCAGTGCTGGGAATACTGTCACAACGGAGGCACCTGTGCCGGCTTCCCCATCTGGCATGCCCACGTGCCGCTGTCCCACTGGCTTCA
CGGGCCCCAAATGCACCGCACAGGTGTGTGCAGGCTACTGCTCTAACAACAGCACCTGCACCGTCAACCAGGGCAACCAGCCCCA
GTGCCGATGTCTACCTGGCTTCCTGGGCGACCGTTGCCAGTACCGGCAGTGCTCTGGCTTCTGTGAGAACTTTGGCACCTGTCAGA
TGGCTGCTGATGGCTCCCGACAATGTCGCTGCACCGTCTACTTTGAGGGACCAAGGTGTGAGGTGAACAAGTGTAGTCGCTGTCTC
CAAGGACCCTGCTGTGACTCAATAAGCAGACAGGGATGCATGCAACTGCACTGATGGCCGGGTAGCCCCCAGTTGTCTGACCT
GCATCGACTGAGCAATAGGTGGCCTCCTGCACCATGAACAGCAAGATGATGCCTGAGTGCCAGTGCCCGCCCATATGACAGG
ACCCCGGTGCGAGGAGCAGGTTGTTAGTCAGCAACAGCCTGGGCATATGGCCTCCATCCTGATCCCTCTGCTGCTGCTTCTCCTGC
TGCTTCTGGTGGCTGGCGTGGTGTTCTGGTATAAGCGGCGAGTCCGAGGGGCTAAGGCTTCCAGCACCAGCGGATGACCAATGG
GGCCATGAATGTGGAAATTGGAAACCCTACCTACAAGATGTATGAAGGTGGAGAGCCCGATGATGTCGGGGGCCTACTGGATGCT
GATTTTGCCCTTGACCCTGACAAGCCTACCAACTTCACCAACCCAGTGTATGCCACGCTCTACATGGGGGCCACGGCAGCCGCC
```

FIG.2 (Continued)

```
ATTCCCTGGCCAGCACGGACGAGAAGCGAGAACTGCTGGGCCGGGGACCTGAAGACGAGATAGGAGATCCCTTGGCATAGGGCC
CTGCCCGACGGATGTCCCCAGAAAGCCCCCTGCCACATGAGTCTTTCAATGAACCCCCTCCCCAGCCGGCCCTTCTCCGGCCCTG
CCGGGTGTACAAATGTAAAAATGAAGGAATTACTTTTTATATGTGAGCGAGCAACCGAGCAAGCACAGTATTATCTCTTTGCATTT
CCTTCCTGCCTGCTCCTCAGTATCCCCCCCATGCTGCCTTGAGGGGGCGGGGAGGGCTTTGTGGCTCAAAGGTATGAAGGAGTCCA
CATGTTCCCTACCGAGCATACCCCTGGAAGCTGGCCGGCACGGCCTCCCCACCACGCCTGTGCAAGACACTCAACGGGGCTCCGTG
TCCCAGCTTTCCTTTCCTTGGCTCTCTGGGGTTAGTTCAGGGGAGGTGGAGTCCTCTGCTGACCCTGTCTGGAAGATTTGGCTCTAG
CTGAGGAAGGAGTCTTTTAGTTGAGGGAAGTCACCCCAAACCCCAGCTCCCACTTTCAGGGGCACCTCTCAGATGGCCATGCTCA
GTATCCCTTCCAGACAGGCCCTCCCCTCTCTAGCGCCCCCTCTGTGGCTCCTAGGGCTGAACACATTCTTTGGTAACTGTCCCCCAA
GCCTCCCATCCCCTGAGGGCCAGGAAGAGTCGGGGCACACCAAGGAAGGGCAAGCGGGCAGCCCCATTTGGGGACGTGAACG
TTTTAATAATTTTTGCTGAATTCCTTTACAACTAAATAACACAGATATTGTTATAAATAAAATTGTAAAAAAGGAAAAAAAAAAG
AAAAGAAAAGAAAAGAAAAAAAAAAAAAAAAAAA
```

(SEQ ID NO: 5)

>gi|170932496|ref|NM_000527.3| Homo sapiens low density lipoprotein receptor (LDLR), mRNA

```
ACATTTGAAAATCACCCCACTGCAAACTCCTCCCCCTGCTAGAAACCTCACATTGAAATGCTGTAAATGACGTGGGCCCCGAGTG
CAATCGCGGGAAGCCAGGGTTTCCAGCTAGGACACAGCAGGTCGTGATCCGGGTCGGGACACTGCCTGGCAGAGGCTGCGAGCA
TGGGGCCCTGGGGCTGGAAATTGCGCTGGACCGTCGCCTTGCTCCTCGCCGCGGCGGGGACTGCAGTGGGCGACAGATGCGAAA
GAAACGAGTTCCAGTGCCAAGACGGGAAATGCATCTCCTACAAGTGGGTCTGCGATGGCAGCGCTGAGTGCCAGGATGGCTCTGA
TGAGTCCCAGGAGACGTGCTTGTCTGTCACCTGCAAATCCGGGGACTTCAGCTGTGGGGGCCGTGTCAACCGCTGCATTCCTCAGT
TCTGGAGGTGCGACGGACATGGACATGCGACAAGACGGCTCAGACGAGCAAAGGCTGTCCCCCCAAGACGTGCTCCCAGGACGAGT
TTCGCTGCCACGATGGGAAGTGCATCTCTCGGCAGTTCGTCTGTGACTCAGACCGGGACTGCTTGGACGGCTCAGACGAGGCCTC
CTGCCCCGGTGCTCACCTGTGGTCCCGCCAGCTTCCAGTGCAACAGCTCCACCTGCATCCCCCAGCTGTGGGCCTGCGACAACGACC
CCGACTGCGAAGATGGCTCGGATGAGTGGCCGCAGCCGTGTAGGGGTCTTTACGTGTTCCAAGGGGACAGTAGCCCCTGCTCGGC
CTTCGAGTTCCACTGCCTAAGTGGCGAGTGCATCCACTCCAGCTGGCGCTGTGATGGTGGCCCCGACTGCAAGGACAAATCTGAC
GAGGAAAACTGCGCTGTGGCCACCTGTCGCCCTGACGAATTCCAGTGCTCTGATGAAACTGCATCCATGGCAGCCGGCAGTGTG
ACCGGGAATATGACTGCAAGGACATGAGCGATGAAGTTGGCTGCGTCAATGTGACACTCTGCGAGGGACCCAACAAGTTCAAGT
GTCACAGCGGCGAATGCATCACCCTGGACAAAGTCTGCAACATGGCTAGAGACTGCCGGGACTGGTCAGATGAACCCATCAAAG
AGTGCGGGACCAACGAATGCTTGGACAACAACGGCGGCTGTTCCCACGTCTGCAATGACCTTAAGATCGGCTACGAGTGCCTGTG
CCCCGACGGCTTCCAGCTGGTGGCCCAGCGAAGATGCGAAGATATCGATGAGTGTCAGGATCCGACACCTGCAGCCAGCTCTGC
GTGAACCTGGAGGGTGGCTACAAGTGCCAGTGTGAGGAAGGCTTCCAGCTGGACCCCCACACGAAGGCCTGCAAGGCTGTGGGC
TCCATCGCCTACCTCTTCTTCACCAACCGGCACGAGGTCAGGAAGATGACGCTGGACCGGAGCGAGTACACCAGCCTCATCCCCA
ACCTGAGGAACGTGGTCGCTCTGGACACGGAGGTGGCCAGCAATAGAATCTACTGGTCTGACCTGTCCCAGAGAATGATCTGCAG
CACCCAGCTTGACAGAGCCCACGGCGTCTCTTCCTATGACACCGTCATCAGCAGAGACATCCAGGCCCCCGACGGGCTGGCTGTG
GACTGGATCCACAGCAACATCTACTGGACCGACTCTGTCCTGGGCACTGTCTCTGTTGCGGATACCAAGGGCGTGAAGAGGAAA
CGTTATTCAGGGAGAACGGCTCCAAGCCAAGGGCCATCGTGGTGGATCCTGTTCATGGCTTCATGTACTGGACTGACTGGGGAAC
TCCCGCCAAGATCAAGAAAGGGGGCCTGAATGGTGTGGACATCTACTCGCTGGTGACTGAAACATTCAGTGGCCCAATGGCATC
ACCCTAGATCTCCTCAGTGGCCCTCTACTGGGTTGACTCCAACCTACATCTCAAGCATCGATGTCAACGGGGCAACCG
GAAGACCATCTTGGAGGATGAAAAGAGGCTGGCCCACCCCTTCTCCTTGGCCGTCTTTGAGGACAAAGTATTTTGGACAGATATC
ATCAACGAAGCCATTTTCAGTGCCAACCGCCTCACAGGTTCCGATGTCAACTTGTTGGCTGAAAACCTACTGTCCCCAGAGGATAT
GGTTCTCTTCCACAAACCTCACCCAGCCAAGAGGAGTGAACTGGTGTGAGAGGACCACCCTGAGCAATGGCGGCTGCCAGTATCTG
TGCCTCCCTGCCCCGCAGATCAACCCCCACTCGCCCAAGTTTACCTGCGCCTGCCCCGACGGCATGCTGCTGGCCAGGGACATGA
GGACGTGCCTCACAGAGGCTGAGGCTGCAGTGGCCACCCAGGAGCACATCCACCGTCAGGCCTAAAGGTCAGTCCACAGCCGTAA
GGACACAGCACAACAACCCACCCGACCTGTTCCCGACACCTCCCGGCTGCCTGGGCCACCCCTGGGCTCACCACGGTGGATAGT
GACAATGTCTCACCAAGCTCTGGGCGACGTTGCTGGCAGAGGAAATGAGAAGAAGCCCAGTAGCGTGAGGGCTCTGTCCATTGTC
CTCCCCATCGTGCTCCTCGTCTTCCTTTGCCTGGGGGTCTTCCTTCTATGGAAGAACTGGCGGCTTAAGAACATCAACAGCATCAA
CTTTGACAACCCCGTCTATCAGAAGACCACAGAGGATGAGGTCCACATTTGCCACAACCAGGACGGCTACAGCTACCCCTCGAGA
CAGATGGTCAGTCTGGAGGATGACGTGGCCGTGAACATCTGCCTGGAGTCCCGTCCCTGCCCAGAACCCTTCCTGAGACCTCGCCG
GCCTTGTTTATTCAAAGACAGAAGACAGACCAAAGACATTCCTCTGAGCTTGTTTTATTACATCTGGGAGGCAGAAC
AGGCTTCGGACAGTGCCCATGCAATGGCTTGGGTTGGGATTTTGGTTTCTTCCTTTCCTGTGAAGGATAAGAGAAACAGGCCCGG
GGGGACCAGGATGACACCTCCATTTCTCTCCAGGAAGTTTGAGTTTCTCTCCACCGTGACACAATCCTCAAACATGGAAGATGAA
AGGGGAGGGGATGTCAGGCCCAGAAGGCAAGTGGCTTTCAACACACAACAGCAGATGGCACCAACGGGACCCCTGGCCCTGC
TCATCCACCAATCTCTAAGCCAAACCCCTAAACTCAGGAGTCAACGTGTTACCTCTTCTATGCAAGCCTTGCTAGACAGCCAGGT
TAGGCCTTTGCCCTGTCACCCCCGGAATCATGACCCCACCCAGTGTCTTTCGAGGTGGGTTTGTACCTCCTTAAGCCAGGAAAGGGAT
TCATGGCGTCGGAAATGATCTGGCTGAATCCGTGGTGGCACCGAGACCAAACTCATTCACCAAATGACCACTTCCCAGAGCCA
GAGCCTGAGTCACTGGTCACCCTTAATATTTATTAAGTGCCTGAGACACCCGGTTACCTTGGCCGTGAGGACACGTGGCCTGCACC
CAGGTGTGGCTGTCAGGACACCAGCCTGGTGCCCATCCTCCCGACCCCTACCCACTTCCATTCCCGTGGTCTCCTTGCACTTTCTCA
GTTCAGAGTTGTACACTGTGTACATTTGGCATTTGTGTTATTATTTTGCACTGTTTCTGTCGTGTGTGTTGGGATGGGATCCCAGG
CCAGGGAAAGCCCGTGTCAATGAATGCCGGGGACAGAGAGGGGCAGGTTGACCGGGACTTCAAAGCCGTGATCGTGAATATCGA
GAACTGCCATTGTCGTCTTTATGTCCGCCCACCTAGTGCTTCCACTCTATGCAAATGCCTCAAATGCCATTCACTTCCCCAATCTTG
TCGTTGATGGGTATGTGTTTAAAACATGCACGGTGAGGCTGGCCGGCACAGTGGCTCACGCCTGTAATCCCAGCACTTTGGGAGGCCG
AGGCCGGTGGATCATGAGGTCAGGAGATCGAGACCATCCTGGCTAACACGTGAAACCCCGTCTCTACTAAAAATACAAAAAATT
AGCCGGGCGTGGTGGCGGGCACCTGTAGTCCCAGCTACTCGGGAGGCTGAGGCAGGAGAATGGCGTGAACCCGGGAAGCGGAGC
```

FIG.2 (Continued)

```
TTGCAGTGAGCCGAGATTGCGCCACTGCAGTCCGCAGTCTGGCCTGGGCGACAGAGCGAGACTCCGTCTCAAAAAAAAAAAACA
AAAAAAAAACCATGCATGGTGCATCAGCAGCCCATGGCCTCTGGCCAGGCATGGCGAGGCTGAGGTGGGAGGATGGTTTGAGCTC
AGCCATTTGAGGCTGTCGTGAGCTATGATTATGCCACTGCTTTCCAGCCTGGGCAACATAGTAAGACCCCATCTCTTAAAAAATGA
ATTTGGCCAGACACAGGTGCCTCACGCCTGTAATCCCAGCACTTTGGGAGGCTGAGCTGGATCACTTGAGTTCAGGAGTTGGAGA
CCAGGCCTGAGCAACAAAGCGAGATCCCATCTCTACAAAAAACCAAAAAGTTAAAAATCAGCTGGGTACGGTGGCACGTGCCTGT
GATCCCAGCTACTTGGGAGGCTGAGGCAGGAGGATCGCCTGAGCCCAGGGAGGTGGAGGTTGCAGTGAGCCATGATCGAGCCACT
GCACTCCAGCCTGGGCAACAGATGAAGACCCTATTTCAGAAATACAACTATAAAAAAATAAATAAATCCTCCAGTCTGGATCGTT
TGACGGGACTTCAGGTTCTTTCTGAAATCGCCGTGTTACTGTTGCACTGATGTCCGGAGAGACAGTGACAGCCTCCGTCAGACTCC
CGCGTGAAGATGTCACAAGGGATTGGCAATTGTCCCCAGGGACAAAACACTGTGTCCCCCCCAGTGCAGGGAACCGTGATAAGC
CTTTCTGGTTTCGGAGCACGTAAATGCGTCCCTGTACAGATAGTGGGGATTTTTTGTTATGTTTGCACTTTGTATATTGGTTGAAAC
TGTTATCACTTATATATATATATATATACACACATATATATAAAATCTATTTATTTTTGCAAACCCTGGTTGCTGTATTGTTCAGTGA
CTATTCTCGGGGCCCTGTGTAGGGGGTTATTGCCTCTGAAATGCCTCTTCTTTATGTACAAAGATTATTTGCACGAACTGGACTGTG
TGCAACGCTTTTGGGAGAATGATGTCCCCGTTGTATGTATGAGTGGCTTCTGGGAGATGGGTGTCACTTTTTAAAACCACTGTATA
GAAGGTTTTTGTAGCCTGAATGTCTTACTGTGATCAATTAAATTTCTTAAATGAACCAATTTGTCTAAA
```

(SEQ ID NO: 6)

>gi|48762938|ref|NM_000041.2| Homo sapiens apolipoprotein receptor E (APOE), mRNA

```
GGGATCCTTGAGTCCTACTCAGCCCCAGCGGAGGTGAAGGACGTCCTTCCCCAGGAGCCGACTGGCCAATCACAGGCAGGAAGA
TGAAGGTTCTGTGGGCTGCGTTGCTGGTCACATTCCTGGCAGGATGCCAGGCCAAGGTGGAGCAAGCGGTGGAGACAGAGCCGG
AGCCCGAGCTGCGCCAGCAGACCGAGTGGCAGAGCGGCCAGCGCTGGGAACTGGCACTGGGTCGCTTTTGGGATTACCTGCGCTG
GGTGCAGACACTGTCTGAGCAGGTGCAGGAGGAGCTGCTCAGCTCCCAGGTCACCCAGGAACTGAGGGCGCTGATGGACGAGAC
CATGAAGGAGTTGAAGGCCTACAAAATCGGAACTGGAGGAACAACTGACCCCGGTGGCGGAGGAGACGCGGGCACGGCTGTCCAA
GGAGCTGCAGGCGGCGCAGGCCCGGCTGGGCGCGGACATGGAGGACGTGTGCGGCCGCCTGGTGCAGTACCGCGGCGAGGTGCA
GGCCATGCTCGGCCAGAGCACCGAGGAGCTGCGGGTGCGCCTCGCCTCCCACCTGCGCAAGCTGCGTAAGCGGCTCCTCCGCGAT
GCCGATGACCTGCAGAAGCGCCTGGCAGTGTACCAGGCCGGGGCCCGCGAGGGCGCCGAGCGCGGCCTCAGCGCCATCCGCGAG
CGCCTGGGGCCCCTGGTCGAACAGGGCCGCGTGCGGGCCGCCACTGTGGGCTCCCTGGCGCCAGCCGCTACAGGAGCGGGCCCA
GGCCTGGGGCGCAGGCTGCGCGCGGGACTGGAGGCAGGTGGCGGAGGACATGGCCGGCCCGGGGTGCGGGCCGGCCTGGGCGA
GGCCGAGGGTGCGCGCGCCAAGCTGGAGGAGCAGGCCCCAGCCAGATACGCCTGCAGGCCGAGGCCTTCCAGGCCCGCCTCAAGAGCT
GGTTCGAGCCCCTGGTGGAAGACATGCAGCGCCAGTGGGCCGGCTGGTGGAGAAGGTGCAGGCTGCCGTGGCCACCAGCGCCG
CCCCTGTGCCCAGCGACAATCACTGAACGCCGAAGCCTGCAGCCATGCGACCCCACGCCACCCCGTGCCTCCTGCCTCCGCGCAG
CCTGCAGCGGGAGACCCTGTCCCCGCCCCAGCCGTCCTCCTGGGGTGGACCCTAGTTTAATAAAGATTCACCAAGTTTCACGCAA
AAAAAAAAAAAAAAAAAAAAAAAAAAAAAAAAAAAAAAAAA
```

(SEQ ID NO: 7)

>gi|4557320|ref|NM_000039| Homo sapiens apolipoprotein A-I (APOA1), mRNA

```
AGAGACTGCGAGAAGGAGGTCCCCCACGGCCCTTCAGGATGAAAGCTGCGGTGCTGACCTTGGCCGTGCTCTTCCTGACGGGGAG
CCAGGCTCGGCATTTCTGGCAGCAAGATGAACCCCCCAGAGCCCCTGGGATCGAGTGAAGGACCTGGCCACTGTGTACGTGGAT
GTGCTCAAAGACAGCGGCAGAGACTATGTGTCCCAGTTTGAAGGCTCCGCCTTGGGAAAACAGCTAAACCTAAAGCTCCTTGACA
ACTGGGACAGCGTGACCTCCACCTTCAGCAAGCTGCGCGAACAGCTCGGCCCTGTGACCCAGGAGTTCTGGGATAACCTGGAAAA
GGAGACAGAGGGCCTGAGGCAGGAGATGAGCAAGGACCTGGAGGAGGTGAAGGCCAAGGTGCAGCCCTACCTGGACGACTTCC
AGAAGAAGTGGCAGGAGGAGATGGAGCTCTACCGCCAGAAGGTGGAGCCGCTGCGCGCAGAGCTCCAAGAGGGCGCGCGCCAG
AAGCTGCACGAGCTGCAAGAGAAGCTGAGCCCACTGGGCGAGGAGATGCGCGACCGCGCGCGCGCCCATGTGGACGCGCTGCGC
ACGCATCTGGCCCCCTACAGCGACGAGCTGCGCCAGCGCTTGGCCGCGCGCCTTGAGGCTCTCAAGGAGAACGGCGGCGCCAGA
CTGGCCGAGTACCACGCCAAGGCCACCGAGCATCTGAGCACGCTCAGCGAGAAGGCCAAGCCCGCGCTCGAGGACCTCCGCCAA
GGCCTGCTGCCCGTGCTGGAGAGCTTCAAGGTCAGCTTCCTGAGCGCTCTCGAGGAGTACACTAAGAAGCTCAACACCCAGTGAG
GCGCCCGCCGCCGCCCCCCTTCCCGGTGCTCAGAATAAACGTTTCCAAAGTGGG
```

FIG.3

Natural antisense sequence (AK311445): SEQ ID NO: 8
ACGCCCGGGAACCCCCGACCCCTCTGAGCCCCGGGTACTGCGCCCGGGTCTCCACGCCCAGAGATGCTCCCCGGTCTCCACCGTC
GGGCAAGCCCCAAGCGCAGCAGCGCAGAGTCCTGGGGTCACCAGAGCTCGTACTAGGACATCGTCTCCCCATTTAACACCGCCTC
CGGTCCCATCTGAGTTGCAAGTGGTGGGGATGTGGGGCTCCGGATCAAAGTCCCCGAAACCGAGCACTTCCCGAAGCCTCCTTGG
CCTCGAAACAAAACAATAACGCCCAACTCCATCATATTCCAGAACTCCCACCACCTGCATACAGACATTCAGCTGCACAAGCCCC
CTCCATGCTACAGTCAACAGATCTCCAGGCCACGGCTCAAGCCCAGGTACTCACATCAGTGGTCTATCAACACTCAGGACAGAC
CCATAGAAGAGGCCCAAGCAGGCCCTGGAAGTGCATGTGGAGGCCACCAGGCAAGGAATTCTGGAGTCCCAGGTACTCATAACT
CTGGGGTGGCATGGCCCCTTTGCACCATGGACTGTTTGCCCTTAGAAAGGGATGGATCTGAGCTGGGCGCAGTGGCTCATGCCTGTA
ATCCCAGCACTTTGGGAGGCCAAGGTGGGCAGCTCACCTCAGGTCAGGTTGGTCTCAAACTCCTGACCTCAGGCGATCCACCTCA
GCCTCTCAAAGTGCTGGAATTATAGGTGTGAGCCCACTGTGCCCCAGCCCAAAATCATTCTTTTTTGGAATTTTGAAGCATATAATTCC
AAAAGGTATGAAGGTAATCACTTAGATTGCTCTAATAAGGGAATGGGAACAGTTAAGTCCTATACAAATAAGACAAAGATAAGA
TACTACAAAAAGGGGATGAGCCCAAGAAAAAAATCAAAGTCCCAGAGAGAGAACAGCCATTGATTCTAAATACACAAGTCTATG
GCCCCAACCCAAACTTGTTTCACTAAGAACAACCTGTGGTTTCGAGAATCTGGTCATCCCCCACAGTGAATACATGAACACATTGT
AATGTTTGAAATGTTTATTTTTCTTGTTGATTTCTTACTGTTAGAAGAGCTAAGTGATTTGGCCCAAAGTGGCTAAGTGATTCGGCC
AGTTTGTACACAGGGATATAAGTTTGCTGACACCAAGCTCATACTTTACAAATGTAATATCTTCATAAAACAAAAATACTGGGCC
GGGCGCGGTGGCTCACGCCTGTAATCCCAGCATTTTGGGAGGCCGAGGCGGGCGGATCATGAGATCAGGAGATCGAGACCATCC
TGGCTAGCAGGGTGAAGCCCCG

Natural antisense sequence (BF133827): SEQ ID NO: 9
CAAAATGGCGTGCTACCCCTGTCCAACCTTGTCTGTAGACAGAGTCAATTGAACACTGTCTTTGGGACTTCCGTGCAACTGAGGTGG
GCGGGCTTGAAGCACAAAGCTTTCAGGGAGAACCAAACTTTATGCCCAAGCTGCTCTCTGCCACCCACAGGGTAAATGAATCTCA
TACAGGAAAGGCAAGAGACATGTGACACTGTTGTCTGATGGTCACAAGTCAAGCTTTTTAAAAAGCAGCCTGATATTGTGAGCTA
ACATGGCTTTCTGTAATTGAATGCAATGTATTTTCTATGCTTGTCTGGGTAAAGTTGACCTTGGTTTGATTTAGCTCAAGCAATATT
TCAACAGTGCACTGGGGCTCTGAGTCCCCTGACTACTGTTTGACTAGAGCCAGGCTCTGCCCTGGATGGCAACCAACAGCCCAGG
CTCTGGGCACAGCCGGGCTTTGACAGGTCTGGGGAAATGTTCACCGGAGATGAAAGGTTTCAAACTATGAAACTCTAAAATCTC
AAGTCAAAACTTTTGACAAGCACACACAGGACATGAATTACAATCACCCGAAGATTTTTACAGGCTTCTCAATTTTAATGACATGC
TGACACGTGTCATCAGATCTCACAACAAGATGACACATGGGTGTCAGGTATGGCGCAGAAGACTAGAGTCGGGGTGTAACCAAT
GAGCCATTGTCTGTTGGACACAGGCGAATTCGGCAAACGGACAGTGCTGGAGGCAGAAGGGTTTAAAGAAGGCAGGAAAGCCCAT
GTTTAACAGAATGGGGTGACGAAGAGGGATGGGAAGGTCTAACTCACCCGGGGGTGGGGGCACCAGGGGGGCCCACGGACACA
GAAAACCACGCAGGTCAGGCACCTACAAAGACCGAAGGAAAAAGGGACCACGCAGAAATCACTCACG

Natural antisense sequence (Hs.668679): SEQ ID NO: 10
AAAGTCCAAGGTGGGAACAGATAGGTCTGGGGGCATGGGGCTGGGCCTAATAGGGGCCGGGCATGGATGGGCCTCTCCTGCTC
ACCGATCCTGGGCTGGGCATCTTGTCCTTGGTGGGTGGGGGCCAAGGAAGGAGTGGTGGGCTTGGCCCAGAGTCTGGTGTGGCT
GTGACTGACCACAGCTTGTGATGCCCCAGCCAAGACCTCAGGCACACCCCGTCCCCCACTCCGCCCCCCTGGGTTAGACAACTG
AGAGTCACAGTGTGGTGGGAGAAGGGACGTCATTCCTCTAAGGGACAAGCTTTTGCCCCTCCCCACACCAGGGCAGGTACTTAT
GTCGGGGCTTATGCAGGGCAGAAGGGCTTTGGCCAGGTCAGCTGCCAGGGGCTGGGGCCAGGCTCCCAGGGTCTGGCGTGGT
GCATCAGGGGCCTGGTGGGGCTTACCGAGGATGACGGGCCGTGTGTGGTTACTGAGCTCAGCCTTGGGCGTGGTGTGCGGGGG
AAGAGCACATTGAGTGAGCCAGAAGGGGCGGCAGGAGGGAGCAGCAGCCCAGCAGCAGCGTCACCCACTGCCATGGGGAGCC
GGGCGGCCCCATTCCAGCCCTGGTGCCTACTGCCAGAGAAAGCGGCACTGGGCTGTCCTTATCTGGTGTGGGAGTGGGAGGGGCC
CTAGGGCCAGTGGGAGGGAGCGTAGCAAAGCTGGGCCAGTGGGGGTTGTGGCCAGAGATTGCCGGAAAGGGGCACAGCCTCAGGGAGCCGGC
TCTGGGCCTGGGTTCAGTTCCGCCTTCTTCTCTTGGCCCAGGGGAAACAGAGCCGGGCAGCAGGAGGGCCCAGAACTACACAAT
GTTTTATTGAAAAGTCAGGCCTCAGCTCAGCTGTCTCCATTCGGCTCAGCTTGGTGGGGGGCCCTGCCCATAGTAGACTGAGCCA
GATCTTCCTGCAGGCAGCTGGGCTGGACTCCCTCCCTGGCTACCCTTCCCTTCGTCTCTGATGGTGACATCCAAACAATAAATATG
CAATAAATAGCGCTCCTGGGCTGGCCGGGCCGGCTGCCTTCAAACCCCACTCGGCCCCTACCAGTCTTCTCTGGCCAGGACAGG
CCTACTGGGGTGCTAGATAGTAAAGTCCCCAAACATCCCAGGGTCCCACAAGACCTGGGATCCATCTCCATTTTGAGGCCCAGGC
CTGGTTCCAAGGAGACCTAGCAAAGCTGGGTCCAGGACAGGGCCCACGCAAGCAGGGCTGGCACGTGGGTGCTGGGAAGAGGCT
GTTACCCCAGACCACAGCTTGTTATGTCCTGGCCAAGACCTCGACTCCAGGCCACAAGATGACACTGGGCTCAGGAGTAGATGGT
GATGACTTCACGGCCACCACCGCGCACCAACAGCACCCGCTCAAGGCCCTCGGTCAGCACCTCGAGGAACTCCATGTAGTTCTCG
TCGCCCTCACTGTTCCTGGGTGGGCCAGGCATGTTTAGGAGAACCAGGCGGGCGTCGTGGGAGCGCGTGACAATGACTTCATTGA
GCTTCACAGCAGTGTGCATGCGCC

Natural antisense sequence (Hs.593769): SEQ ID NO: 11
TTTAAANGTTTGATGTTTATTGGTGGTGTCTGATGAGCGTTTCTCTTGTCCAGACTGTGTTTCTCTCTCCAGACCAGCTCCCAGGGTA
CAGGGGGTGGGGAGTAGGTGGTAGCTGTGTCAGTGCTGGGCCCTGGNGCCACTCCCTAGGGAAGAGCAGGTGGGGCCTCGGGGG
GTCTGGCCCTAGCTCTGGCAGATCCATCCTCAGTGAAGCACATCCCTGGGGCAAAGGCACTCCTGAGGCCAAGACCAGCATGGGC
TTGATGGAGCCACCCCAGGGAGCCCCAAGAGAGATGAAGCCATCAATAAAGCGGNCCTTCCAGGCCTGGGNCT

FIG.3 (Continued)

Natural antisense sequence (Hs.387239): SEQ ID NO: 12
TGTCACTCTGACCTCAGTGTAGGCACTGCCTCCTCTGGGAAGTCTTTGCTGACCTGAAAGGCTCAGCCTCTTGTGCTTCCTAAGCTT
TTCTCAGAGCATTTAGCTTCATTAGTAATTAAACTTCCATTAGTGAAATGATCTGATTAATGGTTGTCACTCCCAGATTTTAATTCT
AACTTTTTTTTTTTTTTTTTTTGAGACCCAGTCTCTTTTTTTTTGAGACAGTCTCATTCTGCCCCCCAGTCTGGAGTGCAACGAC
GTGATCTCGGCTCACGGTGACCTCCACCTCCCAGGTTCAAGTGATTCTCGTGCCTCAGCCTCCTGAGTAGCTGGGACGACAGATGC
ATGCCACCACGCCTGGCAAATATTTTGTATTTTAGTAGAGACGGGGGTTTCTGCCGTGTTGGCCTGGCTGGTCTCAAACTCCTGAG
TTCGGGTGATCCAGCCTGCCTCGCCCGGGGTGCCGGGATTACAGGCGTGAGCCACCGTGCCCGGCCTCTAAACACTTGTGGCC
CTGTCATTCACCCAGCACTCAAAAGGTCGTCTCACCTGCCCTTTGGGAGCTGGGAGAGACAGTCAAATTGTCACCGCCCCCCCA
CCGCCCCGTGCTCCTCTGACAGGGCTGTGGGTGGAGCCAGCTCCAGTCCCCGCGCCCAGCACAGAGGCAGGCACGGTGCACACTG
CCTCAACAGCTCGACCAGGAGAGTGGGCAGCTGTACATCTAGGGTGCCCAGCTCAGTCCCAGGCCTCAGCAGAGCCCATCTTGCC
TCACTGCACACAGCACTGAGCCTGTGGCTGGTGAGGAGTGAAACCTAGTGTGGGACTCTAGTGCCTCCCTTCAACCTGAAACATA
GCCATCAGGGCTTACGGTAGCAAAGGAAGGTCTTTATTCAGGAGGCGGGCTCTGGGCTGGCAGTCGGGGATGCAGGGGGGACC
CTGGCGGTAGGCACCCAGCAGGATGGCATTGATGTGCTCCAGGGTCAGGTTGCTGAAGACCATGTTCAGATGCTGTATCCCGTGC
AGGGGCAGCAGGTGCACAGGCTGTGGCTGGCGGCCCTGCCACAGGCCACAGAGCTCGGTGCTGCGGGTCGCCACCGTGTCATCA
CCATCCTCATAGAGCACACCCACAGGGTCCGTGTAGGGGAAGCCGTGGTCGTAGATGTAGGTGCGGGGCGTGGGCAGGCCCACG
CCGTAAAGACAGTATACTTCCACACCAGGTGCTGGGAGTCCTGCCAGGAGGTCACGTGACTGCAGCCACATGTACCAGCCTTCCT
CAAAGTGCAGGTCTGCAAAGAAGCGTTGGAAGTCACGGCCTGTGTAGTTGAAGCTGGGTGTGGAAATGAACACGTGGTCCTCAG
GCCACGCCATGCGAGAGGGAAACATCCAGGGGGAGGTGGTGGTTATGCGCTGCTCCTCTTTCAGCTTGATGCTGGACATGATGGG
GATGCCCTGGTTGTCACCTGTGGATATGGAGCAAGGTGGGACAGGGAGCCAGGCCTGGCTACCCCTGGCCCACAACCTGCTGAGT
GTAGGCTCAGCCAGATGCTCAATCTTGTCCCTGCCCAATCTAGACACAGACTCTAAGCCACAGGCTTGAGCAGGCCTGATATTCA
ATGATGCTCAGTGTCAGCTTACTCAATGAGAAGCCCTGATAAGACCTCTGTTGGGTGGAGCTGTAGGGCTTCAAAAGGATGGCAG
GGACAGGCACCATGGCTCACCCCTGTAATCCCGGCACTTTGGGAGGCTGAGGCAGGAGGATCACTTGAGGCCAGGAGTCCGTGA
CCAGACTGGGCAATGCAGTGAGACCCTGTCTCTAC

Natural antisense sequence (Hs.711951): SEQ ID NO: 13
TGTTTTTTTTTTTTTTTTAAAGAGATGGAGTCCTGATCTGTCGCCCAGGCTGGAGTTCAGTGGCACAATATTGGCCCACTGCAAC
CCTTGAACCTTCCCGGTTCAAGTGATTCTCCTGCCTAGGTCTTCTGAGTAGCTGGGATTACAGGTGCCCACCACCACGCCCAGCTA
ATTTTTGTGGTTTTAGTAGAGACGGAGTTTTGCCATGTTGGCCAAGCTAGTCTCAAACTCCTGACCTCAAGTGATCGGCCGGCCTC
AGCCTCCCAAAGTGCTGGGATTACAGGCTTGAGCCACTGCGCCTGGCCCAGTTTCCCATGTCTTGAGGCACCACTACCCATGCAC
CTCAGAATCCTCCCTTGCCTTTATCCCTTTGATACAGCACATCCCAAAGTGAATCCCCACATGGTCCCTGGTTGCTCAGACTCAGT
GAAAAAAAAATGAATGGTCAAGTGAGTTTTGGAAAACCCCAAACGCTTGAAAAATTCTTGGCACACATAAACATATTCAAGGCTC
TGAGAAGTTCTGCAGCACAA

Natural antisense sequence (DC401271): SEQ ID NO: 14
ACCATTCAGCTGCACCCAGATGCCCAAGAGCAATGAGCCCACACGCAGAGCTGGAGGACCTGAAAGGCAACCTCCAAGTCCCA
GATCATGTCTCTGTGGGGTCTGGTCTCCAAGATGCCCCCAGAAAAAGTGCAGCGGCTCTATGTCGACTTTCCCCAACACCTGCGGC
ATCTTCTGGGTGACTGGCTGGAGAGCCAGCCCTGGGAGTTCCTGGTCGGCTCCGACGCCTTCTGCTGCAACTTGGCTAGTGCCCTA
CTTTCAGACACTGTCCAGCACCTTCAGGCCTCGGTGGGAGAGCAGGGGGAGGGGAGCACCATCTTGCAACACATCAGCACCCTTG
AGAGCATATATCAGAGGGACCCCCTGAAGCTGGTGGCCACTTTCAGACAAATACTTCAAGGAGAGAAAAAAGCTGTTATGGAAC
AGTTCCGCCACTTGCCAATGCCTTTCCACTGGAAGCAGGAAGAACTCAAGTTTAAGACAGGCTTGCGGAGGCTGCAGCACCGAGT
AGGGGAGATCCACCTTCTCCGAGAAGCCCTGCAGAAGGGGG

Natural antisense sequence (BM933147): SEQ ID NO: 15
TGTGACACCCTTCCTCACGCTTAGACAGCAAAGTTGCCTCGGAAGAGAAGAGAAGCCTGCATGGGAATGGCCAGCACATCCTAAA
TGCTCCAGTGGCCCGTGGTTCGTCCCTTCGTCTCATTGACTGCCACAGACAGGAAGTAGGCTCAGGGACTTGGCACCTACCCAACA
GCAGGACGTCCTTTCTGGCCATACTCCTGAGGGTAACAAAATCACATGGAAGCCCAAAGCAAGCCAGGCTCAGGCTCCTCTGCCC
TCTGCTACTTAACAATGTCCGTCCTCCCCAGCCCCCCTGCAGATGCTTCTGTATGGGAAAGCCCCTCTGCATCTAATGACACTCTG
CTTTCAAAGACGGGACAGTCCCTGGTCTCTGGAGAGTGACCATTCGTGGCCTTCTCAGTTGACACTTCTCCGCTGAGGCATCCCTT
AGCCCTGAACCAGAAATGAAAGAGCCGGCTCAGAGTTGCAAAGGAAAGAATAGCCATCAATCTGCTCCTGTGTGCAAGGAGCACAG
ACCTGGTCTCAGACTCTGCCCGTCTCCCCCGCTTCCCTGCCCTCTGAGTGACTCACGGTGCAGGCTGAGGGAGATGTTGATGGTAT
GCTCATCCACAAAGCCCTTCAGGCCAGGCATCCGGGCAACTTGAGCTGTGTCTGGGCACACTGTCCCAACGTG

Natural antisense sequence (CK626173): SEQ ID NO: 16
GACTTTATCTGCACTGTTTCAACAGCAGGTAGCCAGCCGTCTTTTACTGCCTGCCTCTGGCTGAAGCTCGGCCCACACTATCAG
GACTCAGCCCTGTAGGGATGACTCTGCCACAACAGCTACAGCACCAGCTGGCACAAATGGCTTTCTCTCCAACTTCCTCAGGCTTCC
CTGAGTCACTGCCCAGCCCTAGGACTGGCAACACCCTGGCCCTGCTCACCCATCCACCCTTGCCAAGAGGGAAAGAGGGAAGAAG
CCTGCAGAGAGCTGGTGCCCTGCTTCCAGATGCTGCTCCATTCTCAGGCCAAGCCTCAAGATGGGGGGAACCTGAGTGGGAGCCT
CTCTCCTGCTTGCGTTCCCTCCACTTCTGGGAAAGCAGGGCAGTGACAGTCCCTGTTCTCATGTGTCTCCCCTTGGCTGGCCTC
CCTCACCTCCCAAAGACCAGGCAGGGTCCCATTCAGCAGACCTGACTGTAAGGAATTGGCAAGAAATGACGTCCCTAGCCAGCC
TGGCCTCCCCTTTGGTATTTTTGCAGCTGGAGATTATTAGTCTCAAGCAAAACTCCTTTGTTATCCAAGCCCACTCCACCACATTAT
TTTCCTCTCTCCTAAA

FIG.3 (Continued)

Natural antisense sequence (AW544265): SEQ ID NO: 17
GACAGGGTCTTATTCTGCAGCTCGGGTTGACCTGGAATTCTCCAGGCAGACCATTCTGGCCTTACGTTCACTGACATCCACCTGCC
TCTGCCTCCTGAGTGCTGCTGTTAAGGAGTAGTTCCAGCCTATAGTGTTCTGAAATACTGTTATTTACTGTAATGATAGCCAAAG
CTAAAATGAGTTAAGAATAGTTCCTTTCTTACTCGCTGTCTCGTTCCTCATTCACTTGCCCCATCTTCGTGCCCTCAGAACTACCCC
ACCCCCAATCCTCCTTTAGCCCCAGAGCCTTCTCTGAACCCTACCCCTTGCTTCCTGTCAGCATCTCAGGGCCCCCTCTTTGCTTCC
TTAATCTCTACTGGAAACACAGAGAACTCCCCTGCCCTCTGCCATTCTTCTGCTGGAGCTACCTTCCCACCCTTGTGCAAGCCAGG
CCCCTCATACCCAAGCAGGTGACACCATCTGTGTCCAAC

Natural antisense sequence (bloflor.aApr07): SEQ ID NO: 18
GAGCTGCGCTCACCGCTGTTGCCTGATTTTGGTCTAAGTGAAGGCTTGCGGTTCAGATTCCAACAACTTCCCTTTGTAAAGGAAAT
GGACAAGAAACTCCCCCCTGGATATGCCTTGAAGCCAGCTACAGCGTGAGGTGGTGCAGCTAGAAAGTGCTAGAAACACACACC
AGCTCTCAGAAGTCTGGAGGAAAACATCAGGGGTGTAGTCTCCTTGACAACAGAGGAAACATCACATTCTCAGCCATCCCGGGAG
AGAGAAACTAAAGTGATGAACAAACAAGGCCTTGCCTAAGACTTCCTTAACATTTTCTCTTAAGGAAGAGGTTGATTGAGGAAAA
ATCGCCGCTTGGACAGCTGAACCGAAGCCATTCACAGCCTCTGAAGAAGCGAGGCCACCCCAGGGGGTCGGTCCCGGGGATAG
CTGCCCCACCGTGGCTGAAGATCTCGGCTGCAGACCAAGGAGGGCGGGAGATTCTGAGGCAACGTTTCAACCTCGTAAGGAA
CCGAGGCCTTGAGGGTGGCCGGGGCCCCTCTGTGAACTTGATCGGGGCTGGTGGGGCGAGGGCGCCCCCAGGACAAGGTGGG
GACGGAGGTGTCGCCACAGAGCACAGCGGAAACCGGGGACTTCGCCAGGAGGGCCAGGATAACGGAGGGCGACTCGTGTATGT
CGCGGAGGCGGCTCCGGGGACCCGGGACTTG

Natural antisense sequence (sherflor.aApr07): SEQ ID NO: 19
GGGGCTCCCTCTCAACCTATTCTGGCGCCTGGAGCAAGCCTTACCTGCAGTCCCGCCGCGGCGAGGAGCAAGGCGACGGTCCAG
CGCAATTTCCAGCCCCAGGGCCCCATGCTCGCAGCCTCTGCCAGGCAGTGTCCCGACCCGGATCACGACCTGCTGTGTCCTAGCTG
GAAACCCTGGCTTCCCGCGATTGCACTCGGGGCCCACGTCATTTACAGCATTTCAATGTGAGGTTTCTAGCAGGGGGAGGAGTTTG
CAGTGGGGTGATTTTCAAATGTCTTCACCTCACTGCAAGAGGAGGAGTTTCGAACGGCCGATGTGACATCGGCTTTTAACCCGTG
AAGCTCTGATTCCCACTCCAGTCCTTCGAAAGTGTCGCCAGGGCAGGCGACTTGATTGTTGTATTTGGGTCTCCGGTGAAGAGCT
GACGCCCCCTCAAAATTGGAAACGCATCTTCTGAAAGATCCTCCTGAAATTTCTCGATGTTTAACTGTTAACATTTTGCTGTTGTTG
TCCACAGAAGGATAACAACAGCCTTTCAAGATCCTCCAATAGCCTAATGCCATTGTCCTCTCTGCCTCAAAAGGAAAACACTAAA
AATGTTGGGAACTTCCGCCACTTTCTATATTTGCCTTTTCCTTTCTAGGAATTGTGTATAGATTTTTAGCTTCCTTTCGTTGTATATT
GTTTTTACATTGTTATTCCAAATCACCTAATAGACACTGATCAATCAGGAAT

Natural antisense sequence (Hs.626623): SEQ ID NO: 20
CCCACGTATATTTTTTGTTGTTTTTGTTTTTTTCTGTAAAATGTCCCGGTTCTTCCATAACTTATAAACATGATTTATACCGAGGA
GATGGGAAAGTGGACGGGGCAGGGTGGACTGACCGGGGATGGGGAAGCTCCTCTCGCTGCCCCCTCGGGGCGGGCCCAGGCCCT
TTGGAGGATGGGGACGCCAGGACACTCCTCCCTGAGGTTGCTGGCCGCCTCTGCCCTGGTGCTGTGAAGTCAGAGCCCCGATACT
CCCCGTCCACCTGCCAGTTCACAAACTTCGACTGCTGGGTCTGGATGGCCATCTTGGACCTGAGACCGGGGCCCAGCTGGTGAAT
GACC

Natural antisense sequence (Hs.714236): SEQ ID NO: 21
ACCATCTTTTTTTTTCTTTTATGCGTGAAACTTGGTGAATCTTTATTAAACTAGGGTCCACCCCAGGAGGACGGCTGGGGCGGG
GACAGGGTCTCCCGCTGCACGCTGCGCTGAGGCAGGAGGGCACGGGGTGGCGTGGGGTCGCATGGCTGCAGGCTTCGGCGTTCAG
TGATTGTCGCTGGGCACAGGGGCGGCGCTGGTGCCCACGGCAGCCTGCACCTTCTCCACCAGCCCGGCCCACTGGCGCTGCATGT
CTTCCACCAGGGGCTCGAACCAGCTCTTGAGGCGGGCCTGGAAGGCCTCGGCCTGCAGGCGTATCTGCTGGGCCTGCTCCTCCAG
CTTGGCGCGCACCTCCGCCACCTGCTCCTTCACCTCGTCCAGGCGGTCGCGGGTCCGGCTGCCCATCTCCTCCATCCGCGCGCGCA
GCCGCTCGCCCCAGGCCTGGGCCCGCTCCTGTAGCGGCTGGCCGGCCAGGGAGCCCACAGTGGCGGCCCGCACGCGGCCCTGTTC
CACCAGGGGCCCCAGGCGCTCGCGGATGCGCTGAGGCCGCGCTCGGCGCCCTCGCGGGCCCCGGCCTGGTACACTGCCAGGCGCT
TCTGCAGGTCATCGGCATCGCGGAGGAGCCTTCTTACGCAGCTTGCGCAGGTGGGAGGCGAGGCGCACCCGCAGCCTCCTCGGTGCT
CTGGCCGAGCATGGCCTGCACCTCGCCGGCGGTACTGCACCAGTGGCCGCACACGTCCTCCATGTCCGCGCCCAGCCGGCCTGC
GCCGCCTGCAGCTCCTTGGACAGCCGTGCCCGCGTCTCCTCCGCCACCGGGGTCAGTTGTTCCTCCAGTTCCGATTTGTAGGCCTT
CAACTCCTTCATG

Natural antisense sequence (DA327409 extended): SEQ ID NO: 22
CAGCTTCTCTTGCAGCTCGTGCAGCTTCTGGCGCGCGCCCTCTTGGAGCTCTGCGCGCAGCGGCTCCACCTTCTGGCGGTAGAGCT
CCATCTCCTCCTGCCACTTCTTCTGGAAGTCGTCCAGATCCAAATGGCAAACCTTCTTCATCCACCAGGACCCAACCCACAGGCTA
CTTATTGCTGGAAACCTACGTTGTTCCTTGGATTGAAGTAATCTCTCCCTCTTCTGGTGCGCCCACAGCACTTGCACCAACAGTGG
GTACCCAACAGACTAGCGTGCCTGCCGAAGAAGAGGGTCCTCTGCAGGGGACAATGGGGAATTATGCTCTCCAGACTTTCT
ACACACACAAGTCACACAGGAAGGAAGGTAAAGAGAAACTAGAGAAAATAATTTTTGAAGAAAAACATTTCAGGAAGTATTGAA
AGTACACGGTAACTCAGCCTGGCGCAGGGGTGGAGGGCAGCAGCACTGTTGCTGCAGCTATGCTCCTTCCTCAGTGCCCTGCAC
ACCCCGGGACTTGCTCGGTGAGCATCTCTCGTGTCAGTGACAGCTAGTGTGA

FIG.4

| Sequence ID | Sequence Name | Sequence |
|---|---|---|
| SEQ ID NO: 23 | CUR-0521 | UUGUAAAGUAUGAGCUUGGUGUCAGCA |
| SEQ ID NO: 24 | CUR-0519 | AAUCAAUGGCUGUUCUCUCUCUGGGAC |
| SEQ ID NO: 25 | CUR-0523 | ACCUAUAAUUCCAGCACUUUGAGAGGC |
| SEQ ID NO: 26 | CUR-1214 | C*C*C*A*C*C*A*C*T*T*G*C*A*A*C*T*C*A*G*A |
| SEQ ID NO: 27 | CUR-1215 | T*T*C*G*G*A*A*G*T*G*C*T*C*G*G*T*T*T*C*G |
| SEQ ID NO: 28 | CUR-1216 | C*C*C*A*G*C*T*C*A*G*A*T*C*C*A*T*C*C*T*T |
| SEQ ID NO: 29 | CUR-1217 | G*C*C*T*C*T*T*C*T*A*T*G*G*T*C*T*G*T*C |
| SEQ ID NO: 30 | CUR-1218 | G*C*C*A*T*G*C*C*A*C*C*C*A*G*A*G*T*T*A |
| SEQ ID NO: 31 | CUR-1219 | G*C*T*G*T*T*C*T*C*T*C*T*C*T*G*G*G*A*C*T*T |
| SEQ ID NO: 32 | CUR-1220 | G*T*T*C*C*C*A*T*T*C*C*C*T*T*A*T*T*A*G |
| SEQ ID NO: 33 | CUR-1221 | C*G*A*A*T*C*A*C*T*T*A*G*C*C*A*C*T*T*T*G |
| SEQ ID NO: 34 | CUR-1222 | C*T*G*G*G*A*T*T*A*C*A*G*G*C*G*T*G*A*G*C |
| SEQ ID NO: 35 | CUR-1087 | C*A*T*G*T*C*T*T*C*C*T*G*C*C*T*T*T*C*C*T*G*T |
| SEQ ID NO: 36 | CUR-1088 | G*C*T*C*A*C*A*A*T*A*T*C*A*G*G*C*T*G*C*T*T |
| SEQ ID NO: 37 | CUR-1089 | T*C*A*A*C*T*T*T*A*C*C*C*A*G*A*C*A*A*G*C*A |
| SEQ ID NO: 38 | CUR-1090 | G*G*A*C*A*G*G*G*T*A*G*C*A*A*C*G*C*C*A*T*T |
| SEQ ID NO: 39 | CUR-1091 | C*C*A*C*C*T*C*A*G*T*T*G*C*A*C*G*G*A*A |
| SEQ ID NO: 40 | CUR-1092 | T*T*G*G*G*C*A*T*A*G*A*A*G*T*T*T*G*G*T*T*C |

FIG.5

| Sequence ID | Sequence Name | Sequence |
|---|---|---|
| SEQ ID NO: 41 | CUR-0476 | GUGGUCAGUCACAGCCACACCAGACUU |
| SEQ ID NO: 42 | CUR-0478 | GUCCCUUCUCCCACCACACUGUGACUC |
| SEQ ID NO: 43 | CUR-0480 | CAGCACUGACACAGCUACCACCUACUC |
| SEQ ID NO: 44 | CUR-0444 | UGUGCUUCACUGAGGAUGGAUCUGCCA |
| SEQ ID NO: 45 | CUR-0446 | AGAGAAACGCUCAUCAGACACCACCAA |
| SEQ ID NO: 46 | CUR-0448 | CUUAGGAAGCACAAGAGGCUGAGCCUU |
| SEQ ID NO: 47 | CUR-0450 | CCUGGCUCCCUGUCCCACCUUGCUCCA |
| SEQ ID NO: 48 | CUR-0452 | GUUCAUUUCCACACCCAGCUUCAACUA |
| SEQ ID NO: 49 | CUR-0541 | A*G*A*C*C*T*A*T*C*T*G*T*T*C*C*C*A*C*C |
| SEQ ID NO: 50 | CUR-0542 | G*T*C*A*G*T*C*A*C*A*G*C*C*A*C*A*C*C*A*G |
| SEQ ID NO: 51 | CUR-0815 | C*C*T*A*T*C*T*G*T*T*C*C*C*A*C*C*T*T*G |
| SEQ ID NO: 52 | CUR-0816 | G*T*C*A*C*A*G*C*C*A*C*A*C*C*A*G*A*C*T*T |
| SEQ ID NO: 53 | CUR-0817 | T*C*C*C*T*T*C*T*C*C*C*A*C*C*A*C*A*C*T*G*T |
| SEQ ID NO: 54 | CUR-0818 | C*T*C*C*T*C*A*A*T*G*T*G*C*T*C*T*T*C*C*C |
| SEQ ID NO: 55 | CUR-0819 | C*C*C*A*C*T*C*C*C*A*C*A*C*C*A*G*A*T*A |
| SEQ ID NO: 56 | CUR-0820 | A*A*C*A*G*C*C*T*C*T*T*C*C*C*A*G*C*A*C*C |
| SEQ ID NO: 57 | CUR-0821 | C*A*C*C*A*T*C*T*A*C*T*C*C*T*G*A*G*C*C*C |
| SEQ ID NO: 58 | CUR-0822 | T*C*A*T*T*G*T*C*A*C*G*C*G*C*T*C*C*C*A*C |

FIG.6

| Sequence ID | Antisense Sequence Name | Sequence |
|---|---|---|
| SEQ ID NO: 59 | CUR-0767 | T*C*C*C*A*G*C*T*A*C*T*C*A*G*A*A*G*A*C*C*T |
| SEQ ID NO: 60 | CUR-0768 | T*G*G*G*C*G*A*C*A*G*A*T*C*A*G*G*A*C*T*C |
| SEQ ID NO: 61 | CUR-0769 | C*T*G*A*G*G*T*G*C*A*T*G*G*G*T*A*G*T*G*G*T |
| SEQ ID NO: 62 | CUR-0770 | G*C*C*G*A*T*C*A*C*T*T*G*A*G*G*T*C*A*G*G*A |
| SEQ ID NO: 63 | CUR-0771 | A*T*T*A*G*C*T*G*G*G*C*G*T*G*G*T*G*G*T*G |
| SEQ ID NO: 64 | CUR-0772 | G*C*T*C*T*G*C*G*T*G*T*G*G*G*C*T*C*A*T*T |
| SEQ ID NO: 65 | CUR-0773 | G*T*C*C*C*T*C*T*G*A*T*A*T*A*T*G*C*T*C*T*C |
| SEQ ID NO: 66 | CUR-0774 | C*T*T*G*A*G*T*T*C*T*T*C*C*T*G*C*T*T*C*C*A |
| SEQ ID NO: 67 | CUR-0775 | T*C*T*C*C*A*G*C*C*A*G*T*C*A*C*C*C*A*G*A |
| SEQ ID NO: 68 | CUR-1017 | C*C*A*T*C*A*A*C*A*T*C*T*C*C*C*T*C*A*G*C*C |
| SEQ ID NO: 69 | CUR-1018 | C*T*T*C*T*T*C*C*T*C*T*T*T*C*C*C*T*C*T*T |
| SEQ ID NO: 70 | CUR-1019 | A*C*A*G*C*A*G*C*A*A*C*T*C*A*G*G*A*G*G*C*A |
| SEQ ID NO: 71 | CUR-1020 | G*G*G*T*A*G*T*T*C*T*G*A*G*G*G*C*A*C*G*A |
| SEQ ID NO: 72 | CUR-1021 | A*G*G*C*A*G*G*T*G*G*A*T*G*T*C*A*G*T*G |
| SEQ ID NO: 73 | CUR-1022 | G*G*G*T*A*G*G*G*T*T*C*A*G*A*G*A*A*G*G*C |

FIG.7

| Sequence ID | Antisense Sequence Name | Sequence |
|---|---|---|
| SEQ ID NO: 74 | CUR-1054 | A*C*T*C*C*T*C*C*T*C*T*T*G*C*A*G*T*G*A*G |
| SEQ ID NO: 75 | CUR-1055 | G*C*T*G*T*T*G*T*T*A*T*C*C*T*T*C*T*G*T*G |
| SEQ ID NO: 76 | CUR-1056 | A*T*C*G*C*G*G*G*A*A*G*C*C*A*G*G*G*T*T*T |
| SEQ ID NO: 77 | CUR-1057 | G*C*C*A*G*A*A*T*A*G*G*T*T*G*A*G*A*G*G*G*A |
| SEQ ID NO: 78 | CUR-1058 | G*C*C*G*T*T*C*G*A*A*A*C*T*C*C*T*C*C*T*C*T |
| SEQ ID NO: 79 | CUR-1059 | G*G*T*T*T*C*C*G*C*T*G*T*G*C*T*C*T*G*T*G |
| SEQ ID NO: 80 | CUR-1060 | A*C*G*T*G*C*C*T*C*A*G*A*A*T*C*T*C*C*C |
| SEQ ID NO: 81 | CUR-1061 | T*T*C*C*T*C*A*A*T*C*A*A*C*C*T*C*T*T*C*C*T |
| SEQ ID NO: 82 | CUR-1062 | G*T*G*A*T*G*T*T*T*C*C*T*C*T*G*T*T*G*T*C |
| SEQ ID NO: 83 | CUR-1063 | C*A*C*T*T*T*C*T*A*G*C*T*G*C*A*C*C*A*C*C |

FIG.8

| Sequence ID | Antisense Sequence Name | Sequence |
|---|---|---|
| SEQ ID NO: 84 | CUR-0973 | C*C*G*T*C*C*A*C*T*T*T*C*C*C*A*T*C*T*C*C*T |
| SEQ ID NO: 85 | CUR-0974 | C*C*C*G*T*C*C*A*C*T*T*T*C*C*C*A*T*C*T*C |
| SEQ ID NO: 86 | CUR-0975 | C*T*T*C*A*C*A*G*C*A*C*C*A*G*G*G*C*A*G*A |
| SEQ ID NO: 87 | CUR-0976 | C*C*C*A*G*C*A*G*T*C*G*A*A*G*T*T*T*G*T*G*A |
| SEQ ID NO: 88 | CUR-0977 | C*C*G*G*T*C*T*C*A*G*G*T*C*C*A*A*G*A*T*G |
| SEQ ID NO: 89 | CUR-0978 | T*G*G*T*G*G*A*G*A*A*G*G*T*G*C*A*G*G*C*T |
| SEQ ID NO: 90 | CUR-0979 | G*A*T*T*C*A*C*C*A*A*G*T*T*T*C*A*C*G*C*A*T |
| SEQ ID NO: 91 | CUR-0980 | G*A*C*G*A*G*G*T*G*A*A*G*G*A*G*C*A*G*G*T |
| SEQ ID NO: 92 | CUR-0981 | T*C*G*G*A*A*C*T*G*G*A*G*G*A*A*C*A*A*C*T*G |

FIG. 9

SEQ ID NO: 93- TGGAGCTCAG TTT
SEQ ID NO: 94- TTTCTCGTGC AGCT
SEQ ID NO: 95- TTCTGGCGCG TGCC
SEQ ID NO: 96- CCCTCGTGGA GCTC
SEQ ID NO: 97- GCCCGCGCGC AGCG
SEQ ID NO: 98- CGGCTCCACC TTCT
SEQ ID NO: 99- CTGGCGGTAG AGCT
SEQ ID NO: 100- GCTCGTGCAG CTTC
SEQ ID NO: 101- CAGCTTCTGG CGCG
SEQ ID NO: 102- GCGCGCAGCG GCTC
SEQ ID NO: 103- TCCACCTTCT GGCG
SEQ ID NO: 104- CGGTGTAGAG CTCC
SEQ ID NO: 105- CCATCTCCTC CTGC
SEQ ID NO: 106- GAAGTCGTCC AGATCCAAA
SEQ ID NO: 107- AAGTCGTCCA GATCCAAAT
SEQ ID NO: 108- AGTCGTCCAG ATCCAAATG
SEQ ID NO: 109- GTCGTCCAGA TCCAAATGG
SEQ ID NO: 110- TCGTCCAGAT CCAAATGGC
SEQ ID NO: 111- CGTCCAGATC CAAATGGCA
SEQ ID NO: 112- GTCCAGATCC AAATGGCAA
SEQ ID NO: 113- TCCAGATCCA AATGGCAAA
SEQ ID NO: 114- CAGATCCAAA TG
SEQ ID NO: 115- AGATCCAAAT GGCAAA
SEQ ID NO: 116- AGATCCAAAT GG
SEQ ID NO: 117- GATCCAAATG GC
SEQ ID NO: 118- ATCCAAATGG CA
SEQ ID NO: 119- TCCAAATGGC AA
SEQ ID NO: 120- CCAAATGGCA AA
SEQ ID NO: 121- CCAAATGGCA AACCTTCTT
SEQ ID NO: 122- ATGGCAAATC TTCTTCATC
SEQ ID NO: 123- AAATGGCAAA CCTTCTTCA
SEQ ID NO: 124- AAATGGCAAA TCTTCTTCA
SEQ ID NO: 125- ATGGCAAACC TTCTTCATC
SEQ ID NO: 126- CCAAATGGCA AATCTTCTT
SEQ ID NO: 127- ATGGCAAACC TTCTT
SEQ ID NO: 128- ATGGCAAATC TTCTT
SEQ ID NO: 129- CTTCTTCATC C
SEQ ID NO: 130- CCAGGACCCA ACCCACA
SEQ ID NO: 131- GCTACTTATT GCTG
SEQ ID NO: 132- TGCTGGAAAC CTAC
SEQ ID NO: 133- TTCCTTGGAT TGAA
SEQ ID NO: 134- GCCCACAGCA CTTGCA
SEQ ID NO: 135- CACCAACAGT GGGTAC
SEQ ID NO: 136- CAACAGACTA GC
SEQ ID NO: 137- GAAGAAGGGG TCCT
SEQ ID NO: 138- GAATTATGCT CTCC
SEQ ID NO: 139- CTCCAGACTT TCTA
SEQ ID NO: 140- AAGTCACACA GGAAGG
SEQ ID NO: 141- GAAACTAGAG AAAA
SEQ ID NO: 142- AATAATTTTT GAAG
SEQ ID NO: 143- GAAGTATTGA AAGT
SEQ ID NO: 144- TGAAAGTACA CGGT
SEQ ID NO: 145- CTGGGGCAGG GGTG
SEQ ID NO: 146- GGGGTGGAGG GCAG
SEQ ID NO: 147- TGCTCCTTCC TCAG
SEQ ID NO: 148- ACCCGGGACT TGCTC
SEQ ID NO: 149- TGTCAGTGAC AGCT
SEQ ID NO: 150- TGTCAGTGAC AGCTAGTGT
SEQ ID NO: 151- GTCAGTGACA GCTAGTGTG

FIG.9 (Continued)

SEQ ID NO: 152- TCAGTGACAG CTAGTGTGA
SEQ ID NO: 153- AGTGACAGCT AGTGTGAGT
SEQ ID NO: 154- TGACAGCTAG TGTGA
SEQ ID NO: 155- TGACAGCTAG TGTGAGTAC
SEQ ID NO: 156- GACAGCTAGT GTGAGTACT
SEQ ID NO: 157- CAGCTAGTGT GAGTACTCT
SEQ ID NO: 158- AGCTAGTGTG AGTACTCTT
SEQ ID NO: 159- GCTAGTGTGA GTACTCTTA
SEQ ID NO: 160- CTAGTGTGAG TACTCTTAT
SEQ ID NO: 161- CTAGTGTGAG TACT
SEQ ID NO: 162- TAGTGTGAGT ACTCTTATG
SEQ ID NO: 163- AGTGTGAGTA CTCTTATGT
SEQ ID NO: 164- GTGTGAGTAC TCTTATGTT
SEQ ID NO: 165- TGTGAGTACT CTTATGTTC
SEQ ID NO: 166- GTGAGTACTC TTATGTTCA
SEQ ID NO: 167- TGAGTACTCT TATGTTCAG
SEQ ID NO: 168- ACTCTTATGT TCAG
SEQ ID NO: 169- TACCTCTTGA CTTT
SEQ ID NO: 170- GACTTTGGGG ACAA
SEQ ID NO: 171- A*A*A*C*T*G*A*G*C*T* C*C*A
SEQ ID NO: 172- A*G*C*T*G*C*A*C*G*A *G*A*A*A
SEQ ID NO: 173- G*G*C*A*C*G*C*G*C*C *A*G*A*A
SEQ ID NO: 174- G*A*G*C*T*C*C*A*C*G *A*G*G*G
SEQ ID NO: 175- C*G*C*T*G*C*G*C*G*C* G*G*G*C
SEQ ID NO: 176- A*G*A*A*G*G*T*G*G*A *G*C*C*G
SEQ ID NO: 177- A*G*C*T*C*T*A*C*C*G* C*C*A*G
SEQ ID NO: 178- G*A*A*G*C*T*G*C*A*C *G*A*G*C
SEQ ID NO: 179- C*G*C*G*C*C*A*G*A*A *G*C*T*G
SEQ ID NO: 180- G*A*G*C*C*G*C*T*G*C *G*C*G*C
SEQ ID NO: 181- C*G*C*C*A*G*A*A*G*G* T*G*G*A
SEQ ID NO: 182- G*G*A*G*C*T*C*T*A*C *A*C*C*G
SEQ ID NO: 183- G*C*A*G*G*A*G*G*A*G* A*T*G*G
SEQ ID NO: 184- T*T*T*G*G*A*T*C*T*G* G*A*C*G*A*C*T*T*C
SEQ ID NO: 185- A*T*T*T*G*G*A*T*C*T* G*G*A*C*G*A*C*T*T
SEQ ID NO: 186- C*A*T*T*T*G*G*A*T*C* T*G*G*A*C*G*A*C*T
SEQ ID NO: 187- C*C*A*T*T*T*G*G*A*T *C*T*G*G*A*C*G*A*C
SEQ ID NO: 188- G*C*C*A*T*T*T*G*G*A T*C*T*G*G*A*C*G*A
SEQ ID NO: 189- T*G*C*C*A*T*T*T*G*G *A*T*C*T*G*G*A*C*G
SEQ ID NO: 190- T*T*G*C*C*A*T*T*T*G *G*A*T*C*T*G*G*A*C
SEQ ID NO: 191- T*T*T*G*C*C*A*T*T*T* G*G*A*T*C*T*G*G*A
SEQ ID NO: 192- C*A*T*T*T*G*G*A*T*C* T*G
SEQ ID NO: 193- TTTGCCATTT GGATCT
SEQ ID NO: 194- C*C*A*T*T*T*G*G*A*T* C*T
SEQ ID NO: 195- G*C*C*A*T*T*T*G*G*A *T*C
SEQ ID NO: 196- T*G*C*C*A*T*T*T*G*G* A*T
SEQ ID NO: 197- T*G*C*C*A*T*T*T*G*G* A*T
SEQ ID NO: 198- T*T*T*G*C*C*A*T*T*T* G*G
SEQ ID NO: 199- A*A*G*A*A*G*G*T*T*T* G*C*C*A*T*T*T*G*G
SEQ ID NO: 200- G*A*T*G*A*A*G*A*A*G* A*T*T*T*T*G*C*C*A*T
SEQ ID NO: 201- T*G*A*A*G*A*A*G*G*T *T*T*G*C*C*A*T*T*T
SEQ ID NO: 202- T*G*A*A*G*A*A*G*A*T *T*T*G*C*C*A*T*T*T
SEQ ID NO: 203- G*A*T*G*A*A*G*A*A*G* G*T*T*T*G*C*C*A*T
SEQ ID NO: 204- A*A*G*A*A*G*A*T*T*T *G*C*C*A*T*T*T*G*G
SEQ ID NO: 205- A*A*G*A*A*G*G*T*T*T* G*C*C*A*T
SEQ ID NO: 206- A*A*G*A*A*G*A*T*T*T *G*C*C*A*T
SEQ ID NO: 207- G*G*A*T*G*A*A*G*A*A* G
SEQ ID NO: 208- T*G*T*G*G*G*T*T*G*G *G*T*C*C*T*G*G
SEQ ID NO: 209- C*A*G*C*A*A*T*A*AG* T*A*G*C
SEQ ID NO: 210- G*T*A*G*G*T*T*T*C*C *A*G*C*A

FIG.9 (Continued)

SEQ ID NO: 211- T*T*C*A*A*T*C*C*A*A*G*G*A*A
SEQ ID NO: 212- T*G*C*A*A*G*T*G*C*T* G*T*G*G*G*C
SEQ ID NO: 213- G*T*A*C*C*C*A*C*T*G T*T*G*G*T*G
SEQ ID NO: 214- G*C*T*A*G*T*C*T*G*T *T*G
SEQ ID NO: 215- A*G*G*A*C*C*C*C*T*T *C*T*T*C
SEQ ID NO: 216- G*G*A*G*A*G*C*A*T*A* A*T*T*C
SEQ ID NO: 217- T*A*G*A*A*A*G*T*C*T* G*G*A*G
SEQ ID NO: 218- C*C*T*T*C*C*T*G*T*G* T*G*A*C*T*T
SEQ ID NO: 219- T*T*T*T*C*T*C*T*A*G *T*T*T*C
SEQ ID NO: 220- C*T*T*C*A*A*A*A*A*T *T*A*T*T
SEQ ID NO: 221- A*C*T*T*TC*A*A*T*A *C*T*T*C
SEQ ID NO: 222- A*C*C*G*T*G*T*A*C*T *T*T*C*A
SEQ ID NO: 223- C*A*C*C*C*C*T*G*C*C *C*C*A*G
SEQ ID NO: 224- C*T*G*C*C*C*T*C*C*A*C*C*C*C
SEQ ID NO: 225- C*T*G*A*G*G*A*A*G*G *A*G*C*A
SEQ ID NO: 226- G*A*G*C*A*A*G*T*C*C *C*G*G*G*T
SEQ ID NO: 227- A*G*C*T*G*T*C*A*C*T* G*A*C*A
SEQ ID NO: 228- A*C*A*C*T*A*G*C*T*G* T*C*A*C*T*G*A*C*A
SEQ ID NO: 229- C*A*C*A*C*T*A*G*C*T *G*T*C*A*C*T*G*A*C
SEQ ID NO: 230- T*C*A*C*A*C*T*A*G*C *T*G*T*C*A*C*T*G*A
SEQ ID NO: 231- A*C*T*C*A*C*A*C*T*A* G*C*T*G*T*C*A*C*T
SEQ ID NO: 232- T*C*A*C*A*C*T*A*G*C *T*G*T*C*A
SEQ ID NO: 233- G*T*A*C*T*C*A*C*A*C *T*A*G*C*T*G*T*C*A
SEQ ID NO: 234- A*G*T*A*C*T*C*A*C*A *C*T*A*G*C*T*G*T*C
SEQ ID NO: 235- A*G*A*G*T*A*C*T*C*A* C*A*C*T*A*G*C*T*G
SEQ ID NO: 236- A*A*G*A*G*T*A*C*T*C *A*C*A*C*T*A*G*C*T
SEQ ID NO: 237- T*A*A*G*A*G*T*A*C*T *C*A*C*A*C*T*A*G*C
SEQ ID NO: 238- A*T*A*A*G*A*G*T*A*C *T*C*A*C*A*C*T*A*G
SEQ ID NO: 239- A*G*T*A*C*T*C*A*C*A* C*T*A*G
SEQ ID NO: 240- C*A*T*A*A*G*A*G*T*A *C*T*C*A*C*A*C*T*A
SEQ ID NO: 241- A*C*A*T*A*A*G*A*G*T *A*C*T*C*A*C*A*C*T
SEQ ID NO: 242- A*A*C*A*T*A*A*G*A*G* T*A*C*T*C*A*C*A*C
SEQ ID NO: 243- G*A*A*C*A*T*A*A*G*A* G*T*A*C*T*C*A*C*A
SEQ ID NO: 244- T*G*A*A*C*A*T*A*A*G*A*G*T*A*C*T*C*A*C
SEQ ID NO: 245- C*T*G*A*A*C*A*T*A*A*G*A*G*T*A*C*T*C*A
SEQ ID NO: 246- C*T*G*A*A*C*A*T*A*A*G*A*G*T
SEQ ID NO: 247- A*A*A*G*T*C*A*A*G*A*G*G*T*A
SEQ ID NO: 248- T*T*G*T*C*C*C*A*A*A*G*T*C
SEQ ID NO: 249- +A*+A*+G*A*A*G*G*T*T*T*G*C*+C*+A*+T
SEQ ID NO: 250- +T*+C*+AC*A*C*T*A*G*C*T*G*+T*+C*+A
SEQ ID NO: 251- A*A*G*A*A*G*G*T*T*T* G*C*C*A*T
SEQ ID NO: 252- T*C*A*C*A*C*T*A*G*C*T*G*T*C*A
SEQ ID NO: 253- CTCCTCCTGC CACTTCTTCT G
SEQ ID NO: 254- CTGGTGGATGAAGAAGGTTTGC
SEQ ID NO: 255- TTTGGATCTGGACGACTTC
SEQ ID NO: 256- +C*+A*+A*T*A*A*G*T*A*G*C*C*+T*+G*+T
SEQ ID NO: 257- +C*+A*+C*G*C*T*A*G*T*C*T*G*+T*+T*+G
SEQ ID NO: 258- +C*+T*+T*C*C*T*T*C*C*T* G*T*+G*+T*+G
SEQ ID NO: 259- +C*+A*+G*G*C*T*G*A*G*T*T*A*+C*+C*+G
SEQ ID NO: 260- +G*+C*T*A*G*T*C*T*G*+T *+T*+G
SEQ ID NO: 261- +G*+T*C*T*G*A*T*G*G*+A* G*+A
SEQ ID NO: 262- GCTAGT
SEQ ID NO: 263- T*G*C*C*A*T*T*T*G*G *A*T*C*T*G*G*A*C*G

FIG.10

| Sequence ID | Sense Sequence Name | Sequence |
|---|---|---|
| SEQ ID NO: 264 | CUR-0521 | CUGACACCAAGCUCAUACUUUACAA |
| SEQ ID NO: 265 | CUR-0519 | CCCAGAGAGAGAACAGCCAUUGATT |
| SEQ ID NO: 266 | CUR-0523 | CUCUCAAAGUGCUGGAAUUAUAGGT |

FIG.11

| Sequence ID | Antisense Sequence Name | Sequence |
|---|---|---|
| SEQ ID NO: 267 | CUR-0476 | GUCUGGUGUGGCUGUGACUGACCAC |
| SEQ ID NO: 268 | CUR-0478 | GUCACAGUGUGGUGGAGAAGGGAC |
| SEQ ID NO: 269 | CUR-0480 | GUAGGUGGUAGCUGUGUCAGUGCTG |
| SEQ ID NO: 270 | CUR-0444 | GCAGAUCCAUCCUCAGUGAAGCACA |
| SEQ ID NO: 271 | CUR-0446 | GGUGGUGUCUGAUGAGCGUUUCUCT |
| SEQ ID NO: 272 | CUR-0448 | GGCUCAGCCUCUUGUGCUUCCUAAG |
| SEQ ID NO: 273 | CUR-0450 | GAGCAAGGUGGGACAGGGAGCCAGG |
| SEQ ID NO: 274 | CUR-0452 | GUUGAAGCUGGGUGUGGAAAUGAAC |

FIG.12

SEQ ID NO: 275- TTTGGATCTGGACGACTTC
SEQ ID NO: 276- CTCCTCCTGCCACTTCTTCTG
SEQ ID NO: 277- CTGGTGGATGAAGAAGGTTTGC
SEQ ID NO: 278- +G*+C*T*A*G*T*C*T*G*A*+T*+G (CUR-962)
SEQ ID NO: 279- +G*+T*C*T*G*A*T*G*G*A*+A*+G*+A (CUR-963)

SEQUENCE LISTING

```
<160> NUMBER OF SEQ ID NOS: 279

<210> SEQ ID NO 1
<211> LENGTH: 10412
<212> TYPE: DNA
<213> ORGANISM: Homo sapiens
<300> PUBLICATION INFORMATION:
<308> DATABASE ACCESSION NUMBER: NM_005502
<309> DATABASE ENTRY DATE: 2010-08-15
<313> RELEVANT RESIDUES IN SEQ ID NO: (1)..(10412)

<400> SEQUENCE: 1
gtaattgcga gcgagagtga gtggggccgg gacccgcaga gccgagccga cccttctctc        60
ccgggctgcg gcagggcagg gcggggagct ccgcgcacca acagagccgg ttctcagggc       120
gctttgctcc ttgttttttc cccggttctg ttttctcccc ttctccggaa ggcttgtcaa       180
ggggtaggag aaagagacgc aaacacaaaa gtggaaaaca gttaatgacc agccacggcg       240
tccctgctgt gagctctggc cgctgccttc cagggctccc gagccacacg ctgggggtgc       300
tggctgaggg aacatggctt gttggcctca gctgaggttg ctgctgtgga agaacctcac       360
tttcagaaga agacaaacat gtcagctgct gctggaagtg gcctggcctc tatttatctt       420
cctgatcctg atctctgttc ggctgagcta cccaccctat gaacaacatg aatgccattt       480
tccaaataaa gccatgccct ctgcaggaac acttccttgg gttcagggga ttatctgtaa       540
tgccaacaac ccctgtttcc gttacccgac tcctggggag gctcccggag ttgttggaaa       600
ctttaacaaa tccattgtgg ctcgcctgtt ctcagatgct cggaggcttc ttttatacag       660
ccagaaagac accagcatga aggacatgcg caaagttctg agaacattac agcagatcaa       720
gaaatccagc tcaaacttga agcttcaaga tttcctggtg gacaatgaaa ccttctctgg       780
gttcctgtat cacaacctct ctctcccaaa gtctactgtg gacaagatgc tgagggctga       840
tgtcattctc cacaaggtat ttttgcaagg ctaccagtta catttgacaa gtctgtgcaa       900
tggatcaaaa tcagaagaga tgattcaact tggtgaccaa gaagtttctg agctttgtgg       960
cctaccaagg gagaaactgg ctgcagcaga gcgagtactt cgttccaaca tggacatcct      1020
```

```
gaagccaatc ctgagaacac taaactctac atctcccttc ccgagcaagg agctggctga    1080
agccacaaaa acattgctgc atagtcttgg gactctggcc caggagctgt tcagcatgag    1140
aagctggagt gacatgcgac aggaggtgat gtttctgacc aatgtgaaca gctccagctc    1200
ctccacccaa atctaccagg ctgtgtctcg tattgtctgc gggcatcccg agggaggggg    1260
gctgaagatc aagtctctca actggtatga ggacaacaac tacaaagccc tctttggagg    1320
caatggcact gaggaagatg ctgaaacctt ctatgacaac tctacaactc cttactgcaa    1380
tgatttgatg aagaatttgg agtctagtcc tctttcccgc attatctgga aagctctgaa    1440
gccgctgctc gttgggaaga tcctgtatac acctgacact ccagccacaa ggcaggtcat    1500
ggctgaggtg aacaagacct tccaggaact ggctgtgttc catgatctgg aaggcatgtg    1560
ggaggaactc agcccaaga tctgaccctt catggagaac agccaagaaa tggaccttgt    1620
ccggatgctg ttggacagca gggacaatga ccacttttgg gaacagcagt tggatggctt    1680
agattggaca gcccaagaca tcgtggcgtt tttggccaag cacccagagg atgtccagtc    1740
cagtaatggt tctgtgtaca cctggagaga agctttcaac gagactaacc aggcaatccg    1800
gaccatatct cgcttcatgg agtgtgtcaa cctgaacaag ctagaaccca tagcaacaga    1860
agtctggctc atcaacaagt ccatggagct gctggatgag aggaagttct gggctggtat    1920
tgtgttcact ggaattactc caggcagcat tgagctgccc catcatgtca agtacaagat    1980
ccgaatggac attgacaatg tggagaggac aaataaaatc aaggatgggt actgggaccc    2040
tggtcctcga gctgaccct ttgaggacat gcggtacgtc tggggggggct tcgcctactt    2100 gcaggatgtg gtggagcagg caatcatcag ggtgctgacg ggcaccgaga agaaaactgg    2160
tgtctatatg caacagatgc cctatccctg ttacgttgat gacatctttc tgcgggtgat    2220
gagccggtca atgcccctct tcatgacgct ggcctggatt tactcagtgg ctgtgatcat    2280
caagggcatc gtgtatgaga aggaggcacg gctgaaagag accatgcgga tcatgggcct    2340
ggacaacagc atcctctggt ttagctggtt cattagtagc ctcattcctc ttcttgtgag    2400
cgctggcctg ctagtggtca tcctgaagtt aggaaacctg ctgccctaca gtgatcccag    2460
cgtggtgttt gtcttcctgt ccgtgtttgc tgtggtgaca atcctgcagt gcttcctgat    2520
tagcacactc ttctccagag ccaacctggc agcagcctgt gggggcatca tctacttcac    2580
gctgtacctg ccctacgtcc tgtgtgtggc atggcaggac tacgtgggct tcacactcaa    2640
gatcttcgct agcctgctgt ctcctgtggc ttttgggttt ggctgtgagt actttgccct    2700
ttttgaggag cagggcattg gagtgcagtg ggacaacctg tttgagagtc ctgtggagga    2760
agatggcttc aatctcacca cttcggtctc catgatgctg tttgacaccct tcctctatgg    2820 ggtgatgacc tggtacattg aggctgtctt tccaggccag tacggaattc ccaggccctg    2880
gtattttcct tgcaccaagt cctactggtt tggcgaggaa agtgatgaga agagccaccc    2940
tggttccaac cagaagagaa tatcagaaat ctgcatggag gaggaaccca cccacttgaa    3000
gctgggcgtg tccattcaga acctggtaaa agtctaccga gatgggatga aggtggctgt    3060
cgatggcctg gcactgaatt tttatgaggg ccagatcacc tccttcctgg gccacaatgg    3120
agcggggaag acgaccacca tgtcaatcct gaccggggttg ttccccccga cctcgggcac    3180
cgcctacatc ctgggaaaag acattcgctc tgagatgagc accatccggc agaacctggg    3240
ggtctgtccc cagcataacg tgctgtttga catgctgact gtcgaagaac acatctggtt    3300
ctatgcccgc ttgaaagggc tctctgagaa gcacgtgaag gcgagatgg agcagatggc    3360 cctggatgtt ggtttgccat caagcaagct gaaaagcaaa acaagccagc tgtcaggtgg    3420
```

-continued

```
aatgcagaga aagctatctg tggccttggc ctttgtcggg ggatctaagg ttgtcattct   3480
ggatgaaccc acagctggtg tggacccttα ctcccgcagg ggaatatggg agctgctgct   3540
gaaataccga caaggccgca ccattattct ctctacacac cacatggatg aagcggacgt   3600
cctggggggac aggattgcca tcatctccca tgggaagctg tgctgtgtgg gctcctccct   3660
gtttctgaag aaccagctgg gaacaggcta ctacctgacc ttggtcaaga agatgtgga    3720
atcctccctc agttcctgca gaaacagtag tagcactgtg tcatacctga aaaggagga    3780
cagtgtttct cagagcagtt ctgatgctgg cctgggcagc gaccatgaga gtgacacgct   3840
gaccatcgat gtctctgcta tctccaacct catcaggaag catgtgtctg aagcccggct   3900
ggtggaagac atagggcatg agctgaccta tgtgctgcca tatgaagctg ctaaggaggg   3960
agcctttgtg gaactctttc atgagattga tgaccggctc tcagacctgg gcatttctag   4020
ttatggcatc tcagagacga ccctggaaga aatattcctc aaggtggccg aagagagtgg   4080
ggtggatgct gagacctcag atggtaccctt gccagcaaga cgaaacaggc gggccttcgg   4140
ggacaagcag agctgtcttc gcccgttcac tgaagatgat gctgctgatc caaatgattc   4200
tgacatagac ccagaatcca gagagacaga cttgctcagt gggatggatg gcaaagggtc   4260
ctaccaggtg aaaggctgga aacttacaca gcaacagttt gtggcccttt tgtggaagag   4320
actgctaatt gccagacgga gtcggaaagg atttttgct cagattgtct tgccagctgt    4380
gtttgtctgc attgcccttg tgttcagcct gatcgtgcca ccctttggca agtacccccag  4440
cctggaactt cagccctgga tgtacaacga acagtacaca tttgtcagca atgatgctcc    4500
tgaggacacg ggaaccctgg aactcttaaa cgccctcacc aaagaccctg gcttcgggac    4560
ccgctgtatg gaaggaaacc caatcccaga cacgccctgc caggcagggg aggaagagtg    4620
gaccactgcc ccagttcccc agaccatcat ggacctcttc cagaatggga actggacaat    4680
gcagaaccct tcacctgcat gccagtgtag cagcgacaaa atcaagaaga tgctgcctgt    4740
gtgtccccca ggggcagggg ggctgcctcc tccacaaaga aaacaaaaca ctgcagatat    4800
ccttcaggac ctgacaggaa gaaacatttc ggattatctg gtgaagacgt atgtgcagat    4860
catagccaaa agcttaaaga acaagatctg ggtgaatgag tttaggtatg gcggctttc    4920
cctgggtgtc agtaatactc aagcacttcc tccgagtcaa gaagttaatg atgccatcaa   4980
acaaatgaag aaacacctaa agctggccaa ggacagttct gcagatcgat ttctcaacag   5040
cttgggaaga tttatgacag gactggacac caaaaataat gtcaaggtgt ggttcaataa   5100
caagggctgg catgcaatca gctctttcct gaatgtcatc aacaatgcca ttctccgggc   5160
caacctgcaa aagggagaga accctagcca ttatggaatt actgctttca atcatcccct   5220
gaatctcacc aagcagcagc tctcagaggt ggctctgatg accacatcag tggatgtcct   5280
tgtgtccatc tgtgtcatct ttgcaatgtc cttcgtccca gccagctttg tcgtattcct   5340
gatccaggag cgggtcagca aagcaaaaca cctgcagttc atcagtggag tgaagcctgt   5400
catctactgg ctctctaatt ttgtctggga tatgtgcaat tacgttgtcc ctgccacact   5460
ggtcattatc atcttcatct gcttccagca gaagtcctat gtgtcctcca ccaatctgcc   5520
tgtgctagcc cttctacttt tgctgtatgg gtggtcaatα acacctctca gtacccagc    5580
ctcctttgtg ttcaagatcc ccagcacagc ctatgtggtg ctcaccagcg tgaacctctt   5640
cattggcatt aatggcagcg tggccacctt tgtgctggag ctgttcaccg acaataagct   5700
gaataatatc aatgatatcc tgaagtccgt gttcttgatc ttcccacatt tttgcctggg    5760
```

```
acgagggctc atcgacatgg tgaaaaacca ggcaatggct gatgccctgg aaaggtttgg    5820
ggagaatcgc tttgtgtcac cattatcttg ggacttggtg ggacgaaacc tcttcgccat    5880
ggccgtggaa ggggtggtgt tcttcctcat tactgttctg atccagtaca gattcttcat    5940
caggcccaga cctgtaaatg caaagctatc tcctctgaat gatgaagatg aagatgtgag    6000
gcgggaaaga cagagaattc ttgatggtgg aggccagaat gacatcttag aaatcaagga    6060
gttgacgaag atatatagaa ggaagcggaa gcctgctgtt gacaggattt gcgtgggcat    6120
tcctcctggt gagtgctttg ggctcctggg agttaatggg gctggaaaat catcaacttt    6180
caagatgtta acaggagata ccactgttac cagaggagat gctttcctta acaaaaatag    6240
tatcttatca aacatccatg aagtacatca gaacatgggc tactgccctc agtttgatgc    6300
catcacagag ctgttgactg ggagagaaca cgtggagttc tttgcccttt tgagaggagt    6360
cccagagaaa gaagttggca aggttggtga gtgggcgatt cggaaactgg gcctcgtgaa    6420
gtatggagaa aaatatgctg gtaactatag tggaggcaac aaacgcaagc tctctacagc    6480
catggctttg atcggcggc ctcctgtggt gtttctggat gaacccacca caggcatgga    6540
tcccaaagcc cggcggttct tgtggaattg tgccctaagt gttgtcaagg aggggagatc    6600
agtagtgctt acatctcata gtatggaaga atgtgaagct ctttgcacta ggatggcaat    6660
catggtcaat ggaaggttca ggtgccttgg cagtgtccag catctaaaaa ataggtttgg    6720
agatggttat acaatagttg tacgaatagc agggtccaac ccggacctga gcctgtcca    6780
ggatttcttt ggacttgcat ttcctggaag tgttctaaaa gagaaacacc ggaacatgct    6840
acaataccag cttccatctt cattatcttc tctggccagg atattcagca tcctctccca    6900
gagcaaaaag cgactccaca tagaagacta ctctgtttct cagacaacac ttgaccaagt    6960
atttgtgaac tttgccaagg accaaagtga tgatgaccac ttaaaagacc tctcattaca    7020
caaaaaccag acagtagtgg acgttgcagt tctcacatct tttctacagg atgagaaagt    7080
gaaagaaagc tatgtatgaa gaatcctgtt catacggggt ggctgaaagt aaagaggaac    7140
tagactttcc tttgcaccat gtgaagtgtt gtggagaaaa gagccagaag ttgatgtggg    7200
aagaagtaaa ctggatactg tactgatact attcaatgca atgcaattca atgcaatgaa    7260
aacaaaattc cattacaggg gcagtgcctt tgtagcctat gtcttgtatg gctctcaagt    7320
gaaagacttg aatttagttt tttacctata cctatgtgaa actctattat ggaacccaat    7380
ggacatatgg gtttgaactc acactttttt ttttttttttt gttcctgtgt attctcattg    7440
gggttgcaac aataattcat caagtaatca tggccagcga ttattgatca aaatcaaaag    7500
gtaatgcaca tcctcattca ctaagccatg ccatgcccag gagactggtt tcccggtgac    7560
acatccattg ctgcaatga gtgtgccaga gttattagtg ccaagttttt cagaaagttt    7620
gaagcaccat ggtgtgtcat gctcactttt gtgaaagctg ctctgctcag agtctatcaa    7680
cattgaatat cagttgacag aatggtgcca tgcgtggcta acatcctgct ttgattccct    7740
ctgataagct gttctggtgg cagtaacatg caacaaaaat gtgggtgtct ccaggcacgg    7800
gaaacttggt tccattgtta tattgtccta tgcttcgagc catgggtcta cagggtcatc    7860
cttatgagac tcttaaatat acttagatcc tggtaagagg caaagaatca acagccaaac    7920
tgctggggct gcaagctgct gaagccaggg catgggatta aagagattgt gcgttcaaac    7980
ctagggaagc ctgtgcccat tgtcctgac tgtctgctaa catggtacac tgcatctcaa    8040
gatgtttatc tgacacaagt gtattatttc tggcttttg aattaatcta gaaaatgaaa    8100
agatggagtt gtattttgac aaaaatgttt gtacttttta atgttatttg gaatttaag    8160
```

```
ttctatcagt gacttctgaa tccttagaat ggcctctttg tagaaccctg tggtatagag      8220
gagtatggcc actgccccac tattttatt ttcttatgta agtttgcata tcagtcatga       8280
ctagtgccta gaaagcaatg tgatggtcag gatctcatga cattatattt gagtttcttt      8340
cagatcattt aggatactct taatctcact tcatcaatca aatattttt gagtgtatgc       8400 tgtagctgaa agagtatgta cgtacgtata agactagaga gatattaagt ctcagtacac      8460
ttcctgtgcc atgttattca gctcactggt ttacaaatat aggttgtctt gtggttgtag      8520
gagcccactg taacaatact gggcagcctt tttttttttt ttttaattg caacaatgca       8580 aaagccaaga aagtataagg gtcacaagtc taaacaatga attcttcaac agggaaaaca      8640
gctagcttga aaacttgctg aaaaacacaa cttgtgttta tggcatttag taccttcaaa      8700
taattggctt tgcagatatt ggatacccca ttaaatctga cagtctcaaa tttttcatct      8760
cttcaatcac tagtcaagaa aaatataaaa acaacaaata cttccatatg gagcattttt      8820
cagagttttc taacccagtc ttattttct agtcagtaaa catttgtaaa aatactgttt       8880
cactaatact tactgttaac tgtcttgaga gaaagaaaa atatgagaga actattgttt       8940
ggggaagttc aagtgatctt tcaatatcat tactaacttc ttccactttt tccagaattt      9000
gaatattaac gctaaaggtg taagacttca gatttcaaat taatctttct atattttta      9060 aatttacaga atattatata acccactgct gaaaagaaa aaaatgattg ttttagaagt       9120
taaagtcaat attgatttta aatataagta atgaaggcat atttccaata actagtgata      9180
tggcatcgtt gcattttaca gtatcttcaa aaatacagaa tttatagaat aatttctcct      9240
catttaatat ttttcaaaat caagttatg gtttcctcat tttactaaaa tcgtattcta       9300
attcttcatt atagtaaatc tatgagcaac tccttacttc ggttcctctg atttcaaggc      9360 catatttaa aaaatcaaaa ggcactgtga actattttga agaaaacaca acattttaat       9420
acagattgaa aggacctctt ctgaagctag aaacaatcta tagttataca tcttcattaa      9480
tactgtgtta cctttaaaa tagtaatttt ttacattttc ctgtgtaaac ctaattgtgg       9540
tagaaatttt taccaactct atactcaatc aagcaaaatt tctgtatatt ccctgtggaa      9600
tgtacctatg tgagtttcag aaattctcaa aatacgtgtt caaaaatttc tgcttttgca      9660
tctttgggac acctcagaaa acttattaac aactgtgaat atgagaaata cagaagaaaa      9720
taataagccc tctatacata aatgcccagc acaattcatt gttaaaaaac aaccaaacct      9780
cacactactg tatttcatta tctgtactga aagcaaatgc tttgtgacta ttaaatgttg      9840
cacatcattc attcactgta tagtaatcat tgactaaagc catttgtctg tgttttcttc      9900
ttgtggttgt atatatcagg taaaatattt tccaagagc catgtgtcat gtaatactga       9960
accactttga tattgagaca ttaatttgta cccttgttat tatctactag taataatgta     10020
atactgtaga aatattgctc taattctttt caaaattgtt gcatccccct tagaatgttt     10080
ctatttccat aaggatttag gtatgctatt atcccttctt atacccctaag atgaagctgt    10140 ttttgtgctc tttgttcatc attggccctc attccaagca ctttacgctg tctgtaatgg     10200
gatctatttt tgcactggaa tatctgagaa ttgcaaaact agacaaaagt ttcacaacag     10260
atttctaagt taaatcattt tcattaaaag gaaaaagaa aaaaattttt gtatgtcaat      10320
aactttatat gaagtattaa aatgcatatt tctatgttgt aatataatga gtcacaaaat     10380
aaagctgtga cagttctgtt ggtctacaga aa                                   10412
```

<210> SEQ ID NO 2

<211> LENGTH: 1354
<212> TYPE: DNA
<213> ORGANISM: Homo sapiens
<300> PUBLICATION INFORMATION:
<308> DATABASE ACCESSION NUMBER: NM_000229.1
<309> DATABASE ENTRY DATE: 2010-08-02
<313> RELEVANT RESIDUES IN SEQ ID NO: (1)..(1354)

<400> SEQUENCE: 2

```
ccagggctgg aatggggccg cccggctccc catggcagtg ggtgacgctg ctgctggggc      60
tgctgctccc tcctgccgcc cccttctggc tcctcaatgt gctcttcccc ccgcacacca     120
cgcccaaggc tgagctcagt aaccacacac ggcccgtcat cctcgtgccc ggctgcctgg     180
ggaatcagct agaagccaag ctggacaaac cagatgtggt gaactggatg tgctaccgca     240
agacagagga cttcttcacc atctggctgg atctcaacat gttcctaccc cttggggtag     300
actgctggat cgataacacc agggttgtct acaaccggag ctctgggctc gtgtccaacg     360
cccctggtgt ccagatccgc gtccctggct tggcaagac ctactctgtg gagtacctgg     420
acagcagcaa gctggcaggg tacctgcaca cactggtgca gaacctggtc aacaatggct     480
acgtgcggga cgagactgtg cgcgccgccc cctatgactg gcggctggag cccggccagc     540
aggaggagta ctaccgcaag ctcgcagggc tggtggagga gatgcacgct gcctatggga     600
agcctgtctt cctcattggc cacagcctcg gctgtctaca cttgctctat ttcctgctgc     660
gccagcccca ggcctggaag gaccgctttta ttgatggctt catctctctt ggggctccct     720
ggggtggctc catcaagccc atgctggtct tggcctcagg tgacaaccag gcatcccca     780
tcatgtccag catcaagctg aaagaggagc agcgcataac caccacctcc ccctggatgt     840
ttccctctcg catggcgtgg cctgaggacc acgtgttcat ttccacaccc agcttcaact     900
acacaggccg tgacttccaa cgcttctttg cagacctgca ctttgaggaa ggctggtaca     960
tgtggctgca gtcacgtgac ctcctggcag gactcccagc acctggtgtg gaagtatact    1020
gtctttacgg cgtgggcctg cccacgcccc gcacctacat ctacgaccac ggcttccccc    1080
acacggaccc tgtgggtgtg ctctatgagg atggtgatga cacggtggcg acccgcagca    1140
ccgagctctg tggcctgtgg cagggccgcc agccacagcc tgtgcacctg ctgcccctgc    1200
acgggataca gcatctcaac atggtcttca gcaacctgac cctggagcac atcaatgcca    1260
tcctgctggg tgcctaccgc cagggtcccc ctgcatcccc gactgccagc ccagagcccc    1320
cgcctcctga ataaagacct tcctttgcta ccgt                                1354
```

<210> SEQ ID NO 3
<211> LENGTH: 14905
<212> TYPE: DNA
<213> ORGANISM: Homo sapiens
<300> PUBLICATION INFORMATION:
<308> DATABASE ACCESSION NUMBER: NM_002332.2
<309> DATABASE ENTRY DATE: 2010-08-04
<313> RELEVANT RESIDUES IN SEQ ID NO: (1)..(14905)

<400> SEQUENCE: 3

```
cagcggtgcg agctccaggc ccatgcactg aggaggcgga acaaggggga ccccccagag      60
ctccatcaag cccctccaa aggctcccct accggtcca cgccccccac cccccctccc     120
cgcctcctcc caattgtgca ttttttgcagc cggaggcggc tccgagatgg ggctgtgagc     180
ttcgcccggg gaggggggaaa gagcagcgag gagtgaagcg ggggggtggg gtgaagggtt     240
tggatttcgg ggcaggggggc gcaccccgt cagcaggccc tccccaaggg gctcggaact     300
ctacctcttc acccacgccc ctggtgcgct ttgccgaagg aaagaataag aacagagaag     360
```

```
gaggaggggg aaaggaggaa aagggggacc ccccaactgg gggggtgaa ggagagaagt      420 agcaggacca gaggggaagg ggctgctgct tgcatcagcc cacaccatgc tgaccccgcc      480
gttgctcctg ctgctgcccc tgctctcagc tctggtcgcg gcggctatcg acgccctaa      540 gacttgcagc cccaagcagt ttgcctgcag agatcaaata acctgtatct caaagggctg      600
gcggtgcgac ggtgagaggg actgcccaga cggatctgac gaggcccctg agatttgtcc      660
acagagtaag gcccagcgat gccagccaaa cgagcataac tgcctgggta ctgagctgtg      720
tgttcccatg tcccgcctct gcaatggggt ccaggactgc atggacggct cagatgaggg      780
gccccactgc cgagagctcc aaggcaactg ctctcgcctg gctgccagc accattgtgt        840 ccccacactc gatgggccca cctgctactg caacagcagc tttcagcttc aggcagatgg      900
caagacctgc aaagattttg atgagtgctc agtgtacggc acctgcagcc agctatgcac      960
caacacagac ggctccttca tatgtggctg tgttgaagga tacctcctgc agccggataa     1020
ccgctcctgc aaggccaaga cgagccagt agaccggccc cctgtgctgt tgatagccaa     1080
ctcccagaac atcttggcca cgtacctgag tggggcccag gtgtctacca tcacacctac     1140
gagcacgcgg cagaccacag ccatggactt cagctatgcc aacgagaccg tatgctgggt     1200
gcatgttggg gacagtgctg ctcagacgca gctcaagtgt gcccgcatgc ctggcctaaa     1260
gggcttcgtg gatgagcaca ccatcaacat ctccctcagt ctgcaccacg tggaacagat     1320
ggccatcgac tggctgacag gcaacttcta cttttgtgga gacatcgatg ataggatctt      1380
tgtctgcaac agaaatgggg acacatgtgt cacattgcta gacctggaac tctacaaccc     1440
caagggcatt gccctggacc ctgccatggg gaaggtgttt ttcactgact atgggcagat     1500
cccaaaggtg gaacgctgtg acatggatgg gcagaaccgc accaagctcg tcgacagcaa     1560
gattgtgttt cctcatggca tcacgctgga cctggtcagc cgccttgtct actgggcaga     1620
tgcctatctg gactatattg aagtggtgga ctatgagggc aagggccgcc agaccatcat     1680
ccagggcatc ctgattgagc acctgtacgg cctgactgtg tttgagaatt atctctatgc     1740
caccaactcg gacaatgcca atgcccagca gaagacgagt gtgatccgtg tgaaccgctt     1800
taacagcacc gagtaccagg ttgtcacccg ggtggacaag ggtggtgccc tccacatcta     1860
ccaccagagg cgtcagcccc gagtgaggag ccatgcctgt gaaaacgacc agtatgggaa     1920
gccgggtggc tgctctgaca tctgcctgct ggccaacagc cacaaggcgc ggacctgccg     1980
ctgccgttcc ggcttcagcc tgggcagtga cgggaagtca tgcaagaagc cggagcatga     2040
gctgttcctc gtgtatggca agggccgcc aggcatcatc cggggcatgg atatggggc      2100 caaggtcccg gatgagcaca tgatccccat tgaaaacctc atgaaccccc gagccctgga     2160
cttccacgct gagaccggct tcatctactt tgccgacacc accagctacc tcattggccg     2220
ccagaagatt gatggcactg agcgggagac catcctgaag gacggcatcc acaatgtgga     2280
gggtgtggcc gtgactggaa tgggagacaa tctgtactgg acggacgatg ggcccaaaaa     2340
gacaatcagc gtgccaggc tggagaaagc tgctcagacc cgcaagactt taatcgaggg       2400
caaaatgaca caccccaggg ctattgtggt ggatccactc aatgggtgga tgtactggac     2460
agactgggag gaggacccca aggacagtcg gcgtgggcgg ctggagaggg cgtgatgga      2520 tggctcacac cgagacatct ttgtcacctc caagacagtg cttttggccca atgggctaag     2580 cctggacatc ccggctgggc gcctctactg ggtggatgcc ttctacgacc gcatcgagac     2640
gatactgctc aatggcacag accggaagat tgtgtatgaa ggtcctgagc tgaaccacgc     2700
```

```
ctttggcctg tgtcaccatg gcaactacct cttctggact gagtatcgga gtggcagtgt    2760
ctaccgcttg gaacggggtg taggaggcgc acccccacct gtgacccttc tgcgcagtga    2820 gcggccccc  atctttgaga tccgaatgta tgatgcccag cagcagcaag ttggcaccaa    2880
caaatgccgg gtgaacaatg gcggctgcag cagcctgtgc ttggccaccc ctgggagccg    2940
ccagtgcgcc tgtgctgagg accaggtgtt ggacgcagac ggcgtcactt gcttggcgaa    3000
cccatcctac gtgcctccac cccagtgcca gccaggcgag tttgcctgtg ccaacagccg    3060
ctgcatccag gagcgctgga agtgtgacgg agacaacgat tgcctggaca acagtgatga    3120
ggccccagcc ctctgccatc agcacacctg ccctcggac  cgattcaagt gcagaaacaa    3180
ccggtgcatc cccaaccgct ggctctgcga cggggacaat gactgtggga acagtgaaga    3240
tgagtccaat gccacttgtt cagcccgcac ctgcccccc  aaccagttct cctgtgccag    3300
tggccgctgc atccccatct cctggacgtg tgatctggat gacgactgtg ggaccgctc    3360 tgatgagtct gcttcgtgtg cctatcccac ctgcttcccc ctgactcagt ttacctgcaa    3420
caatggcaga tgtatcaaca tcaactggag atgcgacaat gacaatgact gtggggacaa    3480
cagtgacgaa gccggctgca gccactcctg ttctagcacc cagttcaagt gcaacagcgg    3540
gcgttgcatc cccgagcact ggacctgcga tggggacaat gactgcggag actacagtga    3600
tgagacacac gccaactgca ccaaccaggc cacgaggccc cctggtggct gccacactga    3660
tgagttccag tgccggctgg atggactatg catcccctg  cggtggcgct gcgatgggga    3720
cactgactgc atggactcca gcgatgagaa gagctgtgag ggagtgaccc acgtctgcga    3780
tcccagtgtc aagtttggct gcaaggactc agctcgtgc  atcagcaaag cgtgggtgtg    3840
tgatggcgac aatgactgtg aggataactc ggacgaggag aactgcgagt ccctggcctg    3900
caggccaccc tcgcacccct tgtgccaaca cacctcagtc tgcctgcccc ctgacaagct    3960
gtgtgatggc aacgacgact gtggcgacgg ctcagatgag ggcgagctct gcgaccagtg    4020
ctctctgaat aacggtggct gcagccacaa ctgctcagtg gcacctggcg aaggcattgt    4080
gtgttcctgc cctctgggca tggagctggg gcccgacaac cacacctgcc agatccagag    4140
ctactgtgcc aagcatctca aatgcagcca aaagtgcgac cagaacaagt tcagcgtgaa    4200
gtgctcctgc tacgagggct gggtcctgga acctgacggc gagagctgcc gcagcctgga    4260
ccccttcaag ccgttcatca ttttctccaa ccgccatgaa atccggcgca tcgatcttca    4320
caaaggagac tacagcgtcc tggtgcccgg cctgcgcaac accatcgccc tggacttcca    4380
cctcagccag agcgccctct actgaccga  cgtggtggag gacaagatct accgcgggaa    4440
gctgctggac aacggagccc tgactagttt cgaggtggtg attcagtatg gcctggccac    4500
acccgagggc ctggctgtag actgattgc  aggcaacatc tactgggtgg agagtaacct    4560
ggatcagatc gaggtggcca agctggatgg gaccctccgg accaccctgc tggccggtga    4620
cattgagcac ccaagggcaa tcgcactgga tccccgggat gggatcctgt tttgacaga   4680 ctgggatgcc agcctgcccc gcattgaggc agcctccatg agtggggctg gcgccgcac   4740 cgtgcaccgg gagaccggct ctgggggctg gcccaacggg ctcaccgtgg actacctgga   4800
gaagcgcatc ctttgattg  acgccaggtc agatgccatt tactcagccc gttacgacgg   4860
ctctggccac atggaggtgc ttcggggaca cgagttcctg tcgcacccgt ttgcagtgac   4920
gctgtacggg gggaggtct  actgactga  ctggcgaaca aacacactgg ctaaggccaa   4980
caagtggacc ggccacaatg tcaccgtggt acagaggacc aacacccagc cctttgacct   5040
gcaggtgtac cacccctccc gccagcccat ggctcccaat ccctgtgagg ccaatggggg   5100
```

```
ccagggcccc tgctcccacc tgtgtctcat caactacaac cggaccgtgt cctgcgcctg    5160
cccccacctc atgaagctcc acaaggacaa caccacctgc tatgagttta agaagttcct    5220
gctgtacgca cgtcagatgg agatccgagg tgtggacctg gatgctccct actacaacta    5280
catcatctcc ttcacggtgc ccgacatcga caacgtcaca gtgctagact acgatgcccg    5340
cgagcagcgt gtgtactggt ctgacgtgcg gacacaggcc atcaagcggg ccttcatcaa    5400
cggcacaggc gtggagacag tcgtctctgc agacttgcca aatgcccacg gctggctgt    5460 ggactgggtc tcccgaaacc tgttctggac aagctatgac accaataaga agcagatcaa    5520
tgtggcccgg ctggatggct ccttcaagaa cgcagtggtg cagggcctgg agcagcccca    5580
tggccttgtc gtccacccctc tgcgtgggaa gctctactgg accgatggtg acaacatcag    5640
catggccaac atggatggca gcaatcgcac cctgctcttc agtggccaga agggccccgt    5700
gggcctggct attgacttcc ctgaaagcaa actctactgg atcagctccg ggaaccatac    5760
catcaaccgc tgcaacctgg atgggagtgg gctggaggtc atcgatgcca tgcggagcca    5820
gctgggcaag gccaccgccc tggccatcat gggggacaag ctgtggtggg ctgatcaggt    5880
gtcggaaaag atgggcacat gcagcaaggc tgacggctcg ggctccgtgg tccttcggaa    5940
cagcaccacc ctggtgatgc acatgaaggt ctatgacgag agcatccagc tggaccataa    6000
gggcaccaac ccctgcagtg tcaacaacgg tgactgctcc cagctctgcc tgcccacgtc    6060
agagacgacc cgctcctgca tgtgcacagc cggctatagc ctccggagtg ccagcaggc    6120 ctgcgagggc gtaggttcct ttctcctgta ctctgtgcat gagggaatca ggggaattcc    6180
cctggatccc aatgacaagt cagatgccct ggtcccagtg tccgggacct cgctggctgt    6240
cggcatcgac ttccacgctg aaaatgacac catctactgg gtggacatgg gcctgagcac    6300
gatcagccgg gccaagcggg accagacgtg gcgtgaagac gtggtgacca atggcattgg    6360
ccgtgtggag ggcattgcag tggactggat cgcaggcaac atctactgga cagaccaggg    6420 cttttgatgtc atcgaggtcg cccggctcaa tggctccttc cgctacgtgg tgatctccca    6480
gggtctagac aagcccgggg ccatcaccgt ccacccggag aaagggtact tgttctggac    6540
tgagtggggt cagtatccgc gtattgagcg gtctcggcta gatggcacgg agcgtgtggt    6600
gctggtcaac gtcagcatca gctggcccaa cggcatctca gtggactacc aggatgggaa    6660
gctgtactgg tgcgatgcac ggacagacaa gattgaacgg atcgacctgg agacaggtga    6720
gaaccgcgag gtggttctgt ccagcaacaa catggacatg ttttcagtgt ctgtgtttga    6780 ggattttcatc tactggagtg acaggactca tgccaacgc tctatcaagc gcgggagcaa    6840
agacaatgcc acagactccg tgcccctgcg aaccggcatc ggcgtccagc ttaaagacat    6900
caaagtcttc aaccgggacc ggcagaaagg caccaacgtg tgcgcggtgg ccaatggcgg    6960
gtgccagcag ctgtgcctgt accggggccg tgggcagcgg gcctgcgcct gtgcccacgg    7020
gatgctggct gaagacggag catcgtgccg cgagtatgcc ggctacctgc tctactcaga    7080
gcgcaccatt ctcaagagta tccacctgtc ggatgagcgc aacctcaatg cgcccgtgca    7140
gcccttcgag gaccctgagc acatgaagaa cgtcatcgcc ctggcctttg actaccgggc    7200
aggcacctct ccgggcaccc ccaatcgcat cttcttcagc gacatccact ttgggaacat    7260
ccaacagatc aacgacgatg gctccaggag gatcaccatt gtggaaaacg tgggctccgt    7320
ggaaggcctg gcctatcacc gtggctggga cactctctat tggacaagct acacgacatc    7380
caccatcacg cgccacacag tggaccagac ccgcccaggg gccttcgagc gtgagaccgt    7440
```

```
catcactatg tctggagatg accacccacg ggccttcgtt ttggacgagt gccagaacct   7500
catgttctgg accaactgga atgagcagca tcccagcatc atgcgggcgg cgctctcggg   7560
agccaatgtc ctgacccta tcgagaagga catccgtacc cccaatggcc tggccatcga   7620
ccaccgtgcc gagaagctct acttctctga cgccaccctg gacaagatcg agcggtgcga   7680
gtatgacggc tcccaccgct atgtgatcct aaagtcagag cctgtccacc ccttcgggct   7740
ggccgtgtat ggggagcaca ttttctggac tgactgggtg cggcgggcag tgcagcgggc   7800
caacaagcac gtgggcagca acatgaagct gctgcgcgtg gacatccccc agcagcccat   7860
gggcatcatc gccgtggcca acgacaccaa cagctgtgaa ctctctccat gccgaatcaa   7920
caacggtggc tgccaggacc tgtgtctgct cactcaccag ggccatgtca actgctcatg   7980 ccgaggggc cgaatcctcc aggatgacct cacctgccga gcggtgaatt cctcttgccg   8040
agcacaagat gagtttgagt gtgccaatgg cgagtgcatc aacttcagcc tgacctgcga   8100
cggcgtcccc cactgcaagg acaagtccga tgagaagcca tcctactgca actcccgccg   8160
ctgcaagaag actttccggc agtgcagcaa tgggcgctgt gtgtccaaca tgctgtggtg   8220
caacggggcc gacgactgtg gggatggctc tgacgagatc ccttgcaaca agacagcctg   8280
tggtgtgggc gagttccgct gccgggacgg gacctgcatc gggaactcca gccgctgcaa   8340
ccagtttgtg gattgtgagg acgcctcaga tgagatgaac tgcagtgcca ccgactgcag   8400
cagctacttc cgcctgggcg tgaagggcgt gctcttccag ccctgcgagc ggacctcact   8460
ctgctacgca cccagctggg tgtgtgatgg cgccaatgac tgtggggact acagtgatga   8520
gcgcgactgc ccaggtgtga aacgccccag atgccctctg aattacttcg cctgccctag   8580
tgggcgctgc atccccatga gctggacgtg tgacaaagag gatgactgtg aacatggcga   8640
ggacgagacc cactgcaaca gttctgctc agaggcccag tttgagtgcc agaaccatcg   8700
ctgcatctcc aagcagtggc tgtgtgacgg cagcgatgac tgtggggatg gctcagacga   8760
ggctgctcac tgtgaaggca agacgtgcgg cccctcctcc ttctcctgcc ctggcacccca   8820 cgtgtgcgtc cccgagcgct ggctctgtga cggtgacaaa gactgtgctg atggtgcaga   8880
cgagagcatc gcagctggtt gcttgtacaa cagcacttgt gacgaccgtg agttcatgtg   8940
ccagaaccgc cagtgcatcc ccaagcactt cgtgtgtgac cacgaccgtg actgtgcaga   9000
tggctctgat gagtcccccg agtgtgagta cccgacctgc ggcccagtg agttccgctg   9060 tgccaatggg cgctgtctga gctccgcca gtgggagtgt gatggcgaga tgactgcca   9120 cgaccagagt gacgaggctc ccaagaaccc acactgcacc agccaagagc acaagtgcaa   9180
tgcctcgtca cagttcctgt gcagcagtgg gcgctgtgtg gctgaggcac tgctctgcaa   9240
cggccaggat gactgtggcg acagctcgga cgagcgtggc tgccacatca atgagtgtct   9300
cagccgcaag ctcagtggct gcagccagga ctgtgaggac ctcaagatcg gcttcaagtg   9360
ccgctgtcgc cctggcttcc ggctgaagga cgacggccgg acgtgtgctg atgtggacga   9420
gtgcagcacc accttcccct gcagccagcg ctgcatcaac actcatggca gctataagtg   9480
tctgtgtgtg gagggctatg caccccgcgg cggcgacccc cacagctgca aggctgtgac   9540
tgacgaggaa ccgtttctga tcttcgccaa ccggtactac ctgcgcaagc tcaacctgga   9600
cgggtccaac tacacgttac ttaagcaggg cctgaacaac gccgttgcct ggattttga   9660 ctaccgagag cagatgatct actggacaga tgtgaccacc caggcagca tgatccgaag   9720 gatgcacctt aacggagca atgtgcaggt cctacaccgt acaggcctca gcaacccga   9780 tgggctggct gtggactggg tgggtggcaa cctgtactgg tgcgacaaag gccgggacac   9840
```

```
catcgaggtg tccaagctca atggggccta tcggacggtg ctggtcagct ctggcctccg    9900
tgagcccagg gctctggtgg tggatgtgca gaatgggtac ctgtactgga cagactgggg    9960
tgaccattca ctgatcggcc gcatcggcat ggatgggtcc agccgcagcg tcatcgtgga   10020
caccaagatc acatggccca atggcctgac gctggactat gtcactgagc gcatctactg   10080
ggccgacgcc cgcgaggact acattgaatt tgccagcctg gatggctcca atcgccacgt   10140
tgtgctgagc caggacatcc cgcacatctt tgcactgacc ctgtttgagg actacgtcta   10200
ctggaccgac tgggaaacaa agtccattaa ccgagcccac aagaccacgg caccaacaa    10260
aacgctcctc atcagcacgc tgcaccggcc catggacctg catgtcttcc atgccctgcg   10320
ccagccagac gtgcccaatc acccctgcaa ggtcaacaat ggtggctgca gcaacctgtg   10380
cctgctgtcc cccgggggag ggcacaaatg tgcctgcccc accaacttct acctgggcag   10440
cgatgggcgc acctgtgtgt ccaactgcac ggctagccag tttgtatgca agaacgacaa   10500
gtgcatcccc ttctggtgga agtgtgacac cgaggacgac tgcggggacc actcagacga   10560
gcccccggac tgccctgagt tcaagtgccg gcccggacag ttccagtgct ccacaggtat   10620
ctgcacaaac cctgccttca tctgcgatgg cgacaatgac tgccaggaca cagtgacga    10680
ggccaactgt gacatccacg tctgcttgcc cagtcagttc aaatgcacca acaccaaccg   10740
ctgtattccc ggcatcttcc gctgcaatgg gcaggacaac tgcggagatg ggaggatga    10800
gagggactgc cccgaggtga cctgcgcccc caaccagttc cagtgctcca ttaccaaacg   10860
gtgcatcccc cgggtctggg tctgcgaccg ggacaatgac tgtgtggatg gcagtgatga   10920
gcccgccaac tgcacccaga tgacctgtgg tgtggacgag ttccgctgca aggattcggg   10980
ccgctgcatc ccagcgcgtt ggaagtgtga cggagaggat gactgtgggg atggctcgga   11040
tgagcccaag gaagagtgtg atgaacgcac ctgtgagcca taccagttcc gctgcaagaa   11100
caaccgctgc gtgcccggcc gctggcagtg cgactacgac aacgattgcg gtgacaactc   11160
cgatgaagag agctgcaccc ctcggccctg ctccgagagt gagttctcct gtgccaacgg   11220
ccgctgcatc gcggggcgct ggaaatgcga tggagaccac gactgcgcgg acggctcgga   11280
cgagaaagac tgcacccccc gctgtgacat ggaccagttc cagtgcaaga gcggccactg   11340
catcccctg cgctggcgct gtgacgcaga cgccgactgc atggacggca gcgacgagga   11400
ggcctgcggc actggcgtgc ggacctgccc cctggacgag ttccagtgca acaacaccett   11460
gtgcaagccg ctggcctgga gtgcgatgg cgaggatgac tgtgggggaca actcagatga   11520
gaaccccgag gagtgtgccc ggttcgtgtg ccctcccaac cggcccttcc gttgcaagaa   11580
tgaccgcgtc tgtctgtgga tcgggcgcca atgcgatggc acggacaact gtgggggatgg   11640
gactgatgaa gaggactgtg agccccccac agcccacacc ccccactgca aagacaagaa   11700
ggagtttctg tgccggaacc agcgctgcct ctcctcctcc ctgcgctgca acatgttcga   11760
tgactgcggg gacggctctg acgaggagga ctgcagcatc gaccccaagc tgaccagctg   11820
cgccaccaat gccagcatct gtggggacga ggcacgctgc gtgcgcaccg agaaagcggc   11880
ctactgtgcc tgccgctcgg gcttccacac cgtgcccggc cagcccggat gccaagacat   11940
caacgagtgc ctgcgcttcg gcacctgctc ccagctctgc aacaacacca agggcggcca   12000
cctctgcagc tgcgctcgga acttcatgaa gacgcacaac acctgcaagg ccgaaggctc   12060
tgagtaccag gtcctgtaca tcgctgatga caatgagatc cgcagcctgt tcccggcca    12120
ccccattcg gcttacgagc aggcattcca gggtgacgag agtgtccgca ttgatgctat    12180
```

```
ggatgtccat gtcaaggctg gccgtgtcta ttggaccaac tggcacacgg gcaccatctc   12240
ctaccgcagc ctgccacctg ctgcgcctcc taccacttcc aaccgccacc ggcgacagat   12300
tgaccggggt gtcacccacc tcaacatttc agggctgaag atgcccagag gcatcgccat   12360
cgactgggtg gccggaaacg tgtactggac cgactcgggc cgagatgtga ttgaggtggc   12420
gcagatgaag ggcgagaacc gcaagacgct catctcgggc atgattgacg agccccacgc   12480
cattgtggtg gacccactga gggggaccat gtactggtca gactggggca accacccccaa  12540 gattgagacg gcagcgatgg atgggacgct tcgggagaca ctggtgcagg acaacattca   12600
gtggcccaca ggcctggccg tggattatca caatgagcgg ctgtactggg cagacgccaa   12660
gctttcagtc atcggcagca tccggctcaa tggcacggac cccattgtgg ctgctgacag   12720
caaacgaggc ctaagtcacc ccttcagcat cgacgtcttt gaggattaca tctatggtgt   12780
cacctacatc aataatcgtg tcttcaagat ccataagttt ggccacagcc ccttggtcaa   12840
cctgacaggg ggcctgagcc acgcctctga cgtggtcctt taccatcagc acaagcagcc   12900
cgaagtgacc aacccatgtg accgcaagaa atgcgagtgg ctctgcctgc tgagccccag   12960
tgggcctgtc tgcacctgtc ccaatgggaa gcggctggac aacggcacat gcgtgcctgt   13020
gccctctcca acgccccccc cagatgctcc ccggcctgga acctgtaacc tgcagtgctt   13080
caacggtggc agctgtttcc tcaatgcacg gaggcagccc aagtgccgct gccaaccccg   13140
ctacacgggt gacaagtgtg aactggacca gtgctgggag cactgtcgca atgggggcac   13200
ctgtgctgcc tcccctctg gcatgcccac gtgccggtgc cccacgggct tcacgggccc   13260
caaatgcacc cagcaggtgt gtgcgggcta ctgtgccaac aacagcacct gcactgtcaa   13320
ccagggcaac cagccccagt gccgatgcct accggcttc ctgggcgacc gctgccagta   13380
ccggcagtgc tctggctact gtgagaactt tggcacatgc cagatggctg ctgatggctc   13440
ccgacaatgc cgctgcactg cctactttga gggatcgagg tgtgaggtga acaagtgcag   13500
ccgctgtctc gaaggggcct gtgtggtcaa caagcagagt ggggatgtca cctgcaactg   13560
cacggatggc cgggtggccc ccagctgtct gacctgcgtc ggccactgca gcaatggcgg   13620
ctcctgtacc atgaacagca aaatgatgcc tgagtgccag tgcccacccc acatgacagg   13680
gccccggtgt gaggagcacg tcttcagcca gcagcagcca ggacatatag cctccatcct   13740
aatccctctg ctgttgctgc tgctgctggt tctggtggcc ggagtggtat tctggtataa   13800
gcggcgagtc caaggggcta agggcttcca gcaccaacgg atgaccaacg gggccatgaa   13860
cgtggagatt ggaaacccca cctacaagat gtacgaaggc ggagagcctg atgatgtggg   13920
aggcctactg gacgctgact ttgccctgga ccctgacaag cccaccaact tcaccaaccc   13980
cgtgtatgcc acactctaca tggggggcca tggcagtcgc cactccctgg ccagcacgga   14040
cgagaagcga gaactcctgg gccggggccc tgaggacgag atagggggacc ccttggcata   14100 gggccctgcc ccgtcggact gccccagaa agcctcctgc ccctgccgg tgaagtcctt   14160 cagtgagccc ctccccagcc agcccttccc tggccccgcc ggatgtataa atgtaaaaat   14220
gaaggaatta cattttatat gtgagcgagc aagccggcaa gcgagcacag tattatttct   14280
ccatcccctc cctgcctgct ccttggcacc cccatgctgc cttcagggag acaggcaggg   14340
agggcttggg gctgcacctc ctaccctccc accagaacgc accccactgg gagagctggt   14400
ggtgcagcct tccctcccct gtataagaca ctttgccaag gctctcccct ctcgccccat   14460
ccctgcttgc ccgctcccac agcttcctga gggctaattc tgggaaggga gagttctttg   14520
ctgcccctgt ctggaagacg tggctctggg tgaggtaggc gggaaaggat ggagtgtttt   14580
```

```
agttcttggg ggaggccacc ccaaacccca gccccaactc caggggcacc tatgagatgg      14640
ccatgctcaa ccccccctccc agacaggccc tccctgtctc cagggccccc accgaggttc      14700
ccagggctgg agacttcctc tggtaaacat tcctccagcc tcccctcccc tggggacgcc      14760
aaggaggtgg gccacaccca ggaagggaaa gcgggcagcc ccgttttggg gacgtgaacg      14820
ttttaataat ttttgctgaa ttcctttaca actaaataac acagatattg ttataaataa      14880
aattgtaaaa aaaaaaaaaa aaaaa                                            14905
```

<210> SEQ ID NO 4
<211> LENGTH: 14907
<212> TYPE: DNA
<213> ORGANISM: Mus musculus
<300> PUBLICATION INFORMATION:
<308> DATABASE ACCESSION NUMBER: NM_008512.2
<309> DATABASE ENTRY DATE: 2010-05-16
<313> RELEVANT RESIDUES IN SEQ ID NO: (1)..(14907)

<400> SEQUENCE: 4

```
agtcagggga gcagcggtgc gagctccagg ccagtgcact gaggaggcgg aaacggggga        60 gccccctagtg ctccatcagg cccctaccaa ggcaccccca tcgggtccac gccccccacc      120
ccccaccccg cctcctccca attgtgcatt tttgcagcca gaggcggctc cgagatgggg      180
ctgtgagctt cgccctggga gggggagagg agcgaggagt aaagcagggg tgaagggttc      240
gaatttgggg gcaggggggcg caccgcgtc agcaggccct tcccaggggg ctcggaactg      300
taccatttca cctatgcccc tggttcgctt tgcttaagga aaggataaga atagaagagt      360
cggggagagg aagataaagg gggacccccc aattgggggg ggcgaggaca agaagtaaca      420
ggaccagagg gtgggggctg ctgtttgcat cggcccacac catgctgacc ccgccgttgc      480
tgctgctgct gccgctgctt tcagctctgg tctccggggc cactatggat gcccctaaaa      540
cttgcagccc taagcagttt gcctgcagag accaaatcac ctgtatctca aagggctggc      600
ggtgtgacgg tgaaagagat tgccccgacg gctctgatga agcccctgag atctgtccac      660
agagtaaagc ccagagatgc ccgccaaatg agcacagttg tctggggact gagctatgtg      720
tccccatgtc tcgtctctgc aacgggatcc aggactgcat ggatggctca gacgagggtg      780
ctcactgccg agagctccga gccaactgtt ctcgaatggg ttgtcaacac cattgtgtac      840
ctacacccag tgggcccacg tgctactgta acagcagctt ccagctgcag gcagatggca      900
agacgtgcaa agattttgac gagtgttccg tgtatggcac ctgcagccag ctttgcacca      960
acacagatgg ctccttcaca tgtggctgtg ttgaaggcta cctgctgcaa ccggacaacc     1020
gctcctgcaa ggccaagaat gagccagtag atcggccgcc agtgctactg attgccaact     1080
ctcagaacat cctagctacg tacctgagtg gggcccaagt gtctaccatc acacccacca     1140
gcacccgaca aaccacggcc atggacttca gttatgccaa tgagaccgta tgctgggtgc     1200
acgttgggga cagtgctgcc cagacacagc tcaagtgtgc ccggatgcct ggcctgaagg     1260
gctttgtgga tgagcatacc atcaacatct ccctcagcct gcaccacgtg agcagatgg     1320 caatcgactg gctgacggga aacttctact ttgtcgacga cattgacgac aggatctttg     1380
tctgtaaccg aaacggggac acctgtgtca ctctgctgga cctggaactc tacaacccca     1440
aaggcatcgc cttggacccc gccatgggga aggtgttctt cactgactac gggcagatcc     1500
caaaggtgga gcgctgtgac atggatggac agaaccgcac caagctggtg gatagcaaga     1560
tcgtgtttcc acacgggcatc accctggacc tggtcagccg cctcgtctac tgggcggacg     1620
```

```
cctacctaga ctacatcgag gtggtagact acgaagggaa gggtcggcag accatcatcc    1680
aaggcatcct gatcgagcac ctgtacggcc tgaccgtgtt tgagaactat ctctacgcca    1740
ccaactcgga caatgccaac acgcagcaga agacgagcgt gatccgagtg aaccggttca    1800
acagtactga gtaccaggtc gtcacccgtg tggacaaggg tggtgccctg catatctacc    1860
accagcgacg ccagccccga gtgcggagtc acgcctgtga gaatgaccag tacgggaagc    1920
caggtggctg ctccgacatc tgcctcctgg ccaacagtca caaggcaagg acctgcaggt    1980
gcaggtctgg cttcagcctg ggaagtgatg ggaagtcttg taagaaacct gaacatgagc    2040
tgttcctcgt gtatggcaag ggccgaccag gcatcattag aggcatggac atgggggcca    2100
aggtcccaga tgagcacatg atccccatcg agaaccttat gaatccacgc gctctggact    2160
tccacgccga gaccggcttc atctactttg ctgacaccac cagctacctc attggccgcc    2220
agaaaattga tggcacggag agagagacta tcctgaagga tggcatccac aatgtggagg    2280
gcgtagccgt ggactggatg ggagacaatc tttactggac tgatgatggc cccaagaaga    2340
ccattagtgt ggccaggctg gagaaagccg ctcagacccg gaagactcta attgagggca    2400
agatgacaca ccccagggcc attgtagtgg atccactcaa tgggtggatg tactggacag    2460
actgggagga ggaccccaag gacagtcggc gagggcggct cgagagggct tggatggacg    2520
gctcacaccg agatatcttt gtcacctcca agacagtgct ttggcccaat gggctaagcc    2580
tggatatccc agccggacgc ctctactggg tggatgcctt ctatgaccga attgagacca    2640
tactgctcaa tggcacagac cggaagattg tatatgaggg tcctgaactg aatcatgcct    2700
tcggcctgtg tcaccatggc aactacctct tttggaccga gtaccggagc ggcagcgtct    2760
accgcttgga acggggcgtg gcaggcgcac cgcccactgt gacccttctg cgcagcgaga    2820
gaccgcctat ctttgagatc cgaatgtacg acgcgcagca gcagcaagtg ggtaccaaca    2880
aatgccgggt aaataacgga ggctgcagca gcctgtgcct cgccaccccc gggagccgcc    2940
agtgtgcctg tgccgaggac caggtgttgg acacagatgg tgtcacctgc ttggcgaacc    3000
catcctacgt gcccccaccc cagtgccagc cgggcgagtt tgcctgtgcc aacaaccgct    3060
gcatccagga gcgctggaag tgtgacggag acaacgactg tctggacaac agcgatgagg    3120
ccccagcact gtgccatcaa cacacctgtc cctcggaccg attcaagtgt gagaacaacc    3180
ggtgtatccc caaccgctgg ctctgtgatg gggataatga ttgtggcaac agcgaggacg    3240
aatccaatgc cacgtgctca gcccgcacct gtccacccaa ccagttctcc tgtgccagtg    3300
gccgatgcat tcctatctca tggacctgtg atctggatga tgactgtggg gaccggtccg    3360
atgagtcagc ctcatgcgcc tacccacct gcttccccct gactcaattt acctgcaaca    3420
atggcagatg tattaacatc aactggcggt gtgacaacga caatgactgt ggggacaaca    3480
gcgacgaagc cggctgcagt cactcctgct ccagtaccca gttcaagtgc aacagtggca    3540
gatgcatccc cgagcactgg acgtgtgatg ggacaatga ttgtggggac tacagcgacg    3600
agacacacgc caactgtacc aaccaggcta caagacctcc tggtggctgc cactcggatg    3660
agttccagtg ccgcctagat ggcctgtgca tcccctgag gtggcgctgc gacggggaca    3720
ccgactgcat ggattccagc gatgagaaga gctgtgaggg cgtgacccat gtttgtgacc    3780
cgaatgtcaa gtttggctgc aaggactccg cccggtgcat cagcaaggcg tgggtgtgtg    3840
atggcgacag cgactgtgaa gataactccg acgaggagaa ctgtgaggcc ctggcctgca    3900
ggccaccctc ccatccctgc gccaacaaca cctctgtctg cctgcctcct gacaagctgt    3960
gcgacggcaa ggatgactgt ggagacggct cggatgaggg cgagctctgt gaccagtgtt    4020
```

```
ctctgaataa tggtggctgt agtcacaact gctcagtggc ccctggtgaa ggcatcgtgt    4080
gctcttgccc tctgggcatg gagctgggct ctgacaacca cacctgccag atccagagct    4140
actgtgccaa gcacctcaaa tgcagccaga agtgtgacca gaacaagttc agtgtgaagt    4200
gctcctgcta cgagggctgg gtcttggagc ctgacgggga agctgccgc agtctggatc     4260
ccttcaaacc gttcatcatc ttctccaacc gccacgagat caggcgcatt gaccttcaca    4320
aggggacta cagcgtccta gtgcctggcc tgcgcaacac tattgccctg gacttccacc    4380
tcagccagag tgccctctac tggaccgacg tggtagagga caagatctac cgtgggaaac    4440
tcctggacaa cggagccctg accagctttg aggtggtgat tcagtatggc ttggccacac    4500
cagagggcct ggctgtagat tggattgcag gcaacatcta ctgggtggag agcaacctgg    4560
accagatcga agtggccaag ctggacggaa ccctccgaac cactctgctg gcgggtgaca    4620
ttgagcaccc gagggccatc gctctggacc ctcgggatgg gattctgttt tggacagact    4680
gggatgccag cctgccacga atcgaggctg cgtccatgag tggggctggc cgccgaacca    4740
tccaccggga gacaggctct gggggctggc ccaacgggct caccgtggat tacctggaga    4800
agcgcatcct ctggattgat gctaggtcag atgccatcta ttcagcccgg tatgacggct    4860
ccggccacat ggaggtgctt cggggacacg agttcctgtc acacccattt gccgtgacac    4920
tgtacggtgg ggaggtgtac tggaccgact ggcgaacaaa tacactggct aaggccaaca    4980
agtggactgg ccacaacgtc accgtggtac agaggaccaa cacccagccc ttcgacctgc    5040
aggtgtatca cccttcccgg cagcccatgg ctccaaaccc atgtgaggcc aatggcggcc    5100
ggggcccctg ttcccatctg tgcctcatca actacaaccg gaccgtctcc tgcgcctgtc    5160
cccacctcat gaagctgcac aaggacaaca ccacctgcta tgagtttaag aagttcctgc    5220
tgtacgcacg tcagatggag atccggggcg tggacctgga tgccccgtac tacaattata    5280
tcatctcctt cacggtgcct gatatcgaca atgtcacggt gctggactat gatgcccgag    5340
agcagcgagt ttactggtct gatgtgcgga ctcaagccat caaaagggca tttatcaacg    5400
gcactggcgt ggagaccgtt gtctctgcag acttgcccaa cgcccacggg ctggctgtgg    5460
actgggtctc ccgaaatctg ttttggacaa gttacgacac caacaagaag cagattaacg    5520
tggcccggct ggacggctcc ttcaagaatg cggtggtgca gggcctggag cagccccacg    5580
gcctggtcgt ccacccgctt cgtggcaagc tctactggac tgatgggggac aacatcagca    5640
tggccaacat ggatgggagc aaccacactc tgctcttcag tggccagaag ggccctgtgg    5700
ggttggccat tgacttccct gagagcaaac tctactggat cagctctggg aaccacacaa    5760
tcaaccgttg caatctggat gggagcgagc tggaggtcat cgacaccatg cggagccagc    5820
tgggcaaggc cactgccctg ccatcatggg ggacaagct gtggtgggca gatcaggtgt    5880
cagagaagat gggcacgtgc aacaaagccg atggctctgg gtccgtggtg ctgcggaaca    5940
gtaccacgtt ggttatgcac atgaaggtgt atgacgagag catccagcta gagcatgagg    6000
gcaccaaccc ctgcagtgtc aacaacggag actgttccca gctctgcctg ccaacatcag    6060
agacgactcg ctcctgtatg tgtacagccg gttacagcct ccggagcgga cagcaggcct    6120
gtgagggtgt gggctctttt ctcctgtact ctgtacatga gggaattcgg gggattccac    6180
tagatcccaa tgacaagtcg gatgccctgg tcccagtgtc cggaacttca ctggctgtcg    6240
gaatcgactt ccatgccgaa aatgacacta tttattgggt ggatatgggc ctaagcacca    6300
tcagcagggc caagcgtgac cagacatggc gagaggatgt ggtgaccaac ggtattggcc    6360
```

```
gtgtggaggg catcgcggtg gactggatcg caggcaacat atactggacg gaccagggct    6420
tcgatgtcat cgaggttgcc cggctcaatg gctcttttcg ttatgtggtc atttcccagg    6480
gtctggacaa gcctcgggcc atcactgtcc acccagagaa ggggtacttg ttctggaccg    6540
agtggggtca ttacccacgt attgagcggt ctcgccttga tggcacagag agagtggtgt    6600
tggttaatgt cagcatcagc tggcccaatg gcatctcagt agactatcag ggcggcaagc    6660
tctactggtg tgatgctcgg atggacaaga tcgagcgcat cgacctggaa acgggcgaga    6720
accgggaggt ggtcctgtcc agcaataaca tggatatgtt ctccgtgtcc gtgtttgagg    6780
acttcatcta ctggagtgac agaactcacg ccaatggctc catcaagcgc ggctgcaaag    6840
acaatgctac agactccgtg cctctgagga caggcattgg tgttcagctt aaagacatca    6900
aggtcttcaa cagggacagg cagaagggta ccaatgtgtg cgcggtagcc aacgcgggt     6960 gccagcagct ctgcttgtat cggggtggcg acagcgagc ctgtgcctgt cccacggga     7020 tgctggcaga agacggggcc tcatgccgag agtacgctgg ctacctgctc tactcagagc    7080
ggaccatcct caagagcatc cacctgtcgg atgagcgtaa cctcaacgca ccggtgcagc    7140
cctttgaaga ccccgagcac atgaaaaatg tcatcgccct ggcctttgac taccgagcag    7200
gcacctcccc ggggacccct aaccgcatct tcttcagtga catccacttt gggaacatcc    7260
agcagatcaa tgacgatggc tcgggcagga ccaccatcgt ggaaaatgtg ggctctgtgg    7320
aaggcctggc ctatcaccgt ggctgggaca cactgtactg gacaagctac accacatcca    7380
ccatcacccg ccacaccgtg gaccagactc gcccaggggc cttcgagagg gagacagtca    7440
tcaccatgtc cggagacgac cacccgagag cctttgtgct ggatgagtgc cagaacctga    7500
tgttctggac caattggaac gagctccatc caagcatcat gcgggcagcc ctatccggag    7560
ccaacgtcct gaccctcatt gagaaggaca tccgcacgcc caatgggttg gccatcgacc    7620
accgggcgga gaagctgtac ttctcggatg ccaccttgga caagatcgag cgctgcgagt    7680
acgacggctc ccaccgctat gtgatcctaa agtcggagcc cgtccacccc tttgggttgg    7740
cggtgtacgg agagcacatt ttctggactg actgggtgcg gcgggctgtg cagcgagcca    7800
acaagtatgt gggcagcgac atgaagctgc ttcgggtgga cattcccag caacccatgg     7860 gcatcatcgc cgtggccaac gacaccaaca gctgtgaact ctccccctgc cgtatcaaca    7920
atggaggctg ccaggatctg tgtctgctca cccaccaagg ccacgtcaac tgttcctgtc    7980
gagggggccg gatcctccag gaggacttca cctgccgggc tgtgaactcc tcttgtcggg    8040
cacaagatga gtttgagtgt gccaatgggg aatgtatcag cttcagcctc acctgtgatg    8100
gcgtctccca ctgcaaggac aagtccgatg agaagccctc ctactgcaac tcacgccgct    8160
gcaagaagac tttccgccag tgtaacaatg gtcgctgtgt atccaacatg ctgtggtgca    8220 atgggcgtgga tgactgtggg gatggctctg atgagattcc ttgcaacaag actgcctgtg    8280
gtgtgggtga ttccgctgcc gggatgggt cctgcatcgg gaactccagt cgctgcaacc      8340
agtttgtgga ttgtgaggat gcctcggatg agatgaattg cagtaccaca gactgcagca    8400
gctatttccg cctgggcgtg aaaggtgtcc tcttccagcc gtgcgagcgg acatccctgt    8460
gctacgcacc tagctgggtg tgtgatgcg ccaacgactg tggagactac agcgatgaac      8520
gtgactgtcc aggtgtgaag cgccctaggt gcccgctcaa ttacttttgcc tgccccagcg    8580 ggcgctgtat ccccatgagc tggacgtgtg acaaggagga tgactgtgag aacggcgagg    8640
acgagaccca ctgcaacaag ttctgctcag aggcacagtt cgagtgccag aaccaccggt    8700
gtatctccaa gcagtggctg tgtgacggta gcgatgattg cggggatggc tccgatgagg    8760
```

```
cagctcactg tgaaggcaag acatgtggcc cctcctcctt ctcctgtccc ggcacccacg    8820
tgtgtgtccc tgagcgctgg ctctgtgatg gcgacaagga ctgtaccgat ggcgcggatg    8880
agagtgtcac tgctggctgc ctgtacaaca gcacctgtga tgaccgtgag ttcatgtgcc    8940
agaaccgctt gtgtattccc aagcatttcg tgtgcgacca tgaccgtgac tgtgctgatg    9000
gctctgatga atcccctgag tgtgagtacc caacctgcgg ccccaatgaa ttccgctgtg    9060
ccaatgggcg ttgtctgagc tcccgtcagt gggaatgtga tggggagaat gactgtcacg    9120
accacagcga tgaggctccc aagaacccac actgcaccag cccagagcac aaatgcaatg    9180
cctcatcaca gttcctgtgc agcagcgggc gctgcgtggc tgaggcgttg ctctgcaacg    9240
gccaggacga ctgtggggac ggttcagacg aacgcgggtg ccatgtcaac gagtgtctca    9300
gccgcaagct cagtggctgc agtcaggact gcgaggacct caagataggc tttaagtgcc    9360
gctgtcgccc gggcttccgg ctaaaggacg atggcaggac ctgtgccgac ctggatgagt    9420
gcagcaccac cttcccctgc agccagctct gcatcaacac ccacggaagt tacaagtgtc    9480
tgtgtgtgga gggctatgca ccccgtggcg gtgaccccca cagctgcaaa gctgtgaccg    9540
atgaggagcc atttctcatc tttgccaacc ggtactacct gcggaagctc aacctggacg    9600
gctccaacta cacactgctt aagcagggcc tgaacaatgc ggtcgccttg gactttgact    9660
accgagagca gatgatctac tggacggacg tgaccaccca gggcagcatg attcgcagga    9720
tgcacctcaa cggcagcaac gtgcaggttc tgcaccggac gggccttagt aacccagatg    9780
ggctggctgt ggactgggtg ggtggcaacc tgtactggtg tgacaagggc agagatacca    9840
ttgaggtgtc caagcttaac ggggcctatc ggacagtgct ggtcagctct ggcctccggg    9900
agcccagagc tctggtagtg gatgtacaga atgggtacct gtactggaca gactggggtg    9960
accactcact gatcggccgg attggcatgg atggatctgg ccgcagcatc atcgtggaca   10020
ctaagatcac atggcccaat ggcctgaccg tggactacgt cacggaacgc atctactggg   10080
ctgacgcccg tgaggactac atcgagttcg ccagcctgga tggctccaac cgtcacgttg   10140
tgctgagcca agacatccca cacatctttg cgctgaccct atttgaagac tacgtctact   10200
ggacagactg ggaaacgaag tccatcaacc gggcccacaa gaccacgggt gccaacaaaa   10260
cactcctcat cagcacccta caccggccca tggacttaca tgtattccac gccctgcgcc   10320
agccagatgt gcccaatcac ccctgcaaag tcaacaatgg tggctgcagc aacctgtgcc   10380
tgctgtcccc tgggggtggt cataaatgcg cctgccccac caacttctat ctgggtggcg   10440
atggccgtac ctgtgtgtcc aactgcacag caagccagtt tgtgtgcaaa aatgacaagt   10500
gcatcccctt ctggtggaag tgtgacacgg aggacgactg tggggatcac tcagacgagc   10560
ctccagactg tccgagttc aagtgccgcc caggccagtt ccagtgctcc accggcatct   10620
gcaccaaccc tgccttcatc tgtgatgggg acaatgactg ccaagacaat agtgatgagg   10680
ccaattgcga cattcacgtc tgcttgccca gccaattcaa gtgcaccaac accaaccgct   10740
gcattcctgg catcttccgt tgcaatgggc aggacaactg cggggacggc gaggatgagc   10800
gggattgccc tgaggtgacc tgcgccccca ccagttcca gtgctccatc accaagcgct   10860
gcatccctcg cgtctgggtc tgtgacaggg ataatgactg tgtggacggc agtgatgagc   10920
ctgccaactg tacccaaatg acctgtggag tggatgagtt ccgctgcaag gattctggcc   10980
gctgcatccc cgcgcgctgg aagtgtgacg gagaagatga ctgtgggat ggttcagatg   11040 agcccaagga agagtgtgat gagcgcacct gtgagccata ccagttccgc tgcaaaaaca   11100
```

```
accgctgtgt cccaggccgt tggcaatgtg actacgacaa cgactgcgga gataactcgg    11160
acgaggagag ctgcacacct cggccctgct ctgagagtga gttttcctgt gccaatggcc    11220
gctgcatcgc tgggcgctgg aagtgtgatg gggaccatga ctgtgccgac ggctcagacg    11280
agaaagactg cacccccgc tgtgatatgg accagttcca gtgcaagagt ggccactgca    11340 tcccctgcg ctggcgctgt gacgcggatg ctgactgtat ggacggcagt gacgaggaag    11400
cctgtggcac tggggtgagg acctgcccat tggatgagtt tcaatgtaac aacaccttgt    11460
gcaagccgct ggcctggaag tgtgatggag aggacgactg tggggacaac tcagatgaga    11520
accccgagga atgcgcccgg ttcatctgcc ctcccaaccg gccttccgc tgcaagaatg    11580 accgagtctg cctgtggatt gggcgccagt gtgatggcgt ggacaactgt ggagatggga    11640
ctgacgagga ggactgtgag cccccacgg cccagaaccc ccactgcaaa gacaagaagg    11700
agttcctgtg ccgaaaccag cgctgtctat catcctccct gcgctgtaac atgttcgatg    11760
actgcggcga tggctccgat gaagaagatt gcagcatcga ccccaagctg accagctgtg    11820
ccaccaatgc cagcatgtgt ggggacgaag ctcgttgtgt gcgcactgag aaagctgcct    11880
actgtgcctg ccgctcgggc ttccatactg tgccgggcca gcccggatgc caggacatca    11940
acgagtgcct gcgctttggt acctgctctc agctctgcaa caacaccaag ggaggccacc    12000
tctgcagctg tgcccgcaac ttcatgaaga cacacaacac ctgcaaagct gaaggctccg    12060
agtaccaggt gctatacatc gcggatgaca acgagatccg cagcttgttc ccgggccacc    12120
cccactcagc ctacgagcag acattccagg gcgatgagag tgtccgcata gatgccatgg    12180
atgtccatgt caaggccggc cgtgtctact ggactaactg gcacacgggc acaatctcct    12240
acaggagcct gccccctgcc gcccctccta ccacttccaa ccgccaccgg aggcagatcg    12300
accggggtgt caccccacctc aatatttcag ggctgaagat gccgagggt atcgctatcg    12360 actgggtggc cgggaatgtg tactggaccg attccggccg agacgtgatt gaggtggcgc    12420
aaatgaaggg cgagaaccgc aagacgctca tctcgggcat gattgatgag ccccatgcca    12480
tcgtggtgga ccctctgagg ggcaccatgt actggtcaga ctgggggaac caccccaaga    12540
ttgaaacagc agcgatggat ggcacccttc gggagactct cgtgcaagac aacattcagt    12600
ggcctacagg gctggctgtg gactatcaca tgaacggct ctactgggca gatgccaagc    12660
tttcggtcat cggcagcatc cggctcaacg gcactgaccc cattgtggct gctgacagca    12720
aacgaggcct aagtcacccc ttcagcatcg atgtgtttga agactacatc tacggagtca    12780
cttacatcaa taatcgtgtc ttcaagatcc acaagtttgg acacagcccc ttgatcaacc    12840 taactgggg cctgagccat gcctctgatg tagtcctta ccatcaacac aagcagcctg    12900
aagtgaccaa cccctgtgac cgcaagaaat gtgaatggct gtgtctgctg agccccagcg    12960
ggcctgtctg cacctgtccc aatggaaaga ggctggataa tggcacctgt gtgcctgtgc    13020
cctctccaac accccctcca gatgcccta ggcctggaac ctgcactctg cagtgcttca    13080
atggtggtag ttgtttcctc aatgctcgga ggcagcccaa gtgccgttgc cagccccgtt    13140
acacaggcga taagtgtgag ctggatcagt gctgggaata ctgtcacaac ggaggcacct    13200
gtgcggcttc cccatctggc atgcccacgt gccgctgtcc cactggcttc acgggcccca    13260
aatgcaccgc acaggtgtgt gcaggctact gctctaacaa cagcacctgc accgtcaacc    13320
agggcaacca gccccagtgc cgatgtctac ctggcttcct gggcgaccgt tgccagtacc    13380
ggcagtgctc tggcttctgt gagaactttg gcacctgtca gatggctgct gatggctccc    13440
gacaatgtcg ctgcaccgtc tactttgagg gaccaaggtg tgaggtgaac aagtgtagtc    13500
```

```
gctgtctcca aggcgcctgt gtggtcaata agcagaccgg agatgtcaca tgcaactgca 13560
ctgatggccg ggtagccccc agttgtctga cctgcatcga tcactgtagc aatggtggct 13620
cctgcaccat gaacagcaag atgatgcctg agtgccagtg cccgccccat atgacaggac 13680
cccggtgcga ggagcaggtt gttagtcagc aacagcctgg gcatatggcc tccatcctga 13740
tccctctgct gctgcttctc ctgctgcttc tggtggctgg cgtggtgttc tggtataagc 13800
ggcgagtccg aggggctaag ggcttccagc accagcggat gaccaatggg gccatgaatg 13860
tggaaattgg aaaccctacc tacaagatgt atgaaggtgg agagcccgat gatgtcgggg 13920
gcctactgga tgctgatttt gcccttgacc ctgacaagcc taccaacttc accaacccag 13980
tgtatgccac gctctacatg gggggccacg gcagccgcca ttccctggcc agcacggacg 14040
agaagcgaga actgctgggc cggggacctg aagacgagat aggagatccc ttggcatagg 14100
gccctgcccc gacggatgtc cccagaaagc cccctgccac atgagtcttt caatgaaccc 14160
cctccccagc cggcccttct ccggccctgc cgggtgtaca aatgtaaaaa tgaaggaatt 14220
actttttata tgtgagcgag caagcgagca agcacagtat tatctctttg catttccttc 14280
ctgcctgctc ctcagtatcc cccccatgct gccttgaggg ggcggggagg gctttgtggc 14340
tcaaaggtat gaaggagtcc acatgttccc taccgagcat acccctggaa gctggcggca 14400
cggcctcccc accacgcctg tgcaagacac tcaacggggc tccgtgtccc agctttcctt 14460
tccttggctc tctggggtta gttcagggga ggtggagtcc tctgctgacc ctgtctggaa 14520
gatttggctc tagctgagga aggagtcttt tagttgaggg aagtcacccc aaaccccagc 14580
tcccactttc aggggcacct ctcagatggc catgctcagt atcccttcca gacaggccct 14640
cccctctcta gcgccccctc tgtggctcct agggctgaac acattctttg gtaactgtcc 14700
cccaagcctc ccatccccct gagggccagg aagagtcggg gcacaccaag gaagggcaag 14760
cgggcagccc cattttgggg acgtgaacgt tttaataatt tttgctgaat tcctttacaa 14820
ctaaataaca cagatattgt tataaataaa attgtaaaaa aggaaaaaaa aaagaaaaga 14880
aaagaaaaga aaaaaaaaaa aaaaaaa 14907

<210> SEQ ID NO 5
<211> LENGTH: 5265
<212> TYPE: DNA
<213> ORGANISM: Homo sapiens
<300> PUBLICATION INFORMATION:
<308> DATABASE ACCESSION NUMBER: NM_000527
<309> DATABASE ENTRY DATE: 2010-08-01
<313> RELEVANT RESIDUES IN SEQ ID NO: (1)..(5265)

<400> SEQUENCE: 5
acatttgaaa atcaccccac tgcaaactcc tccccctgct agaaacctca cattgaaatg 60
ctgtaaatga cgtgggcccc gagtgcaatc gcgggaagcc agggtttcca gctaggacac 120
agcaggtcgt gatccgggtc gggacactgc ctggcagagg ctgcgagcat ggggccctgg 180
ggctggaaat tgcgctggac cgtcgccttg ctcctcgccg cggcggggac tgcagtgggc 240
gacagatgcg aaagaaacga gttccagtgc caagacggga aatgcatctc ctacaagtgg 300
gtctgcgatg gcagcgctga gtgccaggat ggctctgatg agtcccagga gacgtgcttg 360
tctgtcacct gcaaatccgg ggacttcagc tgtgggggcc gtgtcaaccg ctgcattcct 420
cagttctgga ggtgcgatgg ccaagtggac tgcgacaacg gctcagacga gcaaggctgt 480
ccccccaaga cgtgctccca ggacgagttt cgctgccacg atgggaagtg catctctcgg 540
cagttcgtct gtgactcaga ccgggactgc ttggacggct cagacgaggc ctcctgcccg      600
gtgctcacct gtggtcccgc cagcttccag tgcaacagct ccacctgcat cccccagctg      660
tgggcctgcg acaacgaccc cgactgcgaa gatggctcgg atgagtggcc gcagcgctgt      720
aggggtcttt acgtgttcca aggggacagt agccctgct cggccttcga gttccactgc       780
ctaagtggcg agtgcatcca ctccagctgg cgctgtgatg gtggcccga ctgcaaggac       840 aaatctgacg aggaaaactg cgctgtggcc acctgtcgcc ctgacgaatt ccagtgctct      900
gatggaaact gcatccatgg cagccggcag tgtgaccggg aatatgactg caaggacatg      960
agcgatgaag ttggctgcgt taatgtgaca ctctgcgagg acccaacaa gttcaagtgt       1020 cacagcggcg aatgcatcac cctggacaaa gtctgcaaca tggctagaga ctgccgggac      1080
tggtcagatg aacccatcaa agagtgcggg accaacgaat gcttggacaa caacggcggc      1140
tgttcccacg tctgcaatga ccttaagatc ggctacgagt gcctgtgccc cgacggcttc      1200
cagctggtgg cccagcgaag atgcgaagat atcgatgagt gtcaggatcc cgacacctgc      1260
agccagctct gcgtgaacct ggaggtggc tacaagtgcc agtgtgagga aggcttccag       1320
ctggaccccc acacgaaggc ctgcaaggct gtgggctcca tcgcctacct cttcttcacc      1380
aaccggcacg aggtcaggaa gatgacgctg gaccggagca gtacaccag cctcatcccc       1440 aacctgagga acgtggtcgc tctggacacg gaggtggcca gcaatagaat ctactggtct      1500
gacctgtccc agagaatgat ctgcagcacc cagcttgaca gagcccacgg cgtctcttcc      1560
tatgacaccg tcatcagcag agacatccag gccccgacg ggctggctgt ggactggatc       1620
cacagcaaca tctactggac cgactctgtc ctgggcactg tctctgttgc ggataccaag      1680
ggcgtgaaga ggaaaacgtt attcaggag aacggctcca gccaagggc catcgtggtg        1740 gatcctgttc atggcttcat gtactggact gactggggaa ctcccgccaa gatcaagaaa      1800
gggggcctga atggtgtgga catctactcg ctggtgactg aaaacattca gtggcccaat      1860
ggcatcaccc tagatctcct cagtggccgc ctctactggg ttgactccaa acttcactcc      1920
atctcaagca tcgatgtcaa cggggggcaac cggaagacca tcttggagga tgaaaagagg      1980
ctggcccacc ccttctcctt ggccgtcttt gaggacaaag tattttggac agatatcatc      2040
aacgaagcca ttttcagtgc caaccgcctc acaggttccg atgtcaactt gttggctgaa      2100
aacctactgt ccccagagga tatggttctc ttccacaacc tcaccagcc aagaggagtg       2160 aactggtgtg agaggaccac cctgagcaat ggcggctgcc agtatctgtg cctccctgcc      2220
ccgcagatca cccccactc gcccaagttt acctgcgcct gccgacgg catgctgctg         2280 gccagggaca tgaggagctg cctcacagag gctgaggctg cagtggccac ccaggagaca      2340
tccaccgtca ggctaaaggt cagctccaca gccgtaagga cacagcacac aaccacccga      2400
cctgttcccg acacctcccg ctgcctgggg ccaccctg ggctcaccac ggtggagata        2460
gtgacaatgt ctcaccaagc tctgggcgac gttgctggca gaggaaatga gaagaagccc      2520
agtagcgtga gggctctgtc cattgtcctc cccatcgtgc tcctcgtctt cctttgcctg      2580
ggggtcttcc ttctatggaa gaactggcgg cttaagaaca tcaacagcat caactttgac      2640
aaccccgtct atcagaagac cacagaggat gaggtccaca tttgccacaa ccaggacggc      2700
tacagctacc cctcgagaca gatggtcagt ctggaggatg acgtggcgtg aacatctgcc      2760
tggagtcccg tccctgccca gaaccccttcc tgagacctcg ccggccttgt tttattcaaa     2820
gacagagaag accaaagcat tgcctgccag agctttgttt tatatattta ttcatctggg      2880
aggcagaaca ggcttcggac agtgcccatg caatggcttg ggttgggatt ttggtttctt      2940
```

-continued

```
cctttcctcg tgaaggataa gagaaacagg cccgggggga ccaggatgac acctccattt    3000
ctctccagga agttttgagt ttctctccac cgtgacacaa tcctcaaaca tggaagatga    3060
aaggggaggg gatgtcaggc ccagagaagc aagtggcttt caacacacaa cagcagatgg    3120
caccaacggg accccctggc cctgcctcat ccaccaatct ctaagccaaa ccctaaact     3180
caggagtcaa cgtgtttacc tcttctatgc aagccttgct agacagccag gttagccttt    3240
gccctgtcac ccccgaatca tgacccaccc agtgtcttc gaggtggtt tgtaccttcc     3300
ttaagccagg aaagggattc atggcgtcgg aaatgatctg gctgaatccg tggtggcacc    3360
gagaccaaac tcattcacca aatgatgcca cttcccagag gcagagcctg agtcactggt    3420
caccccttaat atttattaag tgcctgagac acccggttac cttggccgtg aggacacgtg   3480
gcctgcaccc aggtgtggct gtcaggacac cagcctggtg cccatcctcc cgaccc       3540
ccacttccat tcccgtggtc tccttgcact ttctcagttc agagttgtac actgtgtaca    3600
tttggcattt gtgttattat tttgcactgt tttctgtcgt gtgtgttggg atgggatccc    3660
aggccaggga aagcccgtgt caatgaatgc cggggacaga gaggggcagg ttgaccggga    3720
cttcaaagcc gtgatcgtga atatcgagaa ctgccattgt cgtctttatg tccgcccacc    3780
tagtgcttcc acttctatgc aaatgcctcc aagccattca cttccccaat cttgtcgttg    3840
atgggtatgt gtttaaaaca tgcacggtga ggccgggcgc agtggctcac gcctgtaatc    3900
ccagcacttt gggaggccga ggcgggtgga tcatgaggtc aggagatcga gaccatcctg    3960
gctaacacgt gaaaccccgt ctctactaaa aatacaaaaa attagccggg cgtggtggcg    4020
ggcacctgta gtcccagcta ctcgggaggc tgaggcagga gaatggtgtg aacccgggaa    4080
gcggagcttg cagtgagccg agattgcgcc actgcagtcc gcagtctggc ctgggcgaca    4140
gagcgagact ccgtctcaaa aaaaaaaaac aaaaaaaaac catgcatggt gcatcagcag    4200
cccatggcct ctggccaggc atggcgaggc tgaggtggga ggatggtttg agctcaggca    4260
tttgaggctg tcgtgagcta tgattatgcc actgcttttcc agcctgggca acatagtaag    4320
accccatctc ttaaaaaatg aatttggcca gacacaggtg cctcacgcct gtaatcccag    4380
cactttggga ggctgagctg gatcactgga gttcaggagt tggagaccag gcctgagcaa    4440
caaagcgaga tcccatctct acaaaaacca aaagttaaa aatcagctgg gtacggtggc     4500
acgtgcctgt gatcccagct acttgggagg ctgaggcagg aggatcgcct gagcccagga    4560
ggtggaggtt gcagtgagcc atgatcgagc cactgcactc cagcctgggc aacagatgaa    4620
gaccctattt cagaaataca actataaaaa aataaataaa tcctccagtc tggatcgttt    4680
gacgggactt caggttcttt ctgaaatcgc cgtgttactg ttgcactgat gtccggagag    4740
acagtgacag cctccgtcag actcccgcgt gaagatgtca caaggggattg gcaattgtcc    4800
ccagggacaa aacactgtgt cccccccagt gcagggaacc gtgataagcc tttctggttt    4860
cggagcacgt aaatgcgtcc ctgtacagat agtggggatt ttttgttatg tttgcacttt    4920
gtatattggt tgaaactgtt atcacttata tatatatata tacacacata tatataaaat    4980
ctatttattt ttgcaaaccc tggttgctgt atttgttcag tgactattct cggggccctg    5040
tgtaggggt tattgcctct gaaatgcctc ttctttatgt acaagatta tttgcacgaa      5100
ctggactgtg tgcaacgctt tttgggagaa tgatgtcccc gttgtatgta tgagtggctt    5160
ctgggagatg ggtgtcactt tttaaaccac tgtatagaag gttttttgtag cctgaatgtc    5220
ttactgtgat caattaaatt tcttaaatga accaatttgt ctaaa                    5265
```

<210> SEQ ID NO 6
<211> LENGTH: 1223
<212> TYPE: DNA
<213> ORGANISM: Homo sapiens
<300> PUBLICATION INFORMATION:
<308> DATABASE ACCESSION NUMBER: NM_000041.2
<309> DATABASE ENTRY DATE: 2010-08-15
<313> RELEVANT RESIDUES IN SEQ ID NO: (1)..(1223)

<400> SEQUENCE: 6

```
gggatccttg agtcctactc agccccagcg gaggtgaagg acgtccttcc ccaggagccg      60
actggccaat cacaggcagg aagatgaagg ttctgtgggc tgcgttgctg gtcacattcc     120
tggcaggatg ccaggccaag gtggagcaag cggtggagac agagcggag cccgagctgc      180
gccagcagac cgagtggcag agcggccagc gctgggaact ggcactgggt cgcttttggg     240
attacctgcg ctgggtgcag acactgtctg agcaggtgca ggaggagctg ctcagctccc     300
aggtcaccca ggaactgagg gcgctgatgg acgagaccat gaaggagttg aaggcctaca     360
aatcggaact ggaggaacaa ctgacccgg tgcggagga cgcgggca cggctgtcca         420
aggagctgca ggcggcgcag gcccggctgg gcgcggacat ggaggacgtg tgcggccgcc     480
tggtgcagta ccgcggcgag gtgcaggcca tgctcggcca gagcaccgag gagctgcggg     540
tgcgcctcgc ctcccacctg cgcaagctgc gtaagcggct cctccgcgat gccgatgacc     600
tgcagaagcg cctggcagtg taccaggccg ggcccgcga gggcgccgag cgcggcctca     660
gcgccatccg cgagcgcctg gggcccctgg tggaacaggg ccgcgtgcgg gccgccactg     720
tgggctccct ggccggccag ccgctacagg agcgggccca ggcctggggc gagcggctgc     780
gcgcgcggat ggaggagatg ggcagccgga cccgcgaccg cctggacgag gtgaaggagc     840
aggtggcgga ggtgcgcgcc aagctggagg agcaggccca gcagatacgc ctgcaggccg     900
aggccttcca ggcccgcctc aagagctggt tcgagcccct ggtggaagac atgcagcgcc     960
agtgggccgg gctggtggag aaggtgcagg ctgccgtggg caccagcgcc gccctgtgc     1020
ccagcgacaa tcactgaacg ccgaagcctg cagccatgcg accccacgcc accccgtgcc     1080
tcctgcctcc gcgcagcctg cagcgggaga ccctgtcccc gccccagccg tcctcctggg     1140
gtggacccta gtttaataaa gattcaccaa gtttcacgca aaaaaaaaa aaaaaaaaa     1200
aaaaaaaaa aaaaaaaaa aaa                                              1223
```

<210> SEQ ID NO 7
<211> LENGTH: 897
<212> TYPE: DNA
<213> ORGANISM: Homo sapiens
<300> PUBLICATION INFORMATION:
<308> DATABASE ACCESSION NUMBER: NM_000039
<309> DATABASE ENTRY DATE: 2010-08-15
<313> RELEVANT RESIDUES IN SEQ ID NO: (1)..(897)

<400> SEQUENCE: 7

```
agagactgcg agaaggaggt cccccacggc ccttcaggat gaaagctgcg gtgctgacct      60
tggccgtgct cttcctgacg gggagccagg ctcggcattt ctggcagcaa gatgaacccc     120
cccagagccc ctgggatcga gtgaaggacc tggccactgt gtacgtggat gtgctcaaag     180
acagcggcag agactatgtg tcccagtttg aaggctccgc cttgggaaaa cagctaaacc     240
taaagctcct tgacaactgg gacagcgtga cctccacctt cagcaagctg cgcgaacagc     300
tcggccctgt gacccaggag ttctgggata acctggaaaa ggagacagag ggcctgaggc     360
aggagatgag caaggatctg gaggaggtga aggccaaggt gcagccctac ctggacgact     420
```

```
tccagaagaa gtggcaggag gagatggagc tctaccgcca gaaggtggag ccgctgcgcg      480
cagagctcca agagggcgcg cgccagaagc tgcacgagct gcaagagaag ctgagcccac      540
tgggcgagga gatgcgcgac cgcgcgcgcg cccatgtgga cgcgctgcgc acgcatctgg      600 cccctacag cgacgagctg cgccagcgct tggccgcgcg ccttgaggct ctcaaggaga        660
acggcggcgc cagactggcc gagtaccacg ccaaggccac cgagcatctg agcacgctca      720
gcgagaaggc caagcccgcg ctcgaggacc tccgccaagg cctgctgccc gtgctggaga      780
gcttcaaggt cagcttcctg agcgctctcg aggagtacac taagaagctc aacacccagt      840
gaggcgcccg ccgccgcccc ccttcccggt gctcagaata aacgtttcca aagtggg         897

<210> SEQ ID NO 8
<211> LENGTH: 1299
<212> TYPE: DNA
<213> ORGANISM: Homo sapiens

<400> SEQUENCE: 8
acgcccggga accccgacc cctctgagcc cggggtactg cgcccgggtc tccacgccca        60
gagatgctcc ccggtctcca ccgtcgggca agccccaagc gcagcagcgc agagtcctgg      120
ggtcaccaga gctcgtacta ggacatcgtc tccccattta acaccgcctc cggtcccatc      180
tgagttgcaa gtggtgggga tgtggggctc cggatcaaag tccccgaaac cgagcacttc      240
ccgaagcctc cttggcctcg aaacaaaaca ataacgccca actccatcat attccagaac      300
tcccaccacc tgcatacaga cattcagctg cacaagcccc ctccatgcta cagtcaacag      360
gatctccagg ccacggctca gcccaggta ctcacatcag tggttctatc aacactcagg       420
acagacccat agaagaggcc caagcaggcc ctggaagtgc atgtggaggc caccaggcaa      480
ggaattctgg agtcccaggt actcataact ctgggtggca tggcccctt gcaccatgga       540 ctgtttgccc ttagaaaggg atggatctga gctgggcgca gtggctcatg cctgtaatcc      600
cagcactttg ggaggccaag gtgggcagct cacctcaggt caggttggtc tcaaactcct      660
gacctcaggc gatccacctc agcctctcaa agtgctggaa ttataggtgt gagccactgt      720
gcccagccca aaatcattct tttttggaatt ttgaagcata taattccaaa aggtatgaag      780
gtaatcactt agattgctct aataagggaa tgggaacagt taagtcctat acaaataaga     840
caaagataag atactacaaa aaggggatga gcccaagaaa aaaatcaaag tcccagagag      900
agaacagcca ttgattctaa atacacaagt ctatggcccc aacccaaact tgtttcacta     960
agaacaacct gtggtttcga gaatctggtc atccccaca gtgaatacat gaacacattg      1020
taatgtttga aatgtttatt tttcttgttg atttcttact gttagaagag ctaagtgatt     1080
tggcccaaag tggctaagtg attcggccag tttgtacaca gggatataag tttgctgaca     1140
ccaagctcat actttacaaa tgtaatatct tcataaaaca aaaatactgg gccgggcgcg     1200
gtggctcacg cctgtaatcc cagcattttg ggaggccgag gcgggcggat catgagatca     1260
ggagatcgag accatcctgg ctagcagggt gaagccccg                            1299

<210> SEQ ID NO 9
<211> LENGTH: 917
<212> TYPE: DNA
<213> ORGANISM: Mus musculus

<400> SEQUENCE: 9
caaaatggcg tgctaccctg tccaaccttg tctgtagaca gagtcaattg aacactgtct       60
```

| | |
|---|---|
| ttgggacttc cgtgcaactg aggtgggcgg gcttgaagca caaagctttc agggagaacc | 120 |
| aaactttatg cccaagctgc tctctgccac ccacagggta aatgaatctc atacaggaaa | 180 |
| ggcaagagac atgtgacact gttgtctgat ggtcacaagt caagcttttt aaaaagcagc | 240 |
| ctgatattgt gagctaacat ggctttctgt aattgaatgc aatgtatttt ctatgcttgt | 300 |
| ctgggtaaag ttgaccttgg tttgatttag ctcaagcaat atttcaacag tgcactgggg | 360 |
| ctctgagtcc cctgactact gtttgactag agccaggctc tgccctggat ggcaaccaac | 420 |
| agcccaggct ctggggcaca gccgggcttt gacaggtctg ggaaatgttt caccggagat | 480 |
| gaaaggtttc aaactatgaa actctaaaat ctcaagtcaa aacttttgac aagcacacac | 540 |
| aggacatgaa ttacaatcac ccgaagattt ttacaggctt ctcaatttta atgacatgct | 600 |
| gacacgtgtc atcagatctc acaacaagat gacacatggg tgtcaggtat ggcgcagaag | 660 |
| actagagtcg gggtgtaacc aatgagcatt gtctgttgga cacaggcgaa ttcggcaaac | 720 |
| ggacagtgct ggaggcagaa gggtttaaag aaggcaggaa agcccatgtt taacagaatg | 780 |
| gggtgacgaa gagggatggg aaggtctaac tcacccgggg gtgggggcac caggggggcc | 840 |
| cacggacaca gaaaaccacg caggtcaggc acctacaaag accgaaggaa aaagggacca | 900 |
| cgcagaaatc actcacg | 917 |

<210> SEQ ID NO 10
<211> LENGTH: 1550
<212> TYPE: DNA
<213> ORGANISM: Homo sapiens

<400> SEQUENCE: 10

| | |
|---|---|
| aaagtccaag gtgggaacag ataggtctgg gggcatgggg gctgggccta ataggggccg | 60 |
| ggcatggatg ggcctctcct gctcaccgat cctgggctgg gcatcttgtc cttggtgggt | 120 |
| gggggccaag gaaggagtgg tgggggcttgg cccagagtct ggtgtggctg tgactgacca | 180 |
| cagcttgtga tgccccagcc aagacctcag gcacaccccg tcccccactc cgccccccct | 240 |
| gggttagaca actgagagtc acagtgtggt gggagaaggg acgtcattcc tctaagggac | 300 |
| aagctttttgg cccctcccca caccagggca ggtacttatg tcgggctta tgcagggcag | 360 |
| aagggctttg gccaggtcag ctgccagggg ctggggccca ggctcccag ggtctggcgt | 420 |
| ggtgcatcag gggcctggtg ggggcttacc gaggatgacg ggccgtgtgt ggttactgag | 480 |
| ctcagccttg ggcgtggtgt gcgggggggaa gagcacattg aggagccaga aggggggcggc | 540 |
| aggagggagc agcagcccca gcagcagcgt cacccactgc catggggagc cgggcggccc | 600 |
| cattccagcc ctggtgccta ctgccagaga aagcggcact gggctgtcct tatctggtgt | 660 |
| gggagtggga ggggccctag gccagtggg agggacggcc tggccagtgg gggttgtggc | 720 |
| cagagattgc cggaaagggg cacagcctca gggagccggc tctgggcctg ggttcagttc | 780 |
| cgccttcttc tcttggcgcc aggggaaaca gagccgggc agcaggaggc ccagaactac | 840 |
| acaatgtttt attgaaaaag tcaggcctca gctcagctgt ctccattcgg ctcagcttgg | 900 |
| tggggggccc tgcccatagt agactgagcc agatcttcct gcaggcagct gggctggact | 960 |
| ccctccctgg ctaccctctcc cttcgtctct gatggtgaca tccaaacaat aaatatgcaa | 1020 |
| taaatagcgc tcctgggctg ggccgggccg gctgccttca aaccccactc ggcccctacc | 1080 |
| agtcttctct ggccaggaca ggcctactgg ggtgctagat agtaaagtcc ccaaacatcc | 1140 |
| cagggtccca caagacctgg gatccatctc cattttgagg cccaggcctg gtttccaagg | 1200 |
| agacctagca aagctgggtc caggacaggg ccaggcaagc agggctggca ggtgggtgct | 1260 |

| | |
|---|---|
| gggaagaggc tgttacccca gaccacagct tgttatgtcc tggccaagac ctcgactcca | 1320 |
| ggccacaaga tgacactggg ctcaggagta gatggtgatg acttcacggc caccaccgcg | 1380 |
| caccaacagc acccgctcaa ggccctcggt cagcacctcg aggaactcca tgtagttctc | 1440 |
| gtcgccctca ctgttcctgg gtgggccagg catgtttagg agaaccaggc gggcgtcgtg | 1500 |
| ggagcgcgtg acaatgactt cattgagctt cacagcagtg tgcatgcgcc | 1550 |

<210> SEQ ID NO 11
<211> LENGTH: 329
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (311)..(311)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t

<400> SEQUENCE: 11

| | |
|---|---|
| tttaangttt gatgtttatt ggtggtgtct gatgagcgtt tctcttgtcc agactgtgtt | 60 |
| tctctctcca gaccagctcc cagggtacag ggggtgggga gtaggtggta gctgtgtcag | 120 |
| tgctgggccc tggngccact ccctagggaa gagcaggtgg ggcctcgggg ggtctggccc | 180 |
| tagctctggc agatccatcc tcagtgaagc acatccctgg ggcaaaggca ctcctgaggc | 240 |
| caagaccagc atgggcttga tggagccacc ccagggagcc ccaagagaga tgaagccatc | 300 |
| aataaagcgg nccttccagg cctgggnct | 329 |

<210> SEQ ID NO 12
<211> LENGTH: 1826
<212> TYPE: DNA
<213> ORGANISM: Homo sapiens

<400> SEQUENCE: 12

| | |
|---|---|
| tgtcactctg acctcagtgt aggcactgcc tcctctggga agtctttgct gacctgaaag | 60 |
| gctcagcctc ttgtgcttcc taagcttttc tcagagcatt tagcttcatt agtaattaaa | 120 |
| cttccattag tgaaatgatc tgattaatgg ttgtcactcc cagattttaa ttctaacttt | 180 |
| tttttttttt tttttttttg agacccagtc tcttttttttt tgagacagtc tcattctgcc | 240 |
| gcccagtctg gagtgcaacg acgtgatctc ggctcacggt gacctccacc tcccaggttc | 300 |
| aagtgattct cgtgcctcag cctcctgagt agctgggacg acagatgcat gccaccacgc | 360 |
| ctggcaaata ttttgtattt tagtagagac ggggggtttct gccgtgttgg cctggctggt | 420 |
| ctcaaactcc tgagttcggg tgatccgcct gcctcggtct cccggggtgc cgggattaca | 480 |
| ggcgtgagcc accgtgcccg gcctctaaac acttgtggcc ctgtcattca cccagcactc | 540 |
| aaaaggtcgt ctcacctgcc cttttgggag ctgggagaga cagctcaaat tgtcaccgcc | 600 |
| cccccaccgc cccgtgctcc tctgacaggg ctgtgggtgg agccagctcc agtccccgcg | 660 |
| cccagcacag aggcaggcac ggtgcacact gcctcaacag ctcgaccagg agagtgggca | 720 |

```
gctgtacatc tagggtgccc agctcagtcc caggcctcag cagagcccat cttgcctcac    780
tgcacacagc actgagcctg tggctggtga ggagtgaaac ctagtgtggg actctagtgc    840
ctcccttcaa cctgaaacat agccatcagg gcttacggta gcaaaggaag gtctttattc    900
aggaggcggg ggctctgggc tggcagtcgg ggatgcaggg ggaccctggc ggtaggcacc    960
cagcaggatg gcattgatgt gctccagggt caggttgctg aagaccatgt tcagatgctg   1020
tatcccgtgc aggggcagca ggtgcacagg ctgtggctgg cggccctgcc acaggccaca   1080
gagctcggtg ctgcgggtcg ccaccgtgtc atcaccatcc tcatagagca cacccacagg   1140
gtccgtgtag gggaagccgt ggtcgtagat gtaggtgcgg ggcgtgggca ggcccacgcc   1200
gtaaagacag tatacttcca caccaggtgc tgggagtcct gccaggaggt cacgtgactg   1260
cagccacatg taccagcctt cctcaaagtg caggtctgca aagaagcgtt ggaagtcacg   1320
gcctgtgtag ttgaagctgg gtgtggaaat gaacacgtgg tcctcaggcc acgccatgcg   1380
agagggaaac atccaggggg aggtggtggt tatgcgctgc tcctctttca gcttgatgct   1440
ggacatgatg gggatgccct ggttgtcacc tgtggatatg gagcaaggtg ggacagggag   1500
ccaggcctgg ctaccctgg cccacaacct gctgagtgta ggctcagcca gatgctcaat   1560
cttgtccctg cccaatctag acacagactc taagccacag gcttgagcag gcctgatatt   1620
caatgatgct cagtgtcagc ttactcaatg agaagccctg ataagacctc tgttgggtgg   1680
agctgtaggg cttcaaaagg atggcaggga caggcaccat ggctcacccc tgtaatcccg   1740
gcactttggg aggctgaggc aggaggatca cttgaggcca ggagtccgtg accagactgg   1800
gcaatgcagt gagaccctgt ctctac                                        1826

<210> SEQ ID NO 13
<211> LENGTH: 536
<212> TYPE: DNA
<213> ORGANISM: Homo sapiens

<400> SEQUENCE: 13
tgtttttttt tttttttttt aaagagatgg agtcctgatc tgtcgcccag gctggagttc     60
agtggcacaa tattgcccca ctgcaaccct tgaaccttcc cggttcaagt gattctcctg    120
cctaggtctt ctgagtagct gggattacag gtgcccacca ccacgcccag ctaattttg    180 tggttttagt agagacggag ttttgccatg ttggccaagc tagtctcaaa ctcctgacct    240
caagtgatcg gccggcctca gcctcccaaa gtgctgggat tacaggcttg agccactgcg    300
cctggcccag ttttcccatg tcttgaggca ccactaccca tgcacctcag aatcctccct    360
tgcctttatc cctttgatac agcacatccc aaagtgaatc cccacatggt ccctggttgc    420
tcagactcag tgaaaaaaaa atgaatggtc aagtgagttt tggaaaaccc caaacgcttg    480
aaaaattctt ggcacacata aacatattca aggctctgag aagttctgca gcacaa        536

<210> SEQ ID NO 14
<211> LENGTH: 551
<212> TYPE: DNA
<213> ORGANISM: Homo sapiens

<400> SEQUENCE: 14
accattcagc tgcacccaga tgccccaaga gcaatgagcc cacacgcaga gctggaggac     60
ctgaaaggca acctccaagt cccagatcat gtctctgtgg ggtctggtct ccaagatgcc    120
cccagaaaaa gtgcagcggc tctatgtcga ctttccccaa cacctgcggc atcttctggg    180
tgactggctg gagagccagc cctgggagtt cctggtcggc tccgacgcct tctgctgcaa    240
```

```
cttggctagt gccctacttt cagacactgt ccagcacctt caggcctcgg tgggagagca    300
gggggagggg agcaccatct tgcaacacat cagcacccct tgagagcatat atcagaggga    360 cccctgaag ctggtggcca ctttcagaca aatacttcaa ggagagaaaa aagctgttat     420
ggaacagttc cgccacttgc caatgccttt ccactggaag caggaagaac tcaagtttaa    480
gacaggcttg cggaggctgc agcaccgagt aggggagatc caccttctcc gagaagccct    540
gcagaagggg g                                                          551
```

<210> SEQ ID NO 15
<211> LENGTH: 672
<212> TYPE: DNA
<213> ORGANISM: Mus musculus

<400> SEQUENCE: 15

```
tgtgacaccc ttcctcacgc ttagacagca aagttgcctc ggaagagaag agaagcctgc     60
atgggaatgg ccagcacatc ctaaatgctc cagtggcccg tggttcgtcc cttcgtctca    120
ttgactgcca cagacaggaa gtaggctcag ggacttggca cctacccaac agcaggacgt    180
cctttctggc catactcctg agggtaacaa aatcacatgg aagcccaaag caagccaggc    240
tcaggctcct ctgccctctg ctacttaaca atgtccgtcc ttccccagcc cccctgcaga    300
tgcttctgta tgggaaagcc cctctgcatc taatgacact ctgctttcaa agacgggaca    360
gtccctggtc tctggagagt gaccattcgt ggccttctca gttgacactt ctccgctgag    420
gcatccctta gccctgaacc agaaatgaaa gagccggctc agagtgaaaa ggaagaatag    480
ccatcaatct gctcctgtgt gcaaggagca cagacctggt ctcagactct gcccgtctcc    540
cccgcttccc tgccctctga gtgactcacg gtgcaggctg agggagatgt tgatggtatg    600
ctcatccaca aagcccttca ggccaggcat ccgggcaact tgagctgtgt ctgggcacac    660
tgtcccaacg tg                                                         672
```

<210> SEQ ID NO 16
<211> LENGTH: 616
<212> TYPE: DNA
<213> ORGANISM: Mus musculus

<400> SEQUENCE: 16

```
gacttttatc tgcactgttt caacagcagg tagccagccg tcttttttact gcctgcctct     60 ggctgaagct cggcccacac tatcaggact cagccctgta gggatgactc tgccacacag    120
ctacagcacc agctggcaca aatggctttc tctccaactt cctcaggctt ccctgagtca    180
ctgcccagcc ctaggactgg caacaccctg gccctgctca ccatccacc cttggcaaga     240 gggaaagagg aagaagcctg cagagagctg gtgcccctgct tccagatgct gctccattct    300
caggccaagc ctcaagatgg ggggaacctg agtgggagcc tctctcctgg cttgcgttcc    360
ctcccacttc tgggaaagca gggcagtgac agtccctgtt ctcatgtgtc tgcccttggc    420
tgggctcccc tcacctcccc aaagaccagg cagggtccca ttcagcagac ctgactgtaa    480
ggaattggca agaaatgacg tccctagcca gcctggcctc cccttggta tttttgcagc     540 tggagattat tagtctcaag caaaactcct ttgttatcca agcccactcc accacattat    600
tttcctctct cctaaa                                                     616
```

<210> SEQ ID NO 17
<211> LENGTH: 471
<212> TYPE: DNA

<213> ORGANISM: Mus musculus

<400> SEQUENCE: 17

| | | | | | |
|---|---|---|---|---|---|
| gacagggtct | tattctgcag | ctcgggttga | cctggaattc | tccaggcaga | ccattctggc | 60 |
| cttacgttca | ctgacatcca | cctgcctctg | cctcctgagt | gctgctgtta | aggagtagtt | 120 |
| ccagcctata | gtgttctgaa | atactgttat | tttactgtaa | tgatagccaa | agctaaaatg | 180 |
| agttaagaat | agttcctttc | ttactcgctg | tctcgttcct | cattcacttg | ccccatcttc | 240 |
| gtgccctcag | aactacccca | cccccaatcc | tcctttagcc | ccagagcctt | ctctgaaccc | 300 |
| taccccttgc | ttcctgtcag | catctcaggg | cccctctttt | gcttccttaa | tctctactgg | 360 |
| aaacacagag | aactcccctg | ccctctgcca | ttcttctgct | ggagctacct | tcccacccTT | 420 |
| gtgcaagcca | ggcccctcat | acccaagcag | gtgacaccat | ctgtgtccaa | c | 471 |

<210> SEQ ID NO 18
<211> LENGTH: 707
<212> TYPE: DNA
<213> ORGANISM: Homo sapiens

<400> SEQUENCE: 18

| | | | | | |
|---|---|---|---|---|---|
| gagctgcgct | caccgctgtt | gcctgatttt | ggtctaagtg | aaggcttgcg | gttcagattc | 60 |
| caacaacttc | cctttgtaaa | ggaaatggac | aagaaactcc | ccctggata | tgccttgaag | 120 |
| ccagctacag | cgtgaggtgg | tgcagctaga | agtgctaga | acacacacc | agctctcaga | 180 |
| agtctggagg | aaaacatcag | gggtgtagtc | tccttgacaa | cagaggaaac | atcacattct | 240 |
| cagccatccc | gggagagaga | aactaaagtg | atgaacaaac | aaggccttgc | ctaagacttc | 300 |
| cttaacattt | tctcttaagg | aagaggttga | ttgaggaaaa | atcgccgctt | ggacagctga | 360 |
| accgaagcca | ttcacagcct | ctgaagaagc | gaggccaccc | cagggggtcg | gtcccggggg | 420 |
| atagctgccc | caccgtggct | gaagatctcg | gctgcagacc | aaggaggggc | ggggagattc | 480 |
| tgaggcaacg | tttcaacctc | gtaaggaacc | gaggccttga | gggtggccgg | ggcccctct | 540 |
| gtgaacttga | tcggggctgg | tggggcgagg | gcgccccca | ggacaaggtg | gggacggagg | 600 |
| tgtcgccaca | gagcacagcg | gaaaccgggg | acttcgccag | gagggcccag | gataacggag | 660 |
| ggcgactcgt | gtatgtcgcg | gaggcggctc | cggggacccg | ggacttg | | 707 |

<210> SEQ ID NO 19
<211> LENGTH: 741
<212> TYPE: DNA
<213> ORGANISM: Homo sapiens

<400> SEQUENCE: 19

| | | | | | |
|---|---|---|---|---|---|
| ggggctccct | ctcaacctat | tctggcgcct | ggagcaagcc | ttacctgcag | tccccgccgc | 60 |
| ggcgaggagc | aaggcgacgg | tccagcgcaa | tttccagccc | cagggcccca | tgctcgcagc | 120 |
| ctctgccagg | cagtgtcccg | acccggatca | cgacctgctg | tgtcctagct | ggaaaccctg | 180 |
| gcttcccgcg | attgcactcg | gggcccacgt | catttacagc | atttcaatgt | gaggtttcta | 240 |
| gcaggggag | gagtttgcag | tggggtgatt | ttcaaatgtc | ttcacctcac | tgcaagagga | 300 |
| ggagtttcga | acgccgatg | tgacatcggc | tttttaaccc | gtgaagctct | gattcccact | 360 |
| ccagtccttc | gaaagtgtcg | ccagggcagg | cgacttgatt | tgttgtattt | gggtctccgg | 420 |
| tgaagagctg | acgccccctc | aaaattggaa | acgcatcttc | tgaaagatcc | tcctgaaatt | 480 |
| tctcgatgtt | taactgttaa | cattttgctg | ttgttgtcca | cagaaggata | acaacagcct | 540 |
| ttcaagatcc | tccaatagcc | taatgccatt | gtcctctctg | cctcaaaagg | aaaacactaa | 600 |

```
aaatgttggg aacttccgcc actttctata tttgcctttt cctttctagg aattgtgtat    660 agattttag cttcctttcg ttgtatattg tttttacatt gttattccaa atcacctaat    720
agacactgat caatcaggaa t                                              741
```

<210> SEQ ID NO 20
<211> LENGTH: 346
<212> TYPE: DNA
<213> ORGANISM: Homo sapiens

<400> SEQUENCE: 20

```
cccacgtata ttttttgttg tttttttgttt tttttctgta aaatgtcccg gttcttccat    60
aacttataaa catgatttat accgaggaga tgggaaagtg gacggggcag ggtggactga   120
ccggggatgg ggaagctcct ctcgctgccc cctcggggcg ggcccaggcc ctttggagga   180
tggggacgcc aggacactcc tccctgaggt tgctggccgc ctctgccctg gtgctgtgaa   240
gtcagagccc cgatactccc cgtccacctg ccagttcaca aacttcgact gctgggtctg   300
gatggccatc ttggacctga gaccggggcc cagctggtga atgacc                  346
```

<210> SEQ ID NO 21
<211> LENGTH: 867
<212> TYPE: DNA
<213> ORGANISM: Homo sapiens

<400> SEQUENCE: 21

```
accatctttt tttttttct tttatgcgtg aaacttggtg aatctttatt aaactagggt     60
ccaccccagg aggacggctg gggcggggac agggtctccc gctgcaggct gcgcggaggc   120
aggaggcacg gggtggcgtg gggtcgcatg gctgcaggct tcggcgttca gtgattgtcg   180
ctgggcacag gggcggcgct ggtgcccacg gcagcctgca ccttctccac cagcccggcc   240
cactggcgct gcatgtcttc caccaggggc tcgaaccagc tcttgaggcg ggcctggaag   300
gcctcggcct gcaggcgtat ctgctgggcc tgctcctcca gcttggcgcg cacctccgcc   360
acctgctcct tcacctcgtc caggcggtcg cgggtccggc tgcccatctc ctccatccgc   420
gcgcgcagcc gctcgcccca ggcctgggcc cgctcctgta gcggctggcc ggccagggag   480
cccacagtgg cggcccgcac gcggccctgt tccaccaggg gccccaggcg ctcgcggatg   540
gcgctgaggc cgcgctcggc gccctcgcgg gccccggcct ggtacactgc caggcgcttc   600
tgcaggtcat cggcatcgcg gaggagccgc ttacgcagct tgcgcaggtg ggaggcgagg   660
cgcacccgca gctcctcggt gctctggccg agcatggcct gcaccgcgcc gcggtactgc   720
accaggcggc cgcacacgtc ctccatgtcc gcgcccagcc gggcctgcgc cgcctgcagc   780
tccttggaca gccgtgcccg cgtctcctcc gccaccgggg tcagttgttc ctccagttcc   840
gatttgtagg ccttcaactc cttcatg                                        867
```

<210> SEQ ID NO 22
<211> LENGTH: 563
<212> TYPE: DNA
<213> ORGANISM: Homo sapiens

<400> SEQUENCE: 22

```
cagcttctct tgcagctcgt gcagcttctg gcgcgcgccc tcttggagct ctgcgcgcag     60
cggctccacc ttctggcggt agagctccat ctcctcctgc cacttcttct ggaagtcgtc   120
cagatccaaa tggcaaacct tcttcatcca ccaggaccca acccacaggc tacttattgc   180
```

```
tggaaaccta cgttgttcct tggattgaag taatctctcc ctcttctggt gcgcccacag    240
cacttgcacc aacagtgggt acccaacaga ctagcgtgcc tgccgaagaa ggggtcctct    300
gacaatcagg ggacaatggg gaattatgct ctccagactt tctacacaca caagtcacac    360
aggaaggaag gtaaagagaa actagagaaa ataattttg aagaaaaaca tttcaggaag    420
tattgaaagt acacggtaac tcagcctggg gcaggggtgg agggcagcag cactgtttgc    480
tgcagctatg ctccttcctc agtgccctgc acacccggga cttgctcggt gagcatctct    540
cgtgtcagtg acagctagtg tga                                           563

<210> SEQ ID NO 23
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 23
uuguaaagua ugagcuuggu gucagca                                        27

<210> SEQ ID NO 24
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 24
aaucaauggc uguucucucu cugggac                                        27

<210> SEQ ID NO 25
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 25
accuauaauu ccagcacuuu gagaggc                                        27

<210> SEQ ID NO 26
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 26
cccaccactt gcaactcaga                                                20

<210> SEQ ID NO 27
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 27
ttcgggaagt gctcggtttc g                                              21

<210> SEQ ID NO 28
<211> LENGTH: 21
<212> TYPE: DNA
<213> ORGANISM: Artificial Sequence
```

```
<220> FEATURE:
<223> OTHER INFORMATION: Antisense oligonucleotide

<400> SEQUENCE: 28
cccagctcag atccatccct t                                              21

<210> SEQ ID NO 29
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 29
gcctcttcta tgggtctgtc                                                20

<210> SEQ ID NO 30
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 30
gccatgccac ccagagtta                                                 19

<210> SEQ ID NO 31
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 31
gctgttctct ctctgggact t                                              21

<210> SEQ ID NO 32
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 32
gttcccattc ccttattag                                                 19

<210> SEQ ID NO 33
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 33
cgaatcactt agccactttg                                                20

<210> SEQ ID NO 34
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 34
ctgggattac aggcgtgagc                                                20
```

<210> SEQ ID NO 35
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 35
catgtctcct gcctttcctg t					21

<210> SEQ ID NO 36
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 36
gctcacaata tcaggctgct t					21

<210> SEQ ID NO 37
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 37
tcaactttac ccagacaagc a					21

<210> SEQ ID NO 38
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 38
ggacagggta gcaacgccat t					21

<210> SEQ ID NO 39
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 39
ccacctcagt tgcacggaa					19

<210> SEQ ID NO 40
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 40
ttgggcatag agtttggttc					20

<210> SEQ ID NO 41
<211> LENGTH: 27
<212> TYPE: DNA
<213> ORGANISM: Artificial Sequence
<220> FEATURE:
<223> OTHER INFORMATION: Antisense oligonucleotide

```
<400> SEQUENCE: 41
guggucaguc acagccacac cagacuu                                              27

<210> SEQ ID NO 42
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 42
gucccuucuc ccaccacacu gugacuc                                              27

<210> SEQ ID NO 43
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 43
cagcacugac acagcuacca ccuacuc                                              27

<210> SEQ ID NO 44
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 44
ugugcuucac ugaggaugga ucugcca                                              27

<210> SEQ ID NO 45
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 45
agagaaacgc ucaucagaca ccaccaa                                              27

<210> SEQ ID NO 46
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 46
cuuaggaagc acaagaggcu gagccuu                                              27

<210> SEQ ID NO 47
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 47
ccuggcuccc ugucccaccu ugcucca                                              27

<210> SEQ ID NO 48
```

```
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 48
guucauuucc acacccagcu ucaacua                                           27

<210> SEQ ID NO 49
<211> LENGTH: 19
<212> TYPE: DNA
<213> ORGANISM: Artificial sequence
<220> FEATURE:
<223> OTHER INFORMATION: Antisense oligonucleotide

<400> SEQUENCE: 49
agacctatct gttcccacc                                                    19

<210> SEQ ID NO 50
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 50
gtcagtcaca gccacaccag                                                   20

<210> SEQ ID NO 51
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 51
cctatctgtt cccaccttg                                                    19

<210> SEQ ID NO 52
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 52
gtcacagcca caccagactc t                                                 21

<210> SEQ ID NO 53
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 53
tcccttctcc caccacactg t                                                 21

<210> SEQ ID NO 54
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 54
```

```
ctcctcaatg tgctcttccc                                              20

<210> SEQ ID NO 55
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 55
cccactccca caccagata                                               19

<210> SEQ ID NO 56
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 56
aacagcctct tcccagcacc                                              20

<210> SEQ ID NO 57
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 57
caccatctac tcctgagccc                                              20

<210> SEQ ID NO 58
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 58
tcattgtcac gcgctcccac                                              20

<210> SEQ ID NO 59
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 59
tcccagctac tcagaagacc t                                            21

<210> SEQ ID NO 60
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 60
tgggcgacag atcaggactc                                              20

<210> SEQ ID NO 61
<211> LENGTH: 21
<212> TYPE: DNA
```

<213> ORGANISM: Artificial Sequence
<220> FEATURE:
<223> OTHER INFORMATION: Antisense oligonucleotide

<400> SEQUENCE: 61
ctgaggtgca tgggtagtgg t         21

<210> SEQ ID NO 62
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 62
gccgatcact tgaggtcagg a         21

<210> SEQ ID NO 63
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 63
attagctggg cgtggtggtg           20

<210> SEQ ID NO 64
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 64
gctctgcgtg tgggctcatt           20

<210> SEQ ID NO 65
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 65
gtccctctga tatatgctct c         21

<210> SEQ ID NO 66
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 66
cttgagttct tcctgcttcc a         21

<210> SEQ ID NO 67
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 67
tctccagcca gtcacccaga           20

<210> SEQ ID NO 68
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 68
ccatcaacat ctccctcagc c                                          21

<210> SEQ ID NO 69
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 69
cttcttcctc tttccctctt                                            20

<210> SEQ ID NO 70
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 70
acagcagcac tcaggaggca                                            20

<210> SEQ ID NO 71
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 71
gggtagttct gagggcacga                                            20

<210> SEQ ID NO 72
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 72
aggcaggtgg atgtcagtg                                             19

<210> SEQ ID NO 73
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 73
gggtagggtt cagagaaggc                                            20

<210> SEQ ID NO 74
<211> LENGTH: 20
<212> TYPE: DNA
<213> ORGANISM: Artificial Sequence
<220> FEATURE:

<223> OTHER INFORMATION: Antisense oligonucleotide

<400> SEQUENCE: 74
actcctcctc ttgcagtgag                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 75
gctgttgtta tccttctgtg                                               20

<210> SEQ ID NO 76
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 76
atcgcgggaa gccagggttt                                               20

<210> SEQ ID NO 77
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 77
gccagaatag gttgagaggg a                                             21

<210> SEQ ID NO 78
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 78
gccgttcgaa actcctcctc t                                             21

<210> SEQ ID NO 79
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 79
ggtttccgct gtgctctgtg                                               20

<210> SEQ ID NO 80
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 80
acgttgcctc agaatctccc                                               20

```
<210> SEQ ID NO 81
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 81
ttcctcaatc aacctcttcc t                                              21

<210> SEQ ID NO 82
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 82
gtgatgtttc ctctgttgtc                                                20

<210> SEQ ID NO 83
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 83
cactttctag ctgcaccacc                                                20

<210> SEQ ID NO 84
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 84
ccgtccactt tcccatctcc t                                              21

<210> SEQ ID NO 85
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 85
cccgtccact ttcccatctc                                                20

<210> SEQ ID NO 86
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 86
cttcacagca ccagggcaga                                                20

<210> SEQ ID NO 87
<211> LENGTH: 21
<212> TYPE: DNA
<213> ORGANISM: Artificial Sequence
<220> FEATURE:
<223> OTHER INFORMATION: Antisense oligonucleotide
```

```
<400> SEQUENCE: 87
cccagcagtc gaagtttgtg a                                              21

<210> SEQ ID NO 88
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 88
ccggtctcag gtccaagatg                                                20

<210> SEQ ID NO 89
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 89
tggtggagaa ggtgcaggct                                                20

<210> SEQ ID NO 90
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 90
gattcaccaa gtttcacgca t                                              21

<210> SEQ ID NO 91
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 91
gacgaggtga aggagcaggt                                                20

<210> SEQ ID NO 92
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 92
tcggaactgg aggaacaact g                                              21

<210> SEQ ID NO 93
<211> LENGTH: 13
<212> TYPE: DNA
<213> ORGANISM: Artificial Sequence
<220> FEATURE:
<223> OTHER INFORMATION: Antisense oligonucleotide

<400> SEQUENCE: 93
tggagctcag ttt                                                       13

<210> SEQ ID NO 94
<211> LENGTH: 14
```

```
<212> TYPE: DNA
<213> ORGANISM: Artificial Sequence
<220> FEATURE:
<223> OTHER INFORMATION: Antisense oligonucleotide

<400> SEQUENCE: 94
tttctcgtgc agct                                                       14

<210> SEQ ID NO 95
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 95
ttctggcgcg tgcc                                                       14

<210> SEQ ID NO 96
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 96
ccctcgtgga gctc                                                       14

<210> SEQ ID NO 97
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 97
gcccgcgcgc agcg                                                       14

<210> SEQ ID NO 98
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 98
cggctccacc ttct                                                       14

<210> SEQ ID NO 99
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 99
ctggcggtag agct                                                       14

<210> SEQ ID NO 100
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 100
```

```
gctcgtgcag cttc                                                          14

<210> SEQ ID NO 101
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 101
cagcttctgg cgcg                                                          14

<210> SEQ ID NO 102
<211> LENGTH: 14
<212> TYPE: DNA
<213> ORGANISM: Artificial sequence
<220> FEATURE:
<223> OTHER INFORMATION: Antisense oligonucleotide

<400> SEQUENCE: 102
gcgcgcagcg gctc                                                          14

<210> SEQ ID NO 103
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 103
tccaccttct ggcg                                                          14

<210> SEQ ID NO 104
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 104
cggtgtagag ctcc                                                          14

<210> SEQ ID NO 105
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 105
ccatctcctc ctgc                                                          14

<210> SEQ ID NO 106
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 106
gaagtcgtcc agatccaaa                                                     19

<210> SEQ ID NO 107
<211> LENGTH: 19
<212> TYPE: DNA
<213> ORGANISM: Artificial Sequence
```

```
<220> FEATURE:
<223> OTHER INFORMATION: Antisense oligonucleotide

<400> SEQUENCE: 107
aagtcgtcca gatccaaat                                                19

<210> SEQ ID NO 108
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 108
agtcgtccag atccaaatg                                                19

<210> SEQ ID NO 109
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 109
gtcgtccaga tccaaatgg                                                19

<210> SEQ ID NO 110
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 110
tcgtccagat ccaaatggc                                                19

<210> SEQ ID NO 111
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 111
cgtccagatc caaatggca                                                19

<210> SEQ ID NO 112
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 112
gtccagatcc aaatggcaa                                                19

<210> SEQ ID NO 113
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 113
tccagatcca aatggcaaa                                                19
```

```
<210> SEQ ID NO 114
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 114
cagatccaaa tg                                                          12

<210> SEQ ID NO 115
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 115
agatccaaat ggcaaa                                                      16

<210> SEQ ID NO 116
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 116
agatccaaat gg                                                          12

<210> SEQ ID NO 117
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 117
gatccaaatg gc                                                          12

<210> SEQ ID NO 118
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 118
atccaaatgg ca                                                          12

<210> SEQ ID NO 119
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 119
tccaaatggc aa                                                          12

<210> SEQ ID NO 120
<211> LENGTH: 12
<212> TYPE: DNA
<213> ORGANISM: Artificial Sequence
<220> FEATURE:
<223> OTHER INFORMATION: Antisense oligonucleotide
```

-continued

<400> SEQUENCE: 120
ccaaatggca aa                                                                12

<210> SEQ ID NO 121
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 121
ccaaatggca aaccttctt                                                         19

<210> SEQ ID NO 122
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 122
atggcaaatc ttcttcatc                                                         19

<210> SEQ ID NO 123
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 123
aaatggcaaa ccttcttca                                                         19

<210> SEQ ID NO 124
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 124
aaatggcaaa tcttcttca                                                         19

<210> SEQ ID NO 125
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 125
atggcaaacc ttcttcatc                                                         19

<210> SEQ ID NO 126
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 126
ccaaatggca aatcttctt                                                         19

<210> SEQ ID NO 127

```
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 127
atggcaaacc ttctt                                                      15

<210> SEQ ID NO 128
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 128
atggcaaatc ttctt                                                      15

<210> SEQ ID NO 129
<211> LENGTH: 11
<212> TYPE: DNA
<213> ORGANISM: Artificial Sequence
<220> FEATURE:
<223> OTHER INFORMATION: Antisense oligonucleotide

<400> SEQUENCE: 129
cttcttcatc c                                                          11

<210> SEQ ID NO 130
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 130
ccaggaccca acccaca                                                    17

<210> SEQ ID NO 131
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 131
gctacttatt gctg                                                       14

<210> SEQ ID NO 132
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 132
tgctggaaac ctac                                                       14

<210> SEQ ID NO 133
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 133
```
ttccttggat tgaa                                         14

<210> SEQ ID NO 134
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 134
gcccacagca cttgca                                       16

<210> SEQ ID NO 135
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 135
caccaacagt gggtac                                       16

<210> SEQ ID NO 136
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 136
caacagacta gc                                           12

<210> SEQ ID NO 137
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 137
gaagaagggg tcct                                         14

<210> SEQ ID NO 138
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 138
gaattatgct ctcc                                         14

<210> SEQ ID NO 139
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 139
ctccagactt tcta                                         14

<210> SEQ ID NO 140
<211> LENGTH: 16
<212> TYPE: DNA

<213> ORGANISM: Artificial Sequence
<220> FEATURE:
<223> OTHER INFORMATION: Antisense oligonucleotide

<400> SEQUENCE: 140
aagtcacaca ggaagg                     16

<210> SEQ ID NO 141
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 141
gaaactagag aaaa                       14

<210> SEQ ID NO 142
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 142
aataattttt gaag                       14

<210> SEQ ID NO 143
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 143
gaagtattga aagt                       14

<210> SEQ ID NO 144
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 144
tgaaagtaca cggt                       14

<210> SEQ ID NO 145
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 145
ctggggcagg ggtg                       14

<210> SEQ ID NO 146
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 146
ggggtggagg gcag                       14

```
<210> SEQ ID NO 147
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 147
tgctccttcc tcag                                                      14

<210> SEQ ID NO 148
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 148
acccgggact tgctc                                                     15

<210> SEQ ID NO 149
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 149
tgtcagtgac agct                                                      14

<210> SEQ ID NO 150
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 150
tgtcagtgac agctagtgt                                                 19

<210> SEQ ID NO 151
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 151
gtcagtgaca gctagtgtg                                                 19

<210> SEQ ID NO 152
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 152
tcagtgacag ctagtgtga                                                 19

<210> SEQ ID NO 153
<211> LENGTH: 19
<212> TYPE: DNA
<213> ORGANISM: Artificial Sequence
<220> FEATURE:
```

<223> OTHER INFORMATION: Antisense oligonucleotide

<400> SEQUENCE: 153
agtgacagct agtgtgagt                                               19

<210> SEQ ID NO 154
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 154
tgacagctag tgtga                                                   15

<210> SEQ ID NO 155
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 155
tgacagctag tgtgagtac                                               19

<210> SEQ ID NO 156
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 156
gacagctagt gtgagtact                                               19

<210> SEQ ID NO 157
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 157
cagctagtgt gagtactct                                               19

<210> SEQ ID NO 158
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 158
agctagtgtg agtactctt                                               19

<210> SEQ ID NO 159
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 159
gctagtgtga gtactctta                                               19

```
<210> SEQ ID NO 160
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 160
ctagtgtgag tactcttat                                              19

<210> SEQ ID NO 161
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 161
ctagtgtgag tact                                                   14

<210> SEQ ID NO 162
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 162
tagtgtgagt actcttatg                                              19

<210> SEQ ID NO 163
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 163
agtgtgagta ctcttatgt                                              19

<210> SEQ ID NO 164
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 164
gtgtgagtac tcttatgtt                                              19

<210> SEQ ID NO 165
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 165
tgtgagtact cttatgttc                                              19

<210> SEQ ID NO 166
<211> LENGTH: 19
<212> TYPE: DNA
<213> ORGANISM: Artificial Sequence
<220> FEATURE:
<223> OTHER INFORMATION: Antisense oligonucleotide
```

```
<400> SEQUENCE: 166
gtgagtactc ttatgttca                                              19

<210> SEQ ID NO 167
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 167
tgagtactct tatgttcag                                              19

<210> SEQ ID NO 168
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 168
actcttatgt tcag                                                   14

<210> SEQ ID NO 169
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 169
tacctcttga cttt                                                   14

<210> SEQ ID NO 170
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 170
gactttgggg acaa                                                   14

<210> SEQ ID NO 171
<211> LENGTH: 13
<212> TYPE: DNA
<213> ORGANISM: Artificial Sequence
<220> FEATURE:
<223> OTHER INFORMATION: Antisense oligonucleotide

<400> SEQUENCE: 171
aaactgagct cca                                                    13

<210> SEQ ID NO 172
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 172
agctgcacga gaaa                                                   14

<210> SEQ ID NO 173
<211> LENGTH: 14
```

```
<212> TYPE: DNA
<213> ORGANISM: Artificial Sequence
<220> FEATURE:
<223> OTHER INFORMATION: Antisense oligonucleotide

<400> SEQUENCE: 173
ggcacgcgcc agaa                                                        14

<210> SEQ ID NO 174
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 174
gagctccacg aggg                                                        14

<210> SEQ ID NO 175
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 175
cgctgcgcgc gggc                                                        14

<210> SEQ ID NO 176
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 176
agaaggtgga gccg                                                        14

<210> SEQ ID NO 177
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 177
agctctaccg ccag                                                        14

<210> SEQ ID NO 178
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 178
gaagctgcac gagc                                                        14

<210> SEQ ID NO 179
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 179
```
cgcgccagaa gctg                                                          14

<210> SEQ ID NO 180
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 180
gagccgctgc gcgc                                                          14

<210> SEQ ID NO 181
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 181
cgccagaagg tgga                                                          14

<210> SEQ ID NO 182
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 182
ggagctctac accg                                                          14

<210> SEQ ID NO 183
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 183
gcaggaggag atgg                                                          14

<210> SEQ ID NO 184
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 184
tttggatctg gacgacttc                                                     19

<210> SEQ ID NO 185
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 185
atttggatct ggacgactt                                                     19

<210> SEQ ID NO 186
<211> LENGTH: 19
<212> TYPE: DNA
<213> ORGANISM: Artificial Sequence

```
<220> FEATURE:
<223> OTHER INFORMATION: Antisense oligonucleotide

<400> SEQUENCE: 186
catttggatc tggacgact                                              19

<210> SEQ ID NO 187
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 187
ccatttggat ctggacgac                                              19

<210> SEQ ID NO 188
<211> LENGTH: 19
<212> TYPE: DNA
<213> ORGANISM: Artificial sequence
<220> FEATURE:
<223> OTHER INFORMATION: Antisense oligonucleotide

<400> SEQUENCE: 188
gccatttgga tctggacga                                              19

<210> SEQ ID NO 189
<211> LENGTH: 19
<212> TYPE: DNA
<213> ORGANISM: Artificial sequence
<220> FEATURE:
<223> OTHER INFORMATION: Antisense oligonucleotide

<400> SEQUENCE: 189
tgccatttgg atctggacg                                              19

<210> SEQ ID NO 190
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 190
ttgccatttg gatctggac                                              19

<210> SEQ ID NO 191
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 191
tttgccattt ggatctgga                                              19

<210> SEQ ID NO 192
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 192
catttggatc tg                                                     12
```

```
<210> SEQ ID NO 193
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 193
tttgccattt ggatct                                                    16

<210> SEQ ID NO 194
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 194
ccatttggat ct                                                        12

<210> SEQ ID NO 195
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 195
gccatttgga tc                                                        12

<210> SEQ ID NO 196
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 196
tgccatttgg at                                                        12

<210> SEQ ID NO 197
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 197
tgccatttgg at                                                        12

<210> SEQ ID NO 198
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 198
tttgccattt gg                                                        12

<210> SEQ ID NO 199
<211> LENGTH: 19
<212> TYPE: DNA
<213> ORGANISM: Artificial Sequence
<220> FEATURE:
<223> OTHER INFORMATION: Antisense oligonucleotide
```

```
<400> SEQUENCE: 199
aagaaggttt gccatttgg                                                19

<210> SEQ ID NO 200
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 200
gatgaagaag atttgccat                                                19

<210> SEQ ID NO 201
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 201
tgaagaaggt ttgccattt                                                19

<210> SEQ ID NO 202
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 202
tgaagaagat ttgccattt                                                19

<210> SEQ ID NO 203
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 203
gatgaagaag gtttgccat                                                19

<210> SEQ ID NO 204
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 204
aagaagattt gccatttgg                                                19

<210> SEQ ID NO 205
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 205
aagaaggttt gccat                                                    15

<210> SEQ ID NO 206
```

```
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 206
aagaagattt gccat                                                        15

<210> SEQ ID NO 207
<211> LENGTH: 11
<212> TYPE: DNA
<213> ORGANISM: Artificial Sequence
<220> FEATURE:
<223> OTHER INFORMATION: Antisense oligonucleotide

<400> SEQUENCE: 207
ggatgaagaa g                                                            11

<210> SEQ ID NO 208
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 208
tgtgggttgg gtcctgg                                                      17

<210> SEQ ID NO 209
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 209
cagcaataag tagc                                                         14

<210> SEQ ID NO 210
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 210
gtaggtttcc agca                                                         14

<210> SEQ ID NO 211
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 211
ttcaatccaa ggaa                                                         14

<210> SEQ ID NO 212
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 212
```
tgcaagtgct gtgggc                                                        16

<210> SEQ ID NO 213
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 213
gtacccactg ttggtg                                                        16

<210> SEQ ID NO 214
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 214
gctagtctgt tg                                                            12

<210> SEQ ID NO 215
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 215
aggacccctt cttc                                                          14

<210> SEQ ID NO 216
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 216
ggagagcata attc                                                          14

<210> SEQ ID NO 217
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 217
tagaaagtct ggag                                                          14

<210> SEQ ID NO 218
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 218
ccttcctgtg tgactt                                                        16

<210> SEQ ID NO 219
<211> LENGTH: 14
<212> TYPE: DNA

```
-continued

<213> ORGANISM: Artificial Sequence
<220> FEATURE:
<223> OTHER INFORMATION: Antisense oligonucleotide

<400> SEQUENCE: 219
ttttctctag tttc                                                        14

<210> SEQ ID NO 220
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 220
cttcaaaaat tatt                                                        14

<210> SEQ ID NO 221
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 221
actttcaata cttc                                                        14

<210> SEQ ID NO 222
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 222
accgtgtact ttca                                                        14

<210> SEQ ID NO 223
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 223 caccccctgcc ccag                                                       14

<210> SEQ ID NO 224
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 224
ctgccctcca cccc                                                        14

<210> SEQ ID NO 225
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 225
ctgaggaagg agca                                                        14
```

<210> SEQ ID NO 226
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 226
gagcaagtcc cgggt                                                    15

<210> SEQ ID NO 227
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 227
agctgtcact gaca                                                     14

<210> SEQ ID NO 228
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 228
acactagctg tcactgaca                                                19

<210> SEQ ID NO 229
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 229
cacactagct gtcactgac                                                19

<210> SEQ ID NO 230
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 230
tcacactagc tgtcactga                                                19

<210> SEQ ID NO 231
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 231
actcacacta gctgtcact                                                19

<210> SEQ ID NO 232
<211> LENGTH: 15
<212> TYPE: DNA
<213> ORGANISM: Artificial Sequence
<220> FEATURE:

<223> OTHER INFORMATION: Antisense oligonucleotide

<400> SEQUENCE: 232
tcacactagc tgtca                                                    15

<210> SEQ ID NO 233
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 233
gtactcacac tagctgtca                                                19

<210> SEQ ID NO 234
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 234
agtactcaca ctagctgtc                                                19

<210> SEQ ID NO 235
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 235
agagtactca cactagctg                                                19

<210> SEQ ID NO 236
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 236
aagagtactc acactagct                                                19

<210> SEQ ID NO 237
<211> LENGTH: 19
<212> TYPE: DNA
<213> ORGANISM: Artificial sequence
<220> FEATURE:
<223> OTHER INFORMATION: Antisense oligonucleotide

<400> SEQUENCE: 237
taagagtact cacactagc                                                19

<210> SEQ ID NO 238
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 238
ataagagtac tcacactag                                                19

```
<210> SEQ ID NO 239
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 239
agtactcaca ctag                                                      14

<210> SEQ ID NO 240
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 240
cataagagta ctcacacta                                                 19

<210> SEQ ID NO 241
<211> LENGTH: 19
<212> TYPE: DNA
<213> ORGANISM: Artificial Seqiuence
<220> FEATURE:
<223> OTHER INFORMATION: Antisense oligonucleotide

<400> SEQUENCE: 241
acataagagt actcacact                                                 19

<210> SEQ ID NO 242
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 242
aacataagag tactcacac                                                 19

<210> SEQ ID NO 243
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 243
gaacataaga gtactcaca                                                 19

<210> SEQ ID NO 244
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 244
tgaacataag agtactcac                                                 19

<210> SEQ ID NO 245
<211> LENGTH: 19
<212> TYPE: DNA
<213> ORGANISM: Artificial Sequence
<220> FEATURE:
<223> OTHER INFORMATION: Antisense oligonucleotide
```

```
<400> SEQUENCE: 245
ctgaacataa gagtactca                                          19

<210> SEQ ID NO 246
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 246
ctgaacataa gagt                                               14

<210> SEQ ID NO 247
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 247
aaagtcaaga ggta                                               14

<210> SEQ ID NO 248
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 248
ttgtccccaa agtc                                               14

<210> SEQ ID NO 249
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 249
aagaaggttt gccat                                              15

<210> SEQ ID NO 250
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 250
tcacactagc tgtca                                              15

<210> SEQ ID NO 251
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 251
aagaaggttt gccat                                              15

<210> SEQ ID NO 252
<211> LENGTH: 15
```

```
<212> TYPE: DNA
<213> ORGANISM: Artificial Sequence
<220> FEATURE:
<223> OTHER INFORMATION: Antisense oligonucleotide

<400> SEQUENCE: 252
tcacactagc tgtca                                                    15

<210> SEQ ID NO 253
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 253
ctcctcctgc cacttcttct g                                             21

<210> SEQ ID NO 254
<211> LENGTH: 22
<212> TYPE: DNA
<213> ORGANISM: Artificial Sequence
<220> FEATURE:
<223> OTHER INFORMATION: Antisense oligonucleotide

<400> SEQUENCE: 254
ctggtggatg aagaaggttt gc                                            22

<210> SEQ ID NO 255
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 255
tttggatctg gacgacttc                                                19

<210> SEQ ID NO 256
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 256
caataagtag cctgt                                                    15

<210> SEQ ID NO 257
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 257
cacgctagtc tgttg                                                    15

<210> SEQ ID NO 258
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 258
```
cttccttcct gtgtg                                            15

<210> SEQ ID NO 259
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 259
caggctgagt taccg                                            15

<210> SEQ ID NO 260
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 260
gctagtctgt tg                                               12

<210> SEQ ID NO 261
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 261
gtctgatgga ga                                               12

<210> SEQ ID NO 262
<211> LENGTH: 6
<212> TYPE: DNA
<213> ORGANISM: Artificial Sequence
<220> FEATURE:
<223> OTHER INFORMATION: Antisense oligonucleotide

<400> SEQUENCE: 262 gctagt                                                      6

<210> SEQ ID NO 263
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 263
tgccatttgg atctggacg                                        19

<210> SEQ ID NO 264
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 23

<400> SEQUENCE: 264
cugacaccaa gcucauacuu uacaa                                 25

<210> SEQ ID NO 265
<211> LENGTH: 25
<212> TYPE: DNA

```
<213> ORGANISM: Artificial Sequence
<220> FEATURE:
<223> OTHER INFORMATION: Reverse complement of the antisense
      oligonucleotide SEQ ID NO: 24

<400> SEQUENCE: 265
cccagagaga gaacagccau ugatt                                           25

<210> SEQ ID NO 266
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 25

<400> SEQUENCE: 266
cucucaaagu gcuggaauua uaggt                                           25

<210> SEQ ID NO 267
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 41

<400> SEQUENCE: 267
gucuggugug gcugugacug accac                                           25

<210> SEQ ID NO 268
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 42

<400> SEQUENCE: 268
gucacagugu gguggagaa gggac                                            25

<210> SEQ ID NO 269
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 43

<400> SEQUENCE: 269
guagguggua gcugugucag ugctg                                           25

<210> SEQ ID NO 270
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 44

<400> SEQUENCE: 270
gcagauccau ccucagugaa gcaca                                           25

<210> SEQ ID NO 271
<211> LENGTH: 25
<212> TYPE: DNA
<213> ORGANISM: Artificial Sequence
```

```
<220> FEATURE:
<223> OTHER INFORMATION: Reverse complement of the antisense
      oligonucleotide SEQ ID NO: 45

<400> SEQUENCE: 271 ggugguguucu gaugagcguu ucuct                                25

<210> SEQ ID NO 272
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 46

<400> SEQUENCE: 272
ggcucagccu cuugugcuuc cuaag                                 25

<210> SEQ ID NO 273
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 47

<400> SEQUENCE: 273
gagcaaggug ggacagggag ccagg                                 25

<210> SEQ ID NO 274
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 48

<400> SEQUENCE: 274
guugaagcug gguguggaaa ugaac                                 25

<210> SEQ ID NO 275
<211> LENGTH: 19
<212> TYPE: DNA
<213> ORGANISM: Artificial Sequence
<220> FEATURE:
<223> OTHER INFORMATION: Probe Sequence

<400> SEQUENCE: 275
tttggatctg gacgacttc                                        19

<210> SEQ ID NO 276
<211> LENGTH: 21
<212> TYPE: DNA
<213> ORGANISM: Artificial Sequence
<220> FEATURE:
<223> OTHER INFORMATION: Forward Primer

<400> SEQUENCE: 276
ctcctcctgc cacttcttct g                                     21

<210> SEQ ID NO 277
<211> LENGTH: 22
<212> TYPE: DNA
<213> ORGANISM: Artificial Sequence
<220> FEATURE:
<223> OTHER INFORMATION: Reverse Primer
```

```
<400> SEQUENCE: 277
ctggtggatg aagaaggttt gc                                        22

<210> SEQ ID NO 278
<211> LENGTH: 12
<212> TYPE: DNA
<213> ORGANISM: Artificial sequence
<220> FEATURE:
<223> OTHER INFORMATION: Antisense oligonucleotide

<400> SEQUENCE: 278
gctagtctgt tg                                                   12

<210> SEQ ID NO 279
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 279
gtctgatgga ga                                                   12
```

TREATMENT OF LIPID TRANSPORT AND METABOLISM GENE RELATED DISEASES BY INHIBITION OF NATURAL ANTISENSE TRANSCRIPT TO A LIPID TRANSPORT AND METABOLISM GENE

The present Application is a Divisional of U.S. Ser. No. 13/318,713 filed Nov. 3, 2011, which is a 371 of International Application No. PCT/US2010/033908 filed May 6, 2010, which claims the priority to U.S. Provisional Patent Application Nos. 61/175,930 filed May 6, 2009, 61/176,267 filed May 7, 2009, 61/180,646 filed May 22, 2009, 61/235,227 filed Aug. 19, 2009, and 61/248,212 filed Oct. 2, 2009, which are incorporated herein by reference in their entireties.

FIELD OF THE INVENTION

Embodiments of the invention comprise oligonucleotides modulating expression and/or function of a Lipid transport and metabolism gene and associated molecules.

BACKGROUND

DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drug, VITRAVENE™ (for treatment of cytomegalovirus retinitis), reflecting that antisense has therapeutic utility.

SUMMARY

This Summary is provided to present a summary of the invention to briefly indicate the nature and substance of the invention. It is submitted with the understanding that it will not be used to interpret or limit the scope or meaning of the claims.

In one embodiment, the invention provides methods for inhibiting the action of a natural antisense transcript by using antisense oligonucleotide(s) targeted to any region of the natural antisense transcript resulting in up-regulation of the corresponding sense gene. It is also contemplated herein that inhibition of the natural antisense transcript can be achieved by siRNA, ribozymes and small molecules, which are considered to be within the scope of the present invention.

One embodiment provides a method of modulating function and/or expression of a Lipid transport and metabolism gene polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of a polynucleotide comprising 5 to 30 consecutive nucleotides within nucleotides 1 to 1299 of SEQ ID NO: 8, 1 to 918 of SEQ ID NO: 9, 1 to 1550 of SEQ ID NO: 10, 1 to 329 of SEQ ID NO: 11, 1 to 1826 of SEQ ID NO: 12, 1 to 536 of SEQ ID NO: 13, 1 to 551 of SEQ ID NO: 14, 1 to 672 of SEQ ID NO: 15, 1 to 616 of SEQ ID NO: 16, 1 to 471 of SEQ ID NO: 17, 1 to 707 of SEQ ID NO: 18, 1 to 741 of SEQ ID NO: 19, 1 to 346 of SEQ ID NO: 20, 1 to 867 of SEQ ID NO: 21, 1 to 563 of SEQ ID NO: 22 (FIG. 3) thereby modulating function and/or expression of the Lipid transport and metabolism gene polynucleotide in patient cells or tissues in vivo or in vitro.

In another preferred embodiment, an oligonucleotide targets a natural antisense sequence of a Lipid transport and metabolism gene polynucleotide, for example, nucleotides set forth in SEQ ID NO: 8 to 22, and any variants, alleles, homologs, mutants, derivatives, fragments and complementary sequences thereto. Examples of antisense oligonucleotides are set forth as SEQ ID NOS: 23 to 263 (FIGS. 4 to 9).

Another embodiment provides a method of modulating function and/or expression of a Lipid transport and metabolism gene polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of the an antisense of the Lipid transport and metabolism gene polynucleotide; thereby modulating function and/or expression of the Lipid transport and metabolism gene polynucleotide in patient cells or tissues in vivo or in vitro.

Another embodiment provides a method of modulating (unction and/or expression of a Lipid transport and metabolism gene polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to a Lipid transport and metabolism gene antisense polynucleotide; thereby modulating function and/or expression of the Lipid transport and metabolism gene polynucleotide in patient cells or (issues in vivo or in vitro.

In a preferred embodiment, a composition comprises one or more antisense oligonucleotides which bind to sense and/or antisense Lipid transport and metabolism gene polynucleotides.

In another preferred embodiment, the oligonucleotides comprise one or more modified or substituted nucleotides.

In another preferred embodiment, the oligonucleotides comprise one or more modified bonds.

In yet another embodiment, the modified nucleotides comprise modified bases comprising phosphorothioate, methylphosphonate, peptide nucleic acids, 2'-O-methyl, fluoro- or carbon, methylene or other locked nucleic acid (LNA) molecules. Preferably, the modified nucleotides are locked nucleic acid molecules, including .alpha.-L-LNA.

In another preferred embodiment, the oligonucleotides are administered to a patient subcutaneously, intramuscularly, intravenously or intraperitoneally.

In another preferred embodiment, the oligonucleotides are administered in a pharmaceutical composition. A treatment regimen comprises administering the antisense compounds at least once to patient; however, this treatment can be modified to include multiple doses over a period of time. The treatment can be combined with one or more other types of therapies.

In another preferred embodiment, the oligonucleotides are encapsulated in a liposome or attached to a carrier molecule (e.g. cholesterol, TAT peptide).

Other aspects are described infra.

BRIEF DESCRIPTION OF THE DRAWINGS

FIG. 1C is a graph of real time PCR results showing the fold change+standard deviation in ABCA1 mRNA after treatment of 3T3 cells with phosphorothioate oligonucleotides introduced using Lipofectamine 2000, as compared to control. Real time PCR results show that the levels of ABCA1 mRNA in 3T3 cells are significantly increased 48 h after treatment with three of the oligos designed to mouse ABCA1 antisense BF133827. Bars denoted as CUR-1087 to CUR-1090, CUR-1092 and CUR-1091 correspond to samples treated with SEQ ID NOS: 35 to 38, 40 and 39 respectively.

FIG. 1D is a graph of real time PCR results showing the fold change+standard deviation in LCAT mRNA after treatment of Hek293 cells with siRNA and phosphorothioate oligonucleotides introduced using Lipofectamine 2000, as compared to control. Real time PCR results show that the levels of the LCAT mRNA in Hek293 cells are significantly increased 48 h after treatment with three of the oligos designed to LCAT antisense Hs.668679. Bats denoted as CUR-0476, CUR-0478. CUR-0822, CUR-0820 and CUR-0819 correspond to samples treated with SEQ ID NOS: 41, 42, 58, 56 and 55 respectively.

FIG. 1N to FIG. 1P represent a graphs of real time PCR results showing the fold change-standard deviation in ApoA1 mRNA after treatment of HepG2 cells with phosphorothioate oligonucleotides introduced using Lipofectamine 2000, as compared to control. Real time PCR results show that the levels of ApoA1 mRNA in HepG2 cells are significantly increased 48 h after treatment with some of the antisense oligonucleotides to ApoA1 antisense DA327409ext. Bars RH3-RH597, correspond to samples treated with SEQ ID NOS 171 to 248 respectively.

FIG. 2 shows
SEQ ID NO: 1: *Homo sapiens* ATP-binding cassette, subfamily A (ABC1) member 1 (ABCA1), mRNA (NCBI Accession No.: NM.sub.--005502).
SEQ ID NO: 2: *Homo sapiens* lecithin-cholesterol acyltransferase (LCAT), mRNA (NCBI Accession No.: NM.sub.--000229.1).
SEQ ID NO: 3: *Homo sapiens* low density lipoprotein receptor-related protein 1 (LRP1). mRNA (NCBI Accession No.: NM.sub.--002332.2).
SEQ ID NO: 4: *Mus musculus* low density lipoprotein receptor-related protein 1 (Lrp1), mRNA (NCBI Accession No.: NM.sub.--008512.2).
SEQ ID NO: 5: *Homo sapiens* low density lipoprotein receptor (LDLR), mRNA (NCBI Accession No.: NM.sub.-000527.3).
SEQ ID NO: 6: *Homo sapiens* apolipoprotein E (APOE), mRNA (NCBI Accession No.: NM.sub.--000041.2).
SEQ ID NO: 7: *Homo sapiens* apolipoprotein A-I (APOA1), mRNA (NCBI Accession No.: NM.sub.--000039).

FIG. 3 shows
SEQ ID NO: 8: Human Natural ABCA1 antisense sequence (AK311445)
SEQ ID NO: 9: Mouse Natural ABCA1 antisense sequence (BF133827)
SEQ ID NO: 10: Human Natural LCAT antisense sequence (Hs.668679)
SEQ ID NO: 11: Human Natural LCAT antisense sequence (Hs.593769)
SEQ ID NO: 12: Human Natural LCAT antisense sequence (Hs.387239)
SEQ ID NO: 13: Human Natural LRP1 antisense sequence (Hs.711951)
SEQ ID NO: 14: Human Natural LRP1 antisense sequence (DC401271)
SEQ ID NO: 15: Human Natural LRP1 antisense sequence (BM933147)
SEQ ID NO: 16: Mouse Natural LRP1 antisense sequence (CK626173)
SEQ ID NO: 17: Mouse Natural LRP1 antisense sequence (AW544265) SEQ ID NO: 18: Human Natural ABCA1 antisense sequence (bloflor.aApr07)
SEQ ID NO: 19: Human Natural ABCA1 antisense sequence (sherflor.aApr07)
SEQ ID NO: 20: Natural APOE antisense sequence (Hs.626623)
SEQ ID NO: 21: Natural APOE antisense sequence (Hs.714236)
SEQ ID NO: 22: Natural APOA1 antisense sequence (DA327409 extended)

FIG. 4 shows the ABCA1 antisense oligonucleotides, SEQ ID NOs: 23 to 40. * indicates phosphothioate bond.

FIG. 5 shows the LCAT antisense oligonucleotides, SEQ ID NOs: 41 to 58. * indicates phosphothioate bond.

FIG. 6 shows the LRP1 antisense oligonucleotides, SEQ ID NOs: 59 to 73. * indicates phosphothioate bond.

FIG. 7 shows the LDLR antisense oligonucleotides, SEQ ID NOs: 74 to 83. * indicates phosphothioate bond.

FIG. 8 shows the ApoE antisense oligonucleotides, SEQ ID NOs: 84 to 92. * indicates phosphothioate bond.

FIG. 9 shows the ApoA1 antisense oligonucleotides, SEQ ID NOs: 93 to 263. * indicates phosphothioate bond.

FIG. 10 shows the ABCA1 sense oligonucleotides, SEQ ID NOs: 264 to 266. The sense oligonucleotides SEQ ID NOs: 264 to 266 are the reverse complements of the antisense oligonucleotides SEQ ID NOs: 23 to 25 respectively.

FIG. 11 shows the LCAT sense oligonucleotides, SEQ ID NOs: 267 to 274. The sense oligonucleotides SEQ ID NOs: 267 to 274 are the reverse complements of the antisense oligonucleotides SEQ ID NOs: 41 to 48 respectively.

FIG. 12 shows:
SEQ ID NOs: 275 to 277: correspond to the probe sequence, forward primer sequence and the reverse primer sequence respectively with respect to the custom designed assay for ApoA1 antisense DA327409ext
SEQ ID NO: 278: corresponds to CUR 962, * indicates phosphothioate bond and + indicates LNA.
SEQ ID NO: 279: corresponds to CUR 963, * indicates phosphothioate bond and + indicates LNA.

DETAILED DESCRIPTION

Figure 1A:
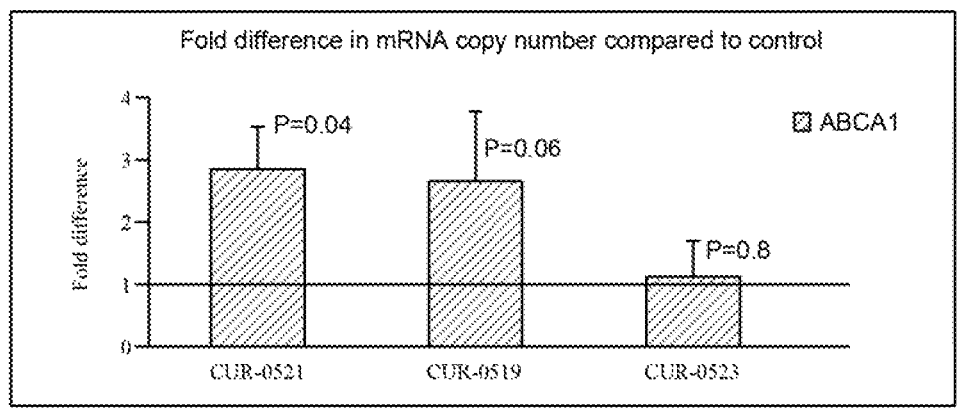
FIG. 1A is a graph of real time PCR results showing the fold change+standard deviation in ABCA1 mRNA after treatment of 518A2 cells with siRNA oligonucleotides introduced using Lipofectamine 2000, as compared to control. Real time PCR results show that the levels of ABCA1 mRNA in 518A2 cells are significantly increased 48 h after treatment with one of the siRNAs designed to ABCA1 antisense AK311445. Bars denoted as CUR-0521, CUR-0519 and CUR-0523 correspond to samples treated with SEQ ID NOS: 23 to 25 respectively.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "mRNA" means the presently known mRNA transcript(s) of a targeted gene, and any further transcripts which may be elucidated.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA (Eguchi et al., (1991) Ann. Rev. Biochem. 60, 631-652). An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoogsteen or reverse Hogsteen types of base pairing, or the like.

The oligonucleotide may be "chimeric", that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register" that is, when the monomers are linked consecutively, as in native DNA, or linked via spacers. The spacers are intended to constitute a covalent "bridge" between the regions and have in preferred cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

As used herein "Lipid transport and metabolism genes" are inclusive of all family members, mutants, alleles, fragments, species, coding and noncoding sequences, sense and antisense polynucleotide strands, etc.

As used herein, the words ATP-binding cassette 1; Lipid transport and metabolism gene; ABC transporter 1; cholesterol efflux regulatory protein (CERP), ABCA1, ABC-1, ABC1, CERP; FLJ14958; HDLDT1; TGD are used interchangeably in the present application.

As used herein, the words Lecithin-cholesterol acyltransferase, LCAT, Phosphatidylcholine-sterol acyltransferase, Phospholipid-cholesterol acyltransferase are used interchangeably in the present application.

As used herein, the words A2MR, Alpha-2-macroglobulin receptor, APOER, Apolipoprotein E receptor, APR, CD91, FLJ16451, IGFBP3R, LRP, LRP-1, MGC88725, Prolow-density lipoprotein receptor-related protein 1, TGFBR5 are used interchangeably in the present application.

As used herein, the words LDLR, FH, FHC, LDLCQ2, LDL receptor, Low-density lipoprotein receptor are used interchangeably in the present application.

As used herein, the words ADZ, Apo-E, ApoE, Apolipoprotein E, LDLCQ5, LPG, MGC1571 are used interchangeably in the present application.

As used herein, the words ApoA1, Apo-A1, Apolipoprotein A1, MGC117399 are used interchangeably in the present application.

As used herein, the term "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

As used herein, the term "target nucleic acid" encompasses DNA, RNA (comprising premRNA and mRNA) transcribed from such DNA and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense" The functions of DNA to be interfered include, for example, replication and transcription. The functions of RNA to be interfered, include all vital functions such as, for example, translocation of the RNA to the she of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences (Caplen, N.J., et al. (2001) Proc. Natl. Acad. Sci. USA 98:9742-9747). In certain embodiments of the present invention, the mediators are 5-25 nucleotide "small interfering" RNA duplexes (siRNAs). The siRNAs are derived from the processing of dsRNA by an RNase enzyme known as Dicer (Bernstein, E., et al. (2001) Nature 409:363-366). siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion (Bernstein, E., et al. (2001) Nature 409:363-366; Boutla, A., et al. (2001) Curr Biol. 11:1776-1780). Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the ease of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

By "enzymatic RNA" is meant an RNA molecule with enzymatic activity (Cech, (1988) J. American. Med. Assoc. 260, 3030-3035). Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al. (1990) Cell, 63, 601-608). This is meant to be a specific example. Those in the art will recognize that this is but one example, and other embodiments can be readily generated using techniques generally known in the art.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphornates, phosphoroselenoate, phosphoramidate, and the like, as more fully described below.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in Benner et at, U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Kornberg and Baker, DNA Replication, 2nd Ed. (Freeman, San Francisco, 1992) as well as their analogs.

"Analogs" in reference to nucleotides includes synthetic nucleotides having modified base moieties and/or modified sugar moieties (sec e.g., described generally by Scheit, Nucleotide Analogs, John Wiley, New York, 1980; Freier & Altmann, (1997) Nucl. Acid. Res., 25(22), 4429-4443, Toulme, J. J., (2001) Nature Biotechnology 19:17-18; Manoharan M., (1999) Biochemica et Biophysica Acta 1489:117-139; Freier S. M., (1997) Nucleic Acid Research, 25:4429-4443, Uhlman, E., (2000) Drug Discovery & Development, 3: 203-213, Herdewin P., (2000) Antisense & Nucleic Acid Drug Dev., 10:297-310); 2'-0, 3'-C-linked [3.2.0] bicycloarabinonucleosides (see e.g. N. K Christiensen, et al, (1998) J. Am. Chem. Soc., 120: 5458-5463; Prakash T P, Bhat B. (2007) Curr Top Med Chem. 7(7):641-9; Cho E J, et al. (2009) Annual Review of Analytical Chemistry, 2, 241-264). Such analogs include synthetic nucleotides designed to enhance binding properties, e.g., duplex or triplex stability, specificity, or the like.

As used herein, "hybridization" means the pairing of substantially complementary strands of oligomeric compounds. One mechanism of pairing involves hydrogen bonding, which may be Watson-Crick, Hoogsteen or reversed Hoogsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal (unction of the target nucleic acid to cause a modulation of (unction and/or activity, and there is a sufficient degree of complementarity to avoid non-specific binding of the antisense compound to non-target nucleic acid sequences under conditions in which specific binding is desired, i.e., under physiological conditions in the ease of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (<0.15M) of salts with inorganic cations such as Na++ or K++ (i.e., low ionic strength), temperature higher than 20.degree. C.-25.degree. C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1.times, sodium chloride-sodium citrate buffer (SSC)/0.1% (w/v) SDS at 60.degree. C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art dial the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., (1990) J. Mol. Biol., 215, 403-410; Zhang and Madden, Genome Res., 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., (1981) 2, 482-489).

As used herein, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 8.3 and the temperature is at least about 30.degree. C. for short oligonucleotides (e.g., 10 to 50 nucleotide). Stringent conditions may also be achieved with the addition of destabilizing agents such as formamide.

As used herein, "modulation" means either an increase (stimulation) or a decrease (inhibition) in the expression of a gene.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

As used herein, "cancer" refers to all types of cancer or neoplasm or malignant tumors found in mammals, including, but not limited to: leukemias, lymphomas, melanomas, carcinomas and sarcomas. The cancer manifests itself as a "tumor" or tissue comprising malignant cells of the cancer. Examples of tumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Additional cancers which can be treated by the disclosed composition according to the invention include but not limited to, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

"Neurological disease or disorder" refers to any disease or disorder of the nervous system and/or visual system. "Neurological disease or disorder" include disease or disorders that involve the central nervous system (brain, brainstem and cerebellum), the peripheral nervous system (including cranial nerves), and the autonomic nervous system (parts of which are located in both central and peripheral nervous system). Examples of neurological disorders include but are not limited to, headache, stupor and coma, dementia, seizure, sleep disorders, trauma, infections, neoplasms, neuroopthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological disorder. The following is a list of several neurological disorders, symptoms, signs and syndromes that can be treated using compositions and methods according to the present invention: acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder, autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (inducting glioblastoma multiforme); spinal tumor; Brown-Sequard syndrome; Canavan disease; carpal tunnel syndrome; causalgia; central pain syndrome; central pontine myelinolysis; cephalic disorder, cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; DandyWalker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy, Erb's palsy; essential tremor; Fabry's disease; Fahr's syndrome; feinting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactic a polyneuritiformis; herpes zoster oticus; herpes zoster. Hirayama syndrome; HIV associated dementia and neuropathy (also neurological manifestations of AIDS); holoprosencephaly, Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Keams-Sayre syndrome; Kennedy disease Kinsboume syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease-neurological sequelae; Machado-Joscph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; p muscular dystrophy; myasthenia gravis; myclinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Neurodegenerative disease or disorder (Parkinson's disease, Huntington's disease, Alzheimer's disease, amyotrophic lateral sclerosis (ALS), dementia, multiple sclerosis and other diseases and disorders associated with neuronal cell death); paramyotonia congenital; paraneoplastic diseases; paroxysmal attacks; Parry Romberg syndrome; Pelizaeus-Merzbacher disease; periodic paralyses; peripheral neuropathy, painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocalleukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy, Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel- Lindau disease; Wallenberg's syndrome; Werdnig-Hoffman disease; West syndrome; whiplash; Williams syndrome; Wildon's disease; and Zellweger syndrome.

An "Inflammation" refers to systemic inflammatory conditions and conditions associated locally with migration and attraction of monocytes, leukocytes and/or neutrophils. Examples of inflammation include, but are not limited to, Inflammation resulting from infection with pathogenic organisms (including gram-positive bacteria, gram-negative bacteria, viruses, fungi, and parasites such as protozoa and helminths), transplant rejection (including rejection of solid organs such as kidney, liver, heart, lung or cornea, as well as rejection of bone marrow transplants including graft-versus-host disease (GVHD)), or from localized chronic or acute autoimmune or allergic reactions. Autoimmune diseases include acute glomerulonephritis; rheumatoid or reactive arthritis; chronic glomerulonephritis; inflammatory bowel diseases such as Crohn's disease, ulcerative colitis and necrotizing enterocolitis; granulocyte transfusion associated syndromes; inflammatory dermatoses such as contact dermatitis, atopic dermatitis, psoriasis; systemic lupus erythematosus (SLE), autoimmune thyroiditis, multiple sclerosis, and some forms of diabetes, or any other autoimmune state where attack by the subject's own immune system results in pathologic tissue destruction. Allergic reactions include allergic asthma, chronic bronchitis, acute and delayed hypersensitivity. Systemic inflammatory disease states include inflammation associated with trauma, burns, reperfusion following ischemic events (e.g. thrombotic events in heart, brain, intestines or peripheral vasculature, including myocardial infarction and stroke), sepsis, ARDS or multiple organ dysfunction syndrome. Inflammatory cell recruitment also occurs in atherosclerotic plaques. Inflammation includes, but is not limited to, Non-Hodgkins lymphoma, Wegener's granulomatosis, Hashimoto's thyroiditis, hepatocellular carcinoma, thymus atrophy, chronic pancreatitis, rheumatoid arthritis, reactive lymphoid hyperplasia, osteoarthritis, ulcerative colitis, papillary carcinoma, Crohn's disease, ulcerative colitis, acute cholecystitis, chronic cholecystitis, cirrhosis, chronic sialadenitis, peritonitis, acute pancreatitis, chronic pancreatitis, chronic Gastritis, adenomyosis, endometriosis, acute cervicitis, chronic cervicitis, lymphoid hyperplasia, multiple sclerosis, hypertrophy secondary to idiopathic thrombocytopenic purpura, primary IgA nephropathy, systemic lupus erythematosus, psoriasis, pulmonary emphysema, chronic pyelonephritis, and chronic cystitis.

A cardiovascular disease or disorder includes those disorders that can either cause ischemia or are caused by reperfusion of the heart. Examples include, but are not limited to, atherosclerosis, coronary artery disease, granulomatous myocarditis, chronic myocarditis (non-granulomatous), primary hypertrophic cardiomyopathy, peripheral artery disease (PAD), stroke, angina pectoris, myocardial infarction, cardiovascular tissue damage caused by cardiac arrest, cardiovascular tissue damage caused by cardiac bypass, cardiogenic shock, and related conditions that would be known by those of ordinary skill in the art or which involve dysfunction of or tissue damage to the heart or vasculature, especially, but not limited to, tissue damage related to a Lipid transport and metabolism gene activation. CVS diseases include, but are not limited to, atherosclerosis, granulomatous myocarditis, myocardial infarction, myocardial fibrosis secondary to valvular heart disease, myocardial fibrosis without infarction, primary hypertrophic cardiomyopathy, and chronic myocarditis (non-granulomatous).

A 'Metabolic disease or disorder' refers to a wide range of diseases and disorders of the endocrine system including, for example, insulin resistance, diabetes, obesity, impaired glucose tolerance, high blood cholesterol, hyperglycemia, hyperinsulinemia, dyslipidemia and hyperlipidemia.

Polynucleotide and Oligonucleotide Compositions and Molecules

Targets

In one embodiment, the targets comprise nucleic acid sequences of a Lipid transport and metabolism genes, including without limitation sense and/or antisense noncoding and/or coding sequences associated with a Lipid transport and metabolism gene.

In one embodiment, the targets comprise nucleic acid sequences of ABCA1, including without limitation sense and/or antisense noncoding and/or coding sequences associated with ABC A1 gene.

In one embodiment, the targets comprise nucleic acid sequences of LCAT, including without limitation sense and/or antisense noncoding and/or coding sequences associated with LCAT gene.

In one embodiment, the targets comprise nucleic acid sequences of LRP1, including without limitation sense and/or antisense noncoding and/or coding sequences associated with LRP1 gene.

In one embodiment, the targets comprise nucleic acid sequences of low density lipoprotein receptor (LDLR), including without limitation sense and/or antisense noncoding and/or coding sequences associated with LDLR.

In one embodiment, the targets comprise nucleic acid sequences of apolipoprotein (ApoA1), including without limitation sense and/or antisense noncoding and/or coding sequences associated with ApoA. Human apolipoprotein A-I (ApoA-I) is the major protein constituent of high-density lipoproteins (HDL and lymph chylomicrons. In human plasma four major circulating lipoproteins have been named: chylomicrons (CM), very low-density lipoproteins (VLDL), low-density lipoproteins (LDL), and high-density lipoproteins (HDL). HDL is involved in the removal of cholesterol from peripheral tissues by transporting it to the liver or to other lipoproteins.

ATP-binding cassette, sub family-A (ABCAI) member I ABCAI functions as a cholesterol efflux pump in the cellular lipid removal pathway.

ATP-binding cassette transporters (ABC-transporter) are members of a protein superfamily that is one of the largest and most ancient families with representatives in all extant phyla from prokaryotes to humans. ABC transporters are transmembrane proteins that utilize the energy of adenosine triphosphate (ATP) hydrolysis to carry out certain biological processes including translocation of various substrates across membranes and non-transport-related processes such as translation of RNA and DNA repair. They transport a wide variety of substrates across extra- and intracellular membranes, including metabolic products, lipids and sterols, and drugs. Proteins are classified as ABC transporters based on the sequence and organization of their ATP-binding cassette (ABC) domain(s). ABC transporters are involved in tumor resistance, cystic fibrosis, bacterial multidrug resistance, and a range of other inherited human diseases.

The membrane-associated protein encoded by ABC1 gene is a member of the superfamily of ATP-binding cassette (ABC) transporters. ABC proteins transport various molecules across extra- and intracellular membranes. ABC genes are divided into seven distinct subfamilies (ABCA, MDRITAP, MRP, ALD, OABP, GCN20, White). This protein is a member of the ABCA subfamily. Members of the ABCA subfamily comprise the only major ABC subfamily found exclusively in multicellular eukaryotes. With cholesterol as its substrate, this protein functions as a cholesterol efflux pump in the cellular lipid removal pathway.

In preferred embodiments, antisense oligonucleotides are used to prevent or treat diseases or disorders associated with ATP-Binding cassette molecules. ATP-binding cassette transporter ABC1 (member 1 of human transporter subfamily ABCA), also known as the cholesterol efflux regulatory protein (CERP) is a protein which in humans is encoded by the ABC1 gene. This transporter is a major regulator of cellular cholesterol and phospholipid homeostasis.

ABC1 is present in high-density lipoproteins (HDL) which permits the removal of excessive cholesterol and phospholipids from human cell membranes. Since this protein is needed throughout the body it is synthesis ubiquitously as a 220-kDa protein. It is present in higher quantities in tissues that shuttle or are involved in the turnover of lipids such as the liver, the small intestine and adipose tissue.

Factors that act upon the ABC1 transporter's expression or its posttranslational modification are also molecules that are involved in its subsequent function like fatty acids, cholesterol and also cytokines and cyclic adenosine monophosphate.

Low-density lipoprotein receptor-related protein 1 (LPR1) is about 4544 amino acids; 504575 Da. It is a heterodimer of an 85-kDa membrane-bound carboxyl subunit and a noncovalently attached 515-kDa amino-terminal subunit. Intracellular domain interacts with MAFB. LPR1 is found in a complex with PIDIIPCLI1, LRP1 and CUBNI. Interacts with SNX17, PIDIIPCLI1, PDGF, LRPAP1 and CUBN. The intracellular domain interacts with SHC1, GULPI and DAB1.

LRP1 is an endocytic receptor involved in endocytosis and in phagocytosis of apoptotic cells; early embryonic development; cellular lipid homeostasis; plasma clearance of chylomicron remnants and activated LRPAP1 (alpha 2-macroglobulin); local metabolism of complexes between plasminogen activators and their endogenous inhibitors. Without wishing to be bound by theory, it may modulate cellular events, such as APP metabolism, kinase-dependent intracellular signaling, neuronal calcium signaling as well as neurotransmission.

High density lipoprotein (HDL) picks up extra cholesterol in the blood and returns it to the liver Low density lipoprotein (or LDL) is the main transporter of cholesterol in the body. But too much LDL over many years can result in atherosclerosis (the narrowing and hardening of arteries) and lead to heart disease or a heart attack. The ratio is determined by dividing the LDL cholesterol into the HDL cholesterol. For example, if a person has an HDL cholesterol of 50 mg/dL and an LDL cholesterol of 150 mg/dL, the HDL/LDL ratio would be 0.33. The goal is to keep the HDL/LDL ratio above 0.3, with the ideal HDL/LDL ratio being above 0.4.

HDL are synthesized de novo in both the liver and small intestine as protein-rich disc-shaped particles. The primary apoproteins of HDL are apoA-1, apoA-II, apoC-I, apoC-II, and apoE. Newly formed HDL contain very little cholesterol and cholesteryl esters. HDL are converted from their initial discoidal shape into spherical lipoprotein particles through the accumulation of cholesteryl esters in the neutral core of the lipoprotein particle. Cholesterol is accumulated by HDL from chylomicron remnants VLDL remnants (also called intermediate density Lipoproteins or IDL) and directly from cell surface membranes. The cholesterol is esterified through the action of an HDL-associated enzyme lecithin:cholesterol acyltransferase ("LCAT"). For LCAT to transfer a fatty acid from lecithin (phosphatidylcholine) to the C-3-OH group of cholesterol, interaction with ApoA-I found on the HDL surface is required. This accumulation of core cholesteryl esters converts nascent HDL to HDL2 and HDL3. Sec R. I. Levy et al., "The structure, function and metabolism of high-density lipoproteins: A status report," Circulation, vol. 62, pp. IV4-8 (1980); and D. I. Silverman et al., "High-density lipoprotein subfractions," Am. J. Med., vol. 94, pp. 636-45 (1993).

HDL are usually isolated from the plasma by ultracentrifugation. The normal HDL density range is from 1.063 g/mL to 1.21 g/mL, which divides roughly into two ranges HDL2 (1.063 g/mL to 1.125 g/mL) and HDL3 (1.125 g/mL to 1.21 g/mL). More recently, two major populations of particles in HDL have been identified by two dimensional electrophoresis followed by immunoblotting and enzyme-linked differential antibody immunosorbent assay. One of these populations contains particles with apoA-I alone, and the other contains particles with both apoA-I and apoA-II. The relative proportion of apoA-I particles is highest in the HDL2 fraction, while HDL3 is more a combination of apoA-I and apoA-II. See J. C. Fruchart et al., "Apolipoprotein A-containing lipoprotein particles: physiological role, quantification, and clinical significance," Clin. Chem., vol. 38, pp. 793-7 (1992); and B. F. Asztalos et al., "Normolipidemic subjects with low HDL cholesterol levels have altered HDL subpopulations," Arteriosder. Thromb. Vasc. Biol., vol. 17, pp. 1885-1893 (1997).

Human apolipoprotein A-I (ApoA-I) is the major protein constituent of HDL and lymph chylomicrons. ApoA-I is primarily synthesized in the liver and small intestine as a precursor protein (preproapo A-I). Preproapo A-I is cleaved intracellularly to form proapo A-I, the form secreted into the plasma and lymph. In the plasma, six amino acids are cleaved from proapo A-I to form mature ApoA-I.

Mature ApoA-I is a single unglycosylated polypeptide composed of 243 amino acids of known sequence. ApoA-I serves as a cofactor of a plasma enzyme (lecithin-cholesterol acyltransferase (LCAT)), responsible for the formation of most cholesterol esters in plasma. Decreased levels of ApoA-I may result in disorders of the plasma lipid transport system and in the development of coronary heart disease. Low levels of both ApoA-I and HDL has been shown to be a strong risk factor for heart attacks and other atherosclerotic vascular diseases. Sec U.S. Pat. Nos. 5,059,528 and 6,258,596.

Apolipoprotein E (ApoE) is an apoprotein found in the chylomicron and intermediate-density lipoproteins (IDLs) that binds to a specific receptor cm liver cells and peripheral cells. Intermediate-density lipoproteins belong to the lipoprotein particle family and are formed from the degradation of very low-density lipoproteins. IDL is one of the five major groups of lipoproteins (chylomicrons, VLDL, IDL, LDL, HDL) that enable fats and cholesterol to move within the water-based solution of the bloodstream. Apolipoprotein E (ApoE) is important for the normal catabolism of triglyceride-rich lipoprotein constituents.

The APOE gene, ApoE, is mapped to chromosome 19 in a cluster with Apolipoprotein C1 and Apolipoprotein C2. ApoE consists of four exons and three introns, totaling 3597 base pairs. In melanocytic cells APOE gene expression may be regulated by microphthalmia-associated transcription factor (MITF). The gene is polymorphic with three major alleles, ApoE2, ApoE3, ApoE4, which translate into three isoforms of the protein: normal-ApoE-E3; dysfunctional- ApoE-E2 and ApoE-E4. These iso forms differ from each other only by single amino acid substitutions at positions 112 and 158.

Lecithin-cholesterol acyltransferase (LCAT), is a plasma enzyme produced by the liver and catalyzes the conversion of cholesterol to cholesteryl esters on lipoproteins by the transacylation of fatty acid from the sn-2 position of phosphatidylcholine to the 3-hydroxyl group on the A-ring of cholesterol. Most LCAT activity is found on high-density lipoprotein (HDL) but approximately 30% is also on apolipoprotein (Apo) B-containing lipoproteins.

The apolipoprotein E gene is polymorphic with three major alleles, ApoE2, ApoE3, ApoE4. E2 is associated with the genetic disorder type III hyperlipoproteinemia and with both increased and decreased risk for atherosclerosis. E3 is found in approximately 64 percent of the population. It is considered the "neutral" Apo E genotype. E4 may contribute to atherosclerosis and Alzheimer's disease, impaired cognitive function, and reduced neurite outgrowth.

LCAT promotes the reverse cholesterol transport pathway, the pathway by which excess cellular cholesterol is returned to the liver for excretion. Without wishing to be bound by theory, mechanisms include, for example: LCAT increases the level of HDL, which in itself may increase the flux of cholesterol from cells by increasing the amount of extracellular acceptors of cholesterol. Also, esterification of cholesterol by LCAT on HDL could limit the spontaneous back exchange of cholesterol from HDL to cells and promotes the net delivery of cholesterol on HDL and on to the liver.

In preferred embodiments, antisense oligonucleotides are used to prevent or treat diseases or disorders associated with Lipid transport and metabolism gene family members. Exemplary Lipid transport and metabolism gene mediated diseases and disorders which can be treated with cell/tissues regenerated from stem cells obtained using the antisense compounds comprise: a cardiovascular disease or disorder, a metabolic disease or disorder (e.g., diabetes, obesity, dyslipidemia, hyperglycemia, hyperinsulinemia, hypercholesterolemia etc.), a disease or disorder associated with impaired lipid metabolism, a coronary artery disease, atherosclerosis, an HDL metabolism disease or disorder (e.g., familial HDL deficiency (FHD), Sea-blue histiocytosis, Tangier's Disease, Fish-eye disease, LCAT deficiency, low-HDL cholesterolemia etc.), a disease or disorder associated with cellular cholesterol and/or phospholipid homeostasis, Familial amyloid nephropathy, a disease or disorder associated with impaired cholesterol regulation, a disease or disorder associated with a deficiency of the Lipid transport and metabolism gene transporter, Apolipoprotein A-I deficiency, a disease or disorder associated with abnormally fast or abnormally stow rate of cholesterol efflux in a cell, a disease or disorder associated with pancreatic beta cell function, diabetes, a metabolic disease or disorder, arthritis, inflammation, an autoimmune disease or disorder, acquired immune deficiency syndrome (AIDS), inflammation, a neurological disease or disorder, a neurodegenerative disease or disorder, cancer, dyslipidemia, metabolic syndrome, a senile plaque, cerebral amyloid angiopathy, Amyloidosis, glioblastoma, a disease or disorder associated with amyloid deposition, neurofibrillary tangles, choriocarcinoma, astrocytoma, amyloidosis, hyperlipidemia, neoplastic transformation, atherosclerotic plaque, obstruction, metastasis, pulmonary fibrosis, necrosis, shock, melanoma, genetic susceptibility, psoriasis, glioma, neuropathology, a vascular disease, cell damage. Nonsmall cell lung carcinomas (NSCLCs), liposarcoma, an immunodeficiency disease or disorder, an organ transplant rejection, an allergy, glomerulonephritis, venous thrombosis, pathological processes or leukemia, a skeletal disease or disorder, a muscular disease or disorder, a disease or disorder associated with infectious organisms, an immune related disease or disorder, nerve repair and paralysis, neuroendocrine differentiation, systemic non-neuropathic amyloidosis, an amyloid disease, tumor growth dependent on angiogenesis, non-cancerous diseases with symptoms include an increase in angiogenesis, e.g., psoriasis, retinopathy of prematurity, a Choroid disease, neovascular glaucoma, diabetic retinopathy, substance abuse, impaired cognitive function, and reduced neurite outgrowth, ApoE abnormal expression, function, activity as compared to a normal control, psoriasis, a disease or disorder caused by foreign organisms such as viral, bacterial, parasitic, fungal, and the like.

In a preferred embodiment the Lipid transport and metabolism gene antisense oligonucleotides are therapeutically used in organ transplantation (e.g., liver transplant, kidney transplant, bone marrow transplant, heart transplant etc.).

In a preferred embodiment, the oligonucleotides are specific for polynucleotides of a Lipid transport and metabolism gene, which includes, without limitation noncoding regions. The Lipid transport and metabolism gene targets comprise variants of a Lipid transport and metabolism gene; mutants of a Lipid transport and metabolism gene, including SNPs; noncoding sequences of a Lipid transport and metabolism gene; alleles, fragments and the like. Preferably the oligonucleotide is an antisense RNA molecule.

In accordance with embodiments of the invention, the target nucleic acid molecule is not limited to a Lipid transport and metabolism gene polynucleotides alone but extends to any of the isoforms, receptors, homologs, noncoding regions and the like of a Lipid transport and metabolism gene.

In another preferred embodiment, an oligonucleotide targets a natural antisense sequence (natural antisense to the coding and non-coding regions) of a Lipid transport and metabolism gene targets, including, without limitation, variants, alleles, homologs, mutants, derivatives, fragments and complementary sequences thereto. Preferably the oligonucleotide is an antisense RNA or DNA molecule.

In another preferred embodiment, the oligomeric compounds of the present invention also include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound. These compounds are then tested using the methods described herein to determine their ability to inhibit expression of a target nucleic acid.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired. Such conditions include, i.e., physiological conditions in the case of in vivo assays or therapeutic treatment, and conditions in which assays are performed in the case of in vitro assays.

An antisense compound, whether DNA, RNA, chimeric, substituted etc, is specifically hybridizable when binding of the compound to the target DNA or RNA molecule interferes with the normal function of the target DNA or RNA to cause a loss of utility, and there is a sufficient degree of complementarily to avoid non-specific binding of the antisense compound to non-target sequences under conditions in which specific binding is desired, i.e., under physiological conditions in the ease of in vivo assays or therapeutic treatment, and in the ease of in vitro assays, under conditions in which the assays are performed.

In another preferred embodiment, targeting of a Lipid transport and metabolism gene including without limitation, antisense sequences which are identified and expanded, using for example, PCR, hybridization etc., one or more of the sequences set forth as SEQ ID NO: 8 to 22, and the like, modulate the expression or function of a Lipid transport and metabolism gene. In one embodiment, expression or function is up-regulated as compared to a control. In another preferred embodiment, expression or function is down-regulated as compared to a control.

In another preferred embodiment, oligonucleotides comprise nucleic acid sequences set forth as SEQ ID NOS: 23 to 263 including antisense sequences which are identified and expanded, using for example, PCR, hybridization etc. These oligonucleotides can comprise one or mote modified nucleotides, shorter or longer fragments, modified bonds and the like. Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes a Lipid transport and metabolism gene.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In a preferred embodiment, the antisense oligonucleotides bind to the natural antisense sequences of a Lipid transport and metabolism gene and modulate the expression and/or function of a Lipid transport and metabolism gene (SEQ ID NO: 1). Examples of antisense sequences include SEQ ID NOS: 8 to 263.

In another preferred embodiment, the antisense oligonucleotides bind to one or more segments of a Lipid transport and metabolism gene polynucleotide and modulate the expression and/or function of a Lipid transport and metabolism gene. The segments comprise at least five consecutive nucleotides of a Lipid transport and metabolism gene sense or antisense polynucleotides.

In another preferred embodiment, the antisense oligonucleotides are specific for natural antisense sequences of a Lipid transport and metabolism gene wherein binding of the oligonucleotides to the natural antisense sequences of a Lipid transport and metabolism gene modulate expression and/or function of a Lipid transport and metabolism gene.

In another preferred embodiment, oligonucleotide compounds comprise sequences set forth as SEQ ID NOS: 23 to 263, antisense sequences which are identified and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

Since, as is known in the art, the translation initiation codon is typically 5-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to junction in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or mote alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding a Lipid transport and metabolism gene, regardless of the sequences) of such codons. A translation lamination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a targeted region is the intragenic region encompassing the translation initiation or termination codon of the open reading frame (ORF) of a gene.

Another target region includes the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. Another target region for this invention is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In one embodiment, targeting splice sites, i.e., intron-exon junctions or exoneration junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In another preferred embodiment, the antisense oligonucleotides bind to coding and/or non-coding regions of a target polynucleotide and modulate the expression and/or function of the target molecule.

In another preferred embodiment, the antisense oligonucleotides bind to natural antisense polynucleotides and modulate the expression and/or function of the target molecule.

In another preferred embodiment, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, (hereby producing transcripts that terminate at unique polyA sites. Within the context of the invention, the types of variants described herein are also embodiments of target nucleic acids.

The locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure.

Target segments 5-100 nucleotides in length comprising a stretch of at least five (5) consecutive nucleotides selected from within the illustrative preferred target segments are considered to be suitable for targeting as well.

Target segments can include DNA or RNA sequences that comprise at least the 5 consecutive nucleotides from the 5'-terminus of one of the illustrative preferred target segments (the remaining nucleotides being a consecutive stretch of the same DNA or RNA beginning immediately upstream of the 5'-terminus of the target segment and continuing until the DNA or RNA contains about 5 to about 100 nucleotides). Similarly preferred target segments are represented by DNA or RNA sequences that comprise at least the 5 consecutive nucleotides from the 3'-terminus of one of the illustrative preferred target segments (the remaining nucleotides being a consecutive stretch of the same DNA or RNA beginning immediately downstream of the 3'-terminus of the target segment and continuing until the DNA or RNA contains about 5 to about 100 nucleotides). One having skill in the art armed with the target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

In one embodiment it is preferred to target specific nucleic acids by antisense oligonucleotides. Targeting an antisense compound to a particular nucleic acid, is a multistep process. The process usually begins with the identification of a nucleic acid sequence whose function is to be modulated. This may be, for example, a cellular gene (or mRNA transcribed from the gene) whose expression is associated with a particular disorder or disease state, or a non coding polynucleotide such as for example, non coding RNA (ncRNA).

RNAs can be classified into (1) messenger RNAs (mRNAs), which are translated into proteins, and (2) non-protein-coding RNAs (ncRNAs). ncRNAs comprise micro-RNAs, antisense transcripts and other Transcriptional Units (TU) containing a high density of stop codons and lacking any extensive "Open Reading Frame". Many neRNAs appear to start from initiation sites in 3' untranslated regions (3'UTRs) of protein-coding loci. neRNAs are often rare and at least half of the neRNAs that have been sequenced by the FANTOM consortium seem not to be polyadenylated. Most researchers have for obvious reasons focused on polyadenylated mRNAs that are processed and exported to the cytoplasm. Recently, it was shown that the set of non-polyadenylated nuclear RNAs may be very large, and that many such transcripts arise from so-called intergenic regions (Cheng, J. et al. (2005) Science 308 (5725), 1149-1154; Kapranov, P. et al. (2005). Genome Res 15 (7), 987-997). The mechanism by which neRNAs may regulate gene expression is by base pairing with target transcripts. The RNAs that function by base pairing can be grouped into (1) cis encoded RNAs that are encoded at the same genetic location, but on the opposite strand to the RNAs they act upon and therefore display perfect complementarity to their target, and (2) trans-encoded RNAs that are encoded at a chromosomal location distinct from the RNAs they act upon and generally do not exhibit perfect base-pairing potential with their targets.

Without wishing to be bound by theory, perturbation of an antisense polynucleotide by the antisense oligonucleotides described herein can alter the expression of the corresponding sense messenger RNAs. However, this regulation can either be discordant (antisense knockdown results in messenger RNA elevation) or concordant (antisense knockdown results in concomitant messenger RNA reduction). In these cases, antisense oligonucleotides can be targeted to overlapping or non-overlapping parts of the antisense transcript resulting in its knockdown or sequestration. Coding as well as non-coding antisense can be targeted in an identical manner and that either category is capable of regulating the corresponding sense transcripts-either in a concordant or disconcordant manner. The strategies that are employed in identifying new oligonucleotides for use against a target can be based on tire knockdown of antisense RNA transcripts by antisense oligonucleotides or any other means of modulating the desired target.

Strategy 1: In the ease of discordant regulation, knocking down the antisense transcript elevates the expression of the conventional (sense) gene. Should that latter gene encode for a known or putative drug target, then knockdown of its antisense counterpart could conceivably mimic the action of a receptor agonist or an enzyme stimulant.

Strategy 2: in the case of concordant regulation, one could concomitantly knock down both antisense and sense transcripts and thereby achieve synergistic reduction of the conventional (sense) gene expression. If, for example, an antisense oligonucleotide is used to achieve knockdown, then this strategy can be used to apply one antisense oligonucleotide targeted to the sense transcript and another antisense oligonucleotide to the corresponding antisense transcript, or a single energetically symmetric antisense oligonucleotide that simultaneously targets overlapping sense and antisense transcripts.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

In another preferred embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

dsRNA can also activate gene expression, a mechanism that has been termed "small RNA-induced gene activation" or RNAa. dsRNAs targeting gene promoters induce potent transcriptional activation of associated genes. RNAa was demonstrated in human cells using synthetic dsRNAs, termed "small activating RNAs" (saRNAs). It is currently not known whether RNAa is conserved in other organisms.

Small double-stranded RNA (dsRNA), such as small interfering RNA (siRNA) and microRNA (miRNA), have been found to be the trigger of an evolutionary conserved mechanism known as RNA interference (RNAi). RNAi invariably leads to gene silencing via remodeling chromatin to thereby suppress transcription, degrading complementary mRNA, or blocking protein translation. However, in instances described in detail in the examples section which follows, oligonucleotides are shown to increase the expression and/or function of the Lipid transport and metabolism gene polynucleotides and encoded products thereof. dsRNAs may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In a further embodiment, the "preferred target segments" identified herein may be employed in a screen for additional compounds that modulate the expression of a Lipid transport and metabolism gene polynucleotide. "Modulators" are those compounds that decrease or increase the expression of a nucleic acid molecule encoding a Lipid transport and metabolism gene and which comprise at least a 5-nucleotide portion that is complementary to a preferred target segment. The screening method comprises the steps of contacting a preferred target segment of a nucleic acid molecule encoding sense or natural antisense polynucleotides of a Lipid transport and metabolism gene with one or more candidate modulators, and selecting for one or more candidate modulators which decrease or increase the expression of a nucleic acid molecule encoding a Lipid transport and metabolism gene polynucleotide, e.g. SEQ ID NOS: 23 to 263. Once it is shown that the candidate modulator or modulators are capable of modulating (e.g. either decreasing or increasing) the expression of a nucleic acid molecule encoding a Lipid transport and metabolism gene polynucleotide, the modulator may then be employed in further investigative studies of the function of a Lipid transport and metabolism gene polynucleotide, or for use as a research, diagnostic, or therapeutic agent in accordance with the present invention.

Figure 2:
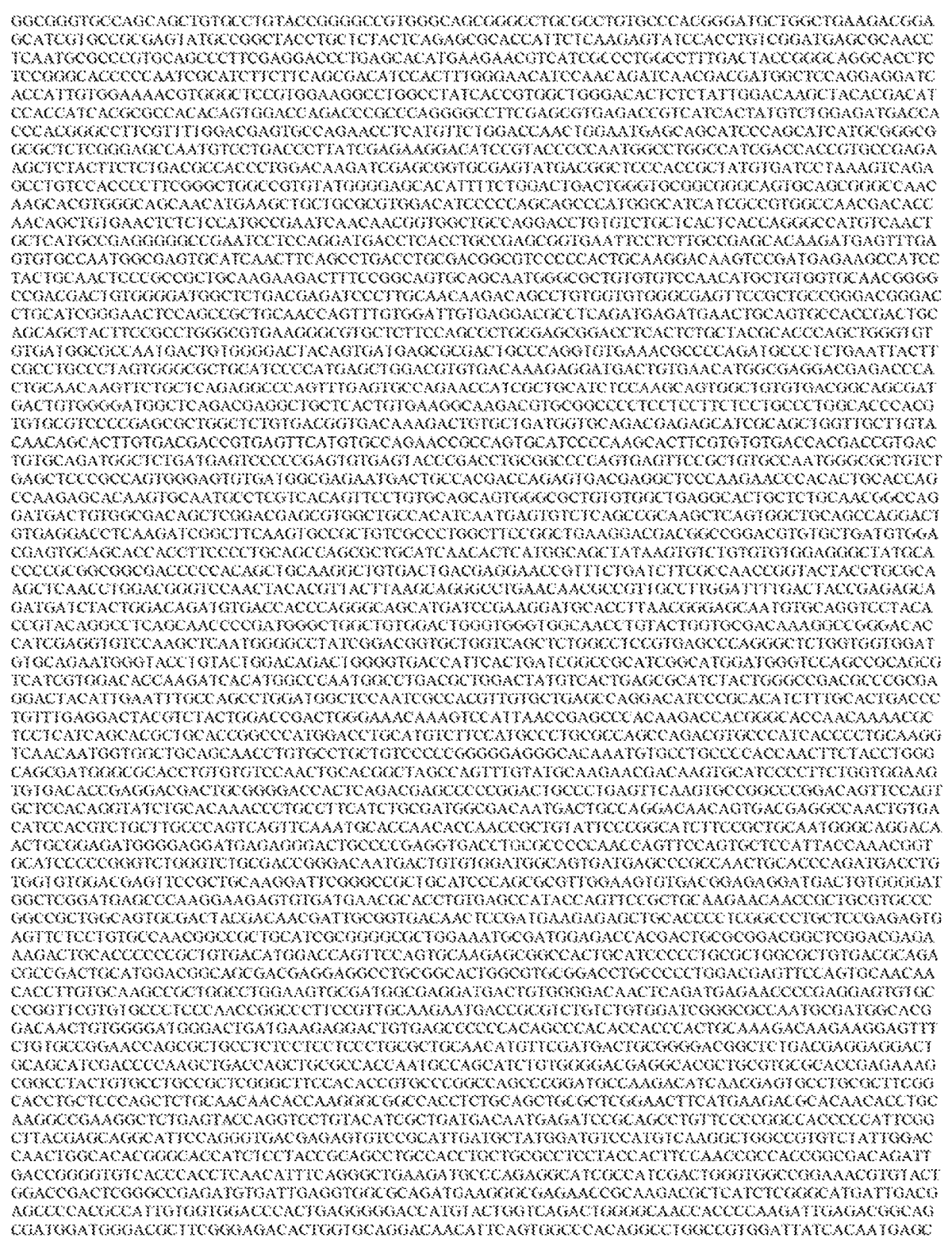

Targeting the natural antisense sequence preferably modulates the function of the target gene. For example, the Lipid transport and metabolism gene (e.g. accession numbers NM.sub.--005502, NM.sub.--000229, NM.sub.--002332, NM.sub.--008512, NM.sub.--000527.3, NM.sub.--000041, NM.sub.--000039, FIG. 2). In a preferred embodiment, the target is an antisense polynucleotide of the Lipid transport and metabolism gene. In a preferred embodiment, an antisense oligonucleotide targets sense and/or natural antisense sequences of a Lipid transport and metabolism gene polynucleotide (e.g. accession numbers NM.sub.--005502, NM.sub.--000229, NM.sub.--002332, NM.sub.--008512, NM.sub.--000527, NM.sub.--000041, NM.sub.--000039, FIG. 2), variants, alleles, isoforms, homologs, mutants, derivatives, fragments and complementary sequences thereto. Preferably the oligonucleotide is an antisense molecule and the targets include coding and noncoding regions of antisense and/or sense Lipid transport and metabolism gene polynucleotides.

The preferred target segments of the present invention may be also be combined with their respective complementary antisense compounds of the present invention to form stabilized double-stranded (duplexed) oligonucleotides.

(Such double stranded oligonucleotide moieties have been shown in the art to modulate target expression and regulate translation as well as RNA processing via an antisense mechanism. Moreover, the double-stranded moieties may be subject to chemical modifications (Fire et al., (1998) Nature, 391, 806-811; Timmons and Fire, (1998) Nature, 395, 854; Timmons et al., (2001) Gene, 263, 103-112; Tabara et al., (1998) Science, 282, 430-431; Montgomery et al., (1998) Proc. Natl. Acad. Sci. USA, 95, 15502-15507; Tuschl et al., (1999) Genes Dev., 13, 3191-3197; Elbashir et al., (2001) Nature, 411, 494-498; Elbashir et al., (2001) Genes Dev. 15, 188-200). For example, such double-stranded moieties have been shown to inhibit the target by the classical hybridization of antisense strand of the duplex to the target, thereby triggering enzymatic degradation of the target (Tijsterman et al., (2002) Science, 295, 694-697).

In a preferred embodiment, an antisense oligonucleotide targets Lipid transport and metabolism gene polynucleotides (e.g. accession numbers NM.sub.--005502, NM.sub.--000229, NM.sub.--002332, NM.sub.--008512. NM.sub.--

000527, NM.sub.--000041, NM.sub.--000039), variants, alleles, isoforms, homologs, mutants, derivatives, fragments and complementary sequences thereto. Preferably the oligonucleotide is an antisense molecule.

In accordance with embodiments of the invention, the target nucleic acid molecule is not limited to Lipid transport and metabolism gene alone but extends to any of the isoforms, receptors, homologs and the like of a Lipid transport and metabolism gene molecule.

In another preferred embodiment, an oligonucleotide targets a natural antisense sequence of a Lipid transport and metabolism gene polynucleotide, for example, polynucleotides set forth as SEQ ID NO: 8 to 22, and any variants, alleles, homologs, mutants, derivatives, fragments and complementary sequences thereto. Examples of antisense oligonucleotides are set forth as SEQ ID NOS: 23 to 263.

In one embodiment, the oligonucleotides are complementary to or bind to nucleic acid sequences of a Lipid transport and metabolism gene antisense, including without limitation noncoding sense and/or antisense sequences associated with a Lipid transport and metabolism gene polynucleotide and modulate expression and/or function of a Lipid transport and metabolism gene molecule.

In another preferred embodiment, the oligonucleotides are complementary to or bind to nucleic acid sequences of a Lipid transport and metabolism gene natural antisense, set forth as SEQ ID NO: 8 to 22 and modulate expression and/or function of a Lipid transport and metabolism gene molecule.

In a preferred embodiment, oligonucleotides comprise sequences of at least 5 consecutive nucleotides of SEQ ID NOS: 23 to 263 and modulate expression and/or function of a Lipid transport and metabolism gene molecule.

The polynucleotide targets comprise Lipid transport and metabolism gene, including family members thereof, variants of a Lipid transport and metabolism gene; mutants of a Lipid transport and metabolism gene, including SNPs; noncoding sequences of a Lipid transport and metabolism gene; alleles of a Lipid transport and metabolism gene; species variants, fragments and the like. Preferably the oligonucleotide is an antisense molecule.

In another preferred embodiment, the oligonucleotide targeting Lipid transport and metabolism gene polynucleotides, comprise: antisense RNA, interference RNA (RNAi), short interfering RNA (siRNA); micro interfering RNA (miRNA); a small, temporal RNA (stRNA); or a short, hairpin RNA (shRNA); small RNA-induced gene activation (RNAa); or, small activating RNA (saRNA).

In another preferred embodiment, targeting of a Lipid transport and metabolism gene polynucleotide, e.g. SEQ ID NO: 8 to 22 modulate the expression or function of these targets. In one embodiment, expression or function is up-regulated as compared to a control. In another preferred embodiment, expression or function is down-regulated as compared to a control.

In another preferred embodiment, antisense compounds comprise sequences set forth as SEQ ID NOS: 23 to 263. These oligonucleotides can comprise one or more modified nucleotides, shorter or longer fragments, modified bonds and the like.

In another preferred embodiment, SEQ ID NOS: 23 to 263 comprise one or more LNA nucleotides.

The modulation of a desired target nucleic acid can be carried out in several ways known in the art. For example, antisense oligonucleotides, siRNA etc. Enzymatic nucleic acid molecules (e.g., ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript (Zaug et al., 324, Nature 429 15186; Cech, 260 JAMA 3030, 1988; and Jefferies et al., 17 Nucleic Acids Research 1371, 1989).

Because of their sequence-specificity, trans-cleaving enzymatic nucleic acid molecules show promise as therapeutic agents for human disease (Usman & McSwiggen, (1995) Ann. Rep. Med. Chem. 30, 285-294; Christoffersen and Marr, (1995) J. Med. Chem. 38, 2023-2037). Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, (1979) Proc. R. Soc. London, B 205, 435) haw been used to evolve new nucleic acid catalysts capable of catalyzing a variety of reactions, such as cleavage and ligation of phosphodiester linkages and amide linkages, (Joyce, (1989) Gene, 82, 83-87; Beaudry et al., (1992) Science 257, 635-641; Joyce, (1992) Scientific American 267, 90-97; Breaker et al., (1994) TIBTECH 12, 268; Bartel et al, (1993) Science 261:1411-1418; Szostak, (1993) TIBS 17, 89-93; Kumar et al, (1995) FASEB J., 9, 1183; Breaker, (1996) Curr. Op. Biotech., 7, 442).

The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 mM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min−1. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural selfcleaving ribozymes. It is then possible that the structures of certain selfcleaving ribozymes may be optimized to give maximal catalytic activity, or that entirely new RNA motifs can be made that display significantly faster rates for RNA phosphodiester cleavage.

Intermolecular cleavage of an RNA substrate by an RNA catalyst that fits the "hammerhead" model was first shown in 1987 (Uhlenbeck, O. C. (1987) Nature, 328: 596-600). The RNA catalyst was recovered and reacted with multiple RNA molecules, demonstrating that it was truly catalytic.

Catalytic RNAs designed based on the "hammerhead" motif have been used to cleave specific target sequences by making appropriate base changes in the catalytic RNA to maintain necessary base pairing with the target sequences (Haseloff and Gerlach, (1988) Nature, 334, 585; Walbot and Bruening, (1988) Nature, 334, 196; Uhlenbeck, O. C. (1987) Nature, 328: 596-600; Koizumi, M., et al. (1988) FEBS Lett., 228: 228-230). This has allowed use of the catalytic RNA to cleave specific target sequences and indicates that catalytic RNAs designed according to the "hammerhead" model may possibly cleave specific substrate RNAs in vivo, (sec Haseloff and Gerlach, (1988) Nature, 334, 585; Walbot and Bruening, (1988) Nature, 334, 196; Uhlenbeck, O. C. (1987) Nature, 328: 596-600).

RNA interference (RNAi) has become a powerful tool for modulating gene expression in mammals and mammalian cells. This approach requires the delivery of small interfering RNA (siRNA) either as RNA itself or as DNA, using an expression plasmid or virus and the coding sequence for small hairpin RNAs that are processed to siRNAs. This system enables efficient transport of the pre-siRNAs to the cytoplasm where they are active and permit the use of regulated and tissue specific promoters for gene expression.

In a preferred embodiment, an oligonucleotide or antisense compound comprises an oligomer or polymer of ribonucleic acid (RNA) and/or deoxyribonucleic acid (DNA), or a mimetic, chimera, analog or homolog thereof. This term includes oligonucleotides composed of naturally occurring nucleotides, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

According to the present invention, the oligonucleotides or "antisense compounds" include antisense oligonucleotides (e.g. RNA, DNA, mimetic, chimera, analog or homolog thereof), ribozymes, external guide sequence (EGS) oligonucleotides, siRNA compounds, single- or double-stranded RNA interference (RNAi) compounds such as siRNA compounds, saRNA, aRNA, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, fix example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines (Hammond et al., (1991) Nat. Rev. Genet., 2, 110-119; Matzke et al., (2001) Curr. Opin. Genet. Dev., 11, 221-227; Sharp, (2001) Genes Dev., 15, 485-490). When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

The antisense compounds in accordance with this invention can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound of the invention comprises from 5 to about 80 nucleotides, and a double-stranded antisense compound of the invention (such as a dsRNA, for example) comprises a sense and an antisense strand or portion of 5 to about 80 nucleotides in length. One of ordinary skill in the art will appreciate that this comprehends antisense portions of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range therewithin.

In one embodiment, the antisense compounds of the invention have antisense portions of 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31.32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length.

In one embodiment, the antisense or oligonucleotide compounds of the invention have antisense portions of 12 or 13 to 30 nucleotides in length. One having ordinary skill in the art will appreciate that this embodies antisense compounds having antisense portions of 12, 13, 14, 15, 16, 17, 18, 19, 20, 21, 22, 23, 24, 25, 26, 27, 28, 29 or 30 nucleotides in length, or any range therewithin.

In another preferred embodiment, the oligomeric compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In another preferred embodiment, the antisense oligonucleotides, such as for example, nucleic acid molecules set forth in SEQ ID NOS: 8 to 263 comprise one or more substitutions or modifications, in one embodiment, the nucleotides are substituted with locked nucleic acids (LNA).

In another preferred embodiment, the oligonucleotides target one or more regions of the nucleic acid molecules sense and/or antisense of coding and/or non-coding sequences associated with Lipid transport and metabolism gene and the sequences set forth as SEQ ID NOS: 1 to 7 and 8 to 22. The oligonucleotides are also targeted to overlapping regions of SEQ ID NOS: 1 to 7 and 8 to 22.

Certain preferred oligonucleotides of this invention are chimeric oligonucleotides. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the an. In one preferred embodiment, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater is the affinity of the oligonucleotide for the target.

Chimeric antisense compounds of the invention may be formed as composite structures of two or more oligonucleotides, modified oligonucleotides, oligonucleosides and/or oligonucleotides mimetics as described above. Such; compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In another preferred embodiment, the region of the oligonucleotide which is modified comprises at least one nucleotide modified at the 2' position of the sugar, most preferably a 2'-Oalkyl, 2'-O-alkyl-O-alkyl or 2'-fluoro-modified nucleotide. In other preferred embodiments, RNA modifications include 2-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. Some desirable modifications can be found in De Mesmaeker et al. (1995) Acc. Chem. Res., 28:366-374.

Specific examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, —N(CH3)-O—CH2 (known as a methylene (methylimino) or MMI backbone), CH2-O—N (CH3-CH2, CH2-N(CH3)-N(CH3)-CH2 and O—N(CH3)-CH2-CH2 backbones, wherein the native phosphodiester backbone is represented as O—P—O—CH). The amide backbones disclosed by Dc Mesmaeker et al. (1995) Acc. Chem. Res. 28:366-374 are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone (Nielsen et al. (1991) Science 254, 1497). Oligonucleotides may also comprise one or more substituted sugar moieties. Preferred oligonucleotides comprise one of the following at the 2' position: OH, SH, SCH3, F, OCN, OCH3 OCH3, OCH3O (CH2)n CH3, O(CH2)n NH2 or O(CH2)n CH3 where n is from 1 to about 10; C1 to C10 lower alkyl, alkoxyalkoxy, substituted lower alkyl, alkaryl or aralkyl; Cl; Br; CN; CF3; OCF3; O—, S, or N-alkyl; O—, S, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator, a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH2 CH2 OCH3, also known as 2'-O-(2-methoxyethyl)] (Martin et al., (1995) Helv. Chim. Acta, 78, 486). Other preferred modifications include 2'-methoxy (2'-O—CH3), 2'-propoxy (2-OCH2 CH2CH3) and 2'-fluoro (2-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 3-Me-C), 5-hydroxymethylcytosine (BMC), glycosyl HMC and gentobiosyl BMC, as well as synthetic nucleotides, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. (Kornberg, A., DNA Replication, W. H. Freeman & Co., San Francisco, 1980, pp 75-77; Gebeyehu, G., (1987) et al. Nucl. Acids Res. 15:4513). A "universal" base known in the art, e.g., inosine, may be included. 5-Me-C substitutions have been shown to increase nucleic acid duplex stability by 0.6-1,2.degree. C. (Sanghvi, Y. S., in Crooke, S. T, and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., (1989) Proc. Natl. Acad. Sci. USA 86, 6553), cholic acid (Manoharan et al. (1994) Bioorg. Med. Chem. Let. 4, 1053), a thioether, e.g., hexyl-S-tritylthiol (Manoharan et al. (1992) Ann. N.Y. Acad. Sci. 660, 306; Manoharan et al. (1993) Bioorg. Med. Chem. Let 3, 2765), a thiocholesterol (Oberhauser et al., (1992) Nucl. Acids Res. 20, 533), an aliphatic chain, e.g., dodecandiol or undecyl residues (Saison-Behmoaras et al. EMBO J. 1991, 10, 111; Kabanov et al. (1990) FEBS Lett. 259, 327; Svinarchuk et al. (1993) Biochimie 75, 49), a phospholipid, e.g., di-hexadecyl-rac-glyccrol or triethylammonium 1,2-di-O-hexadecyl-rac-glycero-3-H-phosphonate (Manoharan et al. (1995) Tetrahedron Lett. 36, 3651; Shea et al. (1990) Nucl. Acids Res. 18, 3777), a polyamine or a polyethylene glycol chain (Manoharan et al. (1995) Nucleosides & Nucleotides, 14, 969), or adamantane acetic acid (Manoharan et al. (1995) Tetrahedron Lett 36, 3651). Oligonucleotides comprising lipophilic moieties, and methods for preparing such oligonucleotides are known in the art, for example, U.S. Pat. Nos. 5,138,045, 5,218,105 and 5,459, 255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary drill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc (Uhlman, et al. (2000) Current Opinions in Drug Discovery & Development Vol. 3 No 2). This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, most preferably less than about 50% LNA monomers and that their sizes are between about 5 and 25 nucleotides, more preferably between about 12 and 20 nucleotides.

Preferred modified oligonucleotide backbones comprise, but not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3-5' linkages, 2'-5' linked analogs of these, and those having inverted polarity wherein the adjacent pairs of nucleoside units are linked 3-5' to 5'-3' or 2'-5' to S'-2'. Various salts, mixed salts and free acid forms are also included.

Representative United States patents that teach the preparation of the above phosphorus containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholine linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides comprise, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen, et al. (1991) Science 254, 1497-1500.

In another preferred embodiment of the invention the oligonucleotides with phosphorothioate backbones and oligonucleosides with heteroatom backbones, and in particular —CH2-NH—O—CH2-, —CH2-N(CH3)-O—CH2-known as a methylene (methylimino) or MMI backbone, —CH2-O—N(CH3)-CH2-, —CH2N(CH3)-N(CH3) CH2- and —O—N(CH3)-CH2-CH2- wherein the native phosphodiester backbone is represented as —O—P—O—CH2- of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O alkyl-O-alkyl, wherein the alkyl, alkenyl and alkynyl may be substituted or unsubstituted C to (TO alkyl or C2 to CO alkenyl and alkynyl. Particularly preferred are O (CH2)n OmCH3, O(CH2)n, OCH3, O(CH2)nNH2, O(CH2)nCH3, O(CH2)nONH2, and O(CH2nON(CH2)nCH3)2 where n and m can be from 1 to about 10. Other preferred oligonucleotides comprise one of the following at the 2' position: C to CO, (lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification comprises 2'-methoxyethoxy (2'-O—CH2CH2OCH3, also known as 2'-O-(2-methoxyethyl) or 2-MOE) (Martin et al., (1995) Helv. Chim. Acta, 78, 486-504) i.e., an alkoxyalkoxy group. A further preferred modification comprises 2-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2.

Other preferred modifications comprise 2'-methoxy (2'-OCH3), 2'-aminopropoxy (2-OCH2CH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646, 265; 5,658,873; 5,670,633; and 5,700,920, each of which is herein incorporated by reference.

Oligonucleotides may also comprise nucleobase (often referred to in the art simply as "base") modifications or substitutions. As used herein, "unmodified" or "natural" nucleotides comprise the purine bases adenine (A) and guanine (G), and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Further, nucleotides comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleotides are particularly useful for increasing the binding affinity of the oligomeric compounds of the invention. These comprise Substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds. 'Antisense Research and Applications', CRC Press, Boca Raton, 1993, pp. 276-278) and are presently preferred base substitutions, even more particularly when combined with 2'-Omethoxyethyl sugar modifications.

Representative United States patents that teach the preparation of the above noted modified nucleotides as well as other modified nucleotides comprise, but are not limited to, U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety (Letsinger et al., (1989) Proc. Natl. Acad. Sci. USA, 86, 6553-6556), cholic acid (Manoharan et al., (1994) Bioorg. Med. Chem. Let., 4, 1053-1060), a thioether, e.g., hexyl-S-tritylthiol (Manoharan et al., (1992) Ann. N. Y. Acad. Sci., 660, 306-309; Manoharan et al., (1993) Bioorg. Med. Chem. Let, 3, 2765-2770), a thiocholesterol (Oberhauser et al., (1992) Nucl. Acids Res., 20, 533-538), an aliphatic chain, e.g., dodecandiol or undecyl residues (Kabanov et al., (1990) FEBS Lett, 259, 327-330; Svinarchuk et al., (1993) Biochimie 75, 49-54), a phospholipid, e.g., di-hexadecyl-rac-glycerol or triethylammonium 1,2-di-O-hexadecyl-rac-glycero-3-H-phosphonate (Manoharan et al., (1995) Tetrahedron Lett, 36, 3651-3654; Shea et al., (1990) Nucl. Acids Res., 18, 3777-3783), a polyamine or a polyethylene glycol chain (Mancharan et al., (1995) Nucleosides & Nucleotides, 14, 969-973), or adamantane acetic acid (Manoharan et al., (1995) Tetrahedron Lett., 36, 3651-3654), a palmityl moiety (Mishra et al., (1995) Biochim Biophys. Acta, 1264, 229-237), or an octa-decylamine or hexylamino-carbonyl-t oxycholesterol moiety (Crooke et al., (1996) J. Pharmacol. Exp. Ther., 277, 923-937).

Representative United States patents that teach the preparation of such oligonucleotides conjugates comprise, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203; 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, each of which is herein incorporated by reference.

Drug Discovery:

The compounds of the present invention can also be applied in the areas of drug discovery and target validation. The present invention comprehends the use of the compounds and preferred target segments identified herein in drug discovery efforts to elucidate relationships dial exist between a Lipid transport and metabolism gene polynucleotide and a disease state, phenotype, or condition. These methods include detecting or modulating a Lipid transport and metabolism gene polynucleotide comprising contacting a sample, tissue, cell, or organism with the compounds of the present invention, measuring the nucleic acid or protein level of a Lipid transport and metabolism gene polynucleotide and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Assessing Up-Regulation or Inhibition of Gene Expression:

Transfer of an exogenous nucleic acid into a host cell or organism can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysis. For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense modulatory activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non coding region can be used. Each control gene is assembled by inserting each coding region between a reporter coding region and its poly(A) signal. These plasmids would produce an mRNA with a reporter gene in the upstream portion of the gene raid a potential RNAi target in the 3' non-coding region. The effectiveness of individual antisense oligonucleotides would be assayed by modulation of the reporter gene. Reporter genes useful in the methods of the present invention include acetohydroxyacid synthase (AHAS), alkaline phosphatase (AP), beta galactosidase (LacZ), beta glucoronidase (GUS), chloramphenicol acetyl-transferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

Lipid transport and metabolism gene protein and mRNA expression can be assayed using methods known to those of skill in the art and described elsewhere herein. For example, immunoassays such as the ELISA can be used to measure protein levels. Lipid transport and metabolism gene antibodies for ELiSAs are available commercially, e.g., from R&D Systems (Minneapolis, Minn.), Abeam, Cambridge, Mass.

In embodiments, Lipid transport and metabolism gene expression (e.g., mRNA or protein) in a sample (e.g., cells or tissues in vivo or in vitro) treated using an antisense oligonucleotide of the invention is evaluated by comparison with Lipid transport and metabolism gene expression in a control sample. For example, expression of the protein or nucleic acid can be compared using methods known to those of skill in the art with that in a mock-treated or untreated sample. Alternatively, comparison with a sample treated with a control antisense oligonucleotide (e.g., one having an altered or different sequence) can be made depending on the information desired. In another embodiment, a difference in the expression of the Lipid transport and metabolism gene protein or nucleic acid in a treated vs. an untreated sample can be compared with the difference in expression of a different nucleic acid (including any standard deemed appropriate by the researcher, e.g., a housekeeping gene) in a treated sample vs. an untreated sample.

Observed differences can be expressed as desired, e.g., in the form of a ratio or fraction, for use in a comparison with control. In embodiments, the level of a Lipid transport and metabolism gene mRNA or protein, in a sample treated with an antisense oligonucleotide of the present invention, is increased or decreased by about 1.25-fold to about 10-fold or more relative to an untreated sample or a sample treated with a control nucleic acid. In embodiments, the level of a Lipid transport and metabolism gene mRNA or protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more.

Kits, Research Reagents, Diagnostics, and Therapeutics

The compounds of the present invention can be utilized for diagnostics, therapeutics, and prophylaxis, and as research reagents and components of kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are useful as tools in differential and/or combinatorial analyses to elucidate expression patterns of a portion or the entire complement of genes expressed within cells and tissues.

As used herein the term "biological system" or "system" is defined as any organism, cell, cell culture or tissue that expresses, or is made competent to express products of the Lipid transport and metabolism genes. These include, but are not limited to, humans, transgenic animals, cells, cell cultures, tissues, xenografts, transplants and combinations thereof.

As one non limiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, (2000) FEBS Lett., 480, 17-24; Celis, et al., (2000) FEBS Lett, 480, 2-16), SAGE (serial analysis of gene expression) (Madden, et al., (2000) Drug Discov. Today, 5, 415-425), READS (restriction enzyme amplification of digested cDNAs) (Prashar and Weissman, (1999) Methods Enzymol., 303, 258-72), TOGA (total gene expression analysis) (Sutcliffe, et al., (2000) Proc. Natl. Acad. Sci. U.S.A., 97, 1976-81), protein arrays and proteomics (Celis, et al., (2000) FEBS Lett., 480, 2-16; Jungblut, et al., Electrophoresis, 1999, 20, 2100-10), expressed sequence tag (EST) sequencing (Celis, et al., FEBS Lett, 2000, 480, 2-16; Larsson, et al., J. Biotechnol., 2000, 80, 143-37), subtractive RNA fingerprinting (SuRF) (Fuchs, et al., (2000) Anal. Biochem. 286, 91-98; Larson, et al., (2000) Cytometry 41, 203-208), subtractive cloning, differential display (DD) (Jurecic and Belmont, (2000) Curr Opin. Microbiol. 3, 316-21), comparative genomic hybridization (Carulli, et al., (1998) J. Cell Biochem. Suppl., 31, 286-96), FISH (fluorescent in situ hybridization) techniques (Going and Gusterson, (1999) Eur. J. Cancer, 35, 1895-904) and mass spectrometry methods (To, Comb. (2000) Chem. High Throughput Screen, 3, 235-41).

The compounds of the invention are useful for research and diagnostics, because these compounds hybridize to nucleic acids encoding a Lipid transport and metabolism gene. For example, oligonucleotides that hybridize with such efficiency and under such conditions as disclosed herein as to be effective Lipid transport and metabolism gene modulators are effective primers or probes under conditions favoring gene amplification or detection, respectively. These primers and probes are useful in methods requiring the specific detection of nucleic acid molecules encoding a Lipid transport and metabolism gene and in the amplification of said nucleic acid molecules for detection or for use in further studies of a Lipid transport and metabolism gene. Hybridization of the antisense oligonucleotides, particularly the primers and probes, of the invention with a nucleic acid encoding a Lipid transport and metabolism gene can be detected by means known in the art. Such means may include conjugation of an enzyme to the oligonucleotide, radiolabeling of the oligonucleotide, or any other suitable detection means. Kits using such detection means for detecting the level of a Lipid transport and metabolism gene in a sample may also be prepared.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of a Lipid transport and metabolism gene polynucleotide is treated by administering antisense compounds in accordance with this invention. For example, in one non-limiting embodiment, the methods comprise the step of administering to the animal in need of treatment, a therapeutically effective amount of a Lipid transport and metabolism gene modulator. The Lipid transport and metabolism gene modulators of the present invention effectively modulate the activity of a Lipid transport and metabolism gene or modulate the expression of a Lipid transport and metabolism gene protein. In one embodiment, the activity or expression of a Lipid transport and metabolism gene in an animal is inhibited by about 10% as compared to a control. Preferably, the activity or expression of a Lipid transport and metabolism gene in an animal is inhibited by about 30%. More preferably, the activity or expression of a Lipid transport and metabolism gene in an animal is inhibited by 50% or more. Thus, the oligomeric compounds modulate expression of a Lipid transport and metabolism gene mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

In one embodiment, the activity or expression of a Lipid transport and metabolism gene and/or in an animal is increased by about 10% as compared to a control. Preferably, the activity or expression of a Lipid transport and metabolism gene in an animal is increased by about 30%. More preferably, the activity or expression of a Lipid transport and metabolism gene in an animal is increased by 50% or mare. Thus, the oligomeric compounds modulate expression of a Lipid transport and metabolism gene mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

For example, the reduction of the expression of a Lipid transport and metabolism gene may be measured in serum, blood, adipose tissue, liver or any other body fluid, tissue or organ of the animal. Preferably, the cells contained within said fluids, tissues or organs being analyzed contain a nucleic acid molecule encoding Lipid transport and metabolism gene peptides and/or the Lipid transport and metabolism gene protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

Conjugates

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-Hphosphonate, a polyamine or a polyethylene glycol chain, or adamantane acetic add, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotides conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,165; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Although, the antisense oligonucleotides do not need to be administered in the context of a vector in order to modulate a target expression and/or function, embodiments of the invention relates to expression vector constructs for the expression of antisense oligonucleotides, comprising promoters, hybrid promoter gene sequences and possess a strong constitutive promoter activity, or a promoter activity which can be induced in the desired case.

In an embodiment, invention practice involves administering at least one of the foregoing antisense oligonucleotides with a suitable nucleic acid delivery system. In one embodiment, that system includes a non-viral vector operably linked to the polynucleotide. Examples of such nonviral vectors include the oligonucleotide alone (e.g. any one or more of SEQ ID NOS: 23 to 263) or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutination virus of Japan-liposome (HVJ) complex. Preferably, the viral vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthqpox or avipox vectors, herpesvirus vectors such as a herpes simplex I virus (HSV) vector [Geller, A. I. et al., (1995) J. Neurochem, 64: 487; Lim, F., et al., in DNA Cloning: Mammalian Systems, D. Glover, Ed. (Oxford Univ. Press, Oxford England) (1995); Geller, A. I. et al., (1993) Proc Natl. Acad. Sci.: USA.: 90 7603; Geller, A. I., et al., (1990) Proc Natl. Acad. Sci USA: 87:1149), Adenovirus Vectors (LeGal LaSalle et al., Science, 259:988 (1993); Davidson, et al., (1993) Nat Genet. 3: 219; Yang, et al., (1995) J. Virol. 69: 2004) and Adeno-associated Virus Vectors (Kaplitt, M. G., et al., (1994) Nat Genet. 8:148).

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are Anther described in U.S. Pat. No. 6,287,860, which is incorporated herein by reference.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

For treating tissues in the central nervous system, administration can be made by, e.g., injection or infusion into the cerebrospinal fluid. Administration of antisense RNA into cerebrospinal fluid is described, e.g., in U.S. Pat. App. Pub. No. 2007/0117772, "Methods for slowing familial ALS disease progression," incorporated herein by reference in its entirety.

When it is intended that the antisense oligonucleotide of the present invention be administered to cells in the central nervous system, administration can be with one or more agents capable of promoting penetration of the subject antisense oligonucleotide across the blood-brain barrier. Injection can be made, e.g., in the entorhinal cortex or hippocampus. Delivery of neurotrophic factors by administration of an adenovirus vector to motor neurons in muscle tissue is described in, e.g., U.S. Pat. No. 6,632,427, "Adeno-viral-vector-mediated gene transfer into medullary motor neurons," incorporated herein by reference. Delivery of vectors directly to the brain, e.g., the striatum, the thalamus, the hippocampus, or the substantia nigra, is known in the art and described, e.g., in U.S. Pat. No. 6,756,523, "Adenovirus vectors for the transfer of foreign genes into cells of the central nervous system particularly in brain," incorporated herein by reference. Administration can be rapid as by injection or made over a period of time as by slow infusion or administration of slow release formulations.

The subject antisense oligonucleotides can also be linked or conjugated with agents that provide desirable pharmaceutical or pharmacodynamic properties. For example, the antisense oligonucleotide can be coupled to any substance, known in the art to promote penetration or transport across the blood-brain barrier, such as an antibody to the transferrin receptor, and administered by intravenous injection. The antisense compound can be linked with a vital vector, for example, that makes the antisense compound more effective and/or increases the transport of the antisense compound across the blood-brain barrier. Osmotic blood brain barrier disruption can also be accomplished by, e.g., infusion of sugars including, but not limited to, meso erythritol, xylitol, D(+) galactose, D(+) lactose, D(+) xylose, dulcitol, myo-inositol, L(−) fructose, D(−) mannitol, D(+) glucose, D(+) arabinose, D(−) arabinose, cellobiose, D(+) maltose, D(+)

raffinose, L(>) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids including, but not limited to, glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 4,866,042, "Method for the delivery of genetic material across the blood brain barrier," U.S. Pat. No. 6,294,520, "Material for passage through the blood-brain barrier," and U.S. Pat. No. 6,936,589, "Parenteral delivery systems," all incorporated herein by reference in their entirety.

The subject antisense compounds may be admixed, encapsulated, conjugated or otherwise associated with other molecules, molecule structures or mixtures of compounds, for example, liposomes, receptor-targeted molecules, oral, rectal, topical or other formulations, for assisting in uptake, distribution and/or absorption. For example, cationic lipids may be included in the formulation to facilitate oligonucleotide uptake. One such composition shown to facilitate uptake is LIPOFECTIN (available from GIBCO-BRL, Bethesda, Md.).

Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carriers) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogeneous systems of one liquid dispersed in another in the form of droplets usually exceeding 0.1 .mu m in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "stoically stabilized" liposomes, a term which, as used herein, refers to liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoyl-phosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein by reference. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein by reference.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bischloroethyl-nitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexyl-nitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclo-phosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drags and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. For example, the first target may be a particular antisense sequence of a Lipid transport and metabolism gene, and the second target may be a region from another nucleotide sequence. Alternatively, compositions of the invention may contain two or more antisense compounds targeted to different regions of the same Lipid transport and metabolism gene nucleic acid target. Numerous examples of antisense compounds are illustrated herein and others may be selected from among suitable compounds known in the art. Two or mote combined compounds may be used together or sequentially.

Dosing:

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drag accumulation in the body of the patient Persons of ordinary skill can easily determine optimum dosages, dosing methodologies and repetition rates. Optimum dosages may vary depending on the relative potency of individual oligonucleotides, and can generally be estimated based on EC50s found to be effective in in vitro and in vivo animal models. In general, dosage is from 0.01 .mu.g to 100 g per kg of body weight and may be given once or more daily, weekly, monthly or yearly, or even once every 2 to 20 years. Persons of ordinary skill in the art can easily estimate repetition rates for dosing based on measured residence times and concentrations of the drag in bodily fluids or tissues. Following successful treatment, it may be desirable to have the patient undergo maintenance therapy to prevent the recurrence of the disease state, wherein the oligonucleotide is administered in maintenance doses, ranging from 0.01 .mu.g to 100 g per kg of body weight, once or more daily, to once every 20 years.

In embodiments, a patient is treated with a dosage of drag that is at least about 1, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100 mg/kg body weight. Certain injected dosages of antisense oligonucleotides are described, e.g., in U.S. Pat. No. 7,563,884, "Antisense modulation of PTP1B expression," incorporated herein by reference in its entirety.

While various embodiments of (be present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document. Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1 Design of Antisense Oligonucleotides Specific for a Nucleic Acid Molecule Antisense to a Lipid Transport and Metabolism Gene and/or a Sense Strand of a Lipid Transport and Metabolism Gene Polynucleotide As indicated above the term "oligonucleotide specific for" or "oligonucleotide targets" refers to an oligonucleotide having a sequence (i) capable of forming a stable complex with a portion of the targeted gene, or (ii) capable of forming a stable duplex with a portion of an mRNA transcript of the targeted gene.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the ease of in vitro assays.

The hybridization properties of the oligonucleotides described herein can be determined by one or more in vitro assays as known in the art. For example, the properties of the oligonucleotides described herein can be obtained by determination of binding strength between the target natural antisense and a potential drug molecules using melting curve assay.

The binding strength between the target natural antisense and a potential drug molecule (Molecule) can be estimated using any of the established methods of measuring the strength of intermolecular interactions, for example, a melting curve assay.

Melting curve assay determines the temperature at which a rapid transition from double-stranded to single-stranded conformation occurs for the natural antisense/Molecule complex. This temperature is widely accepted as a reliable measure of the interaction strength between the two molecules.

A melting curve assay can be performed using a cDNA copy of the actual natural antisense RNA molecule or a synthetic DNA or RNA nucleotide corresponding to the binding site of the Molecule. Multiple kits containing all necessary reagents to perform this assay are available (e.g. Applied Biosystems Inc. MeltDoctor kit). These kits include a suitable buffer solution containing one of the double strand DNA (dsDNA) binding dyes (such as ABI HRM dyes, SYBR Green, SYTO, etc.). The properties of the dsDNA dyes are such that they emit almost no fluorescence in free form, but are highly fluorescent when bound to dsDNA.

To perform the assay the cDNA or a corresponding oligonucleotide are mixed with Molecule in concentrations defined by the particular manufacturer's protocols. The mixture is heated to 95.degree. C. to dissociate all pre-formed dsDNA complexes, then slowly cooled to room temperature or other lower temperature defined by the kit manufacturer to allow the DNA molecules to anneal. The newly formed complexes are then slowly heated to 95.degree. C. with simultaneous continuous collection of data on the amount of fluorescence that is produced by the reaction. The fluorescence intensity is inversely proportional to the amounts of dsDNA present in the reaction. The data can be collected using a real time PCR instrument compatible with the kit (e.g. ABI's StepOne Plus Real Time PCR System or LightTyper instrument, Roche Diagnostics, Lewes, UK).

Melting peaks are constructed by plotting the negative derivative of fluorescence with respect to temperature (-d (Fluorescence)/dT) on the y-axis) against temperature (x-axis) using appropriate software (for example LightTyper (Roche) or SDS Dissociation Curve, ABI). The data is analyzed to identify the temperature of the rapid transition from dsDNA complex to single strand molecules. This temperature is called Tm and is directly proportional to the strength of interaction between the two molecules. Typically, Tm will exceed 40.degree. C.

Example 2 Modulation of a Lipid Transport and Metabolism Gene Polynucleotide Treatment of 518A2 Cells with Antisense Oligonucleotides 518A2 cells obtained from Albert Einstein-Montefiore Cancer Center, NY were grown in growth media (MEM/EBSS (Hyclone cat # SH30024, or Mediatech cat # MT-10-010-CV)+10% FBS (Mediatech cat # MT35-011-CV)+penicillin/streptomycin (Mediatech cat # MT30-002-CI)) at 37.degree. C. and 5% CO2. One day before the experiment the cells were replated at the density of 1.5.times. 105/ml into 6 well plates and incubated at 37.degree. C. and 5% CO2. On the day of the experiment the media in the 6 well plates was changed to fresh growth media. All antisense oligonucleotides were diluted to the concentration of 20 nM. Two .mu.l of this solution was incubated with 400 .mu.l of Opti-MEM media (Gibco cat #319854)70) and 4 .mu.l of Lipofectamine 2000 (Invitrogen cat #11668019) at room temperature for 20 min and applied to each well of the 6 well plates with 518A2 cells. A Similar mixture including 2 .mu.l of water instead of the oligonucleotide solution was used for the mock-transfected controls. After 3-18 h of incubation at 37.degree. C. and 5% CO2 the media was changed to fresh growth media. 48 h after addition of antisense oligonucleotides the media was removed and RNA was extracted from the cells using SV Total RNA Isolation System from Promega (cat #23105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat # AB1453B) or High Capacity cDNA Reverse Transcription Kit (cat #4368813 as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay by Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Results

Real time PCR results show that the levels of ABCA1 mRNA in 518A2 cells are significantly increased 48 h after treatment with one of the siRNAs designed to ABCA1 antisense AK311445 (FIG. 1A).

Figure 1B:
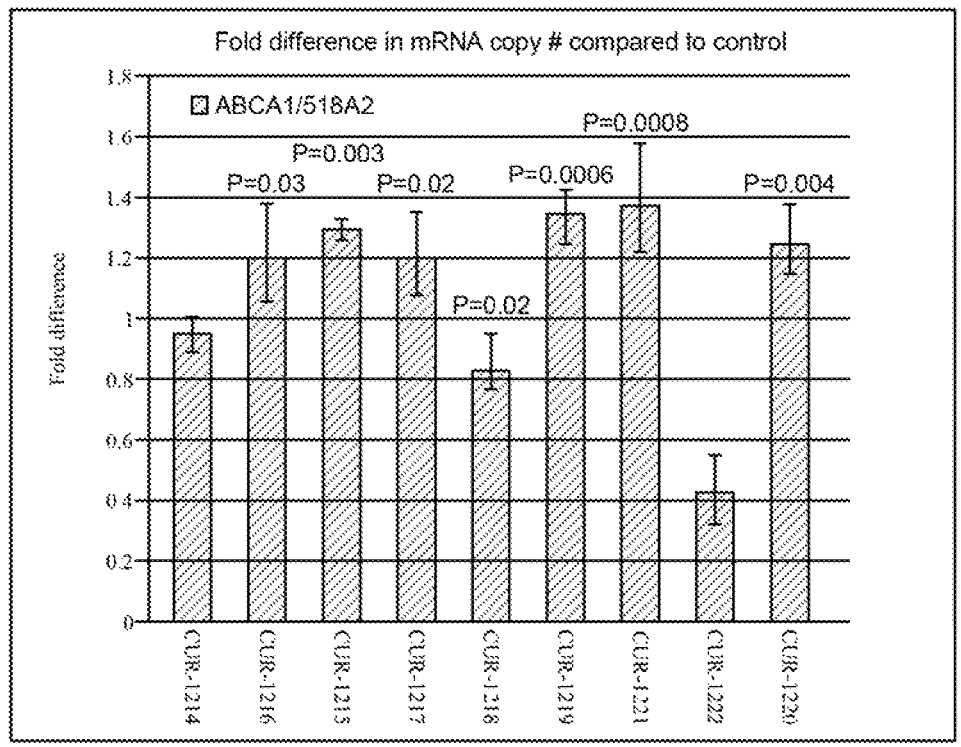
FIG. 1B is a graph of real time PCR results showing the fold changer-standard deviation in ABCA1 mRNA after treatment of 518A2 cells with phosphorothioate oligonucleotides introduced using Lipofectamine 2000, as compared to control. Real time PCR results show that the levels of ABCA1 mRNA in 518A2 cells are significantly increased 48 h after treatment with six of the oligos designed to ABCA1 antisense AK311445. Bars denoted as CUR-1214 to CUR-1222 correspond to samples treated with SEQ ID NOS: 26 to 34 respectively.

Real time PCR results show that the levels of ABCA1 mRNA in 518A2 cells are significantly increased 48 h after treatment with six of the oligos designed to ABCA1 antisense AK311445 (FIG. 1B).

Treatment of 3T3 Cells with Antisense Oligonucleotides

3T3 cells from ATCC (cat # CRL-1658) were grown in growth media (MEM/EBSS (Hyclone cat # SH30024, or Mediatech cat # MT-10-010-CV)+10% FBS (Mediatech cat # MT35-011-CV)+penicillin/streptomycin (Mediatech cat # MT30-002-CI)) at 37.degree. C. and 5% CO.sub.2. One day before the experiment the cells were replated at the density of 1.5.times. 10.sup.5/ml into 6 well plates and incubated at 37.degree. C. and 5% CO.sub.2. On the day of the experiment the media in the 6 well plates was changed to fresh growth media. All antisense oligonucleotides were diluted to the concentration of 20 .mu.M. Two .mu.l of this solution was incubated with 400 .mu.l of Opti-MEM media (Gibco cat #31985-070) and 4 .mu.l of Lipofectamine 2000 (Invitrogen cat #11668019) at room temperature for 20 min and applied to each well of the 6 well plates with 3T3 cells. A Similar mixture including 2 .mu.l of water instead of the oligonucleotide solution was used for the mock-transfected controls. After 3-18 h of incubation at 37.degree. C. and 5% CO.sub.2 the media was changed to fresh growth media. 48 h after addition of antisense oligonucleotides the media was removed and RNA was extracted from the cells using SV Total RNA Isolation System from Promega (cat # Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cal # AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay by Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Results:

Real time PCR results show that the levels of ABCA1 mRNA in 3T3 cells are significantly increased 48 h after treatment with three of the oligos designed to mouse ABCA1 antisense BF133827 (FIG. 1C).

Figure 1E:
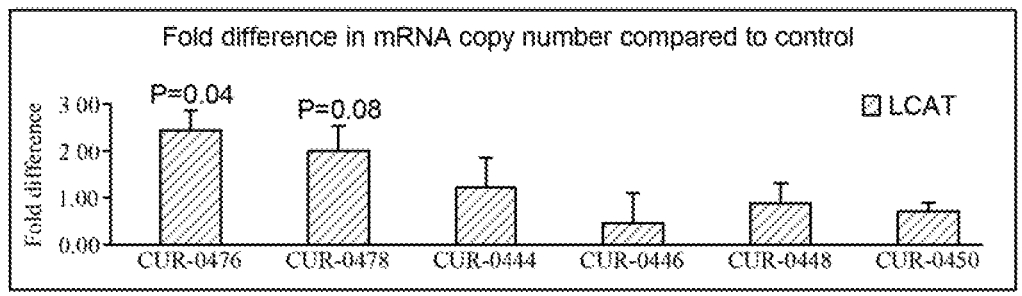
FIG. 1E is a graph of real time PCR results showing the fold changer-standard deviation in LCAT mRNA after treatment of HepG2 cells with siRNA oligonucleotides introduced using Lipofectamine 2000, as compared to control. Real time PCR results show that the levels of the LCAT mRNA in HepG2 cells are significantly increased 48 h after treatment with two of the oligos designed to LCAT antisense Hs.668679. Bars denoted as CUR-0476, CUR-0478, CUR-0444, CUR-0446, CUR-0448 and CUR-0450 correspond to samples treated with SEQ ID NOS: 41, 42, and 44 to 47 respectively.
Figure 1F:
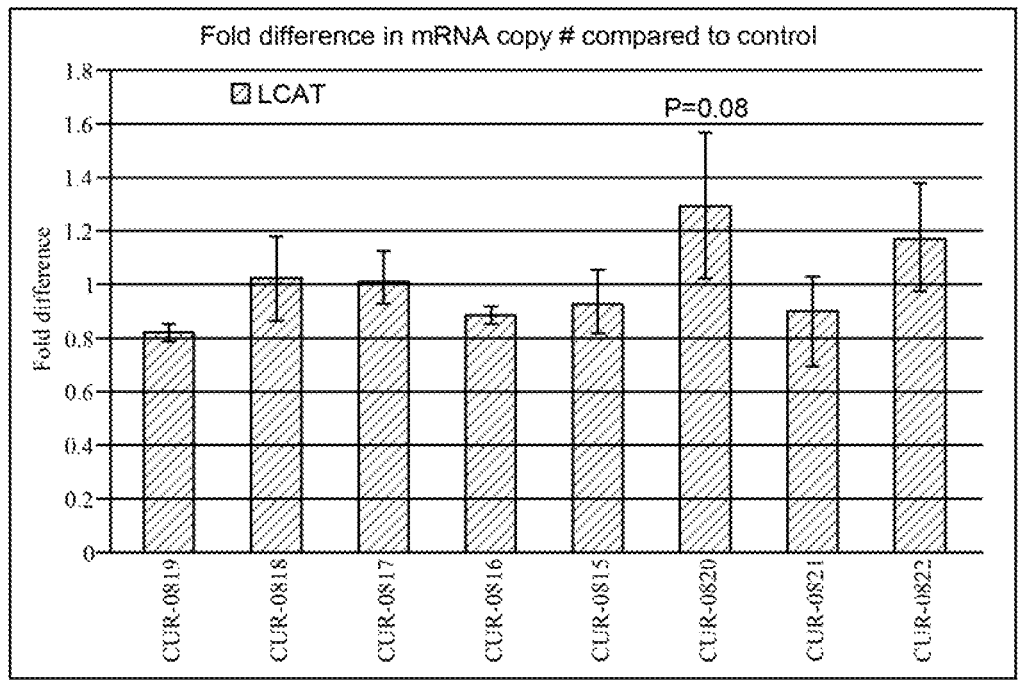
FIG. 1F is a graph of real time PCR results showing the fold change+standard deviation in LCAT mRNA after treatment of HepG2 cells with phosphorothioate oligonucleotides introduced using Lipofectamine 2000, as compared to control. Real time PCR results show that the levels of the LCAT mRNA in HepG2 cells are significantly increased 48 h after treatment with one of the oligos designed to LCAT antisense Hs.668679. Bars denoted as CUR-0819, CUR-0818, CUR-0817, CUR-0816, CUR-0815, CUR-0820, CUR-0821 and CUR-0822 correspond to samples treated with SEQ ID NOS: 55, 54, 53, 52, 51 and 56 to 58 respectively.
Figure 1G:
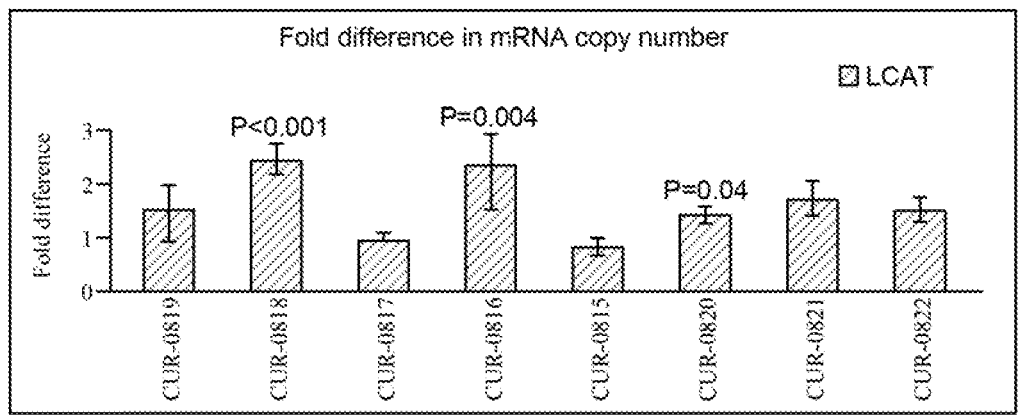
FIG. 1G is a graph of real time PCR results showing the fold change+standard deviation in LCAT mRNA after treatment of Veto cells with phosphorothioate oligonucleotides introduced using Lipofectamine 2000, as compared to control. Real time PCR results show that the levels of the LCAT mRNA in Veto cells are significantly increased 48 h after treatment with one of the oligos designed to LCAT antisense Hs.668679. Bats denoted as CUR-0819, CUR-0818, CUR-0817, CUR-0816, CUR-0815, CUR-0820, CUR-0821 and CUR-0822 correspond to samples treated with SEQ ID NOS: 55, 54, 53, 52, 51 and 56 to 58 respectively.
Figure 1H:
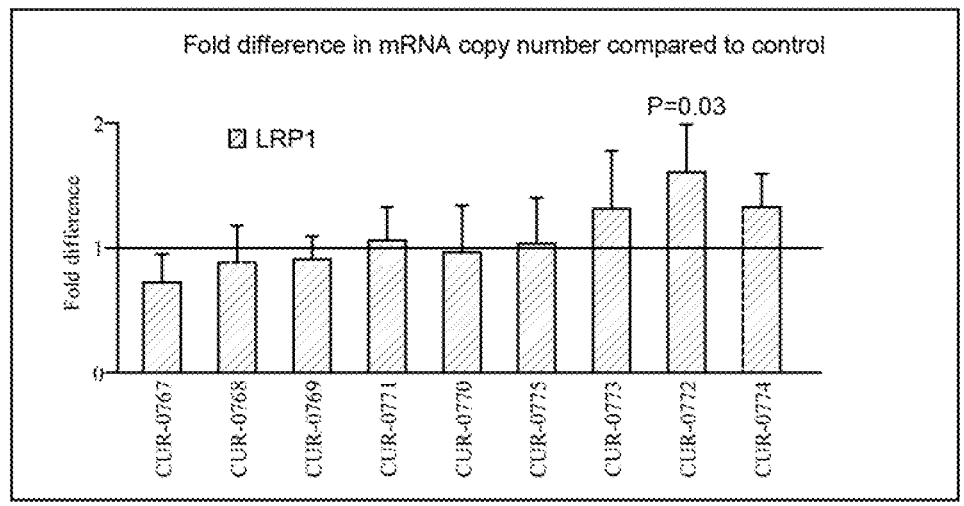
FIG. 1H is a graph of real time PCR results showing the fold change+standard deviation in LRP1 mRNA after treatment of HepG2 cells with phosphorothioate oligonucleotides introduced using Lipofectamine 2000, as compared to control. Real Time PCR results show that levels of LRP1 mRNA in HepG2 cells are significantly increased 48 h after treatment with oligos to LRP1 antisense DC401271. Bars denoted as CUR-0767 to CUR-0769, CUR-0771, CUR-0770, CUR-0775, CUR-0773, CUR-0772 and CUR-0774 correspond to samples treated with SEQ ID NOS; 59 to 61, 63, 62, 67, 65, 64 and 66 respectively.
Figure 1I:
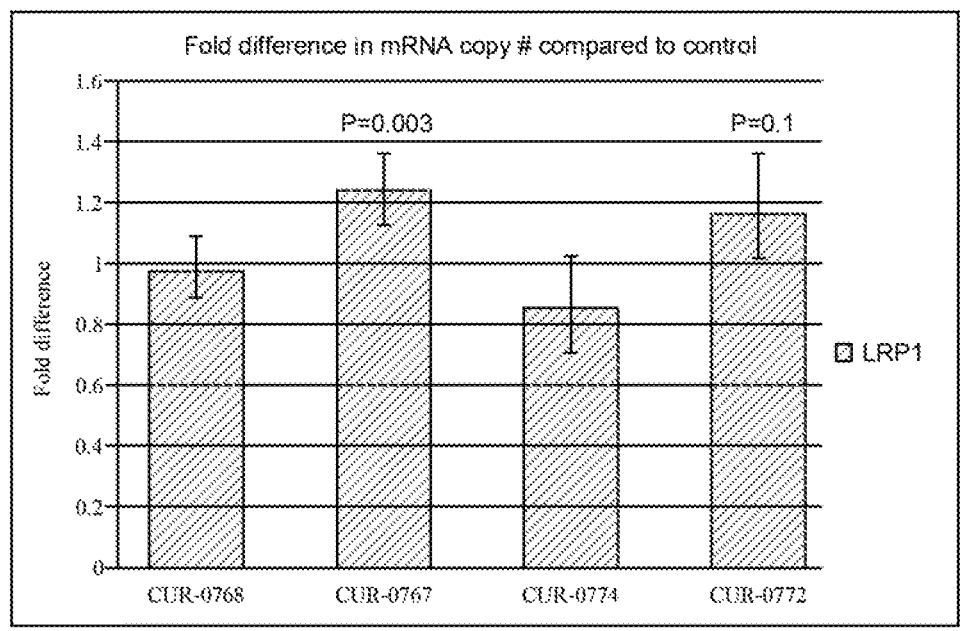
FIG. 1I is a graph of real time PCR results showing the fold change-standard deviation in LRP1 mRNA after treatment of Vero cells with phosphorothioate oligonucleotides introduced using Lipofectamine 2000, as compared to control. Real Time PCR results show that levels of LRP1 mRNA in Vero cells are significantly increased 48 h after treatment with oligos to LRP1 antisense DC401271 and Hs.711951. Bars denoted as CUR-0768, CUR-0767, CUR-0774 and CUR-0772 correspond to samples treated with SEQ ID NOS: 60, 59, 66 and 64 respectively.
Figure 1J:
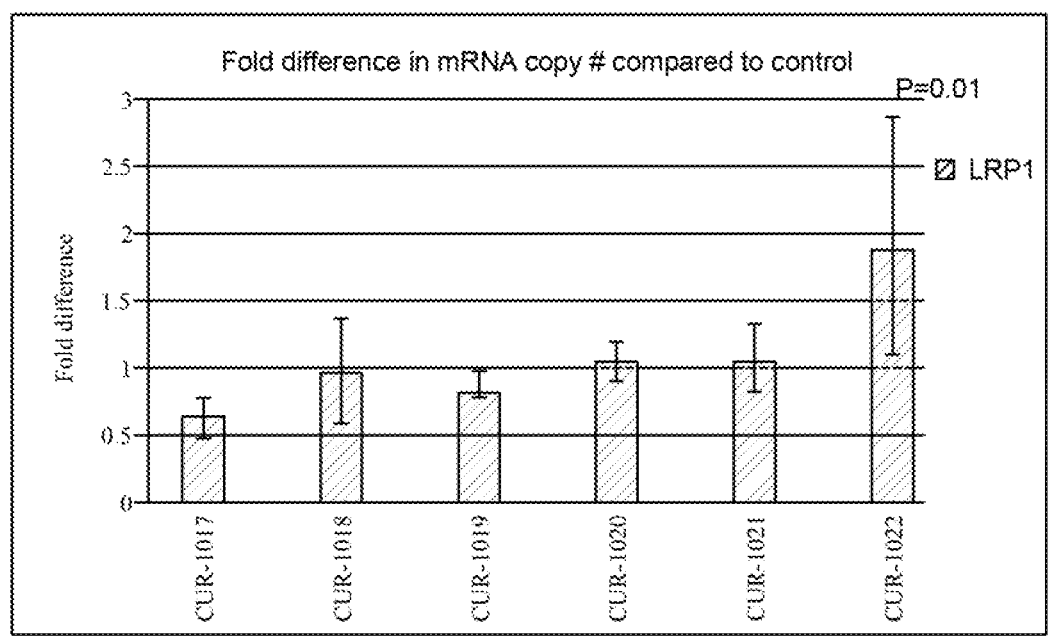
FIG. 1J is a graph of real time PCR results showing the fold change+standard deviation in LRP1 mRNA after treatment of 3T3 cells with phosphorothioate oligonucleotides introduced using Lipofectamine 2000, as compared to control. Real Time PCR results show that levels of LRP1 mRNA in 3T3 cells are significantly increased 48 h after treatment with oligos to LRP1 antisense DC401271 and AW544265. Bars denoted as CUR-1017 to CUR-1022 correspond to samples treated with SEQ ID NOS: 68 to 73 respectively.

Real Time PCR results show that levels of LRP1 mRNA in 3T3 cells are significantly increased 48 h after treatment with oligos to LRP1 antisense DC401271 and AW544265 (FIG. 1J).

Treatment of HepG2 Cells with Antisense Oligonucleotides

Method 1: Treatment of HepG2 Cells with Naked Antisense Oligonucleotides:

HepG2 cells from ATCC (cat # HB-8065) woe grown in growth media (MEM/EBSS (Hyclone cat # SH30024, or Mediatech cal # MT-10-010-CV)+10% FBS (Mediatech cat # MT35-011-CV)+penicillin/streptomycin (Mediatech cat # MT30-002-CI)) at 37.degree. C. and 5% CO.sub.2. One day before the experiment the cells were replated at the density of 0.5.times.10.sup.4/ml into 6 well plates and incubated at 37.degree. C. and 5% CO.sub.2. On the day of the experiment the media in the 6 well plates was replaced with 1.5 ml/well of fresh growth media. All antisense oligonucleotides were diluted in water to the concentration of 20 .mu.l of this solution was mixed with 400 .mu.l of fresh growth media and applied to each well of the 6 well plates with HepG2 cells. A similar mixture including 2 .mu.l of water instead of the oligonucleotide solution was used for the mock-treated controls. After 3-18 h of incubation at 37.degree. C. and 5% CO.sub.2 the media was changed to fresh growth media. 72 h after addition of antisense oligonucleotides the cells were redosed as described in above. 48-72 h after second dosing the media was removed and RNA was extracted from the cells using SV Total RNA Isolation System from Promega (cat # Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat # AB1453B) as described in the manufacturer's protocol. Hie cDNA from this reverse transcription reaction was used to monitor gene expression by real time PCR using ABI Taqman Gene Expression Mix (cat #4369510) and primers/probes designed by ABI (Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using Mx4000 thermal cycler (Stratagene). Fold change in gene expression after treatment with antisense oligonucleotides was calculated based on the difference in 18S-normalized dCt values between treated and mock-transfected samples.

Method Two: Treatment of HepG2 Cells with Antisense Oligonucleotides:

HepG2 cells from ATCC (cat # HB-8065) were grown in growth media (MEM/EBSS (Hyclone cat # SH30024, or Mediatech cal # MT-10-010-CV)+10% FBS (Mediatech cat # MT35-011-CV)+penicillin/streptomycin (Mediatech cat #

MT30-002-CI)) at 37.degree. C. and 5% CO.sub.2. One day before the experiment the cells were replated at the density of 1.5.times.10.sup.5/ml into 6 well plates and incubated at 37.degree. C. and 5% CO.sub.2. On the day of the experiment the media in the 6 well plates was changed to fresh growth media. All antisense oligonucleotides were diluted to the concentration of 20 .mu.M. 2 .mu.l of this solution was incubated with 400 .mu.l of Opti-MEM media (Gibco cat #31985-070) and 4 .mu.l of Lipofectamine 2000 (Invitrogen cat #11668019) at room temperature for 20 min and applied to each well of the 6 well plates with HepG2 cells. A similar mixture including 2 .mu.l of water instead of the oligonucleotide solution was used for the mock-transfected controls. After 3-18 h of incubation at 37.degree. C. and 5% CO.sub.2 the media was changed to fresh growth media. 48 h after addition of antisense oligonucleotides the media was removed and RNA was extracted from the cells using SV Total RNA Isolation System from Promega (cat # Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat # AB1453B) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using Mx4000 thermal cycler (Stratagene). Fold change in gene expression after treatment with antisense oligonucleotides was calculated based on the difference in 18S-normalized dCt values between treated and mock-transfected samples.
Results Real time PCR results show that the levels of the LCAT mRNA in HepG2 cells are significantly increased 48 h after treatment with two of the oligos designed to LCAT antisense Hs.668679 (FIG. 1E).

Real time PCR results show that the levels of the LCAT mRNA in HepG2 cells are significantly increased 48 h after treatment with one of the oligos designed to LCAT antisense Hs.668679 (FIG. 1F).

Real Time PCR results show that levels of LRP1 mRNA in HepG2 cells are significantly increased 48 h after treatment with oligos to LRP1 antisense DC401271 (FIG. 1H).

Figure 1K:
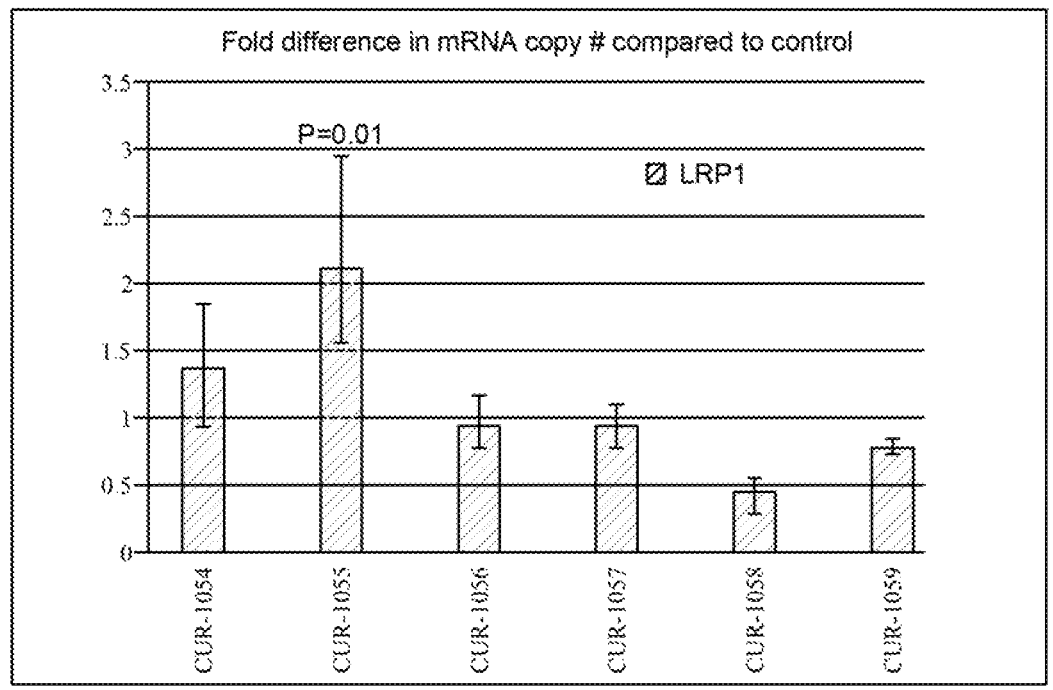
FIG. 1K is a graph of real time PCR results showing the fold change+standard deviation in LDLR mRNA after treatment of HepG2 cells with phosphorothioate oligonucleotides introduced using Lipofectamine 2000, as compared to control. Real Time PCR results show that levels of LDLR mRNA in HepG2 cells are significantly increased 48 h after treatment with antisense oligos to LDLR antisense sherflor.aApr07. Bars denoted as CUR-1054 to CUR-1059 correspond to samples treated with SEQ ID NOS: 74 to 79 respectively.
Figure 1L:
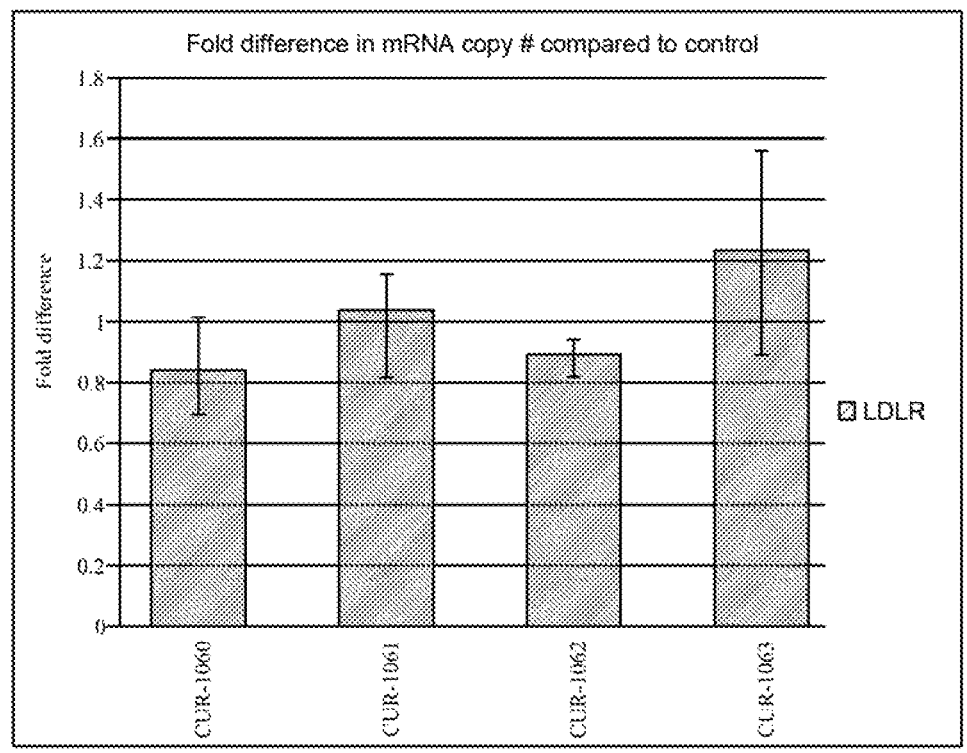
FIG. 1L is a graph of real time PCR results showing the fold change+standard deviation in LDLR mRNA after treatment of HepG2 cells with phosphorothioate oligonucleotides introduced using Lipofectamine 2000, as compared to control. Real Time PCR results show that levels of LDLR mRNA in HepG2 cells after treatment with antisense oligos to LDLR antisense bloflor.aApr07. Bars denoted as CUR-1059 to CUR-1063 correspond to samples treated with SEQ ID NOS: 79 to 83 respectively.

Real Time PCR results show that levels of LDLr mRNA in HepG2 cells are significantly increased 48 h after treatment with antisense oligos to LDLR antisense sherflor.aApr07.Oligos designed to LDLr antisense bloflor.aApr07 (CUR-1059-CUR-1063) did not elevate LDLr levels (FIGS. 1K and 1L).

Figure 1M:
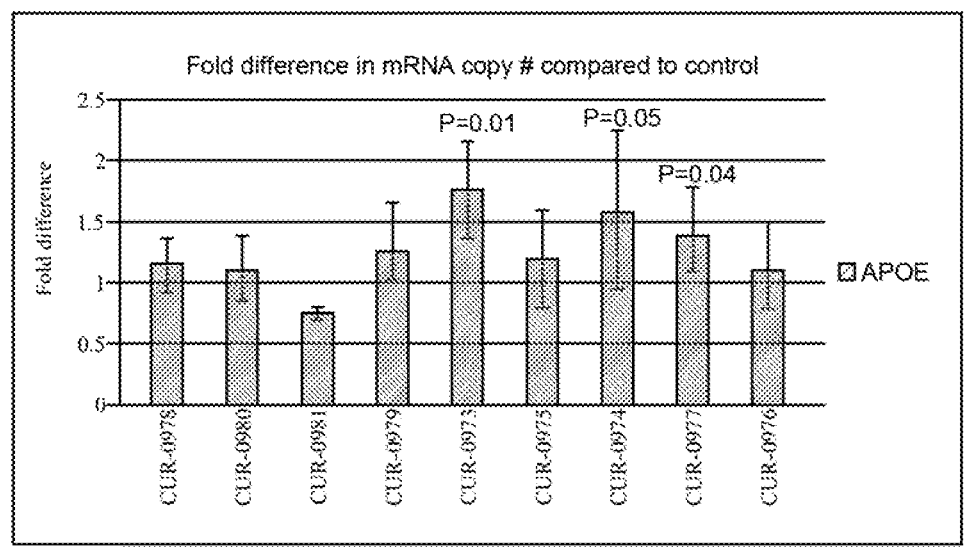
FIG. 1M is a graph of real time PCR results showing the fold change+standard deviation in ApoE mRNA after treatment of HepG2 cells with phosphorothioate oligonucleotides introduced using Lipofectamine 2000, as compared to control. Real time PCR results show that the levels of APOE mRNA in HepG2 cells are significantly increased 48 h after treatment with three of the antisense oligos designed to APOE antisense Hs.626623. Bars denoted as CUR-0978, CUR-0980, CUR-0981, CUR-0979, CUR-0973, CUR-0975, CUR-0974, CUR-0977 and CUR-0976 correspond to samples treated with SEQ ID NOS: 89, 91, 92, 90, 84, 86, 85, 88 and 87 respectively.

Real time PCR results show that the levels of APOE mRNA in HepG2 cells are significantly increased 48 h after treatment with three of the antisense oligos designed to APOE antisense Hs.626623. Oligos designed to APOE4 antisense Hs.714236 did not significantly elevate APOE mRNA (FIG. 1M).

Real time PCR results show that the levels of ApoA1 mRNA in HepG2 cells are significantly increased 48 h after treatment with some of the antisense oligonucleotides to ApoA1 antisense DA327409ext (FIG. 1N to FIG. 1P).

Figure 1Q:
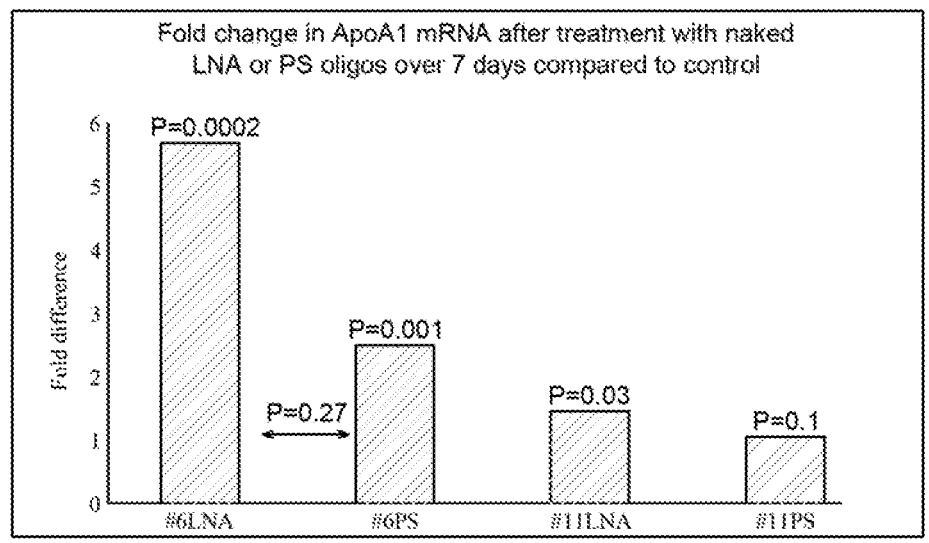
FIG. 1Q is a graph of real time PCR results showing the fold change in ApoA1 mRNA (top panel) and ApoA1 natural antisense DA327409ext RNA (bottom panel) after treatment of HepG2 cells with naked LNA or phosphothioate oligonucleotides over 7 days as compared to control. Bars denoted as #6LN A, #11 LNA, #6PS and #11PS represent SEQ ID NOS 249 to 252 respectively.
Figure 1Q:
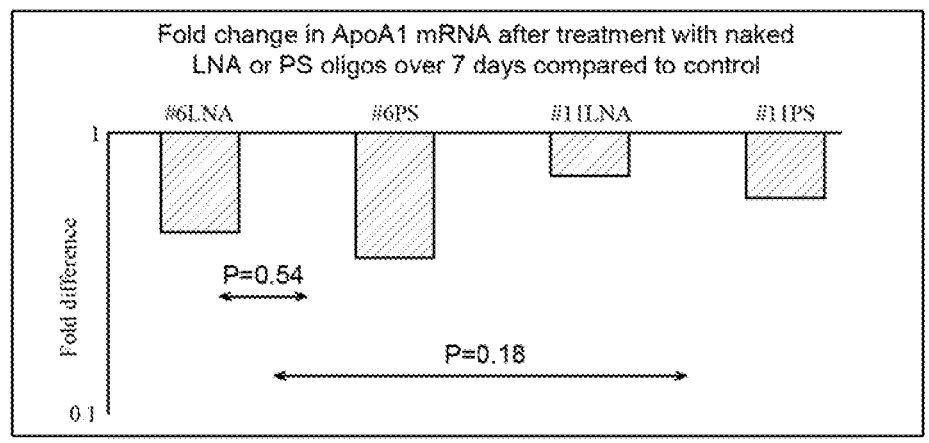

Real time PCR results showing the fold change in ApoA1 mRNA (top panel) and ApoA1 natural antisense DA327409ext RNA (bottom panel) after treatment of HepG2 cells with naked LNA or phosphothioate oligonucleotides over 7 days as compared to control (FIG. 1Q).

Figure 1R:
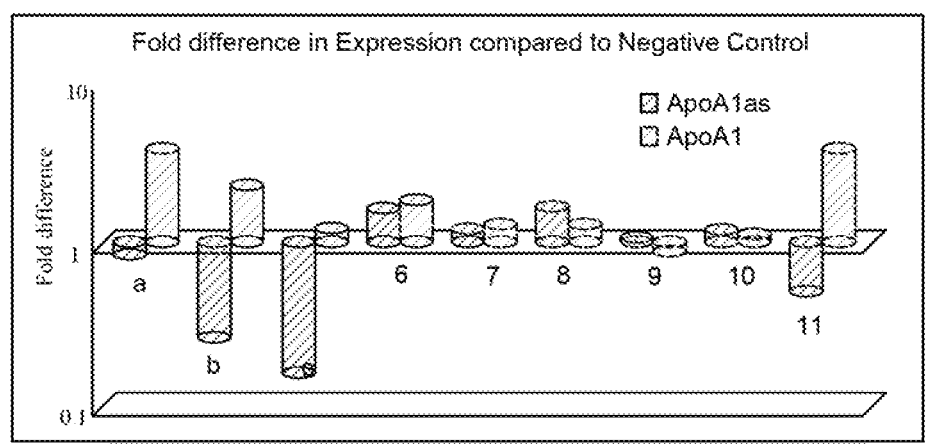
FIG. 1R is a graph of real time PCR results showing the fold change in ApoA1 mRNA (orange bats) and ApoA1 natural antisense DA327409ext RNA (bloc bars) after treatment of HepG2 cells with LNA oligonucleotides. Bars denoted as 6-11 correspond to SEQ ID NOS 249, 257 to 260 and 250.

Real time PCR results showing the fold change in ApoA1 mRNA (orange bars) and ApoA1 natural antisense DA327409ext RNA (blue bars) after treatment of HepG2 cells with LNA oligonucleotides (FIG. 1R). Treatment of Hek293 Cells with Antisense Oligonucleotides.

Hek293 cells from ATCC (cat # CRL-1573) were grown in growth media (MEM/EBSS (Hyclone cat # SH30024, or Mediatech cat # MT-10-010-CV)+10% FBS (Mediatech cat # MT35-011-CV)+penicillin/streptomycin (Mediatech cat # MT30-002-CI)) at 37.degree. C. and 5% CO.sub.2. One day before the experiment the cells were replated at the density of 1.5.times.10.sup.5/ml into 6 well plates and incubated at 37.degree. C. and 5% CO.sub.2. On the day of the experiment the media in the 6 well plates was changed to fresh growth media. All antisense oligonucleotides were diluted to the concentration of 20 .mu.M. Two .mu.l of this solution was incubated with 400 .mu.l of Opti-MEM media (Gibco cat #31985-070) and 4 .mu.l of Lipofectamine 2000 (Invitrogen cat #11668019) at room temperature for 20 min and applied to each well of the 6 well plates with Hek293 cells. A Similar mixture including 2 .mu.l of water instead of the oligonucleotide solution was used for the mock-transfected controls. After 3-18 h of incubation at 37.degree. C. and 5% CO.sub.2 the media was changed to fresh growth media. 48 h after addition of antisense oligonucleotides the media was removed and RNA was extracted from the cells using SV Total RNA Isolation System from Promega (cat # Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat # AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay by Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using using Mx4000 thermal cycler (Stratagene) or StepOne Plus Real Time PCR Machine (Applied Biosystems).

Fold change in gene expression after treatment with antisense oligonucleotides was calculated based on the difference in 18S-normalized dCt values between treated and mock-transfected samples.
Results:

Real Time PCR Results Show that the Levels of the LCAT mRNA in Hek293 Cells are Significantly Increased 48 h after Treatment with Three of the Oligos Designed to LCAT Antisense Hs.668679 (FIG. 1D).

Treatment of Vero 76 Cells with Antisense Oligonucleotides

Vero 76 cells from ATCC (cat # CRL-1587) were grown in growth media (MEM/EBSS (Hyclone cal # SH30024, or Mediatech cat # MT-10-010-CV)+10% FBS (Mediatech cat # MT35-011-CV)+penicillin/streptomycin (Mediatech cat # MT30-002-CI)) at 37.degree. C. and 5% CO.sub.2. One day before the experiment the cells were replated at the density of 1.3.times.10.sup.5/ml into 6 well plates and incubated at 37.degree. C. and 5% CO.sub.2. On the day of the experiment the media in the 6 well plates was changed to fresh growth media. All antisense oligonucleotides were diluted to the concentration of 20 .mu.M. Two .mu.l of this solution was incubated with 400 .mu.l of Opti-MEM media (Gibco cat #31985-070) and 4 .mu.l of Lipofectamine 2000 (Invitrogen cat #11668019) at room temperature for 20 min and applied to each well of the 6 well plates with Vero 76 cells. A Similar mixture including 2 .mu.l of water instead of the oligonucleotide solution was used for the mock-transfected controls. After 3-18 h of incubation at 37.degree. C. and 5% CO.sub.2 the media was changed to fresh growth media. 48 h after addition of antisense oligonucleotides the media was removed and RNA was extracted from the cells using SV Total RNA Isolation System from Promega (cat # Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat # AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay by Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using using Mx4000 thermal cycler (Stratagene) or StepOne Plus Real Time PCR Machine (Applied Biosystems).

Fold change in gene expression after treatment with antisense oligonucleotides was calculated based on the difference in 18S-normalized dCt values between treated and mock-transfected samples.

Results:

Real time PCR results show that the levels of the LCAT mRNA in Veto cells are significantly increased 48 h after treatment with one of the oligos designed to LCAT antisense Hs.668679 (FIG. 1G).

Real Time PCR results show that levels of LRP1 mRNA in Vero cells are significantly increased 48 h after treatment with oligos to LRP1 antisense DC401271 and Hs.711951 (FIG. 11).

Detection Probes Used in Applied Biosystems Gene Expression Assays:

ABCA1: Hs00194045_m1 (human), Mm01350760_m1 (mouse)
LCAT: Hs00173415_m1
LRP1: Hs00233856_m1 (human), Mm00464608_m1 (mouse)
LDLR: Hs00181192_m1
ApoE: Hs00171168_m1
ApoA1: Hs00163641_m1. 18S cat #4319413E
Custom designed assay for ApoA1 antisense DA327409ext:
FAM Jabeled: TTTGGATCTGGACGACTTC (SEQ ID NO: 275)

Example 3 Modulation of a Lipid Transport and Metabolism Gene Expression

Materials and Methods

Cells were treated with either of the following methods:
Method 1: Treatment of HepG2 Cells with Naked Antisense Oligonucleotides:

HepG2 cell were grown in MEM/EBSS (Hyclone cal # SH30024)+10% FBS+penicillin+streptomycin at 37.degree. C. and 5% CO.sub.2. One day before the experiment the cells were replated at the density of 1.5.times.10.sup.4/ml into 6 well plates and left at 37.degree. C. and 5% CO.sub.2. On the day of the experiment the media in the 6 well plates was changed to fresh MEM/EBSS+10% FBS. All antisense oligonucleotides manufactured by IDT were diluted to the concentration of 20 .mu.M. 2 .mu.l of this solution was incubated with 400 .mu.l of Opti-MEM media (Gibco cat #31985-070) and applied to each well of the 6 well plates with HepG2 cells. Similar mixture including 2 .mu.l of water instead of the oligonucleotide solution was used for the mock-transfected controls. 72 h after addition of antisense oligonucleotides the media was removed and the dosing procedure was repeated as described in above.

48-72 h after repeated dosing RNA was extracted from the cells using SV Total RNA Isolation System from Promega (cat # Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat # AB1453B) as described in the manufacturer's protocol. The cDNA from this reverse transcription reaction was used to monitor gene expression by real lime PCR using ABI Taqman Gene Expression Mix (cat #4369510) and primers/probes designed by ABI (Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using Mx4000 thermal cycler (Stratagene).

Fold change in gene expression after treatment with antisense oligonucleotides was calculated based on the difference in 18S-normalized dCt values between treated and mock-transfected samples.

Primers and probe for the custom designed Taqman assay for the ApoA1 natural antisense DA327409ext. Capital letters indicate unmodified deoxyribonucleotides

```
Probe sequence (FAM labeled)
                             (SEQ ID NO: 275)
TTTGGATCTGGACGACTTC Forward Primer Seq.
                             (SEQ ID NO: 276)
CTCCTCCTGCCACTTCTTCTG Reverse Primer Seq.
                             (SEQ ID NO: 277)
CTGGTGGATGAAGAAGGTTTGC
```

Method Two: Treatment of HepG2 Cells with Antisense Oligonucleotides:

HepG2 cells from ATCC (cat # HB-8065) were grown in growth media (MEM/EBSS (Hyclone cat # SH30024, or Mediatech cat # MT-10-010-CV)+10% FBS (Mediatech cal # MT35-011-CV)+penicillin/streptomycin (Mediatech cat # MT30-002-CI)) at 37.degree. C. and 5% CO.sub.2. One day before the experiment the cells were replated at the density of 1.5.times.10.sup.5/ml into 6 well plates and incubated at 37.degree. C. and 5% CO.sub.2. On the day of the experiment the media in the 6 well plates was changed to fresh growth media. All antisense oligonucleotides were diluted to the concentration of 20 .mu.M. 2 .mu.l of this solution was incubated with 400 .mu.l of Opti-MEM media (Gibco cat #31985-070) and 4 .mu.l of Lipofectamine 2000 (Invitrogen cat #11668019) at room temperature for 20 min and applied to each well of the 6 well plates with HepG2 cells. Similar mixture including 2 .mu.l of water instead of the oligonucleotide solution was used for the mock-transfected controls. After 3-18 h of incubation at 37.degree. C. and 5% CO.sub.2 the media was changed to fresh growth media. 48 h after addition of antisense oligonucleotides the media was removed and RNA was extracted from the cells using SV Total RNA Isolation System from Promega (cal #23105) or RNeasy Total RNA Isolation kit from Qiagen (cat #74181) following the manufacturers' instructions.

600 ng of RNA was added to the reverse transcription reaction performed using Verso cDNA kit from Thermo Scientific (cat # AB1453B) as described in the manufacturer's protocol. The cDNA from this reverse transcription reaction was used to monitor gene expression by real time FCR using ABI Taqman Gene Expression Mix (cat #4369510) and primers/probes designed by ABI (Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using Mx4000 thermal cycler (Stratagene). Fold change in gene expression after treatment with antisense oligonucleotides was calculated based on the difference in 18S-normalized dCt values between treated and mock-transfected samples.

Primers and probe for the custom designed Taqman assay for the ApoA1 natural antisense DA327409ext. Capital letters indicate unmodified deoxyribonucleotides

```
Probe sequence (FAM labeled)
                                (SEQ ID NO: 275)
TTTGGATCTGGACGACTTC Forward Primer Seq.
                                (SEQ ID NO: 276)
CTCCTCCTGCCACTTCTTCTG Reverse Primer Seq.
                                (SEQ ID NO: 277)
CTGGTGGATGAAGAAGGTTTGC
```

Treatment of Primary Monkey Hepatocytes

Primary monkey hepatocytes were introduced into culture by RxGen Inc. and plated in 6 well plates. They were treated with oligonucleotides as follows. The media in the 6 well plates was changed to fresh growth media consisting of William's Medium E (Sigma cat # W4128) supplemented with 5% FBS, 50 U/ml penicillin and 50 ug/ml streptomycin, 4 ug/ml insulin, 1 uM dexamethasone, 10 ug/ml Fungin (InVivogen, San Diego Calif.). All antisense oligonucleotides were diluted to the concentration of 20 .mu.M. 2 .mu.l of this solution was incubated with 400 .mu.l of Opti-MEM media (Gibco cat #31985-070) and 4 .mu.l of Lipofectamine 2000 (Invitrogen cat #11668019) at room temperature for 20 min and applied to each well of the 6 well plates with cells. Similar mixture including 2 .mu.l of water instead of the oligonucleotide solution was used for the mock-transfected controls. After 3-18 h of incubation at 37.degree. C. and 5% CO.sub.2 the media was changed to fresh growth media. 48 b after addition of antisense oligonucleotides the media was removed and RNA was extracted from the cells using SV Total RNA Isolation System from Promega (cal # Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat # AB1453B) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using Mx4000 thermal cycler (Stratagene). Fold change in gene expression after treatment with antisense oligonucleotides was calculated based on the difference in 18S-normalized dCt values between treated and mock-transfected samples.

ELISA was conducted using MabTech Inc. ApoA1 ELISA kit cat #3710-11-6 according to manufacturer's instructions.

Figure 1S:
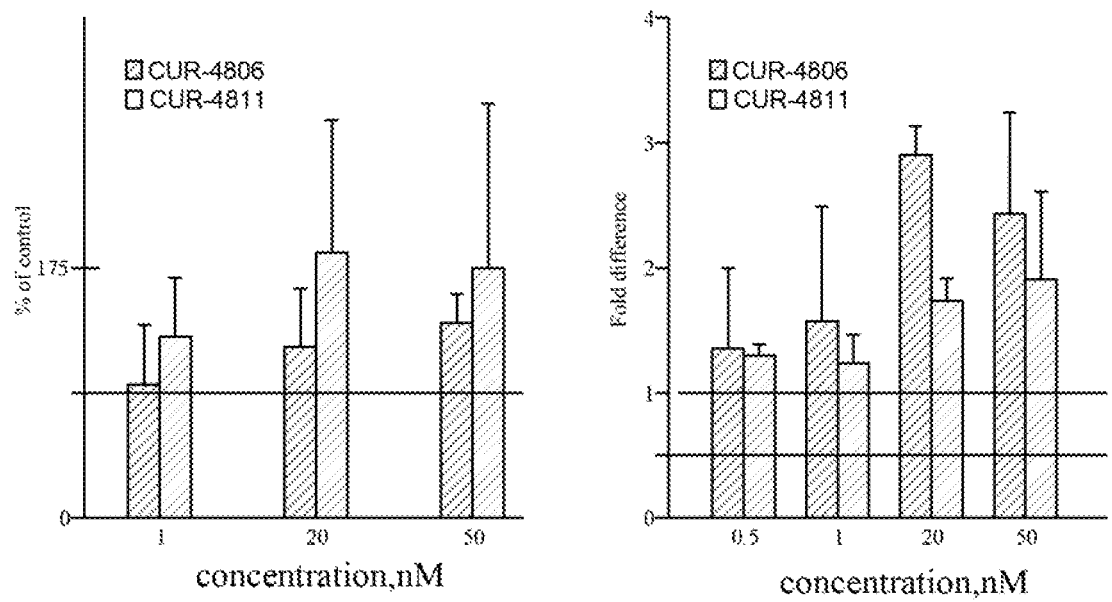
FIG. 1S shows dose dependent increase in ApoA1 mRNA (bottom panel) and protein (top panel) after treatment of HepG2 cells with oligonucleotides. Bars denoted CUR-4806 and CUR-4811 correspond to SEQ ID NOS 249 and 250 respectively.
Figure 1T:
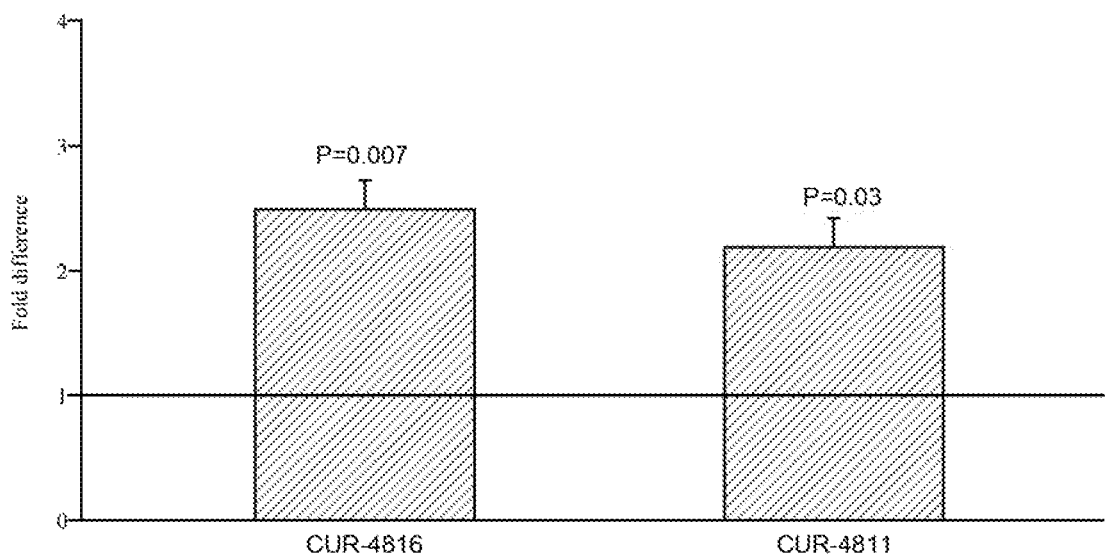
FIG. 1T is a graph of the real time PCR results showing upregulation of the ApoA1 mRNA in primary African green monkey hepatocytes after treatment with oligonucleotides against natural ApoA1 antisense DA327409ext. Bars denoted CUR-4816 and CUR-4811 correspond to SEQ ID NOS: 263 and 250 respectively.

The results are shown in FIG. 1Q to FIG. 1T. FIG. 1Q shows that both oligonucleotides with the phosphothioate backbone, i.e. internucleotide linkages and LNA oligonucleotides were effective in modulating the target gene expression as measured by ApoA1 mRNA (top panel) and ApoA1 antisense DA327409ext RNA (bottom panel) amounts detected. FIG. 1R shows the levels of ApoA1 mRNA (orange bars) and ApoA1 antisense DA327409ext RNA (blue bars) in HepG2 cells treated with oligonucleotides designed against DA327409ext. FIG. 1S shows dose dependent upregulation of ApoA1 mRNA (bottom panel) and protein (top panel) in HepG2 cultures treated with oligonucleotides designed against DA327409ext. Fig. T shows upregulation of ApoA1 mRNA in primary African green monkey hepatocytes after treatment with oligonucleotides designed against DA327409ext.

Example 4: Efficacy and Duration of Action Study of CUR-962 in the African Green Monkey The objective of this study was to assess and compare the effect of antisense knockdown of the discordant noncoding antisense sequences that regulate a Lipid transport and metabolism gene following intravenous administration in a nonhuman primate model. The antisense oligonucleotide test articles designed to inhibit the APOA1 regulatory sequences were designated as CUR-962.

```
CUR-962:
                                (SEQ ID NO: 278)
+G* + C*T* A*G*T* C*T*G* + T* + T* + G

CUR-963 (control):
                                (SEQ ID NO: 279)
+G* + T*C* T*G*A* T*G*G* + A* + G* + A
```

Regulatory Test Guidelines

This study was designed in accordance with accepted toxicological principles and to comply with International Conference of Harmonization (ICH) Harmonized Tripartite Guidelines (Non-Clinical Safety Studies for the Conduct of Human Clinical Trials for Pharmaceuticals ICH M3(m), 2000 Nov. 9), and generally accepted procedures for the testing of therapeutic agents.

Test and Control Articles

Test Article Identity and Preparation

The test article, CUR-962, is a chemically stabilized antisense oligonucleotide. The vehicle for intravenous delivery is phosphate-buffered saline (PBS).

Vehicle Characterization

For the PBS vehicle, the composition, batch number, expiry date and storage conditions (temperature and light/dark) was obtained from the supplier.

Test Article Storage and Handling

The test substance and vehicle were stored according to the received storage conditions supplied by the Sponsor and manufacturer, accordingly.

Analysis of the Test Article Formulations

Samples of the test article formulation will be cryopreserved for analysis of the concentration, stability and homogeneity of the test substance formulations.

Test System Rationale

The primate is a suitable non rodent species, acceptable to regulatory authorities as an indicator of potential hazards, and for which extensive background data are available. The African green monkey specifically is a highly clinically relevant model of multiple human physiologic and disease states.

The intravenous route of administration corresponds to a possible human therapeutic route. The dose of the test articles was based on the results of the dose finding studies of analogous compounds previously performed in the African green monkey.

African green monkey were chosen as the primate of choice as the test substances' target sequence are conserved across species with 100% homology in primates. Additionally, the test substance is a synthetic oligonucleotide. Consequently, dosing in primates allows for a superior assessment of the efficacy of these compounds that would be more reflective of the uptake likely to be seen in humans than in any other species.

Animals

Species: *Chlorocebus sabaeus*, non-human primate
Breed: African green monkey indigenous to St Kitts.
Source: RxGen, Lower Bourryeau, St. Kitts, West Indies.
Expected Age: The test animals were adults.
Expected Body Weight: The monkeys weigh approximately 3-4 kg. The actual range may vary but will be documented in the data.
Sex: The test animals were adult females.
Number of Animals: Ten animals were screened to ensure identification of 8 animals appropriate for enrollment in the study.
Number on Study: Females: 8

Justification for Number on Study:

This study was designed to use the fewest number of animals possible, consistent with the primary objective of evaluating the therapeutic efficacy of the test article in the African green monkey and prior studies of the systemic administration of this type of oligonucleotide in this species.

Animal Specification:

Ten adult African Green monkeys in the weight range of 3 to 4 kg, were employed in the study. The monkeys were drug-naive adult animals humanely trapped from the feral population that inhabits the island. Trapped monkeys were treated with anthelminthics to eliminate any possible intestinal parasite burden and were observed in quarantine for a minimum of 4 weeks prior to screening for study enrollment. The age of trapped monkeys were estimated by size and dentation, with the exclusion of older animals from the study. Prior to study enrollment, a clinical exam was performed on each monkey, including evaluation of locomotion and dexterity. Blood samples were taken and sent to Antech Diagnostics (Memphis, Tenn.) for comprehensive clinical chemistries and a complete blood count and lipid profiles (see sections 9.2 and 319567928 for specifications). Monkeys with abnormal lab values, as determined by comparison to the established normal range for monkeys in the St. Kitts colony, were excluded from the study. In order to identify 8 monkeys that satisfy this criterion, 10 monkeys were screened, with the screening of additional animals as needed. Before study initiation, the selected monkeys will be transferred to individual cages to acclimate to individual housing for a one-week period. Only animals deemed suitable for experimentation will be enrolled in the study. The actual (or estimated) age and weight ranges at the start of the study will be detailed in the raw data and final report Animal Health and Welfare The highest standards of animal welfare were followed and adhered to guidelines stipulated by the St. Kitts Department of Agriculture and the U.S. Department of Health and Human Services. All studies will be conducted in accordance with these requirements and all applicable codes of practice for the care and housing of laboratory animals. All applicable standards for veterinary care, operation, and review as contained in the NIH Guide for the Care and Use of Animals. The St Kilts facility maintains an animal research committee that reviews the protocols and inspects the facilities as required by the Guide. The Foundation has an approved assurance filed with the Office of Laboratory Animal Welfare, as required by the Guide, M4384-01 (Axion Research Foundation/St. Kitts Biomedical Foundation). There are no special nonhuman primate veterinary care issues and biohazard issues raised by the research specified in this study.

Housing and Environment

To allow detection of any treatment-related clinical signs, the animals were housed individually prior to surgery and postoperatively until sacrifice. The primate building in which the individual cages were situated were illuminated entirely by ambient light, which at 17 degrees north latitude approximates a 12 hr. 12 hr light-dark cycle as recommended in the U.S. D.H.H.S guidelines. The RxGen primate building was completely ventilated to the outside. Additional air movement was assured by ceiling fans to maintain a constant target temperature of 23-35.degree. C., as is typical of St. Kitts throughout the year. Twenty-four hour extremes of temperature and relative humidity (which also will not be controlled) were measured daily. During the study, the cages were cleaned at regular intervals.

Diet and Water

Each animal was offered approximately 90 grams per day of a standard monkey chow diet (TekLad, Madison, Wis.). The specific nutritional composition of the diet was recorded. The water was periodically analyzed for microbiological purity. The criteria for acceptable levels of contaminants in stock diet and water supply were within the analytical specifications established by the diet manufacturer and the periodic facility water evaluations, respectively. The water met all criteria necessary for certification as acceptable for human consumption.

Experimental Design

Animal Identification and Randomization

Allocation was done by means of a stratified randomization procedure based on bodyweight and plasma cholesterol profiles. Prior to and after allocation to a group, each animal was identified by a tattoo on the abdomen. Tattoos are placed on all colony animals as a means of identification in the course of routine health inspections. A cage plan was drawn up to identify the individuals housed within, and individual monkeys were further identified by a labeled tag attached to their respective cage.

Group Sizes, Doses and Identification Numbers

The animals were assigned to 2 treatment groups, comprised of 4 monkey's in each group. Specific animal identification numbers were provided to each monkey according to the facility numbering system. This system uniquely identifies each monkey by a letter followed by a three-digit number, e.g. Y032.

Route and Frequency of Administration

Animals were dosed once daily on Days 1, 3, and 5 delivered intravenously by manual infusion over .about. 10 min. The infusion rate will be 24 mL/kg/h. The animals were sedated with ketamine and xylazine prior to and during the dosing procedure. A venous catheter (Terumo mini vein infusion set, 20 gauge needle, or similar appropriate infusion set) was inserted into the saphenous vein. Dosing took place in each monkey between 8:00 and 10:00 a.m. shortly after the animals wake and prior to feeding. A blood sample to assess plasma cholesterol and other lipid levels as described in Blood Chemistry section below, was collected just prior to each infusion. Blood collection preceded feeding at both sampling intervals to minimize dietary effects on cholesterol measurements.

Clinical Observations

All visible signs of reaction to treatment were recorded on each day of dosing. In addition, the animals were examined at least once each week for physical attributes such as appearance and general condition.

Body Weights

Body weights were recorded at weekly intervals during the treatment and post-treatment periods.

Food Consumption

Individual food consumption was not be quantified. Feeding patterns, however, were be monitored and a note made of any major changes.

Mortality and Morbidity

Mortality and morbidity will be recorded. Any decision regarding premature sacrifice will be made after consultation with the Study Director and with the Sponsor's Monitoring Scientist, if possible. Animals that are found dead or killed prematurely will be subjected to necropsy with collection of liver, kidney, heart and spleen lung (issues for histopathology. In the event of premature sacrifice a blood sample will also be taken (if possible) and the parameters determined. Animals that are found dead after regular working hours will be refrigerated overnight and necropsies performed at the start of the next working day. If the condition of an animal requires premature sacrifice, it will be euthanized by intravenous overdose of sodium pentobarbital. All research is governed by the Principles for Use of Animals. RxGcn is required by law to comply with the U.S. Department of Health and Human Services standards for primate facility, which dictates the levels of severity that the procedures within this study, specified as mild, must abide.

Clinical Laboratory Studies

Blood Samples

Three blood samples were obtained from all animals prior to treatment, to establish a plasma cholesterol baseline. Blood samples were collected post treatment and were taken via superficial venipuncture. The volume collected at any one sampling time point was not to exceed 8 ml, which represents approximately 4% total blood volume of an adult monkey.

Animals had blood drawn at two baseline time points and on study days 1, 3, 5, 7, 9, 11, 13 and 15, with continued weekly collection thereafter until total plasma cholesterol normalizes in group 1 (APOA1), if a perturbation is appreciated. Eight milliliters of blood were collected on days 1, 6 and 11 to allow for assessment of clinical chemistries, lipid profiles and coagulation profiles. On all other days only 5 mls of blood were collected, sufficient for clinical chemistries and lipid profiles.

Blood samples were split into three parts on days on which both chemistry and hematology measures will be made. One sample was collected into plasma collection tubes containing 25 .mu.l of heparin and labeled with the study number, dose level, day number, date, unique animal identification number. Following separation 1 ml of plasma was removed to a sterile cryotube carrying the above details and stored appropriately until shipment, for blood chemistry analysis. One aliquot of the plasma (0.5 ml) was removed to a sterile cryotube labeled with the details described above and stored appropriately until shipment for plasma cholesterol distribution and Lipid profile analysis. An additional 1 ml and 0.5 ml aliquot of plasma was flash frozen and stored in liquid nitrogen to serve as back-up samples for potential additional analyses.

Two additional whole blood sample aliquots (2.5 ml each) were treated with acid citrate dextrose (ACD) anticoagulant and labeled, and stored at 4.degree. C. until shipped for coagulation and CBC measures detailed below.

The samples were shipped to arrive within 24 h of sampling, or stored under stable conditions for shipment at a time determined appropriate.

Repeat samples were taken only if the method of sampling or the method of assay was thought to be outside normal quality limits Samples were taken into labeled tubes.

Hematology

A complete blood count (CBC), Prothrombin Time, PTT, Fibrinogen and D-Dimer were measured on all samples collected on days 1, 6 and 11 (and on additional days if perturbations are detected at any of these time points). Blood counts were assessed cm 1 ml of whole blood collected in vacutainers containing EDTA. Coagulation profile determinations were performed on approximately 2.0 mL blood collected in vacutainers containing acid citrate dextrose (ACD) anticoagulant.

Blood Chemistry

Glucose, Blood Urea Nitrogen, Creatinine, Total protein, Albumin, Total bilirubin. Alkaline Phosphatase, Alanine aminotransferase (ALT), Aspartate aminotransferase (AST), Cholesterol, Calcium, Phosphorus, Sodium, Potassium, Chloride, A/G ratio, BUN/Creatine (calculated) Globulins (calculated), Lipase, Amylase, Triglycerides, CPK, Lactate dehydrogenase, Gamma glutamyl transferase (GGT), Magnesium, Total Cholesterol LDL, VLDL, HDL, ApoA1, ApoA2, ApoB, ApoE, ApoLp(a). Superchemistries and LDL and HDL measures were made on every plasma sample. ApoA1 measures were made on select samples after assessment of the LDL and HDL data.

Determinations were performed on approximately 1.0 mL plasma for the superchemistry and 0.5 ml plasma for the cholesterol distribution and Lipid transport and metabolism gene measures. An additional aliquot of plasma was collected and stored for possible future analyses.

Liver Biopsies

A percutaneous liver biopsy was performed on all monkeys at baseline and on days 7 and 17. A 14 gauge biopsy needle (INRAD) will be employed to obtain 2 core biopsies (.about. 1.0 cm in length) from both the right and left lobe of the liver. Successful biopsy was confirmed by visual inspection of the biopsy sample on the biopsy needle prior to subdividing as indicated below.

The samples were pooled and then split in the following manner. Half of one biopsy (.about.0.5 cm) from the left lobe was immersed in paraformaldehyde for sectioning for histopathology and in situ analysis. The remaining half of each of the divided biopsies, as well the other two intact biopsies were immediately immersed in a labeled cryotube containing 2 mls of RNAlater (Qiagen) and incubated at 4.degree. C. overnight, following which the RNAlater was aspirated and the sample tube flash frozen in liquid nitrogen. Following transportation in liquid nitrogen total RNA was isolated employing the Trizol or TriReagent method, with an expected yield of .about.40 .mu.g per 1.0 cm 14 g core biopsy (.about.80-100 .mu.g total for the pooled RNA derived from all 4 pooled core biopsies from a single monkey, absent the component saved for histopathology and in situ). 5 .mu.g of the RNA fraction were used for target-specific real-time qPCR (TaqMan miRNA assay, ABI). The remaining RNA fraction was reserved for possible genome wide expression analysis.

The fixed tissue was processed for paraffin embedding. Sections were stained for H&E and histopathological findings reported under Gross Histological findings. All slides generated in this work carried a label with the study number, dose level, day number, date, unique animal identification number.

Statistical Analysis

Statistics

Descriptive statistics on hematology, clinical chemistries and lipid profiles were performed. Appropriate bioinformatic analyses was conducted on expression data.

Sample Size

Sample size determinations were made cm the basis of prior experiments administering modified antisense oligonucleotides to African green monkeys and resulting clinical chemistry and lipid profile changes and associated variability. The total number of subjects for efficacy evaluation were twenty enrolled animals, with four animals per treatment group, and four additional screened animals.

Figure 1U:
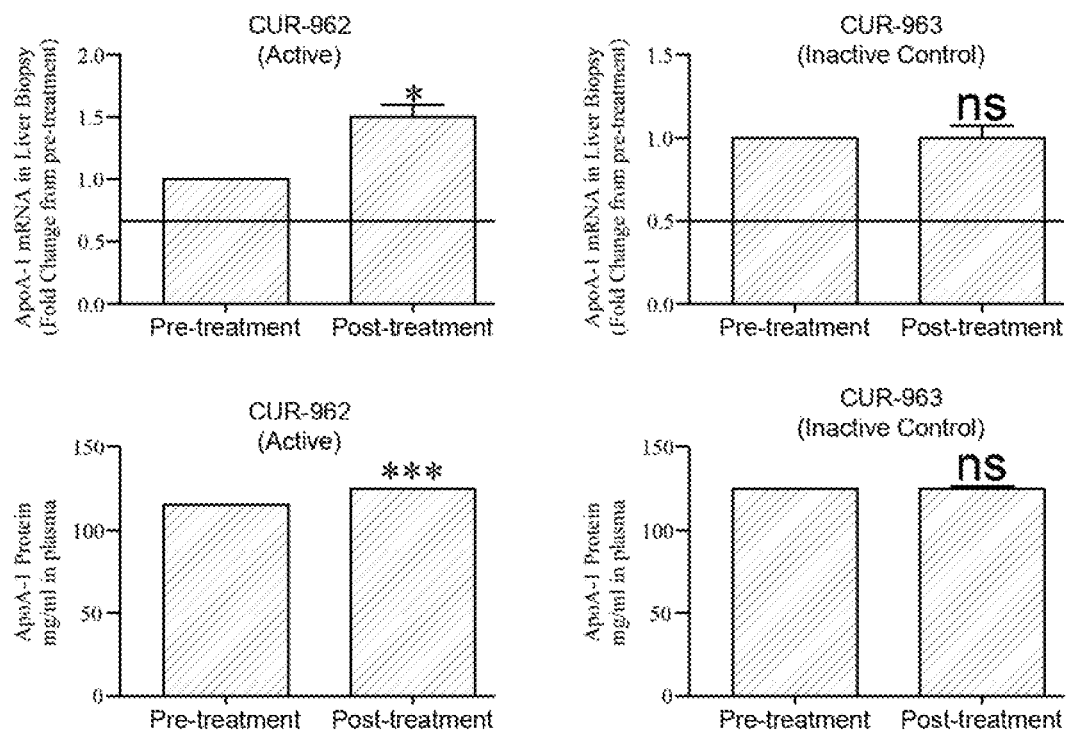
FIG. 1U is a graph showing that ApoA1 mRNA and protein levels increased in monkey liver biopsies after treatment with CUR-962, an oligonucleotide designed to ApoA1 antisense DA327409ext, compared to the baseline levels, as determined by real time PCR and ELISA respectively (right panels). ApoA1 mRNA or protein levels did not change after the same period of time in the control group dosed with an oligonucleotide that showed no effect on ApoA1 levels in vitro (CUR-963) (left panels). Bars denoted CUR-962 and CUR-963 correspond to SEQ ID NOS 260 and 261 respectively.

Results:

The results are shown in the following figures. FIG. 1U: ApoA1 mRNA (top panels) and protein (bottom panels) levels increased in monkey liver biopsies after treatment with CUR-962, an oligonucleotide designed to ApoA1 antisense DA327409ext, compared to the baseline levels, as determined by real time PCR and ELISA respectively (two left panels). ApoA1 mRNA and protein levels did not change after the same period of time in the control group dosed with an oligonucleotide that showed no effect on ApoA1 levels in vitro (CUR-963, two right panels).

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A compound comprising a single stranded synthetic, modified antisense RNA oligonucleotide of 19 to 21 nucleotides in length or an optionally modified double stranded siRNA comprising an oligonucleotide of 19 to 30 nucleotides in length wherein said modifications are selected from: at least one modified sugar moiety; at least one modified internucleotide linkage; at least one modified nucleotide, and combinations thereof; wherein said siRNA oligonucleotide and said single stranded antisense RNA oligonucleotide are each 100% complementary with and specifically hybridize to a target region of a natural antisense polynucleotide of a lipid transport and metabolism gene that is an ABCA1 polynucleotide wherein said natural antisense polynucleotide is SEQ ID NO: 8, and where the antisense RNA oligonucleotide and the siRNA oligonucleotide upregulate the function and/or expression of the ABCA1 polynucleotide in vivo or in vitro as compared to a normal control, and wherein the target region in SEQ ID NO: 8 consists of nucleotides 1-245 and 799-1169, and further wherein the siRNA oligonucleotide and the single stranded oligonucleotide comprise a nucleobase sequence selected from the group consisting of SEQ ID NOS: 27, 28, 29, 31, 32, 33, 35, 38, and 39 wherein each thymine base may be replaced by a uracil base.

2. The siRNA oligonucleotide or single stranded antisense RNA oligonucleotide of claim 1 comprising at least one modified internucleotide linkage selected from the group consisting of phosphorothioate, alkylphosphonate, phosphorodithioate, alkylphosphonothioate, phosphoramidate, carbamate, carbonate, phosphate triester, acetamidate, carboxymethyl ester, and combinations thereof.

3. The siRNA oligonucleotide or single stranded antisense RNA oligonucleotide of claim 1 comprising at least one phosphorothioate internucleotide linkage.

4. The siRNA oligonucleotide or single stranded antisense RNA oligonucleotide of claim 1 comprising a backbone of phosphorothioate internucleotide linkages.

5. The siRNA oligonucleotide or single stranded antisense RNA oligonucleotide of claim 1 comprising at least one modified nucleotide selected from: a peptide nucleic acid, a locked nucleic acid (LNA), an analogue thereof, a derivative thereof, and a combination thereof.

6. The siRNA oligonucleotide or single stranded antisense RNA oligonucleotide of claim 1 comprising a plurality of modified internucleotide linkages selected from: phosphorothioate, alkylphosphonate, phosphorodithioate, alkylphosphonothioate, phosphoramidate, carbamate, carbonate, phosphate triester, acetamidate, carboxymethyl ester, and a combination thereof.

7. The siRNA oligonucleotide or single stranded antisense RNA oligonucleotide of claim 1 comprising a plurality of modifications selected from peptide nucleic acids, locked nucleic acids (LNAs), analogues thereof, derivatives thereof, and a combination thereof.

8. The siRNA oligonucleotide or single stranded antisense RNA oligonucleotide of claim 1 comprising at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and a combination thereof.

9. The siRNA oligonucleotide or single stranded antisense RNA oligonucleotide of claim 1, wherein the oligonucleotide comprises a plurality of modifications, wherein said modifications comprise modified sugar moieties selected from: a 2'-O-methoxyethyl modified sugar moiety, a 2'-methoxy modified sugar moiety, a 2'-O-alkyl modified sugar moiety, a bicyclic sugar moiety, and a combination thereof.

10. A single stranded antisense oligonucleotide comprising a non-naturally occurring modified nucleotide wherein the nucleobase sequence of the oligonucleotide consists of a nucleobase sequence selected from the group consisting of SEQ ID NOS: 27, 28, 29, 31, 32, 33, 35, 38, 39, wherein each thymine base may be replaced with a uracil base.

11. A double stranded RNA oligonucleotide of 19 to 30 nucleotides in length comprising the nucleobase sequence of SEQ ID NO: 23 or 24.

12. A pharmaceutical composition comprising a double-stranded or single stranded antisense oligonucleotide of 19 to 30 nucleotides in length and a pharmaceutically acceptable excipient, wherein the double-stranded or single stranded oligonucleotide comprises a non-naturally occurring nucleotide modification and the nucleobase sequence of any one of SEQ ID NOS; 23, 24, 27, 28, 29, 31, 32, 33, 35, 38 and 39, wherein each thymine base may be replaced by a uracil base.

13. The composition of claim 12, wherein the nucleobase sequence of the single stranded antisense oligonucleotide is selected from the nucleobase sequence of any one of SEQ ID NOS: 27, 28, 29, 31, 32, 33, 35, 38 and 39, wherein each thymine base may be replaced by a uracil base.

14. The composition of claim 12, wherein the double-stranded or single stranded antisense oligonucleotide comprises the nucleobase sequence of SEQ ID NO: 23 or SEQ ID NO: 24.

15. The composition of claim 12, wherein the double-stranded or single stranded antisense oligonucleotide comprises one or more modifications selected from: phosphorothioate, methylphosphonate, peptide nucleic acid, locked nucleic acid (LNA) molecules, and combinations thereof.

* * * * *